US012612631B2

(12) United States Patent
Jiang et al.

(10) Patent No.: US 12,612,631 B2
(45) Date of Patent: Apr. 28, 2026

(54) SMALL RNA MEDICAMENT FOR PREVENTION AND TREATMENT OF INFLAMMATION-RELATED DISEASES AND COMBINATION THEREOF

(71) Applicant: INSTITUTE OF BASIC MEDICAL SCIENCES CHINESE ACADEMY OF MEDICAL SCIENCES, Beijing (CN)

(72) Inventors: Chengyu Jiang, Beijing (CN); Dandan Zhao, Beijing (CN); Yuhao Qin, Beijing (CN); Cong Zhang, Beijing (CN); Yexuan Lin, Beijing (CN)

(73) Assignee: BEIJING BAISHIHEKANG PHARMACEUTICAL TECHNOLOGY (BSJPHARMA) CO., LTD, Beijing (CN)

( * ) Notice: Subject to any disclaimer, the term of this patent is extended or adjusted under 35 U.S.C. 154(b) by 1287 days.

(21) Appl. No.: 17/417,321

(22) PCT Filed: Dec. 25, 2018

(86) PCT No.: PCT/CN2018/123289
§ 371 (c)(1),
(2) Date: Feb. 1, 2022

(87) PCT Pub. No.: WO2020/132844
PCT Pub. Date: Jul. 2, 2020

(65) Prior Publication Data
US 2023/0272402 A1 Aug. 31, 2023

(51) Int. Cl.
C07H 21/04 (2006.01)
A61P 29/00 (2006.01)
C12N 15/113 (2010.01)
C12N 15/85 (2006.01)

(52) U.S. Cl.
CPC .......... C12N 15/1136 (2013.01); A61P 29/00 (2018.01); C12N 15/85 (2013.01); C12N 2310/14 (2013.01); C12N 2330/30 (2013.01); C12N 2330/50 (2013.01)

(58) Field of Classification Search
CPC .......................... C12N 15/113; C12N 2310/11
See application file for complete search history.

(56) References Cited

U.S. PATENT DOCUMENTS 12,253,515 B2 * 3/2025 Asahara .............. G01N 33/574
2017/0342410 A1 11/2017 Hannon et al.

FOREIGN PATENT DOCUMENTS

CN 106687120 A 5/2017
CN 109023536 A 12/2018
EP 3216869 A1 9/2017
WO WO-2012037881 A1 * 3/2012 ......... C12N 15/1093
WO WO 2020/132844 A1 7/2020

OTHER PUBLICATIONS

Elbashir et al. (The EMBO Journal, vol. 20, No. 23, pp. 6877-6888, 2001).*
Fujita et al. (Int. J. Mol. Sci. 2015, 16, 5254-5270).*
Sha et al. (Fertility and Sterility, vol. 96, No. 1, Jul. 2011, 150-155. e5).*
Devroe et al. (BMC Biotechnology 2002, 2, 15, 1-5).*
Ma, Y., et al., "Identification of miRNAs from Dihuang (Rehmannia glutinosa) and Their Regulating Target Function on Human Genes," Chinese Journal of Traditional Medical Science and Technology, 23(4):416-420 (Jul. 20, 2016); Abstract in English.
Xiang, J., et al., "Effect of miRNA from Glycyrrhiza uralensis decoction on gene expression of human immune cells," China Journal of Chinese Materia Medica, 42(9):1752-1756 (May 1, 2017); Abstract in English.
International Search Report and Written Opinion received in PCT Application No. PCT/CN2018/123289 dated Sep. 24, 2019.

* cited by examiner

Primary Examiner — Amy Rose Hudson
(74) Attorney, Agent, or Firm — Crowell & Moring LLP

(57) ABSTRACT

Provided is a small RNA, a composition comprising the small RNA, a method for using same and use of same. The small RNA or composition can inhibit the ability of any one or more of pathways or genes listed in Table 3, or decrease or down regulate the expression level of IL-1 beta, IL-6, and/or TNF-alpha in vitro or in vivo, or treat or prevent IL-1 beta, IL-6, and/or TNF-alpha related diseases and/or increase cell viability in a subject.

15 Claims, 33 Drawing Sheets
Specification includes a Sequence Listing.

A

B

C

D

E

F

K

L

SEQUENCE LISTING

```
<160> NUMBER OF SEQ ID NOS: 239

<210> SEQ ID NO 1
<211> LENGTH: 18
<212> TYPE: RNA
<213> ORGANISM: Artificial sequence
<220> FEATURE:
<223> OTHER INFORMATION: BZL-sRNA-1

<400> SEQUENCE: 1
guucagaguu cuacaguc                                              18

<210> SEQ ID NO 2
<211> LENGTH: 21
<212> TYPE: RNA
<213> ORGANISM: Artificial sequence
<220> FEATURE:
<223> OTHER INFORMATION: BZL-sRNA-2

<400> SEQUENCE: 2
guucagaguu cuacaguccg a                                          21

<210> SEQ ID NO 3
<211> LENGTH: 24
<212> TYPE: RNA
<213> ORGANISM: Artificial sequence
<220> FEATURE:
<223> OTHER INFORMATION: BZL-sRNA-3

<400> SEQUENCE: 3
ucagaguucu acaguccgac gauc                                       24

<210> SEQ ID NO 4
<211> LENGTH: 24
<212> TYPE: RNA
<213> ORGANISM: Artificial sequence
<220> FEATURE:
<223> OTHER INFORMATION: BZL-sRNA-4
```

-continued

```
<400> SEQUENCE: 4
guucagaguu cuacaguccg acga                                        24

<210> SEQ ID NO 5
<211> LENGTH: 20
<212> TYPE: RNA
<213> ORGANISM: Artificial sequence
<220> FEATURE:
<223> OTHER INFORMATION: BZL-sRNA-5

<400> SEQUENCE: 5
ucagucuuuu ucucucuccu                                             20

<210> SEQ ID NO 6
<211> LENGTH: 26
<212> TYPE: RNA
<213> ORGANISM: Artificial sequence
<220> FEATURE:
<223> OTHER INFORMATION: BZL-sRNA-6

<400> SEQUENCE: 6
ucucgcuugg ggugcgagag gucccg                                      26

<210> SEQ ID NO 7
<211> LENGTH: 21
<212> TYPE: RNA
<213> ORGANISM: Artificial sequence
<220> FEATURE:
<223> OTHER INFORMATION: BZL-sRNA-7

<400> SEQUENCE: 7
ucagucuuuu ucucucuccu a                                           21

<210> SEQ ID NO 8
<211> LENGTH: 19
<212> TYPE: RNA
<213> ORGANISM: Artificial sequence
<220> FEATURE:
<223> OTHER INFORMATION: BZL-sRNA-8

<400> SEQUENCE: 8
uccgguaugg ucuaguggc                                              19

<210> SEQ ID NO 9
<211> LENGTH: 20
<212> TYPE: RNA
<213> ORGANISM: Artificial sequence
<220> FEATURE:
<223> OTHER INFORMATION: BZL-sRNA-9

<400> SEQUENCE: 9
uaggaacuuc auaccgugcu                                             20

<210> SEQ ID NO 10
<211> LENGTH: 22
<212> TYPE: RNA
<213> ORGANISM: Artificial sequence
<220> FEATURE:
<223> OTHER INFORMATION: BZL-sRNA-10

<400> SEQUENCE: 10
ucagucuuuu ucucucuccu au                                          22

<210> SEQ ID NO 11
```

-continued

```
<211> LENGTH: 21
<212> TYPE: RNA
<213> ORGANISM: Artificial sequence
<220> FEATURE:
<223> OTHER INFORMATION: BZL-sRNA-11

<400> SEQUENCE: 11
uaggaacuuc auaccgugcu c                                         21

<210> SEQ ID NO 12
<211> LENGTH: 22
<212> TYPE: RNA
<213> ORGANISM: Artificial sequence
<220> FEATURE:
<223> OTHER INFORMATION: BZL-sRNA-12

<400> SEQUENCE: 12
uaggaacuuc auaccgugcu cu                                        22

<210> SEQ ID NO 13
<211> LENGTH: 22
<212> TYPE: RNA
<213> ORGANISM: Artificial sequence
<220> FEATURE:
<223> OTHER INFORMATION: BZL-sRNA-13

<400> SEQUENCE: 13
uggaauguaa agaaguaugg ag                                        22

<210> SEQ ID NO 14
<211> LENGTH: 21
<212> TYPE: RNA
<213> ORGANISM: Artificial sequence
<220> FEATURE:
<223> OTHER INFORMATION: BZL-sRNA-14

<400> SEQUENCE: 14
ugaacacagc uggugguauc u                                         21

<210> SEQ ID NO 15
<211> LENGTH: 20
<212> TYPE: RNA
<213> ORGANISM: Artificial sequence
<220> FEATURE:
<223> OTHER INFORMATION: BZL-sRNA-15

<400> SEQUENCE: 15
gggggcguag cucagauggu                                           20

<210> SEQ ID NO 16
<211> LENGTH: 20
<212> TYPE: RNA
<213> ORGANISM: Artificial sequence
<220> FEATURE:
<223> OTHER INFORMATION: BZL-sRNA-16

<400> SEQUENCE: 16
ggauuugagu aagagcguag                                           20

<210> SEQ ID NO 17
<211> LENGTH: 21
<212> TYPE: RNA
<213> ORGANISM: Artificial sequence
<220> FEATURE:
<223> OTHER INFORMATION: BZL-sRNA-17

<400> SEQUENCE: 17
```

-continued uggauuugag uaagagcgua g                                                    21

<210> SEQ ID NO 18
<211> LENGTH: 22
<212> TYPE: RNA
<213> ORGANISM: Artificial sequence
<220> FEATURE:
<223> OTHER INFORMATION: BZL-sRNA-18

<400> SEQUENCE: 18
auggauuuga guaagagcgu ag                                                   22

<210> SEQ ID NO 19
<211> LENGTH: 25
<212> TYPE: RNA
<213> ORGANISM: Artificial sequence
<220> FEATURE:
<223> OTHER INFORMATION: BZL-sRNA-19

<400> SEQUENCE: 19
guucagaguu cuacaguccg acgau                                               25

<210> SEQ ID NO 20
<211> LENGTH: 26
<212> TYPE: RNA
<213> ORGANISM: Artificial sequence
<220> FEATURE:
<223> OTHER INFORMATION: BZL-sRNA-20

<400> SEQUENCE: 20
guucagaguu cuacaguccg acgauc                                              26

<210> SEQ ID NO 21
<211> LENGTH: 23
<212> TYPE: RNA
<213> ORGANISM: Artificial sequence
<220> FEATURE:
<223> OTHER INFORMATION: BZL-sRNA-21

<400> SEQUENCE: 21
gauggauuug aguaagagcg uag                                                 23

<210> SEQ ID NO 22
<211> LENGTH: 18
<212> TYPE: RNA
<213> ORGANISM: Artificial sequence
<220> FEATURE:
<223> OTHER INFORMATION: BZL-sRNA-22

<400> SEQUENCE: 22
cucuucaacg aggaaugc                                                       18

<210> SEQ ID NO 23
<211> LENGTH: 24
<212> TYPE: RNA
<213> ORGANISM: Artificial sequence
<220> FEATURE:
<223> OTHER INFORMATION: BZL-sRNA-23

<400> SEQUENCE: 23
ggauggauuu gaguaagagc guag                                                24

<210> SEQ ID NO 24
<211> LENGTH: 18
<212> TYPE: RNA

<213> ORGANISM: Artificial sequence
<220> FEATURE:
<223> OTHER INFORMATION: BZL-sRNA-24

<400> SEQUENCE: 24
gaaacggcug cuaauacc                                            18

<210> SEQ ID NO 25
<211> LENGTH: 20
<212> TYPE: RNA
<213> ORGANISM: Artificial sequence
<220> FEATURE:
<223> OTHER INFORMATION: BZL-sRNA-25

<400> SEQUENCE: 25
uggaaacggc ugcuaauacc                                          20

<210> SEQ ID NO 26
<211> LENGTH: 21
<212> TYPE: RNA
<213> ORGANISM: Artificial sequence
<220> FEATURE:
<223> OTHER INFORMATION: BZL-sRNA-26

<400> SEQUENCE: 26
uggauuugag uaagagcaua g                                        21

<210> SEQ ID NO 27
<211> LENGTH: 22
<212> TYPE: RNA
<213> ORGANISM: Artificial sequence
<220> FEATURE:
<223> OTHER INFORMATION: BZL-sRNA-27

<400> SEQUENCE: 27
auggauuuga guaagagcau ag                                       22

<210> SEQ ID NO 28
<211> LENGTH: 18
<212> TYPE: RNA
<213> ORGANISM: Artificial sequence
<220> FEATURE:
<223> OTHER INFORMATION: BZL-sRNA-28

<400> SEQUENCE: 28
ccccgucgug cccggacc                                            18

<210> SEQ ID NO 29
<211> LENGTH: 25
<212> TYPE: RNA
<213> ORGANISM: Artificial sequence
<220> FEATURE:
<223> OTHER INFORMATION: BZL-sRNA-29

<400> SEQUENCE: 29
cggauggauu ugaguaagag cguag                                    25

<210> SEQ ID NO 30
<211> LENGTH: 21
<212> TYPE: RNA
<213> ORGANISM: Artificial sequence
<220> FEATURE:
<223> OTHER INFORMATION: BZL-sRNA-30

<400> SEQUENCE: 30
cuggaaacgg cugcuaauac c                                        21

```
<210> SEQ ID NO 31
<211> LENGTH: 19
<212> TYPE: RNA
<213> ORGANISM: Artificial sequence
<220> FEATURE:
<223> OTHER INFORMATION: BZL-sRNA-31

<400> SEQUENCE: 31
gccccgucgu gcccggacc                                                19

<210> SEQ ID NO 32
<211> LENGTH: 23
<212> TYPE: RNA
<213> ORGANISM: Artificial sequence
<220> FEATURE:
<223> OTHER INFORMATION: BZL-sRNA-32

<400> SEQUENCE: 32
agcuggaaac ggcugcuaau acc                                            23

<210> SEQ ID NO 33
<211> LENGTH: 20
<212> TYPE: RNA
<213> ORGANISM: Artificial sequence
<220> FEATURE:
<223> OTHER INFORMATION: BZL-sRNA-33

<400> SEQUENCE: 33
agccccgucg ugcccggacc                                               20

<210> SEQ ID NO 34
<211> LENGTH: 21
<212> TYPE: RNA
<213> ORGANISM: Artificial sequence
<220> FEATURE:
<223> OTHER INFORMATION: BZL-sRNA-34

<400> SEQUENCE: 34
gagccccguc gugcccggac c                                              21

<210> SEQ ID NO 35
<211> LENGTH: 22
<212> TYPE: RNA
<213> ORGANISM: Artificial sequence
<220> FEATURE:
<223> OTHER INFORMATION: BZL-sRNA-35

<400> SEQUENCE: 35
agagccccgu cgugcccgga cc                                             22

<210> SEQ ID NO 36
<211> LENGTH: 23
<212> TYPE: RNA
<213> ORGANISM: Artificial sequence
<220> FEATURE:
<223> OTHER INFORMATION: BZL-sRNA-36

<400> SEQUENCE: 36
gagagccccg ucgugcccgg acc                                            23

<210> SEQ ID NO 37
<211> LENGTH: 24
<212> TYPE: RNA
<213> ORGANISM: Artificial sequence
<220> FEATURE:
```

-continued

<223> OTHER INFORMATION: BZL-sRNA-37

<400> SEQUENCE: 37
ugagagcccc gucgugcccg gacc                                                    24

<210> SEQ ID NO 38
<211> LENGTH: 25
<212> TYPE: RNA
<213> ORGANISM: Artificial sequence
<220> FEATURE:
<223> OTHER INFORMATION: BZL-sRNA-38

<400> SEQUENCE: 38
gugagagccc cgucgugccc ggacc                                                   25

<210> SEQ ID NO 39
<211> LENGTH: 26
<212> TYPE: RNA
<213> ORGANISM: Artificial sequence
<220> FEATURE:
<223> OTHER INFORMATION: BZL-sRNA-39

<400> SEQUENCE: 39
ggugagagcc ccgucgugcc cggacc                                                  26

<210> SEQ ID NO 40
<211> LENGTH: 27
<212> TYPE: RNA
<213> ORGANISM: Artificial sequence
<220> FEATURE:
<223> OTHER INFORMATION: BZL-sRNA-40

<400> SEQUENCE: 40
gggugagagc cccgucgugc ccggacc                                                 27

<210> SEQ ID NO 41
<211> LENGTH: 28
<212> TYPE: RNA
<213> ORGANISM: Artificial sequence
<220> FEATURE:
<223> OTHER INFORMATION: BZL-sRNA-41

<400> SEQUENCE: 41
agggugagag ccccgucgug cccggacc                                                28

<210> SEQ ID NO 42
<211> LENGTH: 29
<212> TYPE: RNA
<213> ORGANISM: Artificial sequence
<220> FEATURE:
<223> OTHER INFORMATION: BZL-sRNA-42

<400> SEQUENCE: 42
gagggugaga ccccgucgu gcccggacc                                                29

<210> SEQ ID NO 43
<211> LENGTH: 18
<212> TYPE: RNA
<213> ORGANISM: Artificial sequence
<220> FEATURE:
<223> OTHER INFORMATION: CHu-sRNA-1

<400> SEQUENCE: 43
acaacuuuca gcaacgga                                                           18

-continued

```
<210> SEQ ID NO 44
<211> LENGTH: 19
<212> TYPE: RNA
<213> ORGANISM: Artificial sequence
<220> FEATURE:
<223> OTHER INFORMATION: CHu-sRNA-2

<400> SEQUENCE: 44
acaacuuuca gcaacggau                                                    19

<210> SEQ ID NO 45
<211> LENGTH: 20
<212> TYPE: RNA
<213> ORGANISM: Artificial sequence
<220> FEATURE:
<223> OTHER INFORMATION: CHu-sRNA-3

<400> SEQUENCE: 45
acaacuuuca gcaacggauc                                                   20

<210> SEQ ID NO 46
<211> LENGTH: 21
<212> TYPE: RNA
<213> ORGANISM: Artificial sequence
<220> FEATURE:
<223> OTHER INFORMATION: CHu-sRNA-4

<400> SEQUENCE: 46
acaacuuuca gcaacggauc u                                                 21

<210> SEQ ID NO 47
<211> LENGTH: 20
<212> TYPE: RNA
<213> ORGANISM: Artificial sequence
<220> FEATURE:
<223> OTHER INFORMATION: CHu-sRNA-5

<400> SEQUENCE: 47
ugauaugaag cacuguagcu                                                   20

<210> SEQ ID NO 48
<211> LENGTH: 21
<212> TYPE: RNA
<213> ORGANISM: Artificial sequence
<220> FEATURE:
<223> OTHER INFORMATION: CHu-sRNA-6

<400> SEQUENCE: 48
ugauaugaag cacuguagcu c                                                 21

<210> SEQ ID NO 49
<211> LENGTH: 19
<212> TYPE: RNA
<213> ORGANISM: Artificial sequence
<220> FEATURE:
<223> OTHER INFORMATION: CHu-sRNA-7

<400> SEQUENCE: 49
guucagaguu cuacagucc                                                    19

<210> SEQ ID NO 50
<211> LENGTH: 20
<212> TYPE: RNA
<213> ORGANISM: Artificial sequence
<220> FEATURE:
<223> OTHER INFORMATION: CHu-sRNA-8
```

<400> SEQUENCE: 50
guucagaguu cuacaguccg                                        20

<210> SEQ ID NO 51
<211> LENGTH: 19
<212> TYPE: RNA
<213> ORGANISM: Artificial sequence
<220> FEATURE:
<223> OTHER INFORMATION: CHu-sRNA-9

<400> SEQUENCE: 51
uguaguagau uguauaguu                                         19

<210> SEQ ID NO 52
<211> LENGTH: 22
<212> TYPE: RNA
<213> ORGANISM: Artificial sequence
<220> FEATURE:
<223> OTHER INFORMATION: CHu-sRNA-10

<400> SEQUENCE: 52
ugauaugaag cacguagcu cu                                      22

<210> SEQ ID NO 53
<211> LENGTH: 18
<212> TYPE: RNA
<213> ORGANISM: Artificial sequence
<220> FEATURE:
<223> OTHER INFORMATION: CHu-sRNA-11

<400> SEQUENCE: 53
ugauguagua gguuguau                                          18

<210> SEQ ID NO 54
<211> LENGTH: 19
<212> TYPE: RNA
<213> ORGANISM: Artificial sequence
<220> FEATURE:
<223> OTHER INFORMATION: CHu-sRNA-12

<400> SEQUENCE: 54
ugauguagua gauuguaua                                         19

<210> SEQ ID NO 55
<211> LENGTH: 20
<212> TYPE: RNA
<213> ORGANISM: Artificial sequence
<220> FEATURE:
<223> OTHER INFORMATION: CHu-sRNA-13

<400> SEQUENCE: 55
ugauguagua gauuguauag                                        20

<210> SEQ ID NO 56
<211> LENGTH: 21
<212> TYPE: RNA
<213> ORGANISM: Artificial sequence
<220> FEATURE:
<223> OTHER INFORMATION: CHu-sRNA-14

<400> SEQUENCE: 56
ugauguagua gauuguauag u                                      21

<210> SEQ ID NO 57
<211> LENGTH: 22

-continued

```
<212> TYPE: RNA
<213> ORGANISM: Artificial sequence
<220> FEATURE:
<223> OTHER INFORMATION: CHu-sRNA-15

<400> SEQUENCE: 57
ugauguagua gauuguauag uu                                             22

<210> SEQ ID NO 58
<211> LENGTH: 18
<212> TYPE: RNA
<213> ORGANISM: Artificial sequence
<220> FEATURE:
<223> OTHER INFORMATION: CHu-sRNA-16

<400> SEQUENCE: 58
ugcuguagua gguuguau                                                  18

<210> SEQ ID NO 59
<211> LENGTH: 20
<212> TYPE: RNA
<213> ORGANISM: Artificial sequence
<220> FEATURE:
<223> OTHER INFORMATION: CHu-sRNA-17

<400> SEQUENCE: 59
ugauguagua gguuguaugg                                                20

<210> SEQ ID NO 60
<211> LENGTH: 21
<212> TYPE: RNA
<213> ORGANISM: Artificial sequence
<220> FEATURE:
<223> OTHER INFORMATION: CHu-sRNA-18

<400> SEQUENCE: 60
ugauguagua gguuguaugg u                                              21

<210> SEQ ID NO 61
<211> LENGTH: 20
<212> TYPE: RNA
<213> ORGANISM: Artificial sequence
<220> FEATURE:
<223> OTHER INFORMATION: CHu-sRNA-19

<400> SEQUENCE: 61
ugauguagua gguuguauag                                                20

<210> SEQ ID NO 62
<211> LENGTH: 18
<212> TYPE: RNA
<213> ORGANISM: Artificial sequence
<220> FEATURE:
<223> OTHER INFORMATION: CHu-sRNA-20

<400> SEQUENCE: 62
agccggacgg uggccaug                                                  18

<210> SEQ ID NO 63
<211> LENGTH: 21
<212> TYPE: RNA
<213> ORGANISM: Artificial sequence
<220> FEATURE:
<223> OTHER INFORMATION: CHu-sRNA-21

<400> SEQUENCE: 63
```
uaacuuauca gacugauguu g                                                    21

<210> SEQ ID NO 64
<211> LENGTH: 22
<212> TYPE: RNA
<213> ORGANISM: Artificial sequence
<220> FEATURE:
<223> OTHER INFORMATION: CHu-sRNA-22

<400> SEQUENCE: 64
cagcagcaau ucauguuuug ga                                                   22

<210> SEQ ID NO 65
<211> LENGTH: 22
<212> TYPE: RNA
<213> ORGANISM: Artificial sequence
<220> FEATURE:
<223> OTHER INFORMATION: CHu-sRNA-23

<400> SEQUENCE: 65
uaacuuauca gacugauguu ga                                                   22

<210> SEQ ID NO 66
<211> LENGTH: 21
<212> TYPE: RNA
<213> ORGANISM: Artificial sequence
<220> FEATURE:
<223> OTHER INFORMATION: CHu-sRNA-24

<400> SEQUENCE: 66
ugauguagua gguuguauag u                                                    21

<210> SEQ ID NO 67
<211> LENGTH: 22
<212> TYPE: RNA
<213> ORGANISM: Artificial sequence
<220> FEATURE:
<223> OTHER INFORMATION: CHu-sRNA-25

<400> SEQUENCE: 67
ugauguagua gguuguaugg uu                                                   22

<210> SEQ ID NO 68
<211> LENGTH: 19
<212> TYPE: RNA
<213> ORGANISM: Artificial sequence
<220> FEATURE:
<223> OTHER INFORMATION: CHu-sRNA-26

<400> SEQUENCE: 68
uuaaaguaau ccaggauag                                                       19

<210> SEQ ID NO 69
<211> LENGTH: 22
<212> TYPE: RNA
<213> ORGANISM: Artificial sequence
<220> FEATURE:
<223> OTHER INFORMATION: CHu-sRNA-27

<400> SEQUENCE: 69
uguaaacauc cucgacugga aa                                                   22

<210> SEQ ID NO 70
<211> LENGTH: 20
<212> TYPE: RNA
<213> ORGANISM: Artificial sequence -continued
<220> FEATURE:
<223> OTHER INFORMATION: CHu-sRNA-28

<400> SEQUENCE: 70
uuaaaguaau ccaggauagg                                                   20

<210> SEQ ID NO 71
<211> LENGTH: 20
<212> TYPE: RNA
<213> ORGANISM: Artificial sequence
<220> FEATURE:
<223> OTHER INFORMATION: CHu-sRNA-29

<400> SEQUENCE: 71
uuagaguaau ccaggauagg                                                   20

<210> SEQ ID NO 72
<211> LENGTH: 22
<212> TYPE: RNA
<213> ORGANISM: Artificial sequence
<220> FEATURE:
<223> OTHER INFORMATION: CHu-sRNA-30

<400> SEQUENCE: 72
ugauguagua gguuguauag uu                                                22

<210> SEQ ID NO 73
<211> LENGTH: 20
<212> TYPE: RNA
<213> ORGANISM: Artificial sequence
<220> FEATURE:
<223> OTHER INFORMATION: CHu-sRNA-31

<400> SEQUENCE: 73
ugcuguagua gauuguauag                                                   20

<210> SEQ ID NO 74
<211> LENGTH: 20
<212> TYPE: RNA
<213> ORGANISM: Artificial sequence
<220> FEATURE:
<223> OTHER INFORMATION: CHu-sRNA-32

<400> SEQUENCE: 74
uccaguacug ugauaacuga                                                   20

<210> SEQ ID NO 75
<211> LENGTH: 21
<212> TYPE: RNA
<213> ORGANISM: Artificial sequence
<220> FEATURE:
<223> OTHER INFORMATION: CHu-sRNA-33

<400> SEQUENCE: 75
ccuucccuuu guacacaccg c                                                 21

<210> SEQ ID NO 76
<211> LENGTH: 20
<212> TYPE: RNA
<213> ORGANISM: Artificial sequence
<220> FEATURE:
<223> OTHER INFORMATION: CHu-sRNA-34

<400> SEQUENCE: 76
ugcgguagua gguuguaugg                                                   20

```
<210> SEQ ID NO 77
<211> LENGTH: 21
<212> TYPE: RNA
<213> ORGANISM: Artificial sequence
<220> FEATURE:
<223> OTHER INFORMATION: CHu-sRNA-35

<400> SEQUENCE: 77
ugcuguagua gauuguauag u                                                              21

<210> SEQ ID NO 78
<211> LENGTH: 20
<212> TYPE: RNA
<213> ORGANISM: Artificial sequence
<220> FEATURE:
<223> OTHER INFORMATION: CHu-sRNA-36

<400> SEQUENCE: 78
ugauguagua gguugugugg                                                                20

<210> SEQ ID NO 79
<211> LENGTH: 21
<212> TYPE: RNA
<213> ORGANISM: Artificial sequence
<220> FEATURE:
<223> OTHER INFORMATION: CHu-sRNA-37

<400> SEQUENCE: 79
ugauguagua gguugugugg u                                                              21

<210> SEQ ID NO 80
<211> LENGTH: 21
<212> TYPE: RNA
<213> ORGANISM: Artificial sequence
<220> FEATURE:
<223> OTHER INFORMATION: CHu-sRNA-38

<400> SEQUENCE: 80
uuagaguaau ccaggauagg c                                                              21

<210> SEQ ID NO 81
<211> LENGTH: 21
<212> TYPE: RNA
<213> ORGANISM: Artificial sequence
<220> FEATURE:
<223> OTHER INFORMATION: CHu-sRNA-39

<400> SEQUENCE: 81
uuaaaguaau ccaggauagg c                                                              21

<210> SEQ ID NO 82
<211> LENGTH: 19
<212> TYPE: RNA
<213> ORGANISM: Artificial sequence
<220> FEATURE:
<223> OTHER INFORMATION: CHu-sRNA-40

<400> SEQUENCE: 82
agccggacgg uggccaugg                                                                 19

<210> SEQ ID NO 83
<211> LENGTH: 22
<212> TYPE: RNA
<213> ORGANISM: Artificial sequence
<220> FEATURE:
<223> OTHER INFORMATION: CHu-sRNA-41
```

<400> SEQUENCE: 83
ugcuguagua gauuguauag uu                                                    22

<210> SEQ ID NO 84
<211> LENGTH: 19
<212> TYPE: RNA
<213> ORGANISM: Artificial sequence
<220> FEATURE:
<223> OTHER INFORMATION: CHu-sRNA-42

<400> SEQUENCE: 84
aacccguuac cauuacuga                                                        19

<210> SEQ ID NO 85
<211> LENGTH: 21
<212> TYPE: RNA
<213> ORGANISM: Artificial sequence
<220> FEATURE:
<223> OTHER INFORMATION: CHu-sRNA-43

<400> SEQUENCE: 85
aacccguuac cauuacugag u                                                     21

<210> SEQ ID NO 86
<211> LENGTH: 19
<212> TYPE: RNA
<213> ORGANISM: Artificial sequence
<220> FEATURE:
<223> OTHER INFORMATION: CHu-sRNA-44

<400> SEQUENCE: 86
guccaguacu gugauaacu                                                        19

<210> SEQ ID NO 87
<211> LENGTH: 22
<212> TYPE: RNA
<213> ORGANISM: Artificial sequence
<220> FEATURE:
<223> OTHER INFORMATION: CHu-sRNA-45

<400> SEQUENCE: 87
uuaaaguaau ccaggauagg cu                                                    22

<210> SEQ ID NO 88
<211> LENGTH: 21
<212> TYPE: RNA
<213> ORGANISM: Artificial sequence
<220> FEATURE:
<223> OTHER INFORMATION: CHu-sRNA-46

<400> SEQUENCE: 88
uaaguuauca gacugauguu g                                                     21

<210> SEQ ID NO 89
<211> LENGTH: 20
<212> TYPE: RNA
<213> ORGANISM: Artificial sequence
<220> FEATURE:
<223> OTHER INFORMATION: CHu-sRNA-47

<400> SEQUENCE: 89
guccaguacu gugauaacug                                                       20

<210> SEQ ID NO 90

```
<211> LENGTH: 20
<212> TYPE: RNA
<213> ORGANISM: Artificial sequence
<220> FEATURE:
<223> OTHER INFORMATION: CHu-sRNA-48

<400> SEQUENCE: 90
ugcuguagua gguuguauag                                        20

<210> SEQ ID NO 91
<211> LENGTH: 19
<212> TYPE: RNA
<213> ORGANISM: Artificial sequence
<220> FEATURE:
<223> OTHER INFORMATION: CHu-sRNA-49

<400> SEQUENCE: 91
uccugagagg gagccugag                                         19

<210> SEQ ID NO 92
<211> LENGTH: 22
<212> TYPE: RNA
<213> ORGANISM: Artificial sequence
<220> FEATURE:
<223> OTHER INFORMATION: CHu-sRNA-50

<400> SEQUENCE: 92
guucagaguu cuacaguccg ac                                     22

<210> SEQ ID NO 93
<211> LENGTH: 19
<212> TYPE: RNA
<213> ORGANISM: Artificial sequence
<220> FEATURE:
<223> OTHER INFORMATION: CHu-sRNA-51

<400> SEQUENCE: 93
ucccggauag cucagucgg                                         19

<210> SEQ ID NO 94
<211> LENGTH: 21
<212> TYPE: RNA
<213> ORGANISM: Artificial sequence
<220> FEATURE:
<223> OTHER INFORMATION: CHu-sRNA-52

<400> SEQUENCE: 94
gagcuuauca gacugauguu g                                      21

<210> SEQ ID NO 95
<211> LENGTH: 22
<212> TYPE: RNA
<213> ORGANISM: Artificial sequence
<220> FEATURE:
<223> OTHER INFORMATION: CHu-sRNA-53

<400> SEQUENCE: 95
gagcuuauca gacugauguu ga                                     22

<210> SEQ ID NO 96
<211> LENGTH: 19
<212> TYPE: RNA
<213> ORGANISM: Artificial sequence
<220> FEATURE:
<223> OTHER INFORMATION: CHu-sRNA-54

<400> SEQUENCE: 96
```

-continued ucacuccgaa guuucccuc                                                       19

<210> SEQ ID NO 97
<211> LENGTH: 21
<212> TYPE: RNA
<213> ORGANISM: Artificial sequence
<220> FEATURE:
<223> OTHER INFORMATION: CHu-sRNA-55

<400> SEQUENCE: 97
uuucagaguu cuacaguccg a                                                    21

<210> SEQ ID NO 98
<211> LENGTH: 19
<212> TYPE: RNA
<213> ORGANISM: Artificial sequence
<220> FEATURE:
<223> OTHER INFORMATION: DDi-sRNA-1

<400> SEQUENCE: 98
ugauaugaag cacuguagc                                                       19

<210> SEQ ID NO 99
<211> LENGTH: 22
<212> TYPE: RNA
<213> ORGANISM: Artificial sequence
<220> FEATURE:
<223> OTHER INFORMATION: HQi-sRNA-1

<400> SEQUENCE: 99
cccugcccuu guacacaccg cc                                                   22

<210> SEQ ID NO 100
<211> LENGTH: 21
<212> TYPE: RNA
<213> ORGANISM: Artificial sequence
<220> FEATURE:
<223> OTHER INFORMATION: HQi-sRNA-2

<400> SEQUENCE: 100
augguucgau uccggagagg g                                                    21

<210> SEQ ID NO 101
<211> LENGTH: 24
<212> TYPE: RNA
<213> ORGANISM: Artificial sequence
<220> FEATURE:
<223> OTHER INFORMATION: JYH-sRNA-1

<400> SEQUENCE: 101
uucagaguuc uacaguccga cgau                                                 24

<210> SEQ ID NO 102
<211> LENGTH: 18
<212> TYPE: RNA
<213> ORGANISM: Artificial sequence
<220> FEATURE:
<223> OTHER INFORMATION: LQi-sRNA-1

<400> SEQUENCE: 102
gccugucuga gcgucguu                                                        18

<210> SEQ ID NO 103
<211> LENGTH: 18
<212> TYPE: RNA

-continued

```
<213> ORGANISM: Artificial sequence
<220> FEATURE:
<223> OTHER INFORMATION: LQi-sRNA-2

<400> SEQUENCE: 103
ucccugguug auccugcc                                                  18

<210> SEQ ID NO 104
<211> LENGTH: 18
<212> TYPE: RNA
<213> ORGANISM: Artificial sequence
<220> FEATURE:
<223> OTHER INFORMATION: LQi-sRNA-3

<400> SEQUENCE: 104
uagugguaug auucucgc                                                  18

<210> SEQ ID NO 105
<211> LENGTH: 19
<212> TYPE: RNA
<213> ORGANISM: Artificial sequence
<220> FEATURE:
<223> OTHER INFORMATION: LQi-sRNA-4

<400> SEQUENCE: 105
cuuucagcaa cggaucucu                                                 19

<210> SEQ ID NO 106
<211> LENGTH: 26
<212> TYPE: RNA
<213> ORGANISM: Artificial sequence
<220> FEATURE:
<223> OTHER INFORMATION: LQi-sRNA-5

<400> SEQUENCE: 106
cuucagaguu cuacaguccg acgauc                                         26

<210> SEQ ID NO 107
<211> LENGTH: 18
<212> TYPE: RNA
<213> ORGANISM: Artificial sequence
<220> FEATURE:
<223> OTHER INFORMATION: LQi-sRNA-6

<400> SEQUENCE: 107
auccugcugg cgucgcca                                                  18

<210> SEQ ID NO 108
<211> LENGTH: 21
<212> TYPE: RNA
<213> ORGANISM: Artificial sequence
<220> FEATURE:
<223> OTHER INFORMATION: LQi-sRNA-7

<400> SEQUENCE: 108
auccacggcc auaggacuuu g                                              21

<210> SEQ ID NO 109
<211> LENGTH: 21
<212> TYPE: RNA
<213> ORGANISM: Artificial sequence
<220> FEATURE:
<223> OTHER INFORMATION: LQi-sRNA-8

<400> SEQUENCE: 109
uccauggucu agugguuagg a                                              21
```

<210> SEQ ID NO 110
<211> LENGTH: 18
<212> TYPE: RNA
<213> ORGANISM: Artificial sequence
<220> FEATURE:
<223> OTHER INFORMATION: XKC-sRNA-1

<400> SEQUENCE: 110
cgcuggcaag ggcccugg                                                    18

<210> SEQ ID NO 111
<211> LENGTH: 19
<212> TYPE: RNA
<213> ORGANISM: Artificial sequence
<220> FEATURE:
<223> OTHER INFORMATION: XKC-sRNA-2

<400> SEQUENCE: 111
cgcuggcaag ggcccuggg                                                   19

<210> SEQ ID NO 112
<211> LENGTH: 18
<212> TYPE: RNA
<213> ORGANISM: Artificial sequence
<220> FEATURE:
<223> OTHER INFORMATION: CCCCCGGUUCAAUCCCGG

<400> SEQUENCE: 112
cccccgguuc aaucccgg                                                    18

<210> SEQ ID NO 113
<211> LENGTH: 18
<212> TYPE: RNA
<213> ORGANISM: Artificial sequence
<220> FEATURE:
<223> OTHER INFORMATION: XKC-sRNA-4

<400> SEQUENCE: 113
cccccgguuc agucccgg                                                    18

<210> SEQ ID NO 114
<211> LENGTH: 20
<212> TYPE: RNA
<213> ORGANISM: Artificial sequence
<220> FEATURE:
<223> OTHER INFORMATION: XKC-sRNA-5

<400> SEQUENCE: 114
uccauggucu agugguuagg                                                  20

<210> SEQ ID NO 115
<211> LENGTH: 21
<212> TYPE: RNA
<213> ORGANISM: Artificial sequence
<220> FEATURE:
<223> OTHER INFORMATION: XKC-sRNA-6

<400> SEQUENCE: 115
cccacugcua aauuugacug g                                                21

<210> SEQ ID NO 116
<211> LENGTH: 27
<212> TYPE: RNA
<213> ORGANISM: Artificial sequence
<220> FEATURE:

-continued

<223> OTHER INFORMATION: XKC-sRNA-7

<400> SEQUENCE: 116
ccggggcuac gccugucuga gcgucgc                                                    27

<210> SEQ ID NO 117
<211> LENGTH: 24
<212> TYPE: RNA
<213> ORGANISM: Artificial sequence
<220> FEATURE:
<223> OTHER INFORMATION: XKC-sRNA-8

<400> SEQUENCE: 117
ggcuacgccu gucugagcgu cgcu                                                       24

<210> SEQ ID NO 118
<211> LENGTH: 21
<212> TYPE: RNA
<213> ORGANISM: Artificial sequence
<220> FEATURE:
<223> OTHER INFORMATION: YXC-sRNA-1

<400> SEQUENCE: 118
ccgcggggcc ccgucguccc c                                                          21

<210> SEQ ID NO 119
<211> LENGTH: 21
<212> TYPE: RNA
<213> ORGANISM: Artificial sequence
<220> FEATURE:
<223> OTHER INFORMATION: YXC-sRNA-2

<400> SEQUENCE: 119
cccgcggggc cccgucgucc c                                                          21

<210> SEQ ID NO 120
<211> LENGTH: 22
<212> TYPE: RNA
<213> ORGANISM: Artificial sequence
<220> FEATURE:
<223> OTHER INFORMATION: YXC-sRNA-3

<400> SEQUENCE: 120
cccgcggggc cccgucgucc cc                                                         22

<210> SEQ ID NO 121
<211> LENGTH: 22
<212> TYPE: RNA
<213> ORGANISM: Artificial sequence
<220> FEATURE:
<223> OTHER INFORMATION: YXC-sRNA-4

<400> SEQUENCE: 121
ccgcggggcc ccgucguccc cc                                                         22

<210> SEQ ID NO 122
<211> LENGTH: 26
<212> TYPE: RNA
<213> ORGANISM: Artificial sequence
<220> FEATURE:
<223> OTHER INFORMATION: YXC-sRNA-5

<400> SEQUENCE: 122
ugcaaugaug ucaucuuacu acugaa                                                     26

```
<210> SEQ ID NO 123
<211> LENGTH: 23
<212> TYPE: RNA
<213> ORGANISM: Artificial sequence
<220> FEATURE:
<223> OTHER INFORMATION: YXC-sRNA-6

<400> SEQUENCE: 123
cccgcggggc cccgucgucc ccc                                              23

<210> SEQ ID NO 124
<211> LENGTH: 21
<212> TYPE: RNA
<213> ORGANISM: Artificial sequence
<220> FEATURE:
<223> OTHER INFORMATION: YXC-sRNA-7

<400> SEQUENCE: 124
cccaguguuu agacuaccug u                                                21

<210> SEQ ID NO 125
<211> LENGTH: 23
<212> TYPE: RNA
<213> ORGANISM: Artificial sequence
<220> FEATURE:
<223> OTHER INFORMATION: YXC-sRNA-8

<400> SEQUENCE: 125
aggcagugua guuagcugau uga                                              23

<210> SEQ ID NO 126
<211> LENGTH: 21
<212> TYPE: RNA
<213> ORGANISM: Artificial sequence
<220> FEATURE:
<223> OTHER INFORMATION: YXC-sRNA-9

<400> SEQUENCE: 126
ccaguguuua gacuaccugu u                                                21

<210> SEQ ID NO 127
<211> LENGTH: 22
<212> TYPE: RNA
<213> ORGANISM: Artificial sequence
<220> FEATURE:
<223> OTHER INFORMATION: YXC-sRNA-10

<400> SEQUENCE: 127
cccaguguuu agacuaccug uu                                               22

<210> SEQ ID NO 128
<211> LENGTH: 21
<212> TYPE: RNA
<213> ORGANISM: Artificial sequence
<220> FEATURE:
<223> OTHER INFORMATION: YXC-sRNA-11

<400> SEQUENCE: 128
uaauacuguc ugguaaugcc g                                                21

<210> SEQ ID NO 129
<211> LENGTH: 19
<212> TYPE: RNA
<213> ORGANISM: Artificial sequence
<220> FEATURE:
<223> OTHER INFORMATION: YXC-sRNA-12
```

-continued

```
<400> SEQUENCE: 129
uguaguaggu uguauaguu                                                 19

<210> SEQ ID NO 130
<211> LENGTH: 19
<212> TYPE: RNA
<213> ORGANISM: Artificial sequence
<220> FEATURE:
<223> OTHER INFORMATION: YXC-sRNA-13

<400> SEQUENCE: 130
uguaguaggu uguaugguu                                                 19

<210> SEQ ID NO 131
<211> LENGTH: 22
<212> TYPE: RNA
<213> ORGANISM: Artificial sequence
<220> FEATURE:
<223> OTHER INFORMATION: YXC-sRNA-14

<400> SEQUENCE: 131
uaauacuguc ugguaaugcc gu                                             22

<210> SEQ ID NO 132
<211> LENGTH: 19
<212> TYPE: RNA
<213> ORGANISM: Artificial sequence
<220> FEATURE:
<223> OTHER INFORMATION: YXC-sRNA-15

<400> SEQUENCE: 132
ugauguagua gguuguaua                                                 19

<210> SEQ ID NO 133
<211> LENGTH: 23
<212> TYPE: RNA
<213> ORGANISM: Artificial sequence
<220> FEATURE:
<223> OTHER INFORMATION: YXC-sRNA-16

<400> SEQUENCE: 133
uguaaacauc cucgacugga aga                                            23

<210> SEQ ID NO 134
<211> LENGTH: 23
<212> TYPE: RNA
<213> ORGANISM: Artificial sequence
<220> FEATURE:
<223> OTHER INFORMATION: YXC-sRNA-17

<400> SEQUENCE: 134
cagcagcaau ucauguuuug gaa                                            23

<210> SEQ ID NO 135
<211> LENGTH: 22
<212> TYPE: RNA
<213> ORGANISM: Artificial sequence
<220> FEATURE:
<223> OTHER INFORMATION: YXC-sRNA-18

<400> SEQUENCE: 135
ccaguguuua gacuaccugu uc                                             22

<210> SEQ ID NO 136
<211> LENGTH: 23
```

```
<212> TYPE: RNA
<213> ORGANISM: Artificial sequence
<220> FEATURE:
<223> OTHER INFORMATION: YXC-sRNA-19

<400> SEQUENCE: 136
cccaguguuu agacuaccug uuc                                          23

<210> SEQ ID NO 137
<211> LENGTH: 23
<212> TYPE: RNA
<213> ORGANISM: Artificial sequence
<220> FEATURE:
<223> OTHER INFORMATION: YXC-sRNA-20

<400> SEQUENCE: 137
ccccgcgggg ccccgucguc ccc                                          23

<210> SEQ ID NO 138
<211> LENGTH: 20
<212> TYPE: RNA
<213> ORGANISM: Artificial sequence
<220> FEATURE:
<223> OTHER INFORMATION: YXC-sRNA-21

<400> SEQUENCE: 138
ucccugagga gcccuuugag                                              20

<210> SEQ ID NO 139
<211> LENGTH: 19
<212> TYPE: RNA
<213> ORGANISM: Artificial sequence
<220> FEATURE:
<223> OTHER INFORMATION: YXC-sRNA-22

<400> SEQUENCE: 139
ugcuguagua gauuguaua                                               19

<210> SEQ ID NO 140
<211> LENGTH: 21
<212> TYPE: RNA
<213> ORGANISM: Artificial sequence
<220> FEATURE:
<223> OTHER INFORMATION: YXC-sRNA-23

<400> SEQUENCE: 140
aagguuacuu guuaguucag g                                            21

<210> SEQ ID NO 141
<211> LENGTH: 24
<212> TYPE: RNA
<213> ORGANISM: Artificial sequence
<220> FEATURE:
<223> OTHER INFORMATION: YXC-sRNA-24

<400> SEQUENCE: 141
ccccgcgggg ccccgucguc cccc                                         24

<210> SEQ ID NO 142
<211> LENGTH: 19
<212> TYPE: RNA
<213> ORGANISM: Artificial sequence
<220> FEATURE:
<223> OTHER INFORMATION: YXC-sRNA-25

<400> SEQUENCE: 142
```

-continued uguaguaggu ugugugguu                                                                  19

<210> SEQ ID NO 143
<211> LENGTH: 21
<212> TYPE: RNA
<213> ORGANISM: Artificial sequence
<220> FEATURE:
<223> OTHER INFORMATION: YXC-sRNA-26

<400> SEQUENCE: 143
uuaaugcuaa uugugauagg g                                                                21

<210> SEQ ID NO 144
<211> LENGTH: 19
<212> TYPE: RNA
<213> ORGANISM: Artificial sequence
<220> FEATURE:
<223> OTHER INFORMATION: YXC-sRNA-27

<400> SEQUENCE: 144
ugauguagua guuuguaca                                                                   19

<210> SEQ ID NO 145
<211> LENGTH: 20
<212> TYPE: RNA
<213> ORGANISM: Artificial sequence
<220> FEATURE:
<223> OTHER INFORMATION: YXC-sRNA-28

<400> SEQUENCE: 145
ugauguagua guuuguacag                                                                  20

<210> SEQ ID NO 146
<211> LENGTH: 22
<212> TYPE: RNA
<213> ORGANISM: Artificial sequence
<220> FEATURE:
<223> OTHER INFORMATION: YXC-sRNA-29

<400> SEQUENCE: 146
ugauguagua gguugugugg uu                                                               22

<210> SEQ ID NO 147
<211> LENGTH: 21
<212> TYPE: RNA
<213> ORGANISM: Artificial sequence
<220> FEATURE:
<223> OTHER INFORMATION: YXC-sRNA-30

<400> SEQUENCE: 147
ugauguagua guuuguacag u                                                                21

<210> SEQ ID NO 148
<211> LENGTH: 21
<212> TYPE: RNA
<213> ORGANISM: Artificial sequence
<220> FEATURE:
<223> OTHER INFORMATION: YXC-sRNA-31

<400> SEQUENCE: 148
ugcuguagua gguuguauag u                                                                21

<210> SEQ ID NO 149
<211> LENGTH: 22
<212> TYPE: RNA
<213> ORGANISM: Artificial sequence -continued

```
<220> FEATURE:
<223> OTHER INFORMATION: YXC-sRNA-32

<400> SEQUENCE: 149
ugauguagua guuuguacag uu                                      22

<210> SEQ ID NO 150
<211> LENGTH: 22
<212> TYPE: RNA
<213> ORGANISM: Artificial sequence
<220> FEATURE:
<223> OTHER INFORMATION: YXC-sRNA-33

<400> SEQUENCE: 150
ucccugagga gcccuuugag cc                                      22

<210> SEQ ID NO 151
<211> LENGTH: 20
<212> TYPE: RNA
<213> ORGANISM: Artificial sequence
<220> FEATURE:
<223> OTHER INFORMATION: YXC-sRNA-34

<400> SEQUENCE: 151
ugcuguagua gguuguaugg                                         20

<210> SEQ ID NO 152
<211> LENGTH: 21
<212> TYPE: RNA
<213> ORGANISM: Artificial sequence
<220> FEATURE:
<223> OTHER INFORMATION: YXC-sRNA-35

<400> SEQUENCE: 152
ugcuguagua gguuguaugg u                                       21

<210> SEQ ID NO 153
<211> LENGTH: 20
<212> TYPE: RNA
<213> ORGANISM: Artificial sequence
<220> FEATURE:
<223> OTHER INFORMATION: YXC-sRNA-36

<400> SEQUENCE: 153
aacccguuac cauuacugag                                         20

<210> SEQ ID NO 154
<211> LENGTH: 19
<212> TYPE: RNA
<213> ORGANISM: Artificial sequence
<220> FEATURE:
<223> OTHER INFORMATION: YXC-sRNA-37

<400> SEQUENCE: 154
ugcuguagua guuugugcu                                          19

<210> SEQ ID NO 155
<211> LENGTH: 22
<212> TYPE: RNA
<213> ORGANISM: Artificial sequence
<220> FEATURE:
<223> OTHER INFORMATION: YXC-sRNA-38

<400> SEQUENCE: 155
ugcuguagua gguuguauag uu                                      22
```

<210> SEQ ID NO 156
<211> LENGTH: 21
<212> TYPE: RNA
<213> ORGANISM: Artificial sequence
<220> FEATURE:
<223> OTHER INFORMATION: YXC-sRNA-39

<400> SEQUENCE: 156
ugcuguagua guuugugcug u                                                 21

<210> SEQ ID NO 157
<211> LENGTH: 22
<212> TYPE: RNA
<213> ORGANISM: Artificial sequence
<220> FEATURE:
<223> OTHER INFORMATION: YXC-sRNA-40

<400> SEQUENCE: 157
ugcuguagua guuugugcug uu                                                22

<210> SEQ ID NO 158
<211> LENGTH: 19
<212> TYPE: RNA
<213> ORGANISM: Artificial sequence
<220> FEATURE:
<223> OTHER INFORMATION: YXC-sRNA-41

<400> SEQUENCE: 158
ugugaacauc cucgacugg                                                    19

<210> SEQ ID NO 159
<211> LENGTH: 20
<212> TYPE: RNA
<213> ORGANISM: Artificial sequence
<220> FEATURE:
<223> OTHER INFORMATION: YXC-sRNA-42

<400> SEQUENCE: 159
ugugaacauc cucgacugga                                                   20

<210> SEQ ID NO 160
<211> LENGTH: 22
<212> TYPE: RNA
<213> ORGANISM: Artificial sequence
<220> FEATURE:
<223> OTHER INFORMATION: YXC-sRNA-43

<400> SEQUENCE: 160
ugcuguagua gguuguaugg uu                                                22

<210> SEQ ID NO 161
<211> LENGTH: 24
<212> TYPE: RNA
<213> ORGANISM: Artificial sequence
<220> FEATURE:
<223> OTHER INFORMATION: YXC-sRNA-44

<400> SEQUENCE: 161
uaauacugcc ugguaaugau gacu                                              24

<210> SEQ ID NO 162
<211> LENGTH: 21
<212> TYPE: RNA
<213> ORGANISM: Artificial sequence
<220> FEATURE:
<223> OTHER INFORMATION: YXC-sRNA-45

-continued

<400> SEQUENCE: 162
ugugaacauc cucgacugga a                                              21

<210> SEQ ID NO 163
<211> LENGTH: 21
<212> TYPE: RNA
<213> ORGANISM: Artificial sequence
<220> FEATURE:
<223> OTHER INFORMATION: YXC-sRNA-46

<400> SEQUENCE: 163
guccaguacu gugauaacug a                                              21

<210> SEQ ID NO 164
<211> LENGTH: 22
<212> TYPE: RNA
<213> ORGANISM: Artificial sequence
<220> FEATURE:
<223> OTHER INFORMATION: YXC-sRNA-47

<400> SEQUENCE: 164
aacccguuac cauuacugag uu                                             22

<210> SEQ ID NO 165
<211> LENGTH: 21
<212> TYPE: RNA
<213> ORGANISM: Artificial sequence
<220> FEATURE:
<223> OTHER INFORMATION: YXC-sRNA-48

<400> SEQUENCE: 165
agauguagua gguugcauag u                                              21

<210> SEQ ID NO 166
<211> LENGTH: 21
<212> TYPE: RNA
<213> ORGANISM: Artificial sequence
<220> FEATURE:
<223> OTHER INFORMATION: YXC-sRNA-49

<400> SEQUENCE: 166
aggguucgag ugugagcaug c                                              21

<210> SEQ ID NO 167
<211> LENGTH: 18
<212> TYPE: RNA
<213> ORGANISM: Artificial sequence
<220> FEATURE:
<223> OTHER INFORMATION: YXC-sRNA-50

<400> SEQUENCE: 167
ugauaugaag cacuguag                                                  18

<210> SEQ ID NO 168
<211> LENGTH: 19
<212> TYPE: RNA
<213> ORGANISM: Artificial sequence
<220> FEATURE:
<223> OTHER INFORMATION: YXC-sRNA-51

<400> SEQUENCE: 168
aacccguccu caguucgga                                                 19

<210> SEQ ID NO 169

-continued

```
<211> LENGTH: 18
<212> TYPE: RNA
<213> ORGANISM: Artificial sequence
<220> FEATURE:
<223> OTHER INFORMATION: YXC-sRNA-52

<400> SEQUENCE: 169
ugcuaugaag cacuguag                                                          18

<210> SEQ ID NO 170
<211> LENGTH: 19
<212> TYPE: RNA
<213> ORGANISM: Artificial sequence
<220> FEATURE:
<223> OTHER INFORMATION: YXC-sRNA-53

<400> SEQUENCE: 170
ugcuaugaag cacuguagc                                                         19

<210> SEQ ID NO 171
<211> LENGTH: 20
<212> TYPE: RNA
<213> ORGANISM: Artificial sequence
<220> FEATURE:
<223> OTHER INFORMATION: YXC-sRNA-54

<400> SEQUENCE: 171
ugcuaugaag cacuguagcu                                                        20

<210> SEQ ID NO 172
<211> LENGTH: 18
<212> TYPE: RNA
<213> ORGANISM: Artificial sequence
<220> FEATURE:
<223> OTHER INFORMATION: YXC-sRNA-55

<400> SEQUENCE: 172
ugauguagua gauuguau                                                          18

<210> SEQ ID NO 173
<211> LENGTH: 21
<212> TYPE: RNA
<213> ORGANISM: Artificial sequence
<220> FEATURE:
<223> OTHER INFORMATION: YXC-sRNA-56

<400> SEQUENCE: 173
ugcuaugaag cacuguagcu c                                                      21

<210> SEQ ID NO 174
<211> LENGTH: 23
<212> TYPE: RNA
<213> ORGANISM: Artificial sequence
<220> FEATURE:
<223> OTHER INFORMATION: YXC-sRNA-57

<400> SEQUENCE: 174
ucgauccugg cucaggauga acg                                                    23

<210> SEQ ID NO 175
<211> LENGTH: 22
<212> TYPE: RNA
<213> ORGANISM: Artificial sequence
<220> FEATURE:
<223> OTHER INFORMATION: YXC-sRNA-58

<400> SEQUENCE: 175
```
ugcuaugaag cacguagcu cu                                                22

<210> SEQ ID NO 176
<211> LENGTH: 19
<212> TYPE: RNA
<213> ORGANISM: Artificial sequence
<220> FEATURE:
<223> OTHER INFORMATION: YXC-sRNA-59

<400> SEQUENCE: 176
ugauguagua guuugugcu                                                   19

<210> SEQ ID NO 177
<211> LENGTH: 20
<212> TYPE: RNA
<213> ORGANISM: Artificial sequence
<220> FEATURE:
<223> OTHER INFORMATION: YXC-sRNA-60

<400> SEQUENCE: 177
ugauguagua guuugugcug                                                  20

<210> SEQ ID NO 178
<211> LENGTH: 21
<212> TYPE: RNA
<213> ORGANISM: Artificial sequence
<220> FEATURE:
<223> OTHER INFORMATION: YXC-sRNA-61

<400> SEQUENCE: 178
ugauguagua guuugugcug u                                                21

<210> SEQ ID NO 179
<211> LENGTH: 21
<212> TYPE: RNA
<213> ORGANISM: Artificial sequence
<220> FEATURE:
<223> OTHER INFORMATION: YXC-sRNA-62

<400> SEQUENCE: 179
ucuucccagu gcucugaaug u                                                21

<210> SEQ ID NO 180
<211> LENGTH: 22
<212> TYPE: RNA
<213> ORGANISM: Artificial sequence
<220> FEATURE:
<223> OTHER INFORMATION: YXC-sRNA-63

<400> SEQUENCE: 180
ugauguagua guuugugcug uu                                               22

<210> SEQ ID NO 181
<211> LENGTH: 20
<212> TYPE: RNA
<213> ORGANISM: Artificial sequence
<220> FEATURE:
<223> OTHER INFORMATION: YXC-sRNA-64

<400> SEQUENCE: 181
agacacggcc cagacuccua                                                  20

<210> SEQ ID NO 182
<211> LENGTH: 18
<212> TYPE: RNA

-continued

```
<213> ORGANISM: Artificial sequence
<220> FEATURE:
<223> OTHER INFORMATION: YXC-sRNA-65

<400> SEQUENCE: 182
ugauguagua gguugugu                                                           18

<210> SEQ ID NO 183
<211> LENGTH: 20
<212> TYPE: RNA
<213> ORGANISM: Artificial sequence
<220> FEATURE:
<223> OTHER INFORMATION: YXC-sRNA-66

<400> SEQUENCE: 183
guauuguuuc cuacuuuaug                                                         20

<210> SEQ ID NO 184
<211> LENGTH: 21
<212> TYPE: RNA
<213> ORGANISM: Artificial sequence
<220> FEATURE:
<223> OTHER INFORMATION: YXC-sRNA-67

<400> SEQUENCE: 184
guauuguuuc cuacuuuaug g                                                       21

<210> SEQ ID NO 185
<211> LENGTH: 22
<212> TYPE: RNA
<213> ORGANISM: Artificial sequence
<220> FEATURE:
<223> OTHER INFORMATION: YXC-sRNA-68

<400> SEQUENCE: 185
guauuguuuc cuacuuuaug ga                                                      22

<210> SEQ ID NO 186
<211> LENGTH: 20
<212> TYPE: RNA
<213> ORGANISM: Artificial sequence
<220> FEATURE:
<223> OTHER INFORMATION: YXC-sRNA-69

<400> SEQUENCE: 186
uggaaacauc cucgacugga                                                         20

<210> SEQ ID NO 187
<211> LENGTH: 20
<212> TYPE: RNA
<213> ORGANISM: Artificial sequence
<220> FEATURE:
<223> OTHER INFORMATION: YXC-sRNA-70

<400> SEQUENCE: 187
acauuagucu gcacauuggu                                                         20

<210> SEQ ID NO 188
<211> LENGTH: 21
<212> TYPE: RNA
<213> ORGANISM: Artificial sequence
<220> FEATURE:
<223> OTHER INFORMATION: YXC-sRNA-71

<400> SEQUENCE: 188
uggaaacauc cucgacugga a                                                       21
```

-continued

<210> SEQ ID NO 189
<211> LENGTH: 21
<212> TYPE: RNA
<213> ORGANISM: Artificial sequence
<220> FEATURE:
<223> OTHER INFORMATION: YXC-sRNA-72

<400> SEQUENCE: 189
aucuuaucag acugauguug a                                                       21

<210> SEQ ID NO 190
<211> LENGTH: 21
<212> TYPE: RNA
<213> ORGANISM: Artificial sequence
<220> FEATURE:
<223> OTHER INFORMATION: YXC-sRNA-73

<400> SEQUENCE: 190
acauuagucu gcacauuggu u                                                       21

<210> SEQ ID NO 191
<211> LENGTH: 19
<212> TYPE: RNA
<213> ORGANISM: Artificial sequence
<220> FEATURE:
<223> OTHER INFORMATION: YXC-sRNA-74

<400> SEQUENCE: 191
uguucaaauc caugcaaaa                                                          19

<210> SEQ ID NO 192
<211> LENGTH: 19
<212> TYPE: RNA
<213> ORGANISM: Artificial sequence
<220> FEATURE:
<223> OTHER INFORMATION: YXC-sRNA-75

<400> SEQUENCE: 192
ucuuaccgug aguaauaau                                                          19

<210> SEQ ID NO 193
<211> LENGTH: 22
<212> TYPE: RNA
<213> ORGANISM: Artificial sequence
<220> FEATURE:
<223> OTHER INFORMATION: YXC-sRNA-76

<400> SEQUENCE: 193
uaucuuauca gacugauguu ga                                                      22

<210> SEQ ID NO 194
<211> LENGTH: 20
<212> TYPE: RNA
<213> ORGANISM: Artificial sequence
<220> FEATURE:
<223> OTHER INFORMATION: YXC-sRNA-77

<400> SEQUENCE: 194
ucuuaccgug aguaauaaug                                                         20

<210> SEQ ID NO 195
<211> LENGTH: 22
<212> TYPE: RNA
<213> ORGANISM: Artificial sequence
<220> FEATURE:

-continued

<223> OTHER INFORMATION: YXC-sRNA-78

<400> SEQUENCE: 195
uguucaaauc caugcaaaac ug                                              22

<210> SEQ ID NO 196
<211> LENGTH: 20
<212> TYPE: RNA
<213> ORGANISM: Artificial sequence
<220> FEATURE:
<223> OTHER INFORMATION: YXC-sRNA-79

<400> SEQUENCE: 196
uaucaccauc ugaaaucggu                                                 20

<210> SEQ ID NO 197
<211> LENGTH: 23
<212> TYPE: RNA
<213> ORGANISM: Artificial sequence
<220> FEATURE:
<223> OTHER INFORMATION: YXC-sRNA-80

<400> SEQUENCE: 197
uguucaaauc caugcaaaac uga                                             23

<210> SEQ ID NO 198
<211> LENGTH: 20
<212> TYPE: RNA
<213> ORGANISM: Artificial sequence
<220> FEATURE:
<223> OTHER INFORMATION: YXC-sRNA-81

<400> SEQUENCE: 198
ucauaccgug aguaauaaug                                                 20

<210> SEQ ID NO 199
<211> LENGTH: 21
<212> TYPE: RNA
<213> ORGANISM: Artificial sequence
<220> FEATURE:
<223> OTHER INFORMATION: YXC-sRNA-82

<400> SEQUENCE: 199
uaucaccauc ugaaaucggu u                                               21

<210> SEQ ID NO 200
<211> LENGTH: 22
<212> TYPE: RNA
<213> ORGANISM: Artificial sequence
<220> FEATURE:
<223> OTHER INFORMATION: YXC-sRNA-83

<400> SEQUENCE: 200
ugauaugaag cacuguagcu ca                                              22

<210> SEQ ID NO 201
<211> LENGTH: 33
<212> TYPE: RNA
<213> ORGANISM: Artificial sequence
<220> FEATURE:
<223> OTHER INFORMATION: CXL-sRNA-30

<400> SEQUENCE: 201
gggauuguag uucaauuggu cagagcaccg ccc                                  33

-continued

<210> SEQ ID NO 202
<211> LENGTH: 19
<212> TYPE: RNA
<213> ORGANISM: Artificial sequence
<220> FEATURE:
<223> OTHER INFORMATION: PGY-sRNA-21

<400> SEQUENCE: 202
gugcuugaaa uugucggga                                                                                     19

<210> SEQ ID NO 203
<211> LENGTH: 21
<212> TYPE: RNA
<213> ORGANISM: Artificial sequence
<220> FEATURE:
<223> OTHER INFORMATION: PGY-sRNA-22

<400> SEQUENCE: 203
ugaacucuga acuccaguca c                                                                                  21

<210> SEQ ID NO 204
<211> LENGTH: 19
<212> TYPE: RNA
<213> ORGANISM: Artificial sequence
<220> FEATURE:
<223> OTHER INFORMATION: PGY-sRNA-23

<400> SEQUENCE: 204
cccuccgcgg ccagcuucu                                                                                     19

<210> SEQ ID NO 205
<211> LENGTH: 18
<212> TYPE: RNA
<213> ORGANISM: Artificial sequence
<220> FEATURE:
<223> OTHER INFORMATION: PGY-sRNA-24

<400> SEQUENCE: 205
gugucgugag auguuggg                                                                                      18

<210> SEQ ID NO 206
<211> LENGTH: 28
<212> TYPE: RNA
<213> ORGANISM: Artificial sequence
<220> FEATURE:
<223> OTHER INFORMATION: PGY-sRNA-25

<400> SEQUENCE: 206
guucagaguu cuacaguccg acgaucuc                                                                           28

<210> SEQ ID NO 207
<211> LENGTH: 25
<212> TYPE: RNA
<213> ORGANISM: Artificial sequence
<220> FEATURE:
<223> OTHER INFORMATION: PGY-sRNA-26

<400> SEQUENCE: 207
uccggaauga uugggcguaa agcgu                                                                              25

<210> SEQ ID NO 208
<211> LENGTH: 19
<212> TYPE: RNA
<213> ORGANISM: Artificial sequence
<220> FEATURE:
<223> OTHER INFORMATION: PGY-sRNA-27

-continued

<400> SEQUENCE: 208
accgugcgcu ggauuauga                                              19

<210> SEQ ID NO 209
<211> LENGTH: 24
<212> TYPE: RNA
<213> ORGANISM: Artificial sequence
<220> FEATURE:
<223> OTHER INFORMATION: PGY-sRNA-28

<400> SEQUENCE: 209
ucucagguag acaguuucua uggg                                        24

<210> SEQ ID NO 210
<211> LENGTH: 22
<212> TYPE: RNA
<213> ORGANISM: Artificial sequence
<220> FEATURE:
<223> OTHER INFORMATION: PGY-sRNA-29

<400> SEQUENCE: 210
cgauccuggc ucaggaugaa cg                                          22

<210> SEQ ID NO 211
<211> LENGTH: 21
<212> TYPE: RNA
<213> ORGANISM: Artificial sequence
<220> FEATURE:
<223> OTHER INFORMATION: PGY-sRNA-30

<400> SEQUENCE: 211
uuuggauuga agggagcucu g                                           21

<210> SEQ ID NO 212
<211> LENGTH: 19
<212> TYPE: RNA
<213> ORGANISM: Artificial sequence
<220> FEATURE:
<223> OTHER INFORMATION: PGY-sRNA-31

<400> SEQUENCE: 212
agcuuaccaa ggcgaugau                                              19

<210> SEQ ID NO 213
<211> LENGTH: 20
<212> TYPE: RNA
<213> ORGANISM: Artificial sequence
<220> FEATURE:
<223> OTHER INFORMATION: PGY-sRNA-32

<400> SEQUENCE: 213
ccggccccga acccgucggc                                             20

<210> SEQ ID NO 214
<211> LENGTH: 21
<212> TYPE: RNA
<213> ORGANISM: Artificial sequence
<220> FEATURE:
<223> OTHER INFORMATION: PGY-sRNA-6

<400> SEQUENCE: 214
guucagaguu cuacaguccg a                                           21

<210> SEQ ID NO 215
<211> LENGTH: 26

<212> TYPE: RNA
<213> ORGANISM: Artificial sequence
<220> FEATURE:
<223> OTHER INFORMATION: PGY-sRNA-18

<400> SEQUENCE: 215
cggggcuacg ccugucugag cgucgc                                    26

<210> SEQ ID NO 216
<211> LENGTH: 21
<212> TYPE: RNA
<213> ORGANISM: Artificial sequence
<220> FEATURE:
<223> OTHER INFORMATION: sly-miR168b-5p

<400> SEQUENCE: 216
ucgcuuggug caggucggga c                                         21

<210> SEQ ID NO 217
<211> LENGTH: 19
<212> TYPE: RNA
<213> ORGANISM: Artificial sequence
<220> FEATURE:
<223> OTHER INFORMATION: Pab-miR3711

<400> SEQUENCE: 217
ggcccuccuu cuagcgcca                                            19

<210> SEQ ID NO 218
<211> LENGTH: 18
<212> TYPE: RNA
<213> ORGANISM: Artificial sequence
<220> FEATURE:
<223> OTHER INFORMATION: CXL-sRNA-17

<400> SEQUENCE: 218
cagagucgcg cagcggaa                                             18

<210> SEQ ID NO 219
<211> LENGTH: 24
<212> TYPE: RNA
<213> ORGANISM: Artificial sequence
<220> FEATURE:
<223> OTHER INFORMATION: CXL-sRNA-21

<400> SEQUENCE: 219
acagcaggac gguggccaug gaag                                      24

<210> SEQ ID NO 220
<211> LENGTH: 21
<212> TYPE: RNA
<213> ORGANISM: Artificial sequence
<220> FEATURE:
<223> OTHER INFORMATION: ppe-miR169c

<400> SEQUENCE: 220
cagccaagga ugacuugccg g                                         21

<210> SEQ ID NO 221
<211> LENGTH: 21
<212> TYPE: RNA
<213> ORGANISM: Artificial sequence
<220> FEATURE:
<223> OTHER INFORMATION: HJT-sRNA-a2

<400> SEQUENCE: 221
uagcaccauc cgaaaucggu a                                          21

<210> SEQ ID NO 222
<211> LENGTH: 27
<212> TYPE: RNA
<213> ORGANISM: Artificial sequence
<220> FEATURE:
<223> OTHER INFORMATION: HJT-sRNA-h3

<400> SEQUENCE: 222 ugggggcuacg ccugucugag cgucgcu                                   27

<210> SEQ ID NO 223
<211> LENGTH: 21
<212> TYPE: DNA
<213> ORGANISM: Artificial Sequence
<220> FEATURE:
<223> OTHER INFORMATION: random nonsense sequence

<400> SEQUENCE: 223
uucuccgaac gugucacgut t                                          21

<210> SEQ ID NO 224
<211> LENGTH: 21
<212> TYPE: DNA
<213> ORGANISM: Artificial Sequence
<220> FEATURE:
<223> OTHER INFORMATION: primer

<400> SEQUENCE: 224
ctggaagatg gtcgtaccct g                                          21

<210> SEQ ID NO 225
<211> LENGTH: 20
<212> TYPE: DNA
<213> ORGANISM: Artificial Sequence
<220> FEATURE:
<223> OTHER INFORMATION: primer

<400> SEQUENCE: 225
ggtcttgcca gtgagtgtct                                            20

<210> SEQ ID NO 226
<211> LENGTH: 21
<212> TYPE: DNA
<213> ORGANISM: Artificial Sequence
<220> FEATURE:
<223> OTHER INFORMATION: primer

<400> SEQUENCE: 226
ctcgccagtg aaatgatggc t                                          21

<210> SEQ ID NO 227
<211> LENGTH: 21
<212> TYPE: DNA
<213> ORGANISM: Artificial Sequence
<220> FEATURE:
<223> OTHER INFORMATION: primer

<400> SEQUENCE: 227
gtcggagatt cgtagctgga t                                          21

<210> SEQ ID NO 228
<211> LENGTH: 21
<212> TYPE: DNA
<213> ORGANISM: Artificial Sequence -continued

```
<220> FEATURE:
<223> OTHER INFORMATION: primer

<400> SEQUENCE: 228
ggtacatcct cgacggcatc t                                              21

<210> SEQ ID NO 229
<211> LENGTH: 21
<212> TYPE: DNA
<213> ORGANISM: Artificial Sequence
<220> FEATURE:
<223> OTHER INFORMATION: primer

<400> SEQUENCE: 229
gtgcctcttt gctgctttca c                                              21

<210> SEQ ID NO 230
<211> LENGTH: 19
<212> TYPE: DNA
<213> ORGANISM: Artificial Sequence
<220> FEATURE:
<223> OTHER INFORMATION: primer

<400> SEQUENCE: 230
ctgccccaat ccctttatt                                                 19

<210> SEQ ID NO 231
<211> LENGTH: 20
<212> TYPE: DNA
<213> ORGANISM: Artificial Sequence
<220> FEATURE:
<223> OTHER INFORMATION: primer

<400> SEQUENCE: 231
cccaattctc tttttgagcc                                                20

<210> SEQ ID NO 232
<211> LENGTH: 19
<212> TYPE: DNA
<213> ORGANISM: Artificial Sequence
<220> FEATURE:
<223> OTHER INFORMATION: primer

<400> SEQUENCE: 232
gttcccatta gacaactgc                                                 19

<210> SEQ ID NO 233
<211> LENGTH: 18
<212> TYPE: DNA
<213> ORGANISM: Artificial Sequence
<220> FEATURE:
<223> OTHER INFORMATION: primer

<400> SEQUENCE: 233
gattctttcc tttgaggc                                                  18

<210> SEQ ID NO 234
<211> LENGTH: 23
<212> TYPE: DNA
<213> ORGANISM: Artificial Sequence
<220> FEATURE:
<223> OTHER INFORMATION: primer

<400> SEQUENCE: 234
tagtccttcc taccccaatt tcc                                            23
```

-continued

```
<210> SEQ ID NO 235
<211> LENGTH: 21
<212> TYPE: DNA
<213> ORGANISM: Artificial Sequence
<220> FEATURE:
<223> OTHER INFORMATION: primer

<400> SEQUENCE: 235
ttggtcctta gccactcctt c                                      21

<210> SEQ ID NO 236
<211> LENGTH: 19
<212> TYPE: DNA
<213> ORGANISM: Artificial Sequence
<220> FEATURE:
<223> OTHER INFORMATION: primer

<400> SEQUENCE: 236
cctgtagccc acgtcgtag                                         19

<210> SEQ ID NO 237
<211> LENGTH: 22
<212> TYPE: DNA
<213> ORGANISM: Artificial Sequence
<220> FEATURE:
<223> OTHER INFORMATION: primer

<400> SEQUENCE: 237
gggagtagac aaggtacaac cc                                     22

<210> SEQ ID NO 238
<211> LENGTH: 24
<212> TYPE: DNA
<213> ORGANISM: Artificial Sequence
<220> FEATURE:
<223> OTHER INFORMATION: primer

<400> SEQUENCE: 238
cactcacggc aaattcaacg gcac                                   24

<210> SEQ ID NO 239
<211> LENGTH: 22
<212> TYPE: DNA
<213> ORGANISM: Artificial Sequence
<220> FEATURE:
<223> OTHER INFORMATION: primer

<400> SEQUENCE: 239
gactccacga catactcagc ac                                     22
```

SMALL RNA MEDICAMENT FOR PREVENTION AND TREATMENT OF INFLAMMATION-RELATED DISEASES AND COMBINATION THEREOF

RELATED APPLICATIONS

The present patent document is a § 371 filing based on PCT Application Serial No. PCT/CN2018/123289, filed Dec. 25, 2018, contents of which are hereby incorporated by reference in its entirety.

REFERENCE TO APPENDIX [CD ROM/SEQUENCE LISTING]

This application is being filed electronically via EFS-Web and includes an electronically submitted Sequence Listing in .txt format. The .txt file contains a sequence listing entitled "516946_5000004_Seq_Listing_ST25" created on Feb. 1, 2022 and is 44,510 bytes in size. The sequence listing contained in this .txt file is part of the specification and hereby incorporated by reference in its entirety.

TECHNICAL FIELD

The present invention generally relates to the field of nucleic acid therapeutics, and more specifically to small RNAs and methods of use and uses thereof.

BACKGROUND OF THE INVENTION

Inflammation is a very common and important basic pathological process, and a common and frequently-occurring disease of most of the various organs and trauma infections on the body surface. Inflammation can be infectious inflammation caused by infection (such as pneumonia, myocarditis, acute and chronic gastritis, acute and chronic enteritis, acute and chronic hepatitis, acute and chronic nephritis, dermatitis, encephalitis, lymphitis, conjunctivitis, keratitis, iridocyclitis, tympanitis, etc.). It can also be non-infectious inflammation not caused by infection, which is usually closely related to the immunity of the body (such as allergic rhinitis, asthma, pulmonary fibrosis, chronic obstructive pulmonary disease, allergic dermatitis, sickle cell disease, multiple sclerosis, systemic lupus erythematosus, lupus nephritis, etc.). Meanwhile, inflammation is also one of the main predisposing factors of the onset of cancer (such as lung cancer, gastric cancer, colorectal cancer, liver cancer, pancreatic cancer, cervical cancer, breast cancer, leukemia, multiple myeloma, etc.). Also, studies have shown that some inflammatory factors are also related to metabolic diseases (such as diabetes, gout, etc.). Under normal circumstances, inflammation is beneficial and is an automatic defense response of the body. But sometimes inflammation is also harmful, for example, attacks on the own tissues of the body, inflammation that occurs in hyaline tissues, and the like.

The clinical manifestations of inflammation include redness, swelling, fever, pain, dysfunction, etc., while the biochemical indicators of inflammation usually refer to high expression of inflammatory factors which are involved in the inflammation process and mediate the inflammatory response, for example, IL-1beta, IL-6 and TNF-alpha. At present, the prevention and treatment of inflammation is still mainly based on western medicine, but there are also many traditional Chinese medicine products that have certain anti-inflammatory effects, but all have their own unavoidable shortcomings. Therefore, it is still necessary to find novel anti-inflammatory treatment measures.

SUMMARY OF THE INVENTION

This application is partly based on the discovery of a series of small RNAs by the inventors. Unexpectedly, the inventors discovered that the small RNAs or their composition in the present application can reduce or down-regulate the expression level of IL-1beta, IL-6 or/and TNF-alpha and rescue cell death caused by H5N1 infection.

The present invention provides the following:

1. A small RNA comprising:
   (A) The sequence shown in any one of SEQ ID NO. 1-222, preferably the sequence of SEQ ID NO. 20, or complementary sequence thereof;
   (B) A sequence with at least 80%-98% identity with the sequence shown in (A), which has an ability to inhibit any one or more of pathway(s) or gene(s) listed in Table 3;
   (C) A sequence that hybridizes to the sequence shown in (A), preferably a sequence that hybridizes to the sequence shown in (A) under stringent conditions, which has an ability to inhibit any one or more of pathway(s) or gene(s) listed in Table 3;
   (D) A sequence obtained from the sequence shown in (A) by addition, deletion, replacement or insertion of one or more, such as 2, 3, 4, 5, 6, 7, 8 or 9 bases, which has an ability to inhibit any one or more of pathway(s) or gene(s) listed in Table 3; or
   (E) A precursor or modified variant of the sequence shown in (A), (B), (C) or (D), which has an ability to inhibit any one or more of pathway(s) or gene(s) listed in Table 3.

2. The small RNA according to item 1, which has an ability to inhibit the same pathway(s) or gene(s) listed in Table 3, or has an ability to prevent and/or treat IL-1beta, IL-6 or/and TNF-alpha related diseases and/or an ability to improve cell survival rate.

3. The small RNA according to item 2, wherein the small RNA has an ability to reduce or down-regulate the expression level of IL-1beta, IL-6 or/and TNF-alpha and/or has an ability to rescue cell death caused by virus (for example RNA virus, for example avian influenza virus, for example H5N1) infection, Preferably, the small RNA has an ability to reduce or down-regulate the expression level of an inflammatory factor selected form any one of IL-1beta, IL-6 and TNF-alpha, Preferably, the IL-1beta, IL-6 or/and TNF-alpha related disease is selected from any one or more IL-1beta, IL-6 or/and TNF-alpha related diseases listed in the specification, preferably pneumonia, myocarditis, acute and chronic gastritis, acute and chronic enteritis, acute and chronic hepatitis, acute and chronic nephritis, dermatitis, encephalitis, lymphitis, conjunctivitis, keratitis, iridocyclitis, tympanitis, allergic rhinitis, asthma, pulmonary fibrosis, chronic obstructive pulmonary disease, allergic dermatitis, sickle cell disease, multiple sclerosis, systemic lupus erythematosus, lupus nephritis, lung cancer, gastric cancer, colorectal cancer, liver cancer, pancreatic cancer, cervical cancer, breast cancer, leukemia, multiple myeloma, diabetes and gout.

4. The small RNA according to any one of items 1 to 3, wherein the small RNA is in a double-stranded or single-stranded form or a double-stranded and single-stranded hybrid form.

5. The small RNA according to any one of items 1 to 4, wherein the small RNA is a non-natural small RNA.

6. The small RNA according to any one of items 1 to 5, wherein the non-natural small RNA is a small RNA obtained through artificial synthesis or expression of an artificial vector.

7. A nucleic acid sequence or a construct comprising the same, the nucleic acid sequence comprising a sequence encoding the small RNA according to any one of items 1 to 6, wherein preferably the construct is a viral construct, preferably a retroviral construct.

8. A recombinant virus comprising the nucleic acid sequence or construct according to item 7, preferably, the recombinant virus is a retrovirus.

9. An expression vector comprising a sequence encoding the small RNA according to any one of items 1 to 6.

10. A cell comprising the nucleic acid sequence or construct according to item 7, or transfected with the recombinant virus according to item 8, or comprising the expression vector according to item 9.

11. A method for expressing the small RNA according to any one of items 1 to 6, which comprises expressing the cell according to item 10 under suitable conditions and recovering the small RNA according to any one of items 1 to 4.

12. A pharmaceutical composition comprising one or more small RNA(s) according to any one of items 1 to 6, the nucleic acid sequence or construct according to item 7, the recombinant virus according to item 8, the expression vector according to item 9 and/or the cell according to item 10, preferably, said pharmaceutical composition is pharmaceutical composition used for oral, intravenous administration such as bolus injection or continuous perfusion for a period of time, through subcutaneous, intramuscular, intraarterial, intraperitoneal, intrapulmonary, intracerebrospinal, intraarticular, intrasynovial, intrathecal, intralesional, or inhalation routes such as intranasal, usually by intravenous or subcutaneous administration.

13. The pharmaceutical composition according to item 12, which comprises any one or more of Mixture 1 to Mixture 43 in Table 2.

14. The pharmaceutical composition according to item 13, wherein in the pharmaceutical composition, the molar concentration ratio of the small RNA comprising the sequence shown in SEQ ID NO. 20 to other small RNA(s) in the composition is about 2:1.

15. The pharmaceutical composition according to any one of items 12 to 14, which further comprises one or more agent(s) listed in the specification.

16. A kit comprising one or more small RNA(s) according to any one of items 1 to 6, the nucleic acid sequence or construct according to item 7, the recombinant virus according to item 8, the expression vector according to item 9 and/or the cell according to item 10, preferably, said kit further comprises one or more agent(s) listed in the specification.

17. A method for inhibiting any one or more of pathway(s) or gene(s) listed in Table 3 in vitro or in vivo, which comprises administering to a cell or a subject one or more small RNA(s) according to any one of items 1 to 6, the nucleic acid sequence or construct according to item 7, the recombinant virus according to item 8, the expression vector according to item 9, the cell according to item 10, and/or the pharmaceutical composition according to any one of items 12 to 15.

18. A method for reducing or down-regulating the expression level of IL-1beta, IL-6 or/and TNF-alpha in vitro or in vivo and/or improving cell survival rate, which comprises administering to a cell or a subject one or more small RNA(s) according to any one of items 1 to 6, the nucleic acid sequence or construct according to item 7, the recombinant virus according to item 8, the expression vector according to item 9, the cell according to item 10, and/or the pharmaceutical composition according to any one of items 12 to 15.

19. The method according to item 18, wherein the cell survival rate is the cell survival rate in virus (for example RNA virus, for example avian influenza virus, e.g H5N1) infection, preferably, said cell survival rate is improved by rescuing the cell death caused by virus (e.g RNA virus, for example avian influenza virus, for example H5N1) infection.

20. A method for treating or preventing IL-1beta, IL-6 or/and TNF-alpha related diseases and/or virus (for example RNA virus, for example avian influenza virus, for example H5N1) infection in a subject, which comprises administering to a subject one or more small RNA(s) according to any one of items 1 to 6, the nucleic acid sequence or construct according to item 7, the recombinant virus according to item 8, the expression vector according to item 9, the cell according to item 10, and/or the pharmaceutical composition according to any one of items 12 to 15, Preferably, the IL-1beta, IL-6 or/and TNF-alpha related disease is selected from the IL-1beta, IL-6 or/and TNF-alpha related diseases listed in the specification, preferably pneumonia, myocarditis, acute and chronic gastritis, acute and chronic enteritis, acute and chronic hepatitis, acute and chronic nephritis, dermatitis, encephalitis, lymphitis, conjunctivitis, keratitis, iridocyclitis, tympanitis, allergic rhinitis, asthma, pulmonary fibrosis, chronic obstructive pulmonary disease, allergic dermatitis, sickle cell disease, multiple sclerosis, systemic lupus erythematosus, lupus nephritis, lung cancer, gastric cancer, colorectal cancer, liver cancer, pancreatic cancer, cervical cancer, breast cancer, leukemia, multiple myeloma, diabetes and gout.

21. Use of the small RNA according to any one of items 1 to 6, the nucleic acid sequence or construct according to item 7, the recombinant virus according to item 8, the expression vector according to item 9, the cell according to item 10, and/or the pharmaceutical composition according to any one of items 12 to 15, for reducing or down-regulating the expression level of IL-1beta, IL-6 or/and TNF-alpha in vitro or in vivo and/or improving cell survival rate and/or treating or preventing IL-1beta, IL-6 or TNF-alpha related diseases and/or virus (for example RNA virus, for example avian influenza virus, for example H5N1) infection in a subject, Preferably, the IL-1beta, IL-6 or/and TNF-alpha related disease is selected from the IL-1beta, IL-6 or/and TNF-alpha related diseases listed in the specification, preferably pneumonia, myocarditis, acute and chronic gastritis, acute and chronic enteritis, acute and chronic hepatitis, acute and chronic nephritis, dermatitis, encephalitis, lymphitis, conjunctivitis, keratitis, iridocyclitis, tympanitis, allergic rhinitis, asthma, pulmonary fibrosis, chronic obstructive pulmonary disease, allergic dermatitis, sickle cell disease, multiple sclerosis, systemic lupus erythematosus, lupus nephritis, lung cancer, gastric cancer, colorectal cancer, liver cancer, pancreatic cancer, cervical cancer, breast cancer, leukemia, multiple myeloma, diabetes and gout.

22. Use of the small RNAs according to any one of items 1 to 6, the nucleic acid sequence or construct according to item 7, the recombinant virus according to item 8, the expression vector according to item 9, the cell according to item 10, and/or the pharmaceutical composition according to any one of items 12 to 15, in the preparation of a medicament for reducing or down-regulating the expression level of IL-1beta, IL-6 or/and TNF-alpha in vitro or in vivo and/or improving cell survival rate and/or treating or preventing IL-1beta, IL-6 or/and TNF-alpha related diseases and/or virus (for example RNA virus, for example avian influenza virus, for example H5N1) infection in a subject, preferably, the IL-1beta, IL-6 or/and TNF-alpha related disease is selected from the IL-1beta, IL-6 or/and TNF-alpha related diseases listed in the specification, for example, pneumonia, myocarditis, acute and chronic gastritis, acute and chronic enteritis, acute and chronic hepatitis, acute and chronic nephritis, dermatitis, encephalitis, lymphitis, conjunctivitis, keratitis, iridocyclitis, tympanitis, allergic rhinitis, asthma, pulmonary fibrosis, chronic obstructive pulmonary disease, allergic dermatitis, sickle cell disease, multiple sclerosis, systemic lupus erythematosus, lupus nephritis, lung cancer, gastric cancer, colorectal cancer, liver cancer, pancreatic cancer, cervical cancer, breast cancer, leukemia, multiple myeloma, diabetes and gout.

23. A reagent for detecting the small RNA according to any one of items 1 to 6, the nucleic acid sequence or construct according to item 7, the recombinant virus according to item 8, the expression vector according to item 9, the cell according to item 10, and/or the pharmaceutical composition according to any one of items 12 to 15, preferably the reagent is a primer and/or a probe.

24. A kit comprising the reagent according to item 23.

25. A method for detecting whether cells from different sources contain the small RNA according to any one of items 1 to 6 using the reagent according to item 23 or the kit according to item 24, wherein the cell is preferably a plant cell.

US 12,612,631 B2

7 group, in the cell inflammation model after 9 hours of LPS stimulation, with the THP1 cells transfected with the *Houttuynia cordata* (YXC) small RNA 24 hours in advance, as specified in the figure.

Figure 20:
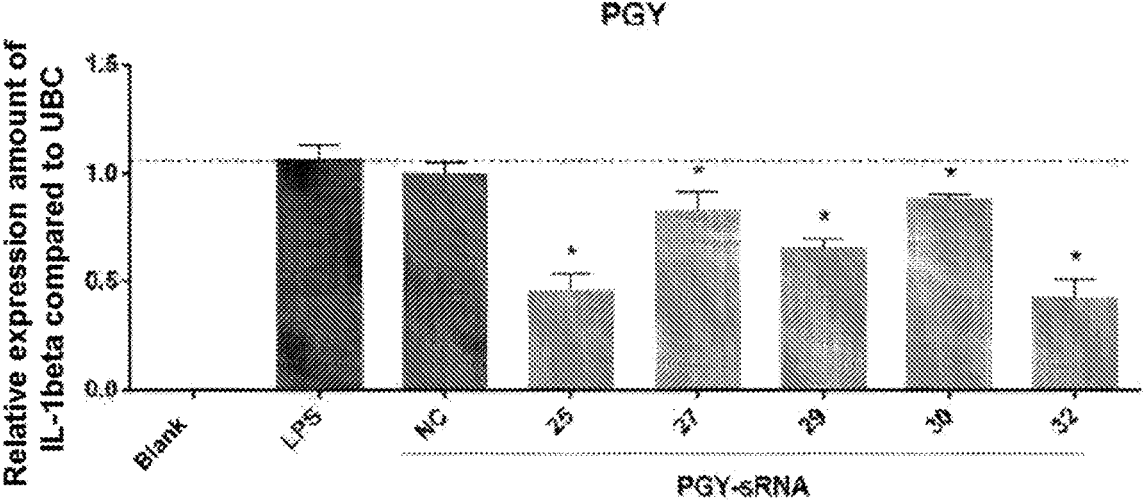

FIG. 20: The expression of the inflammatory factor IL-1beta at mRNA level compared to the control group, in the cell inflammation model after 9 hours of LPS stimulation, with the THP1 cells transfected with the *Taraxacum* (PGY) small RNA 24 hours in advance, as specified in the figure.

Figure 21:
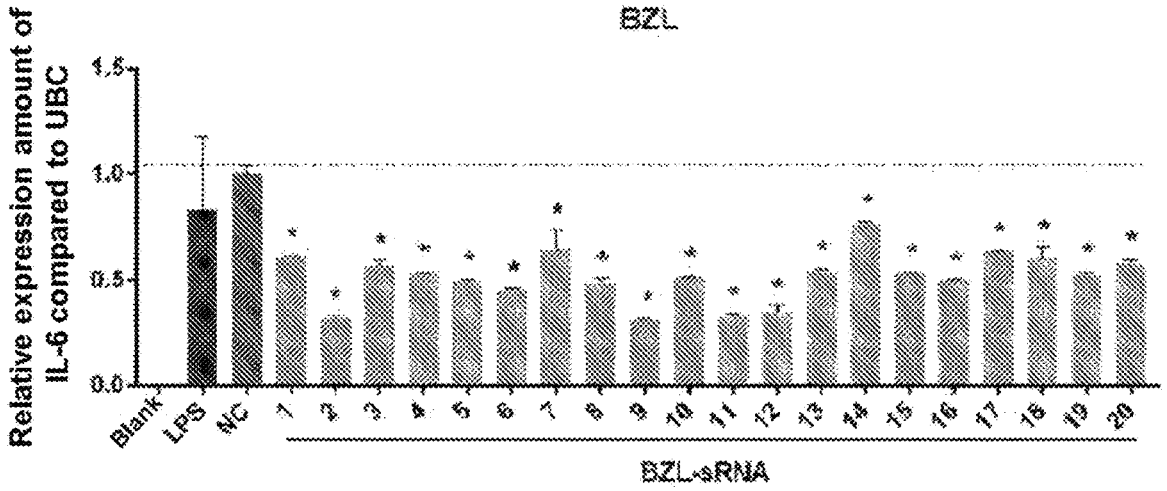
Figure 22:
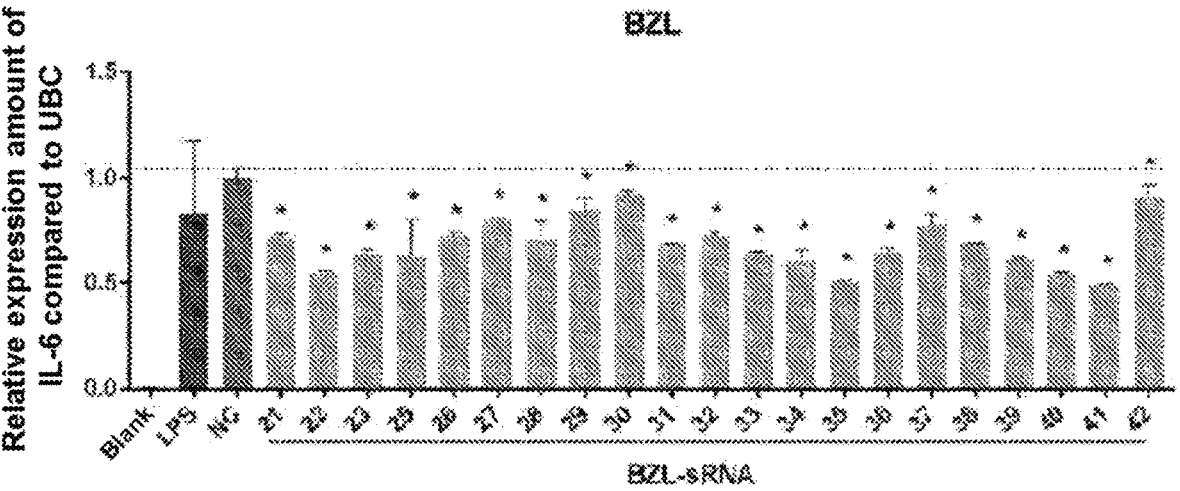

FIG. 21 to FIG. 22: The expression of the inflammatory factor IL-6 at mRNA level compared to the control group, in the cell inflammation model after 9 hours of LPS stimulation, with the THP1 cells transfected with the *Scutellaria barbata* (BZL) small RNA 24 hours in advance, as specified in the figure.

Figure 23:
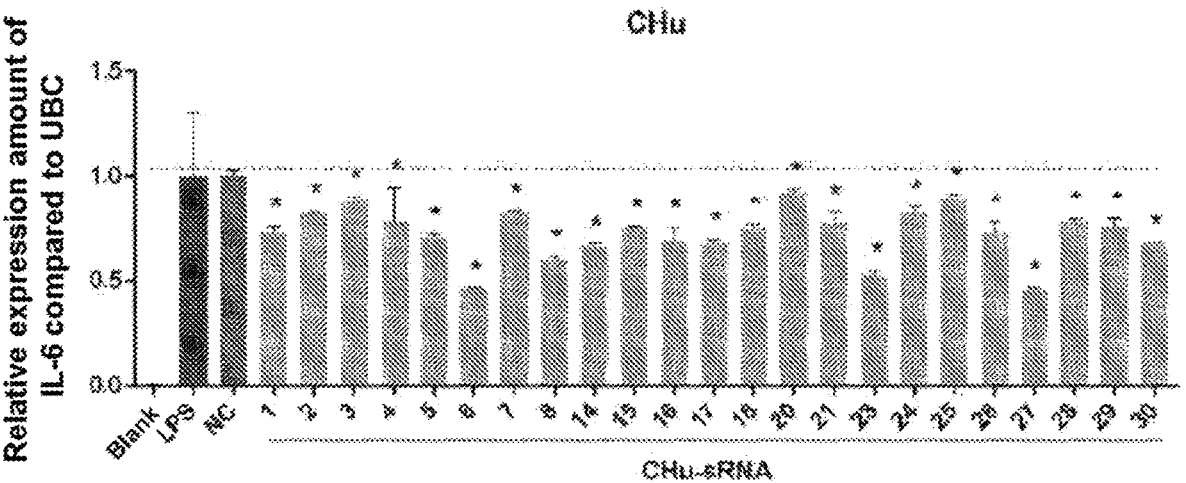
Figure 24:
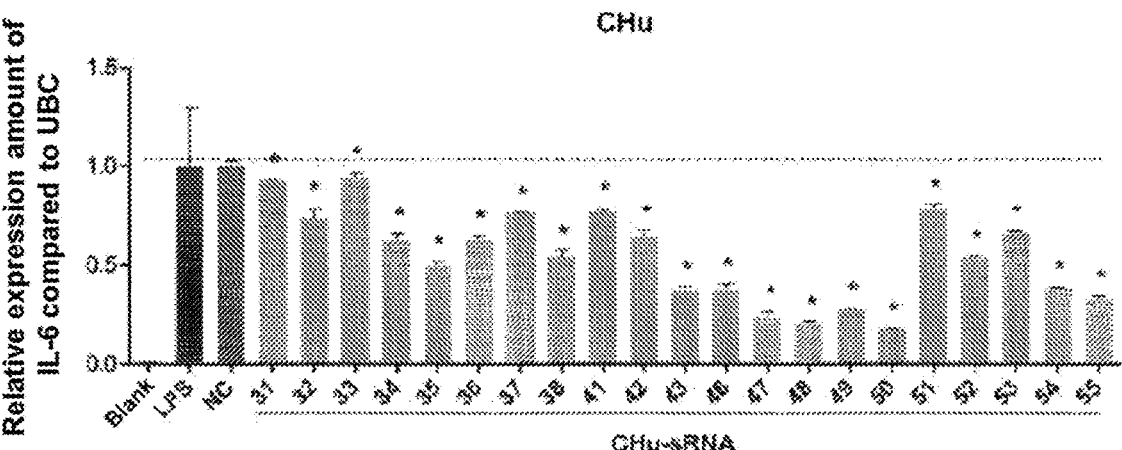

FIG. 23 to FIG. 24: The expression of the inflammatory factor IL-6 at mRNA level compared to the control group, in the cell inflammation model after 9 hours of LPS stimulation, with the THP1 cells transfected with the *Bupleurum* (CHu) small RNA 24 hours in advance, as specified in the figure.

Figure 25:
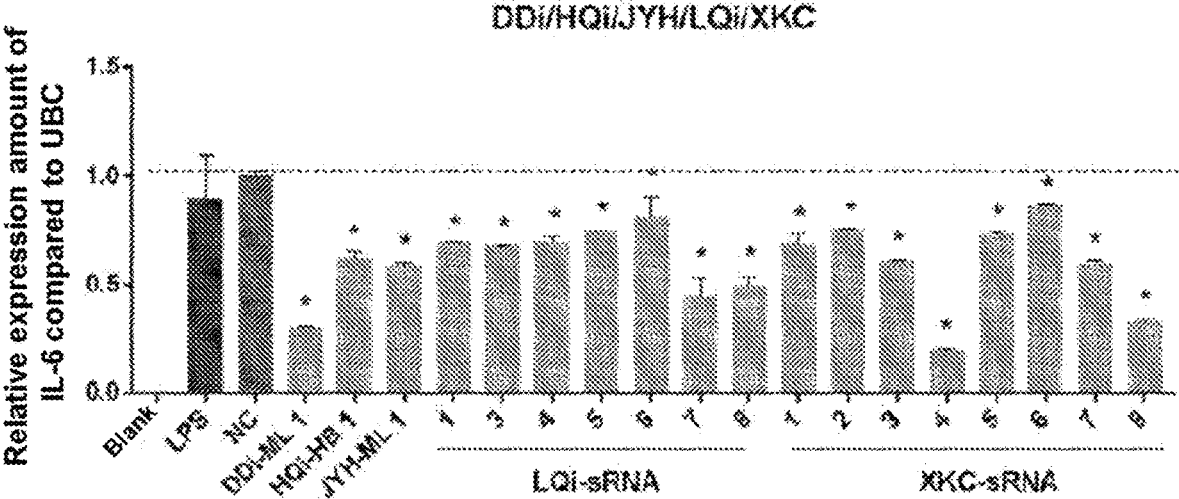

FIG. 25: The expression of the inflammatory factor IL-6 at mRNA level compared to the control group, in the cell inflammation model after 9 hours of LPS stimulation, with the THP1 cells transfected with the *Viola philippica* (DDi), *Scutellaria baicalensis* (HQi), *Lonicera japonica* (JYH), *Fructus forsythiae* (LQi) and *Prunella vulgaris* (XKC) small RNA 24 hours in advance, as specified in the figure.

Figure 26:
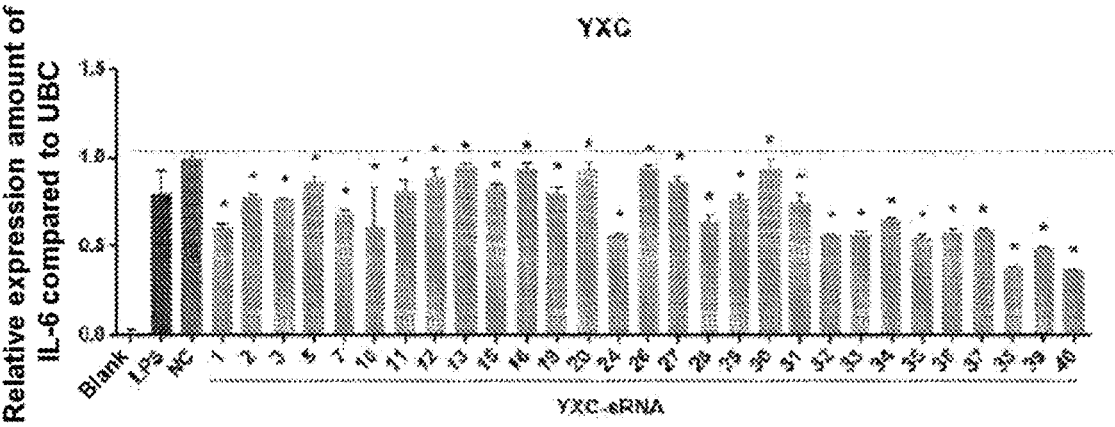
Figure 27:
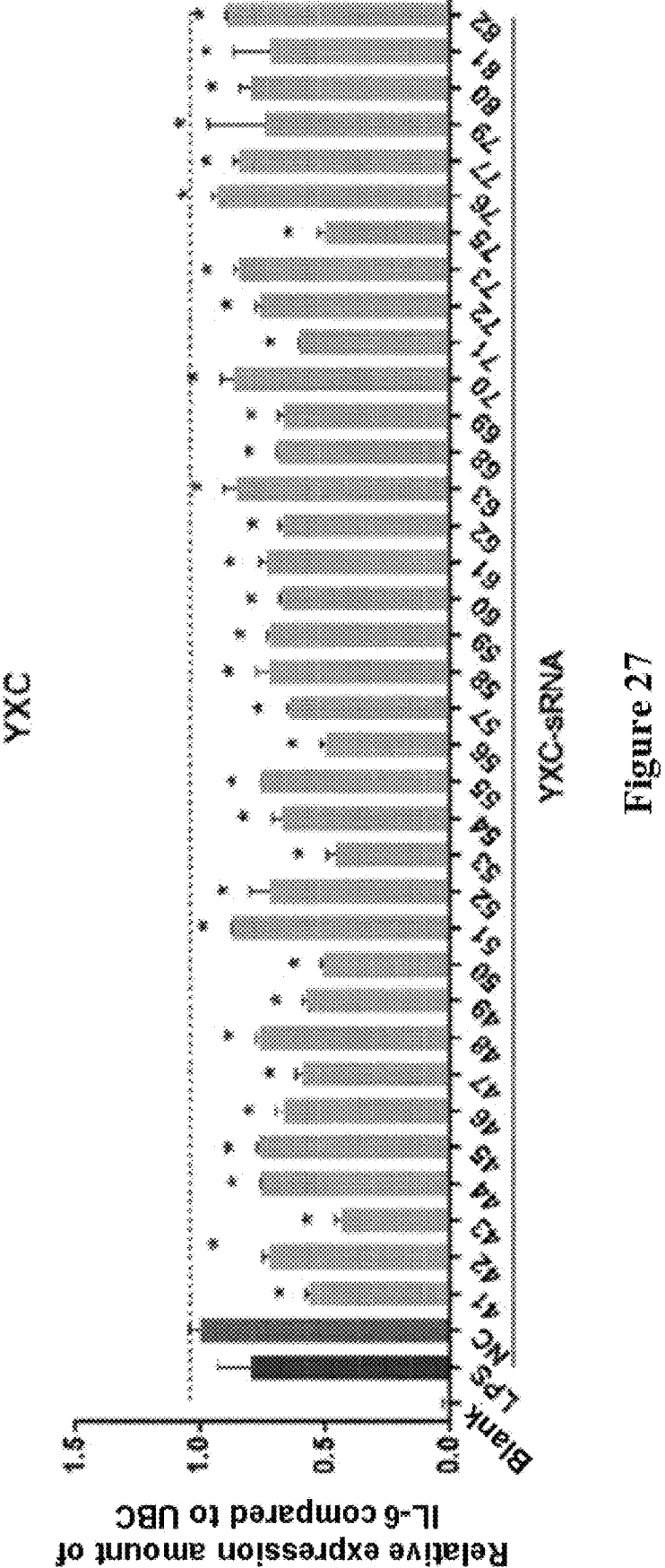

FIG. 26 to FIG. 27: The expression of the inflammatory factor IL-6 at mRNA level compared to the NC group, in the cell inflammation model after 9 hours of LPS stimulation, with the THP-1 cells transfected with the *Houttuynia cordata* (YXC) small RNA 24 hours in advance, as specified in the figure.

Figure 28:
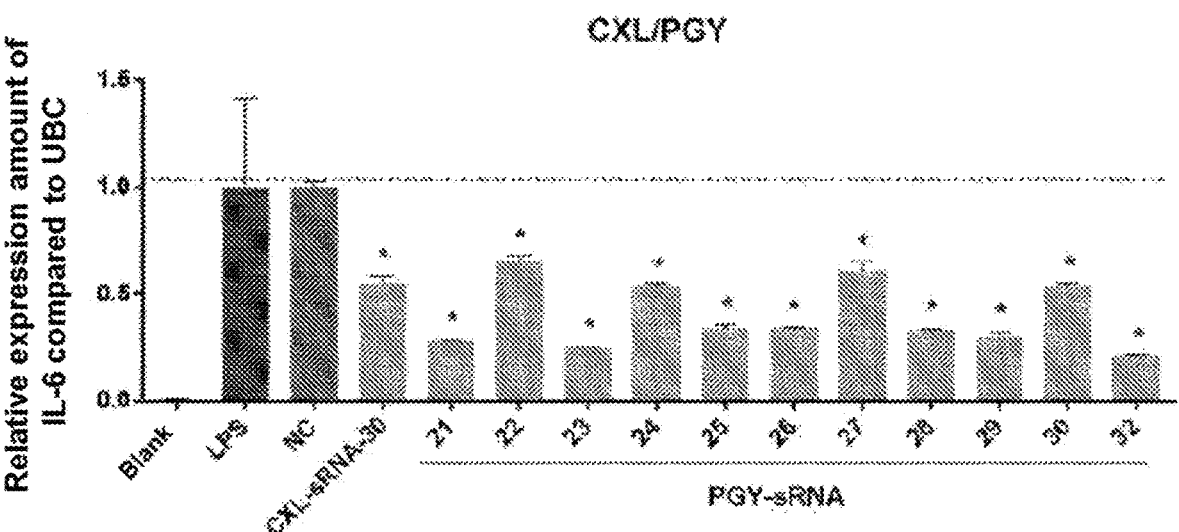

FIG. 28: The expression of the inflammatory factor IL-6 at mRNA level compared to the NC group, in the cell inflammation model after 9 hours of LPS stimulation, with the THP1 cells transfected with the *Andrographis paniculata* (CXL) and *Taraxacum* (PGY) small RNA 24 hours in advance, as specified in the figure.

Figure 29:
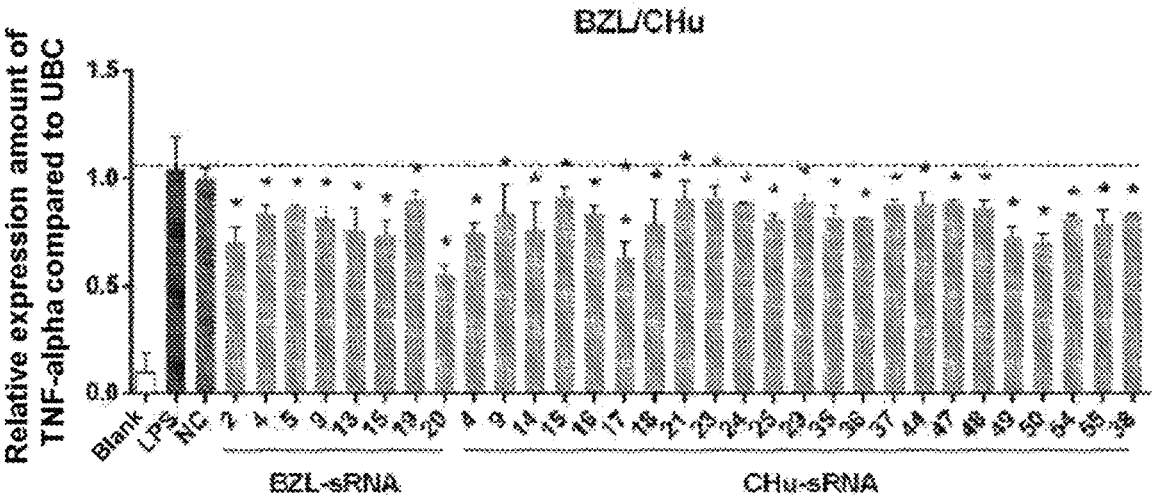

FIG. 29: The expression of the inflammatory factor TNF-alpha at mRNA level compared to the NC group, in the cell inflammation model after 9 hours of LPS stimulation, with the THP1 cells transfected with the *Scutellaria barbata* (BZL) and *Bupleurum* (CHu) small RNA 24 hours in advance, as specified in the figure.

Figure 30:
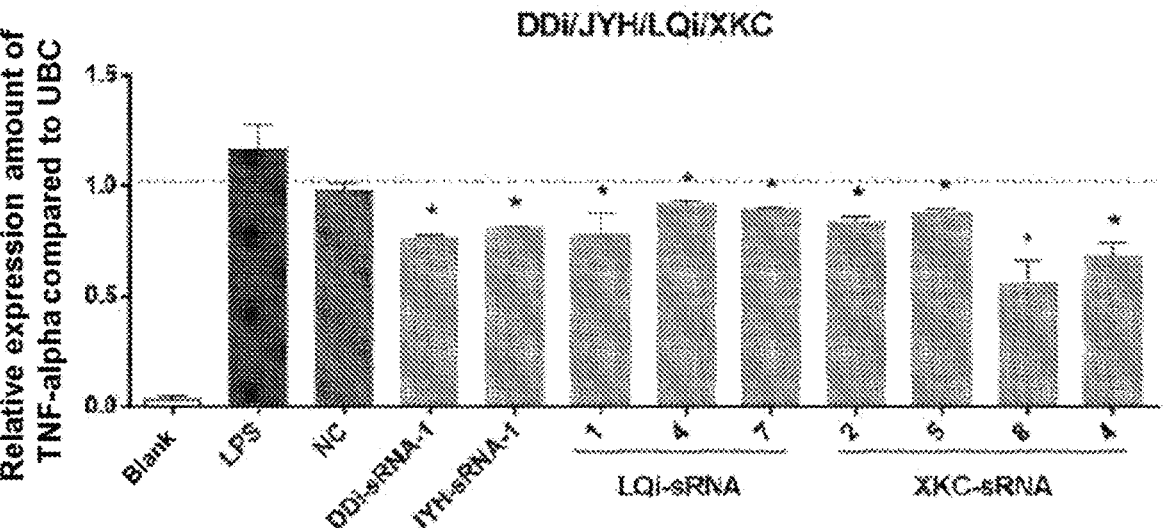

FIG. 30: The expression of the inflammatory factor TNF-alpha at mRNA level compared to the NC group, in the cell inflammation model after 9 hours of LPS stimulation, with the THP1 cells transfected with the *Viola philippica* (DDi), *Lonicera japonica* (JYH), *Fructus forsythiae* (LQi) and *Prunella vulgaris* (XKC) small RNA 24 hours in advance, as specified in the figure.

Figure 31:
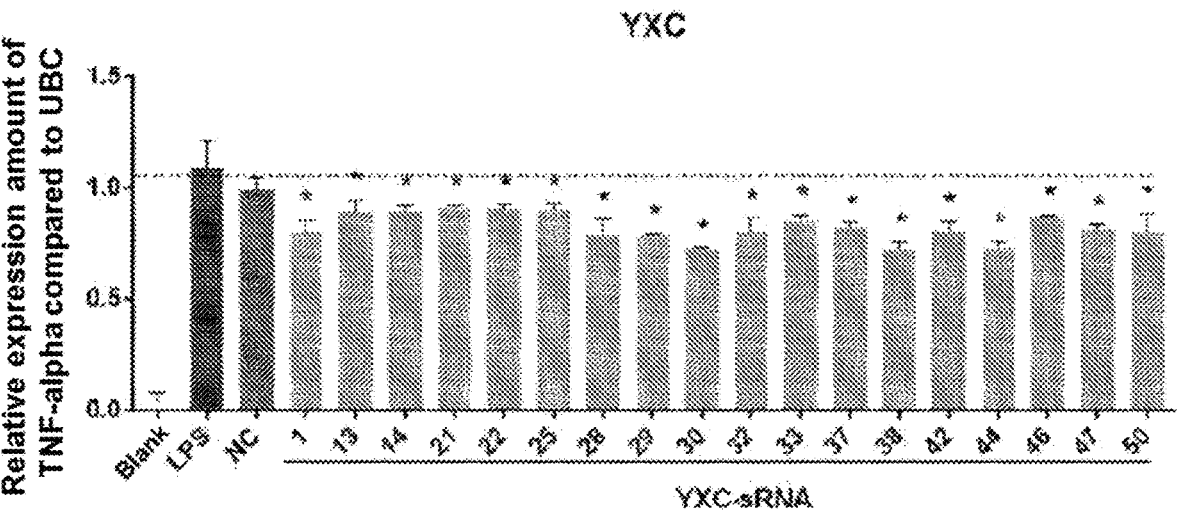
Figure 32:
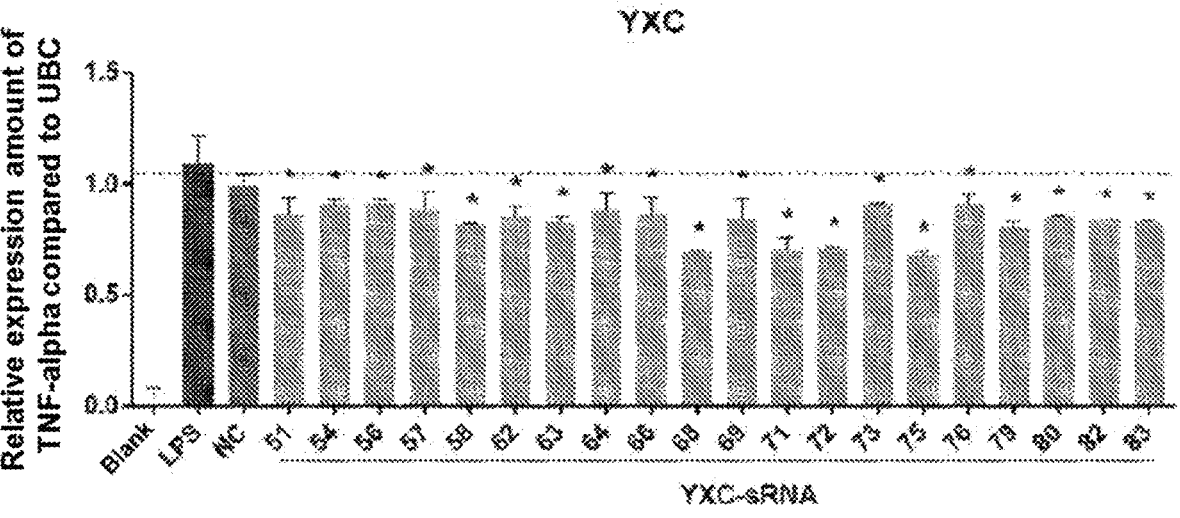

FIG. 31 to FIG. 32: The expression of the inflammatory factor TNF-alpha at mRNA level compared to the NC group, in the cell inflammation model after 9 hours of LPS stimulation, with the THP1 cells transfected with the *Houttuynia cordata* (YXC) small RNA 24 hours in advance, as specified in the figure.

Figure 33:
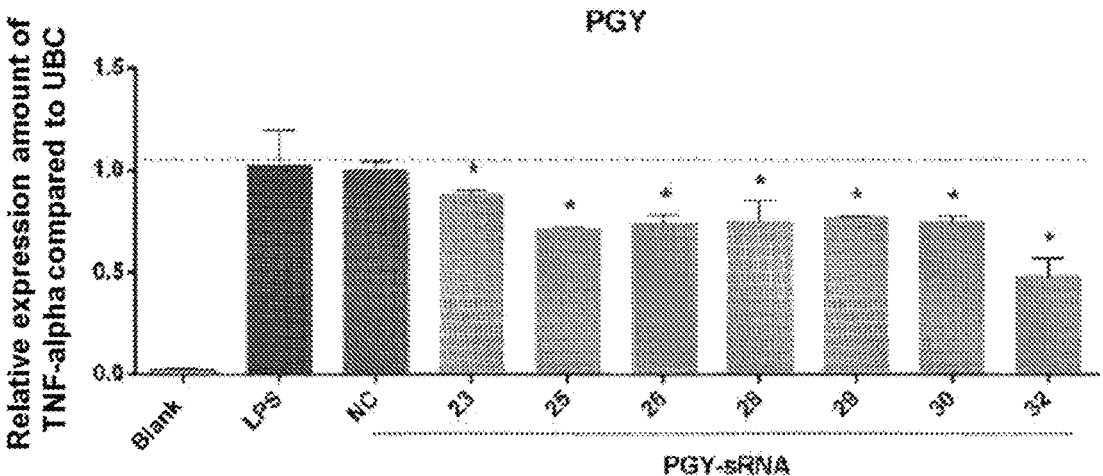

FIG. 33: The expression of the inflammatory factor TNF-alpha at mRNA level compared to the NC group, in the cell inflammation model after 9 hours of LPS stimulation, with the THP1 cells transfected with the *Taraxacum* (PGY) small RNA 24 hours in advance, as specified in the figure.

Figure 34A:
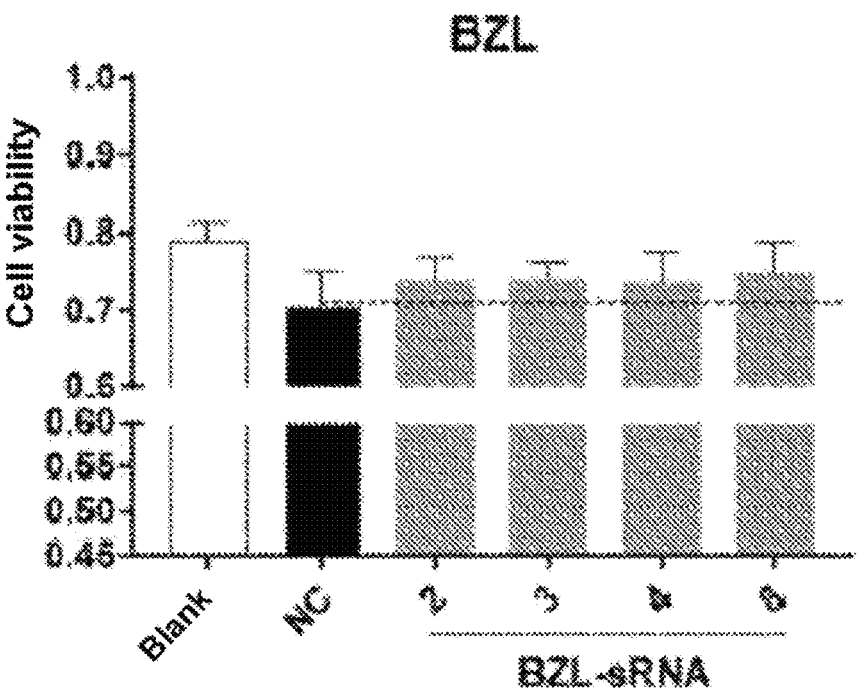
Figure 34B:
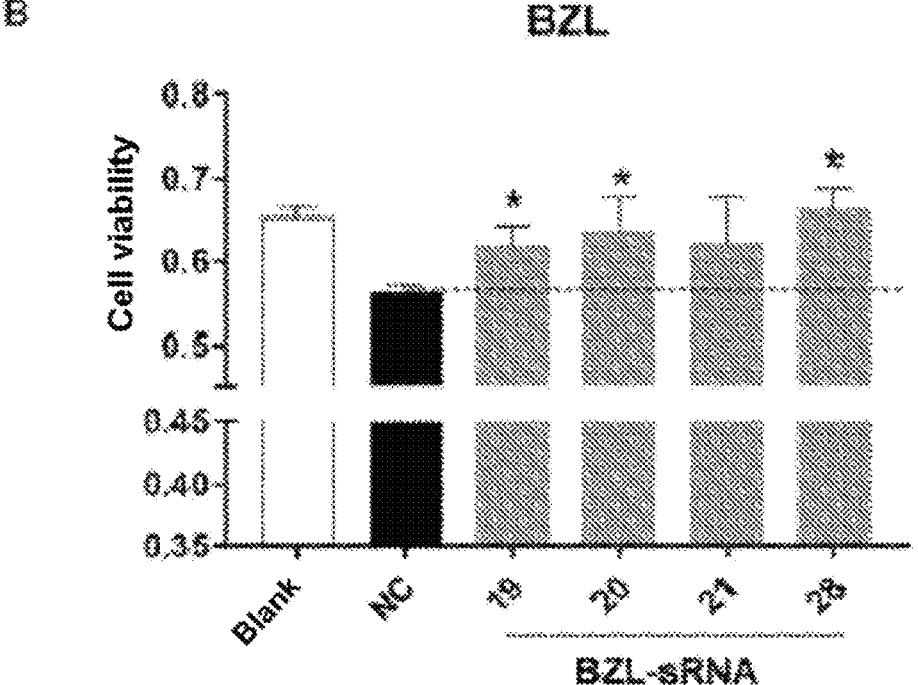
Figure 34C:
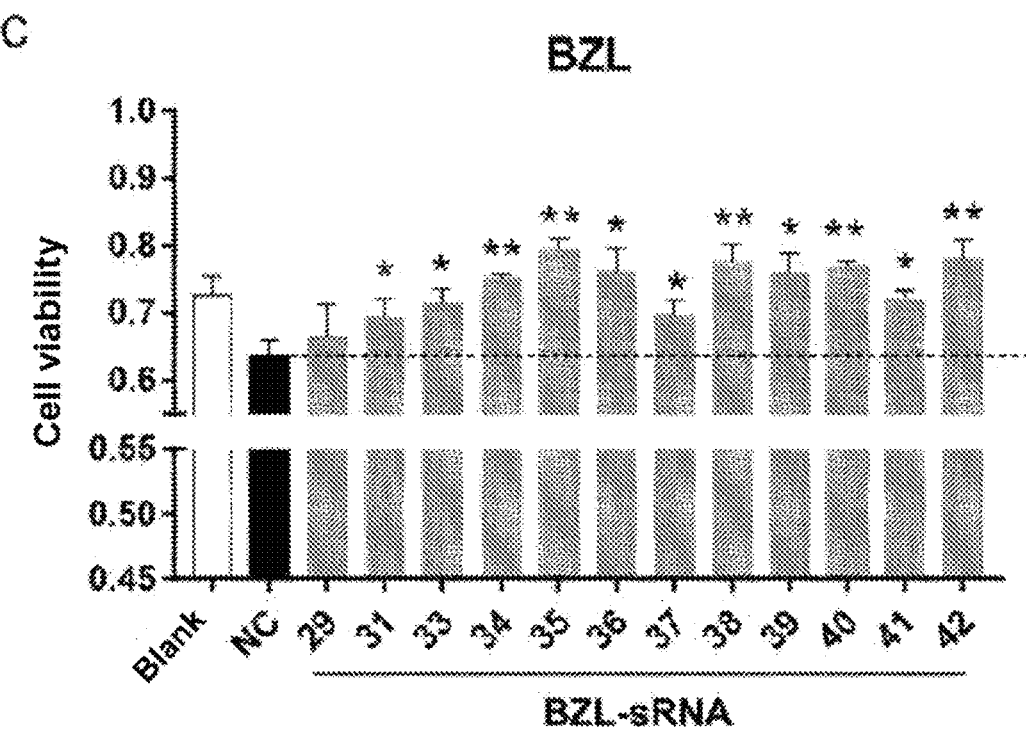
Figure 34D:
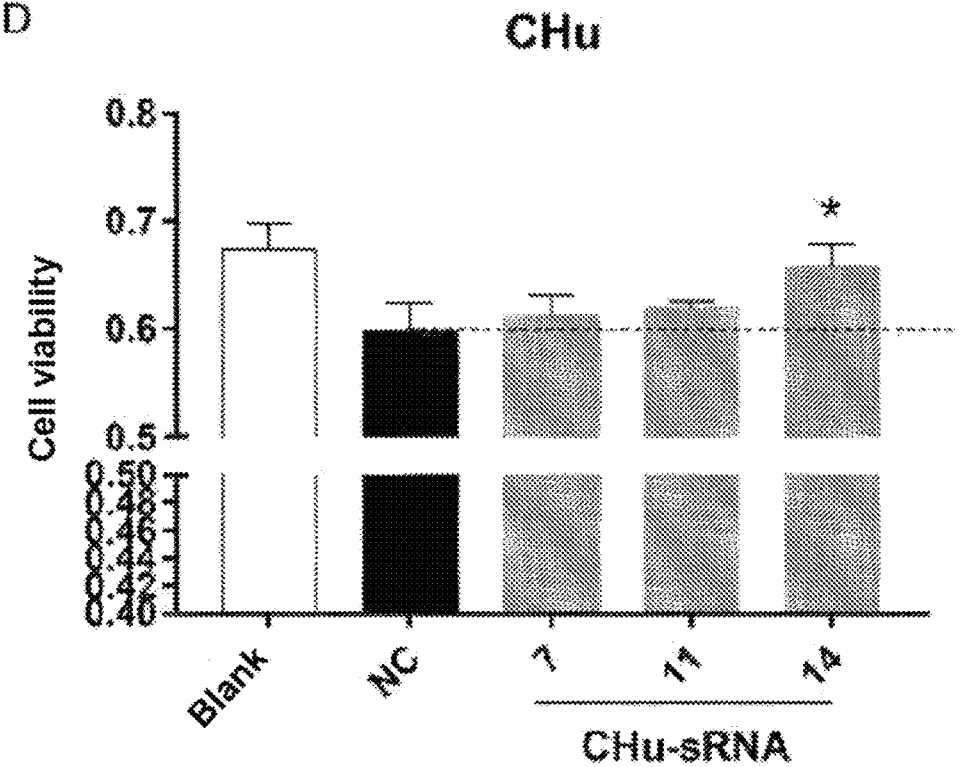
Figure 34E:
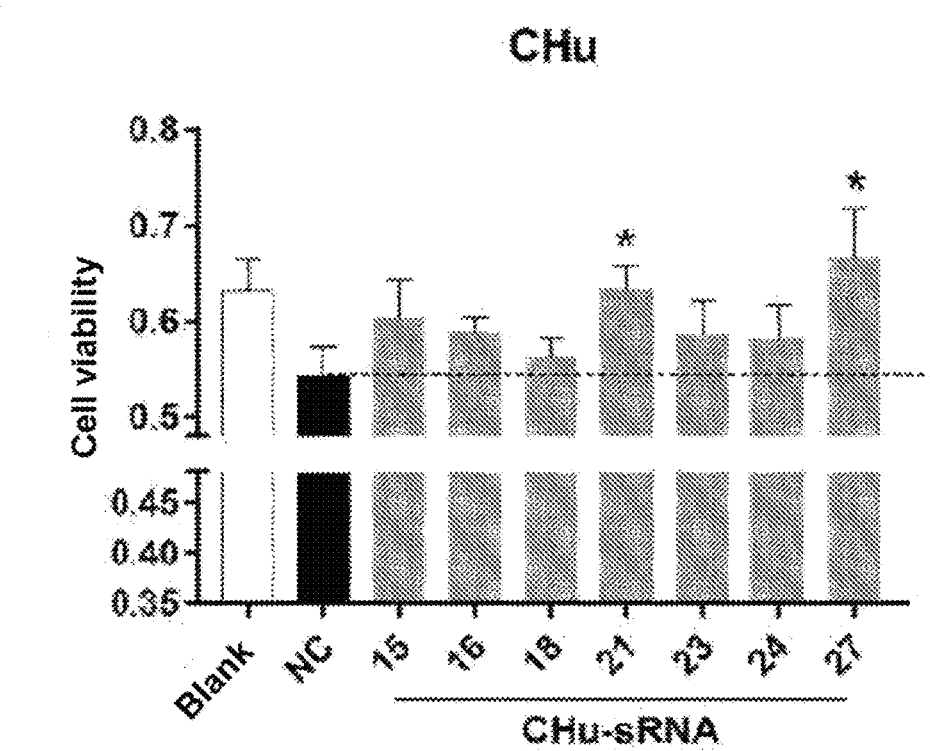
Figure 34F:
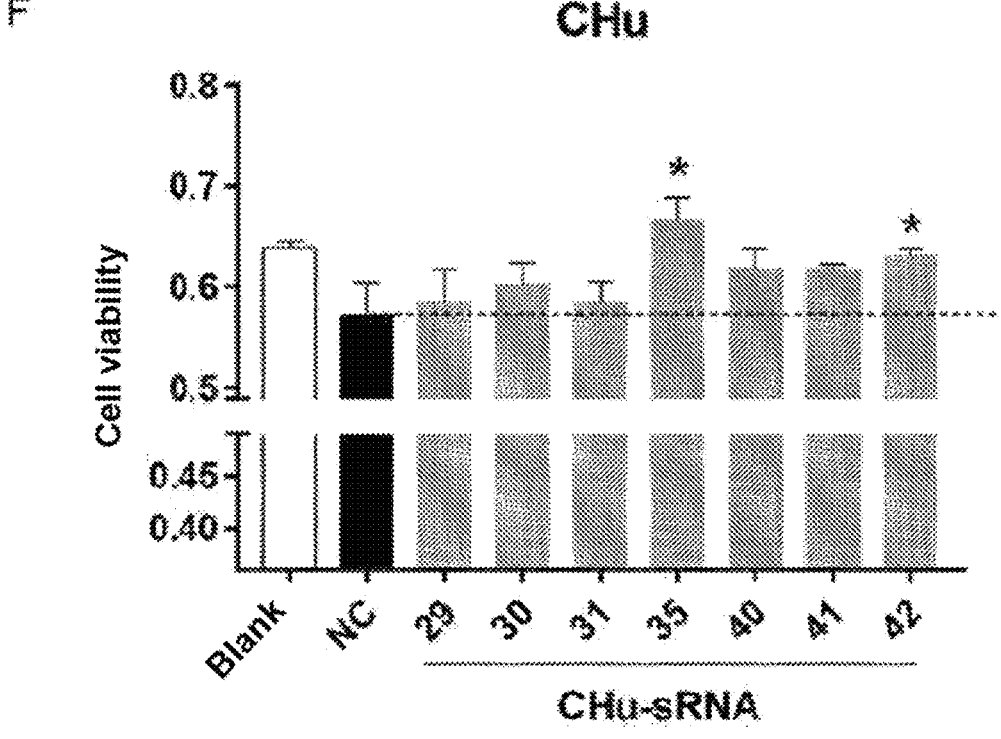
Figure 34G:
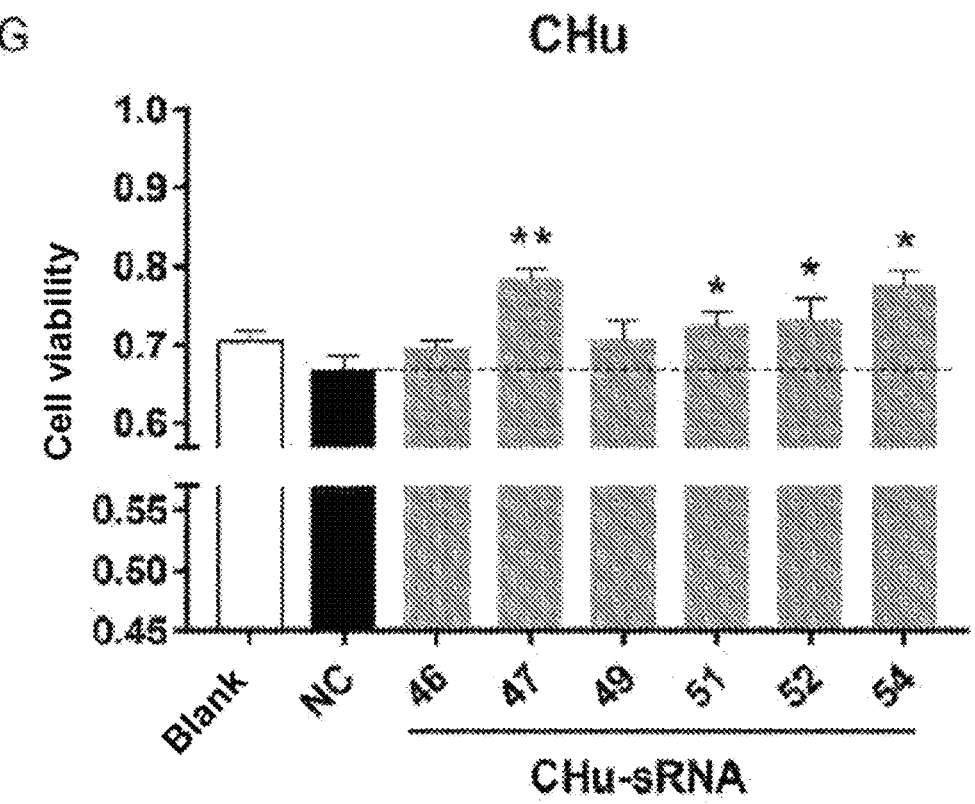

FIG. 34A to FIG. 34C: BZL small RNA: after H5N1 (0.4 M.O.I) infection, the rescue results of the *Scutellaria bar-*

8

Figure 34H:
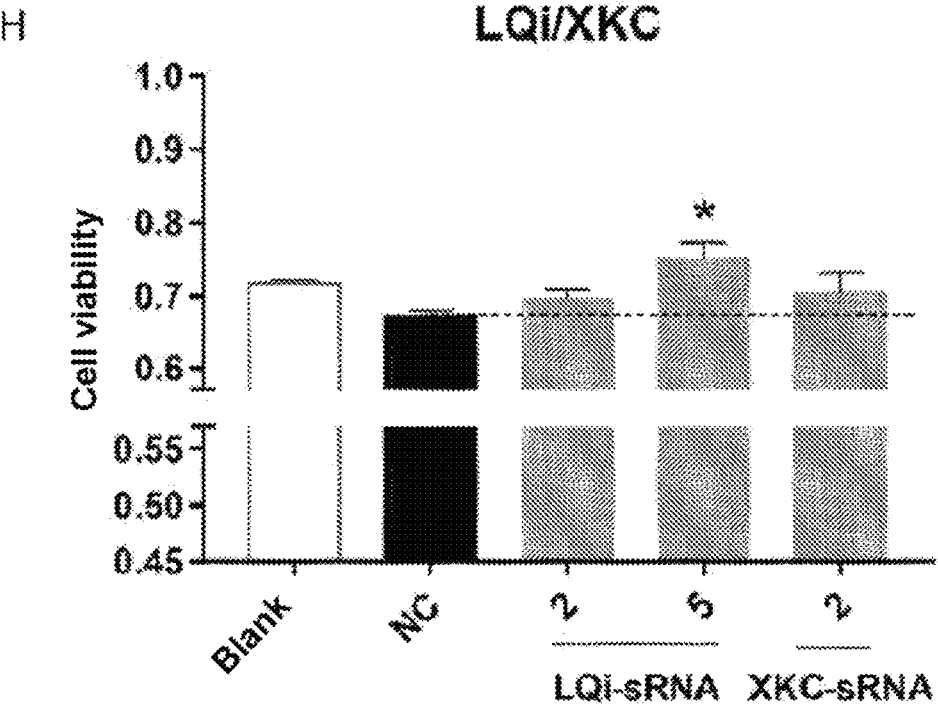
Figure 34I:
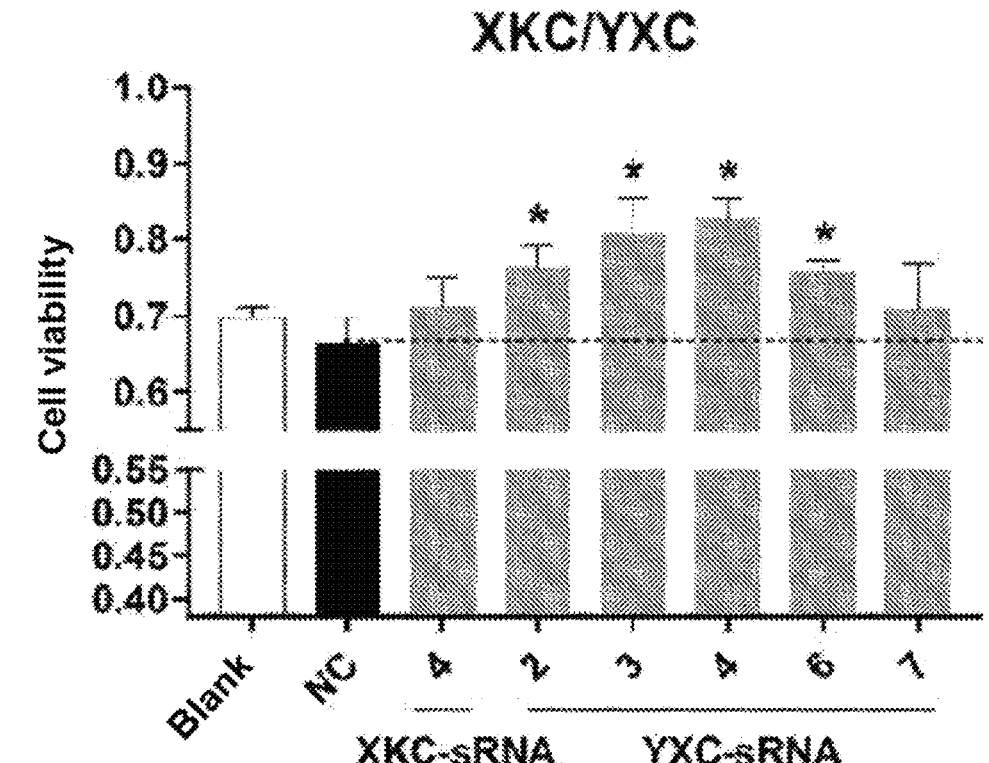
Figure 34J:
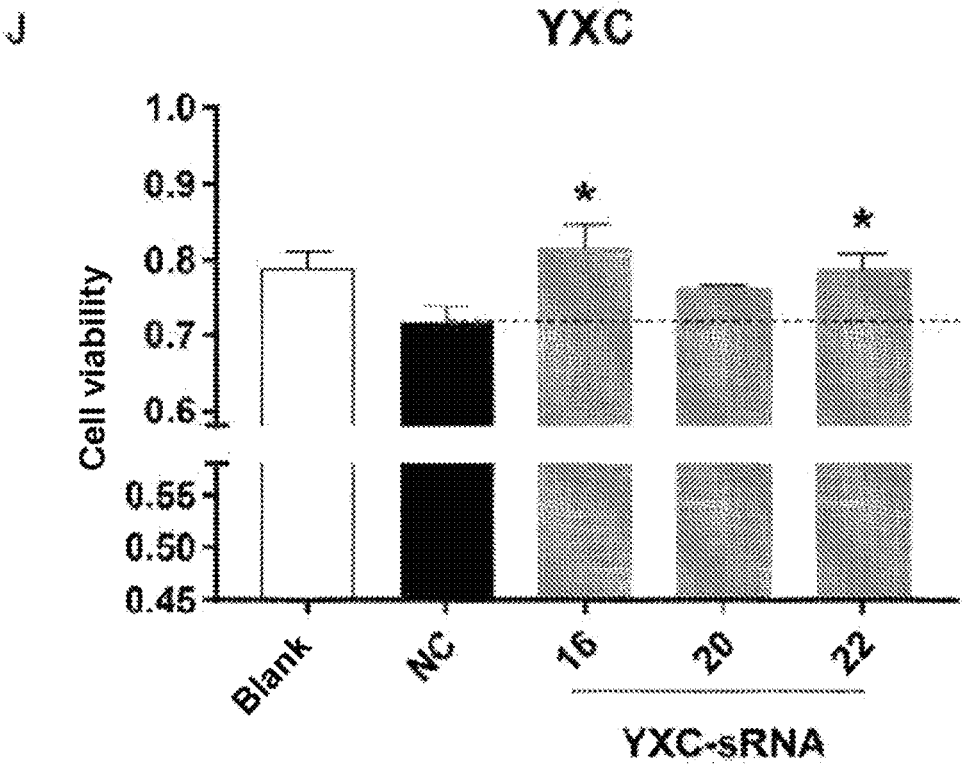
Figure 34K:
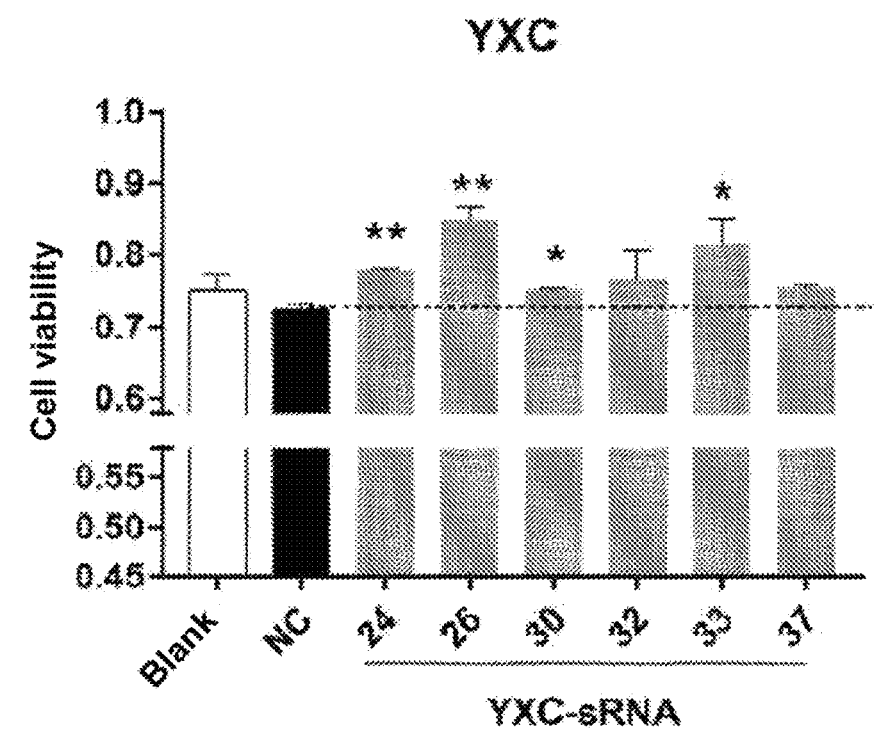
Figure 34L:
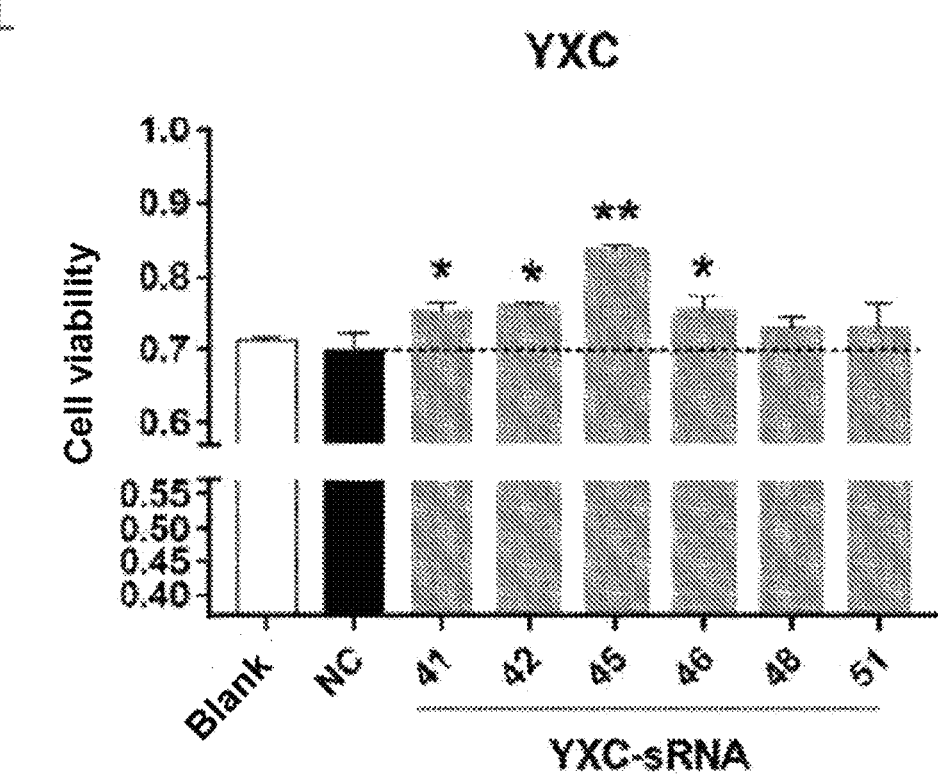
Figure 34M:
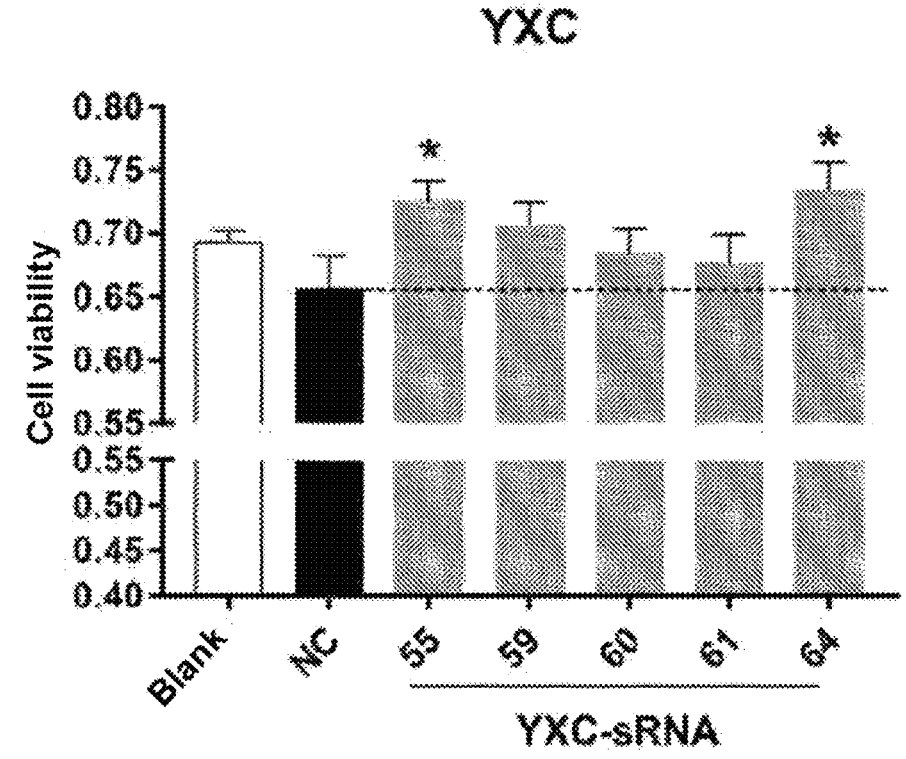

*bata* (BZL) small RNA on cell death, as specified in the figure; FIG. 34D to FIG. 34G: CHu small RNA: after H5N1 (0.4 M.O.I) infection, the rescue results of the *Bupleurum* (CHu) small RNA on cell death, as specified in the figure;

FIG. 34H: LQi/XKC small RNA: after H5N1 (0.4 M.O.I) infection, the rescue results of the *Fructus forsythiae* (LQi)/ *Prunella vulgaris* (XKC) small RNA on cell death, as specified in the figure; FIG. 34I: XKC/YXC small RNA: after H5N1 (0.4 M.O.I) infection, the rescue results of the *Prunella vulgaris* (XKC)/*Houttuynia cordata* (YXC) small RNA on cell death, as specified in the figure; FIG. 34J to FIG. 34N: YXC small RNA: after H5N1 (0.4 M.O.I) infection, the rescue results of *Houttuynia cordata* (YXC) small RNA on cell death, as specified in the figure.

Figure 35:
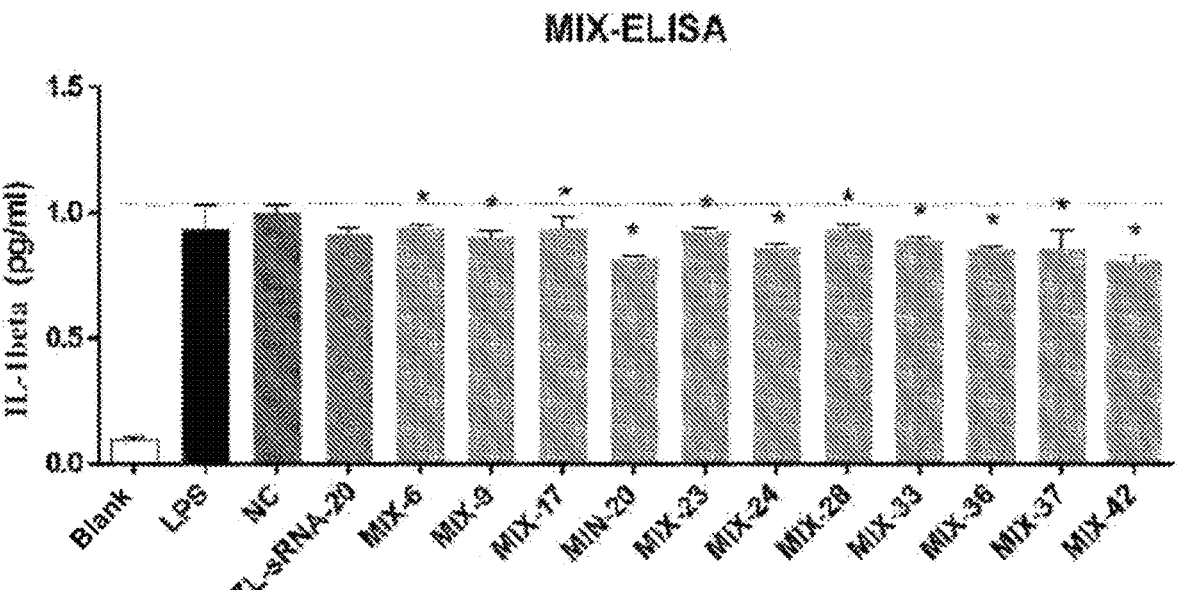

FIG. 35: The expression of the inflammatory factor IL-1beta at protein level compared to the NC group, in the cell inflammation model after 9 hours of LPS stimulation, with the THP1 cells transfected with the small RNA mixtures 24 hours in advance, as specified in the figure.

Figure 36:
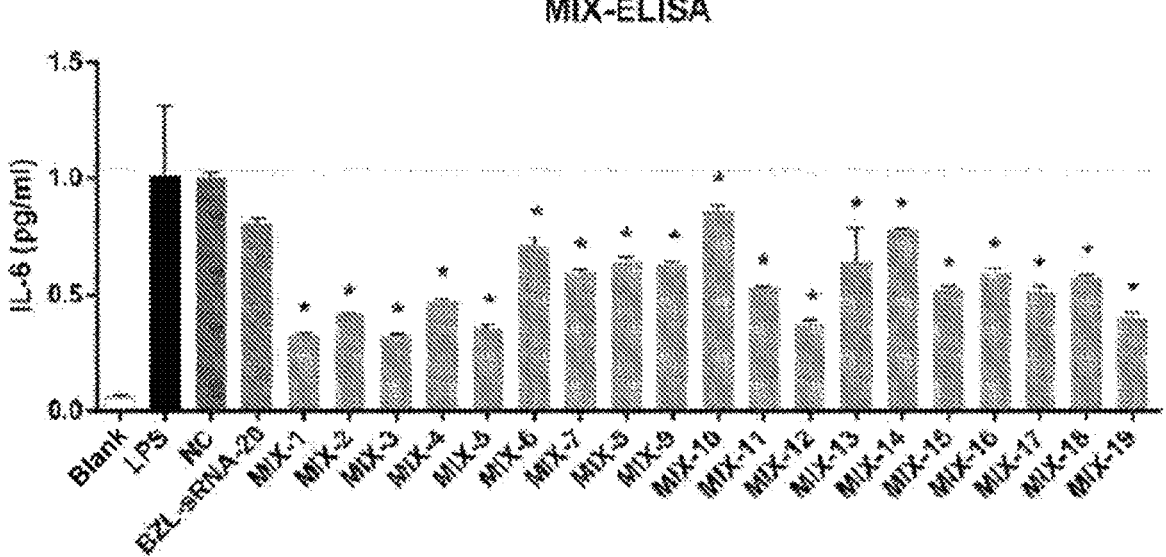
Figure 37:
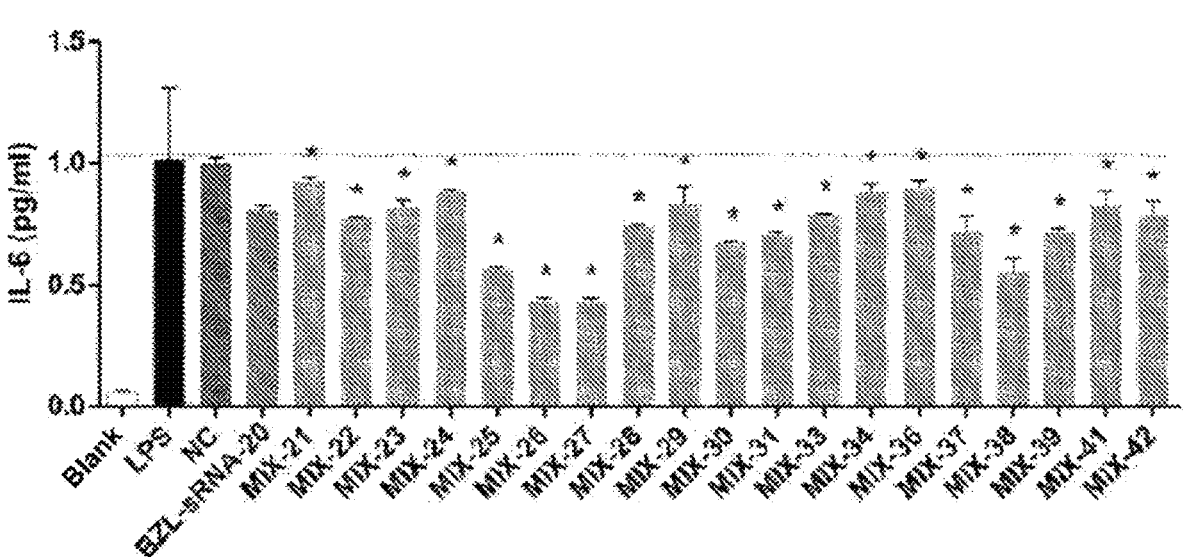

FIG. 36 to FIG. 37: The expression of the inflammatory factor IL-6 at protein level compared to the NC group, in the cell inflammation model after 9 hours of LPS stimulation, with the THP1 cells transfected with the small RNA mixtures 24 hours in advance, as specified in the figure.

Figure 38:
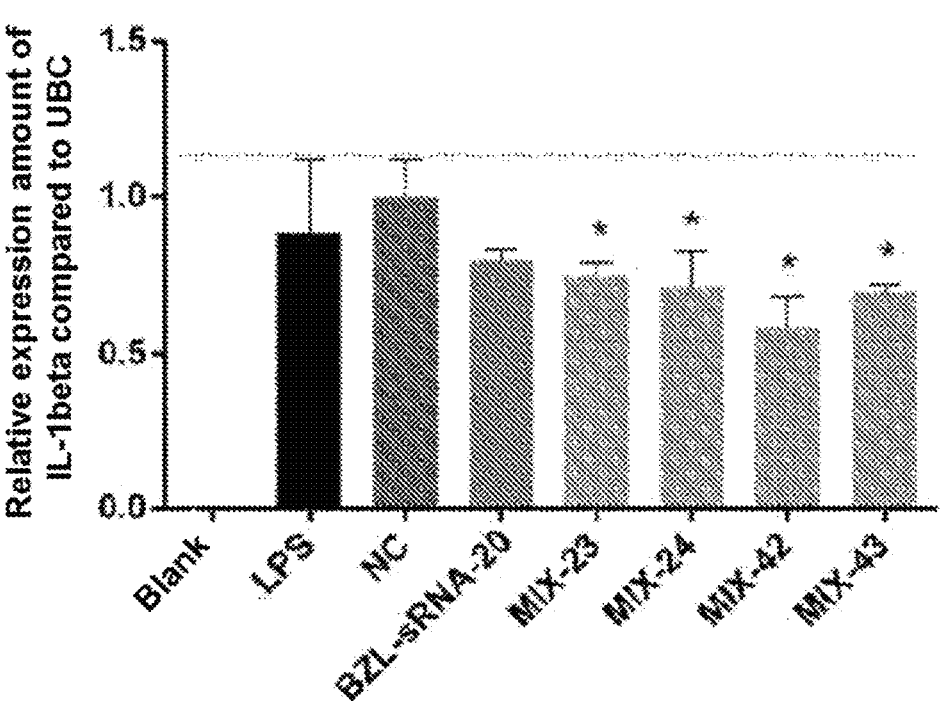

FIG. 38: The expression of the inflammatory factor IL-1beta at mRNA level compared to the NC group, in the cell inflammation model after 9 hours of LPS stimulation, with the THP1 cells transfected with the small RNA mixtures 24 hours in advance, as specified in the figure.

Figure 39:
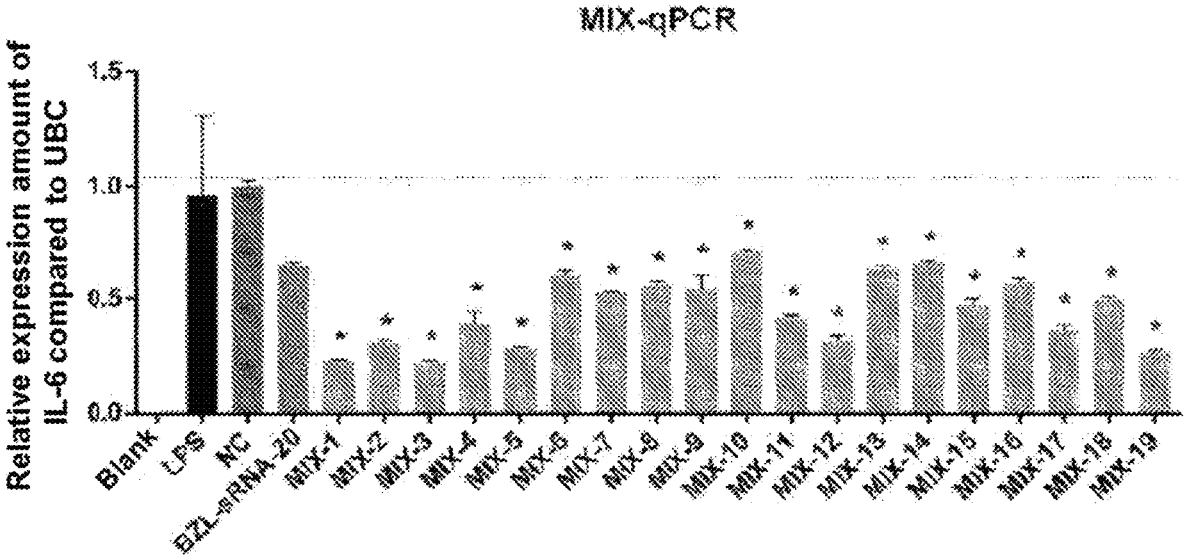
Figure 40:
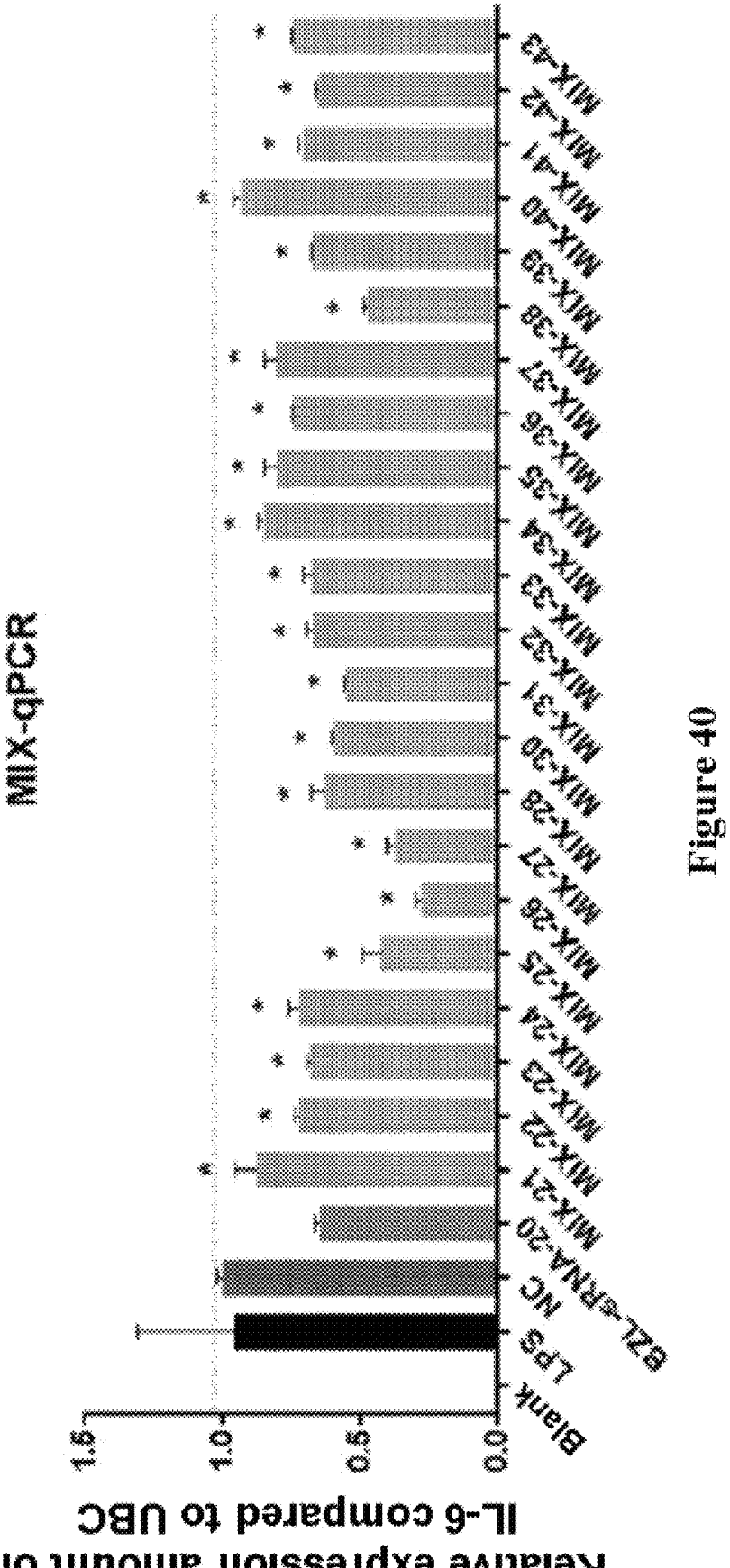

FIG. 39 to FIG. 40: The expression of the inflammatory factor IL-6 at mRNA level compared to the NC group, in the cell inflammation model after 9 hours of LPS stimulation, with the THP1 cells transfected with the small RNA mixtures 24 hours in advance, as specified in the figure.

Figure 41:
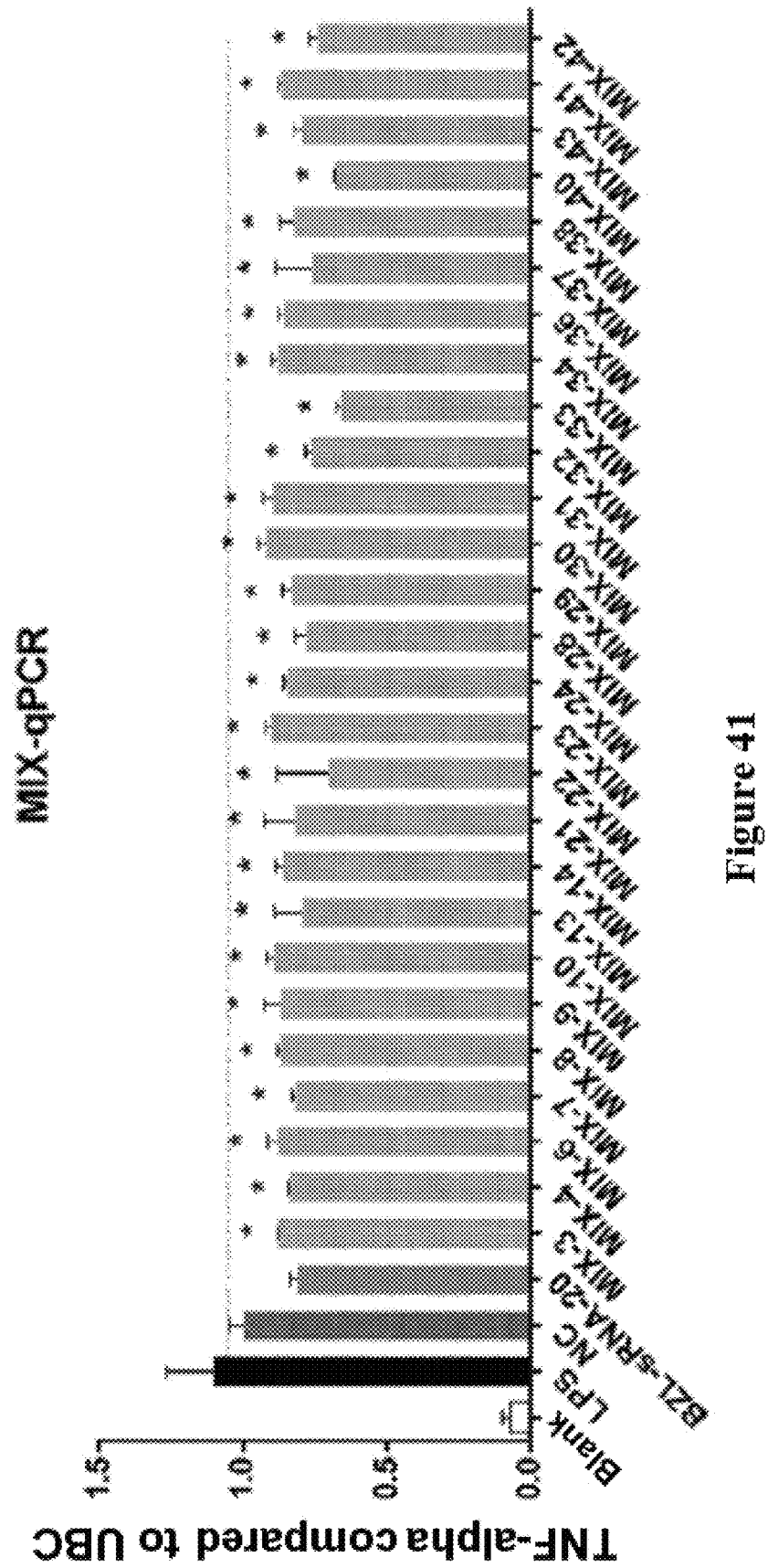

FIG. 41: The expression of the inflammatory factor TNF-alpha at mRNA level compared to the NC group, in the cell inflammation model after 9 hours of LPS stimulation, with the THP1 cells transfected with the small RNA mixtures 24 hours in advance, as specified in the figure.

Figure 42:
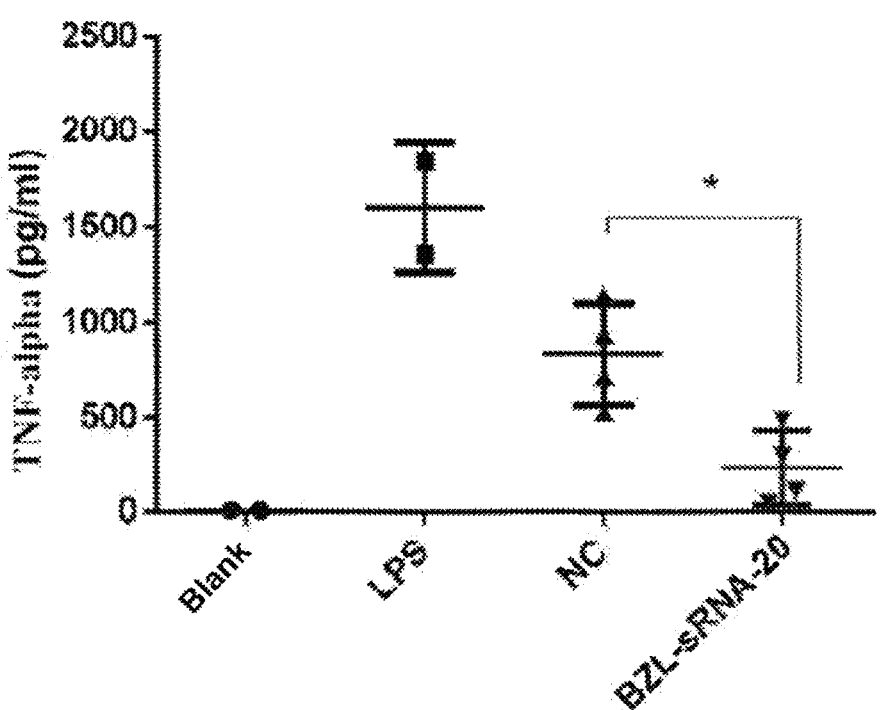

FIG. 42: The expression of the inflammatory factor TNF-alpha at protein level compared to the NC group, in the alveolar lavage fluid of the animal inflammation model after 9 hours of LPS stimulation, wherein the mice were gavaged with small RNA, three days in advance.

Figure 43:
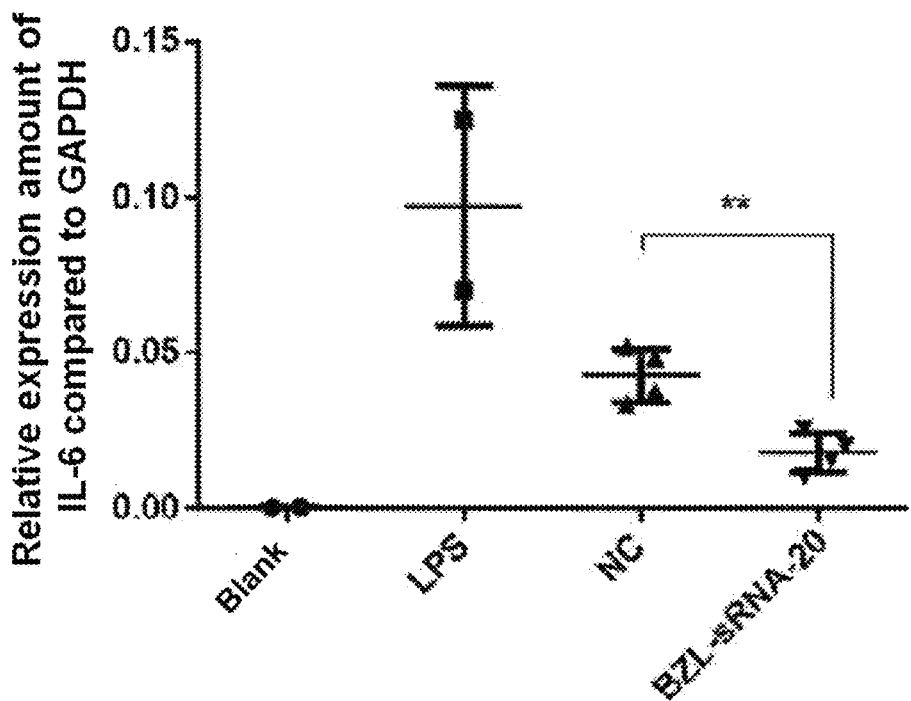

FIG. 43: The expression of the inflammatory factor IL-6 at mRNA level compared to the NC group, in the exfoliated lung cells of the animal inflammation model after 9 hours of LPS stimulation, wherein the mice were gavaged with small RNA, three days in advance.

DETAILED DESCRIPTION OF THE
EMBODIMENT

The invention discloses some small RNAs and the ability thereof to inhibit any one or more of pathway(s) or gene(s) listed in Table 3, or discloses the application thereof in reducing or down-regulating the expression level of IL-1beta, IL-6 or/and TNF-alpha in vivo or in vitro, or in treating or preventing IL-1beta, IL-6 or/and TNF-alpha related diseases and/or H5N1 infection in a subject. Those skilled in the art can learn from the content herein and appropriately improve the process parameters for realization. In particular, it should be pointed out that all similar substitutions and modifications are obvious to those skilled in the art, and they are all deemed to be included in the present invention. The nucleic acid and applications of the present invention have been described through preferred embodiments. It is obvious that relevant personnel can modify or appropriately change and combine the applications described herein without departing from the content, spirit and scope of the present invention to realize and apply the technology of the present invention.

Generally, siRNA, miRNA and other non-coding small RNAs are indiscriminately referred to as small RNAs (sR-NAs). Unless otherwise specified, the term "small RNA (sRNA)" herein refers to various non-coding small RNAs including siRNA and miRNA. The "small" in the term does not limit the RNA to a specific size.

The terms "including", "comprising" and "containing" mean that in addition to the listed characteristic elements, there may be other additional characteristic elements. In particular, it can also consist of only the listed characteristic elements.

The term "subject" refers to, for example, a subject who suffers from inflammation and/or H5N1 infection and needs treatment or who has signs of potential inflammation development and/or who is susceptible to H5N1 infection and in need of prevention.

Sequence "identity" is used herein to describe the relativity between two amino acid sequences or between two nucleotide sequences. For the purpose of the present invention, the sequence identity between two deoxyribonucleotide sequences is determined by using the Needleman-Wunsch algorithm (Needleman and Wunsch, 1970) implemented in the Needle program of the EMBOSS package (EMBOSS: European Molecular Biology Open Software Suite, Rice et al., 2000, Trends Genet. 16:276-277) (preferably version 5.0.0 or later versions). The parameters used are a gap open penalty of 10, a gap extension penalty of 0.5, and the EDNAFULL substitution matrix (EMBOSS version of NCBI NUC4.4). The Needle output (obtained with the -nobrief option) marked as "the longest identity" is used as the percentage identity and calculated as follows:

(Identical deoxyribonucleotides×100)/(Alignment length−total number of gaps in the alignment).

For example, the present invention encompasses the sequences with at least 80%, 85%, 90%, 95%, 96%, 97%, 98%, 99% or 99.9% identity with the sequence shown in any one of SEQ ID NO. 1-222.

As used herein, the term "stringent conditions" may refer to for example hybridization in 4×SSC at 65° C., followed by washing several times in 0.1×SSC at 65° C., for a total of approximately 1 hour. The term "stringent hybridization conditions" used herein can also refer to hybridization in 0.25 M sodium phosphate, 7% SDS pH 7.2, 1 mM EDTA and 1% BSA at 68° C. for 16 hours, followed by washing twice in 2×SSC and 0.1% SDS at 68° C. Those skilled in the art can determine the stringent conditions according to the specific sequence.

The term "cell survival rate" is also called cell viability. In one embodiment, cell survival rate can be calculated by using the MTS detection kit according to the manufacturer's instructions.

The term "IL-1beta, IL-6 or/and TNF-alpha related disease" refers to the diseases characterized in the increase of the expression level of IL-1beta, IL-6 or/and TNF-alpha, such as pneumonia, myocarditis, acute and chronic gastritis, acute and chronic enteritis, acute and chronic hepatitis, acute and chronic nephritis, dermatitis, encephalitis, lymphitis, conjunctivitis, keratitis, iridocyclitis, tympanitis, allergic rhinitis, asthma, pulmonary fibrosis, allergic dermatitis, multiple sclerosis, systemic lupus erythematosus, lung cancer, gastric cancer, colorectal cancer, liver cancer, cervical cancer, breast cancer, leukemia, diabetes and gout, etc.

After long-term research, the inventors have found that the small RNA sequences of the present invention reduce or down-regulate the expression level of IL-1beta, IL-6 or/and TNF-alpha in vivo or in vitro, or treat or prevent IL-1beta, IL-6 or/and TNF-alpha related diseases and/or H5N1 infection (thus rescuing cell death caused by H5N1 infection) in a subject. The small RNA sequences used in the experiment are as shown in Table 1 below.

TABLE 1

| The small RNA sequences used in the experiment, all commercially synthesized. | |
|---|---|
| Name | Sequence |
| BZL-sRNA-1 (SEQ ID NO. 1) | GUUCAGAGUUCUACAGUC |
| BZL-sRNA-2 (SEQ ID NO. 2) | GUUCAGAGUUCUACAGUCCGA |
| BZL-sRNA-3 (SEQ ID NO. 3) | UCAGAGUUCUACAGUCCGACGAUC |
| BZL-sRNA-4 (SEQ ID NO. 4) | GUUCAGAGUUCUACAGUCCGACGA |
| BZL-sRNA-5 (SEQ ID NO. 5) | UCAGUCUUUUCUCUCUCCU |
| BZL-sRNA-6 (SEQ ID NO. 6) | UCUCGCUUGGGGUGCGAGAGGUCCCG |
| BZL-sRNA-7 (SEQ ID NO. 7) | UCAGUCUUUUCUCUCUCCUA |
| BZL-sRNA-8 (SEQ ID NO. 8) | UCCGGUAUGGUCUAGUGGC |
| BZL-sRNA-9 (SEQ ID NO. 9) | UAGGAACUUCAUACCGUGCU |
| BZL-sRNA-10 (SEQ ID NO. 10) | UCAGUCUUUUCUCUCUCCUAU |
| BZL-sRNA-11 (SEQ ID NO. 11) | UAGGAACUUCAUACCGUGCUC |
| BZL-sRNA-12 (SEQ ID NO. 12) | UAGGAACUUCAUACCGUGCUCU |
| BZL-sRNA-13 (SEQ ID NO. 13) | UGGAAUGUAAAGAAGUAUGGAG |
| BZL-sRNA-14 (SEQ ID NO. 14) | UGAACACAGCUGGUGGUAUCU |

TABLE 1-continued

The small RNA sequences used in the experiment,
all commercially synthesized.

| Name | Sequence |
|---|---|
| BZL-sRNA-15 (SEQ ID NO. 15) | GGGGGCGUAGCUCAGAUGGU |
| BZL-sRNA-16 (SEQ ID NO. 16) | GGAUUUGAGUAAGAGCGUAG |
| BZL-sRNA-17 (SEQ ID NO. 17) | UGGAUUUGAGUAAGAGCGUAG |
| BZL-sRNA-18 (SEQ ID NO. 18) | AUGGAUUUGAGUAAGAGCGUAG |
| BZL-sRNA-19 (SEQ ID NO. 19) | GUUCAGAGUUCUACAGUCCGACGAU |
| BZL-sRNA-20 (SEQ ID NO. 20) | GUUCAGAGUUCUACAGUCCGACGAUC |
| BZL-sRNA-21 (SEQ ID NO. 21) | GAUGGAUUUGAGUAAGAGCGUAG |
| BZL-sRNA-22 (SEQ ID NO. 22) | CUCUUCAACGAGGAAUGC |
| BZL-sRNA-23 (SEQ ID NO. 23) | GGAUGGAUUUGAGUAAGAGCGUAG |
| BZL-sRNA-24 (SEQ ID NO. 24) | GAAACGGCUGCUAAUACC |
| BZL-sRNA-25 (SEQ ID NO. 25) | UGGAAACGGCUGCUAAUACC |
| BZL-sRNA-26 (SEQ ID NO. 26) | UGGAUUUGAGUAAGAGCAUAG |
| BZL-sRNA-27 (SEQ ID NO. 27) | AUGGAUUUGAGUAAGAGCAUAG |
| BZL-sRNA-28 (SEQ ID NO. 28) | CCCCGUCGUGCCCGGACC |
| BZL-sRNA-29 (SEQ ID NO. 29) | CGGAUGGAUUUGAGUAAGAGCGUAG |
| BZL-sRNA-30 (SEQ ID NO. 30) | CUGGAAACGGCUGCUAAUACC |
| BZL-sRNA-31 (SEQ ID NO. 31) | GCCCCGUCGUGCCCGGACC |
| BZL-sRNA-32 (SEQ ID NO. 32) | AGCUGGAAACGGCUGCUAAUACC |
| BZL-sRNA-33 (SEQ ID NO. 33) | AGCCCCGUCGUGCCCGGACC |
| BZL-sRNA-34 (SEQ ID NO. 34) | GAGCCCCGUCGUGCCCGGACC |
| BZL-sRNA-35 (SEQ ID NO. 35) | AGAGCCCCGUCGUGCCCGGACC |
| BZL-sRNA-36 (SEQ ID NO. 36) | GAGAGCCCCGUCGUGCCCGGACC |
| BZL-sRNA-37 (SEQ ID NO. 37) | UGAGAGCCCCGUCGUGCCCGGACC |
| BZL-sRNA-38 (SEQ ID NO. 38) | GUGAGAGCCCCGUCGUGCCCGGACC |
| BZL-sRNA-39 (SEQ ID NO. 39) | GGUGAGAGCCCCGUCGUGCCCGGACC |
| BZL-sRNA-40 (SEQ ID NO. 40) | GGGUGAGAGCCCCGUCGUGCCCGGACC |
| BZL-sRNA-41 (SEQ ID NO. 41) | AGGGUGAGAGCCCCGUCGUGCCCGGACC |
| BZL-sRNA-42 (SEQ ID NO. 42) | GAGGGUGAGAGCCCCGUCGUGCCCGGACC |
| CHu-sRNA-1 (SEQ ID NO. 43) | ACAACUUUCAGCAACGGA |
| CHu-sRNA-2 (SEQ ID NO. 44) | ACAACUUUCAGCAACGGAU |
| CHu-sRNA-3 (SEQ ID NO. 45) | ACAACUUUCAGCAACGGAUC |
| CHu-sRNA-4 (SEQ ID NO. 46) | ACAACUUUCAGCAACGGAUCU |
| CHu-sRNA-5 (SEQ ID NO. 47) | UCAUAUGAAGCACUGUAGCU |
| CHu-sRNA-6 (SEQ ID NO. 48) | UGAUAUGAAGCACUGUAGCUC |
| CHu-sRNA-7 (SEQ ID NO. 49) | GUUCAGAGUUCUACAGUCC |
| CHu-sRNA-8 (SEQ ID NO. 50) | GUUCAGAGUUCUACAGUCCG |
| CHu-sRNA-9 (SEQ ID NO. 51) | UGUAGUAGAUUGUAUAGUU |

TABLE 1-continued

The small RNA sequences used in the experiment, all commercially synthesized.

| Name | Sequence |
|------|----------|
| CHu-sRNA-10 (SEQ ID NO. 52) | UGAUAUGAAGCACUGUAGCUCU |
| CHu-sRNA-11 (SEQ ID NO. 53) | UGAUGUAGUAGGUUGUAU |
| CHu-sRNA-12 (SEQ ID NO. 54) | UGAUGUAGUAGAUUGUAUA |
| CHu-sRNA-13 (SEQ ID NO. 55) | UGAUGUAGUAGAUUGUAUAG |
| CHu-sRNA-14 (SEQ ID NO. 56) | UGAUGUAGUAGAUUGUAUAGU |
| CHu-sRNA-15 (SEQ ID NO. 57) | UGAUGUAGUAGAUUGUAUAGUU |
| CHu-sRNA-16 (SEQ ID NO. 58) | UGCUGUAGUAGGUUGUAU |
| CHu-sRNA-17 (SEQ ID NO. 59) | UGAUGUAGUAGGUUGUAUGG |
| CHu-sRNA-18 (SEQ ID NO. 60) | UGAUGUAGUAGGUUGUAUGGU |
| CHu-sRNA-19 (SEQ ID NO. 61) | UGAUGUAGUAGGUUGUAUAG |
| CHu-sRNA-20 (SEQ ID NO. 62) | AGCCGGACGGUGGCCAUG |
| CHu-sRNA-21 (SEQ ID NO. 63) | UAACUUAUCAGACUGAUGUUG |
| CHu-sRNA-22 (SEQ ID NO. 64) | CAGCAGCAAUUCAUGUUUUGGA |
| CHu-sRNA-23 (SEQ ID NO. 65) | UAACUUAUCAGACUGAUGUUGA |
| CHu-sRNA-24 (SEQ ID NO. 66) | UGAUGUAGUAGGUUGUAUAGU |
| CHu-sRNA-25 (SEQ ID NO. 67) | UGAUGUAGUAGGUUGUAUGGUU |
| CHu-sRNA-26 (SEQ ID NO. 68) | UUAAAGUAAUCCAGGAUAG |
| CHu-sRNA-27 (SEQ ID NO. 69) | UGUAAACAUCCUCGACUGGAAA |
| CHu-sRNA-28 (SEQ ID NO. 70) | UUAAAGUAAUCCAGGAUAGG |
| CHu-sRNA-29 (SEQ ID NO. 71) | UUAGAGUAAUCCAGGAUAGG |
| CHu-sRNA-30 (SEQ ID NO. 72) | UGAUGUAGUAGGUUGUAUAGUU |
| CHu-sRNA-31 (SEQ ID NO. 73) | UGCUGUAGUAGAUUGUAUAG |
| CHu-sRNA-32 (SEQ ID NO. 74) | UCCAGUACUGUGAUAACUGA |
| CHu-sRNA-33 (SEQ ID NO. 75) | CCUUCCCUUUGUACACACCGC |
| CHu-sRNA-34 (SEQ ID NO. 76) | UGCGGUAGUAGGUUGUAUGG |
| CHu-sRNA-35 (SEQ ID NO. 77) | UGCUGUAGUAGAUUGUAUAGU |
| CHu-sRNA-36 (SEQ ID NO. 78) | UGAUGUAGUAGGUUGUGUGG |
| CHu-sRNA-37 (SEQ ID NO. 79) | UGAUGUAGUAGGUUGUGUGGU |
| CHu-sRNA-38 (SEQ ID NO. 80) | UUAGAGUAAUCCAGGAUAGGU |
| CHu-sRNA-39 (SEQ ID NO. 81) | UUAAAGUAAUCCAGGAUAGGU |
| CHu-sRNA-40 (SEQ ID NO. 82) | AGCCGGACGGUGGCCAUGG |
| CHu-sRNA-41 (SEQ ID NO. 83) | UGCUGUAGUAGAUUGUAUAGUU |
| CHu-sRNA-42 (SEO ID NO. 84) | AACCCGUUACCAUUACUGA |
| CHu-sRNA-43 (SEO ID NO. 85) | AACCCGUUACCAUUACUGAGU |
| CHu-sRNA-44 (SEQ ID NO. 86) | GUCCAGUACUGUGAUAACU |
| CHu-sRNA-45 (SEQ ID NO. 87) | UUAAAGUAAUCCAGGAUAGGCU |
| CHu-sRNA-46 (SEQ ID NO. 88) | UAAGUUAUCAGACUGAUGUUG |
| CHu-sRNA-47 (SEQ ID NO. 89) | GUCCAGUACUGUGAUAACUG |

TABLE 1-continued

The small RNA sequences used in the experiment,
all commercially synthesized.

| Name | Sequence |
| --- | --- |
| CHu-sRNA-48 (SEQ ID NO. 90) | UGCUGUAGUAGGUUGUAUAG |
| CHu-sRNA-49 (SEQ ID NO. 91) | UCCUGAGAGGGAGCCUGAG |
| CHu-sRNA-50 (SEQ ID NO. 92) | GUUCAGAGUUCUACAGUCCGAC |
| CHu-sRNA-51 (SEO ID NO. 93) | UCCCGGAUAGCUCAGUCGG |
| CHu-sRNA-52 (SEQ ID NO. 94) | GAGCUUAUCAGACUGAUGUUG |
| CHu-sRNA-53 (SEQ ID NO. 95) | GAGCUUAUCAGACUGAUGUUGA |
| CHu-sRNA-54 (SEQ ID NO. 96) | UCACUCCGAAGUUUCCCUC |
| CHu-sRNA-55 (SEQ ID NO. 97) | UUUCAGAGUUCUACAGUCCGA |
| DDi-sRNA-1 (SEQ ID NO. 98) | UGAUAUGAAGCACUGUAGC |
| HQi-sRNA-1 (SEQ ID NO. 99) | CCCUGCCCUUGUACACACCGCC |
| HQi-sRNA-2 (SEQ ID NO. 100) | AUGGUUCGAUUCCGGAGAGGG |
| JYH-sRNA-1 (SEQ ID NO. 101) | UUCAGAGUUCUACAGUCCGACGAU |
| LQi-sRNA-1 (SEQ ID NO. 102) | GCCUGUCUGAGCGUCGUU |
| LQi-sRNA-2 (SEQ ID NO. 103) | UCCCUGGUUGAUCCUGCC |
| LQi-sRNA-3 (SEQ ID NO. 104) | UAGUGGUAUGAUUCUCGC |
| LQi-sRNA-4 (SEQ ID NO. 105) | CUUUCACCAACGGAUCUCU |
| LQi-sRNA-3 (SEQ ID NO. 106) | CUUCAGAGUUCUACAGUCCGACGAUC |
| LQi-sRNA-6 (SEO ID NO. 107) | AUCCUGCUGGCGUCGCCA |
| LQi-sRNA-7 (SEQ ID NO. 108) | AUCCACGGCCAUAGGACUUUG |
| LQi-sRNA-8 (SEO ID NO. 109) | UCCAUGGUCUAGUGGUUAGGA |
| XKC-sRNA-1 (SEQ ID NO. 110) | CGCUGGCAAGGGCCCUGG |
| XKC-sRNA-2 (SEQ ID NO. 111) | CGCUGGCAAGGGCCCUGGG |
| XKC-sRNA-3 (SEQ ID NO. 112) | CCCCCGGUUCAAUCCCGG |
| XKC-sRNA-4 (SEQ ID NO. 113) | CCCCCGGUUCAGUCCCGG |
| XKC-sRNA-5 (SEQ ID NO. 114) | UCCAUGGUCUAGUGGUUAGG |
| XKC-sRNA-6 (SEQ ID NO. 115) | CCCACUGCUAAAUUUGACUGG |
| XKC-sRNA-7 (SEQ ID NO. 116) | CCGGGGCUACGCCUGUCUGAGCGUCGC |
| XKC-sRNA-8 (SEQ ID NO. 117) | GGCUACGCCUGUCUGAGCGUCGCU |
| YXC-sRNA-1 (SEQ ID NO. 118) | CCGCGGGGCCCCGUCGUCCCC |
| YXC-sRNA-2 (SEQ ID NO. 119) | CCCGCGGGGCCCCGUCGUCCC |
| YXC-sRNA-3 (SEQ ID NO. 120) | CCCGCGGGGCCCCGUCGUCCCC |
| YXC-sRNA-4 (SEQ ID NO. 121) | CCGCGGGGCCCCGUCGUCCCCC |
| YXC-sRNA-5 (SEQ ID NO. 122) | UGCAADGAUGUCAUCUUACUACUGAA |
| YXC-sRNA-6 (SEQ ID NO. 123) | CCCGCGGGGCCCCGUCGUCCCCC |
| YXC-sRNA-7 (SEQ ID NO. 124) | CCCAGUGUUUAGACUACCUGU |
| YXC-sRNA-8 (SEQ ID NO. 125) | AGGCAGUGUAGUUAGCUGAUUCA |
| YXC-sRNA-9 (SEQ ID NO. 126) | CCAGUGUUUAGACUACCUGUU |

TABLE 1-continued

The small RNA sequences used in the experiment,
all commercially synthesized.

| Name | Sequence |
|---|---|
| YXC-sRNA-10 (SEQ ID NO. 127) | CCCAGUGUUUAGACUACCUGUU |
| YXC-sRNA-11 (SEQ ID NO. 128) | UAAUACUGUCUGGUAAUGCCG |
| YXC-sRNA-12 (SEQ ID NO. 129) | UGUAGUAGGUUGUAUAGUU |
| YXC-sRNA-13 (SEQ ID NO. 130) | UGUAGUAGGUUGUAUGGUU |
| YXC-sRNA-14 (SEQ ID NO. 131) | UAAUACUGUCUGGUAAUGCCGU |
| YXC-sRNA-15 (SEQ ID NO. 132) | UGAUGUAGUAGGUUGUAUA |
| YXC-sRNA-16 (SEQ ID NO. 133) | UGUAAACAUCCUCGACUGGAAGA |
| YXC-sRNA-17 (SEQ ID NO. 134) | CAGCAGCAAUUCAUGUUUUGGAA |
| YXC-sRNA-18 (SEQ ID NO. 135) | CCAGUGUUUAGACUACCUGUUC |
| YXC-sRNA-19 (SEQ ID NO. 136) | CCCAGUGUUUAGACUACCUGUUC |
| YXC-sRNA-20 (SEQ ID NO. 137) | CCCCCCGGGGCCCCGUCGUCCCC |
| YXC-sRNA-21 (SEQ ID NO. 138) | UCCCUGAGGAGCCCUUUGAG |
| YXC-sRNA-22 (SEQ ID NO. 139) | UGCUGUAGUAGAUUGUAUA |
| YXC-sRNA-23 (SEQ ID NO. 140) | AAGGUUACUUGUUAGUUCAGG |
| YXC-sRNA-24 (SEQ ID NO. 141) | CCCCGCGGGGCCCCGUCGUCCCCC |
| YXC-sRNA-25 (SEQ ID NO. 142) | UGUAGUAGGUUGUGUGGUU |
| YXC-sRNA-26 (SEQ ID NO. 143) | UUAAUGCUAAUUGUGAUAGGG |
| YXC-sRNA-27 (SEQ ID NO. 144) | UGAUGUAGUAGUUUGUACA |
| YXC-sRNA-28 (SEQ ID NO. 145) | UGAUGUAGUAGUUUGUACAG |
| YXC-sRNA-29 (SEQ ID NO. 146) | UGAUGUAGUAGGUUGUGUGGUU |
| YXC-sRNA-30 (SEQ ID NO. 147) | UGAUGUAGUAGUUUGUACAGU |
| YXC-sRNA-31 (SEQ ID NO. 148) | UGCUGUAGUAGGUUGUAUAGU |
| YXC-sRNA-32 (SEQ ID NO. 149) | UGAUGUAGUAGUUUGUACAGUU |
| YXC-sRNA-33 (SEQ ID NO. 150) | UCCCUGAGGAGCCCUUUGAGCC |
| YXC-sRNA-34 (SEQ ID NO. 151) | UGCUGUAGUAGGUUGUAUGG |
| YXC-sRNA-35 (SEQ ID NO. 152) | UGCUGUAGUAGGUUGUAUGGU |
| YXC-sRNA-36 (SEQ ID NO. 153) | AACCCGUUACCAUUACUGAG |
| YXC-sRNA-37 (SEQ ID NO. 154) | UGCUGUAGUAGUUUGUGCU |
| YXC-sRNA-38 (SEQ ID NO. 155) | UGCUGUAGUAGGUUGUAUAGUU |
| YXC-sRNA-39 (SEQ ID NO. 156) | UGCUGUAGUAGUUUGUGCUGU |
| YXC-sRNA-40 (SEQ ID NO. 157) | UGCUGUAGUAGUUUGUGCUGUU |
| YXC-sRNA-41 (SEQ ID NO. 158) | UGUGAACAUCCUCGACUGG |
| YXC-sRNA-42 (SEQ ID NO. 159) | UGUGAACAUCCUCGACUGGA |
| YXC-sRNA-43 (SEQ ID NO. 160) | UGCUGUAGUAGGUUGUAUGGUU |
| YXC-sRNA-44 (SEQ ID NO. 161) | UAAUACUGCCUGGUAAUGAUGACU |
| YXC-sRNA-45 (SEQ ID NO. 162) | UGUGAACAUCCUCGACUGGAA |
| YXC-sRNA-46 (SEQ ID NO. 163) | GUCCAGUACUGUGAUAACUGA |
| YXC-sRNA-47 (SEQ ID NO. 164) | AACCCGUUACCAUUACUGAGUU |

TABLE 1-continued

The small RNA sequences used in the experiment,
all commercially synthesized.

| Name | Sequence |
|------|----------|
| YXC-sRNA-48 (SEQ ID NO. 165) | AGAUGUAGUAGGUUGCAUAGU |
| YXC-sRNA-49 (SEQ ID NO. 166) | AGGGUUCGAGUGUGAGCAUGC |
| YXC-sRNA-50 (SEQ ID NO. 167) | UGAUAUGAAGCACUGUAG |
| YXC-sRNA-51 (SEQ ID NO. 168) | AACCCGUCCUCAGUUCGGA |
| YXC-sRNA-52 (SEQ ID NO. 169) | UGCUAUGAAGCACUGUAG |
| YXC-sRNA-53 (SEQ ID NO. 170) | UGCUAUGAAGCACUGUAGC |
| YXC-sRNA-54 (SEQ ID NO. 171) | UGCUAUGAAGCACUGUAGCU |
| YXC-sRNA-55 (SEQ ID NO. 172) | UGAUGUAGUAGAUUGUAU |
| YXC-sRNA-56 (SEQ ID NO. 173) | UGCUAUGAAGCACUGUAGCUC |
| YXC-sRNA-57 (SEQ ID NO. 174) | UCGAUCCUGGCUCAGGAUGAACG |
| YXC-sRNA-58 (SEQ ID NO. 175) | UGCUAUGAAGCACUGUAGCUCU |
| YXC-sRNA-59 (SEQ ID NO. 176) | UGAUGUAGUAGUUUGUGCU |
| YXC-sRNA-60 (SEQ ID NO. 177) | UGAUGUAGUAGUUUGUGCUG |
| YXC-sRNA-61 (SEQ ID NO. 178) | UGAUGUAGUAGUUUGUGCUGU |
| YXC-sRNA-62 (SEQ ID NO. 179) | UCUUCCCAGUGCUCUGAAUGU |
| YXC-sRNA-63 (SEQ ID NO. 180) | UGAUGUAGUAGUUUGUGCUGUU |
| YXC-sRNA-64 (SEQ ID NO. 181) | AGACACGGCCCAGACUCCUA |
| YXC-sRNA-65 (SEQ ID NO. 182) | UGAUGUAGUAGGUUGUGU |
| YXC-sRNA-66 (SEQ ID NO. 183) | GUAUUGUUUCCUACUUUAUG |
| YXC-sRNA-67 (SEQ ID NO. 184) | GUAUUGUUUCCUACUUUAUGG |
| YXC-sRNA-68 (SEQ ID NO. 185) | GUAUUGUUUCCUACUUUAUGGA |
| YXC-sRNA-69 (SEQ ID NO. 186) | UGGAAACAUCCUCGACUGGA |
| YXC-sRNA-70 (SEQ ID NO. 187) | ACAUUAGUCUGCACAUUGGU |
| YXC-sRNA-71 (SEQ ID NO. 188) | UGGAAACAUCCUCGACUGGAA |
| YXC-sRNA-72 (SEQ ID NO. 189) | AUCUUAUCAGACUGAUGUUGA |
| YXC-sRNA-73 (SEQ ID NO. 190) | ACAUUAGUCUGCACAUUGGUU |
| YXC-sRNA-74 (SEQ ID NO. 191) | UGUUCAAAUCCAUGCAAAA |
| YXC-sRNA-75 (SEQ ID NO. 192) | UCUUACCGUGAGUAAUAAU |
| YXC-sRNA-76 (SEQ ID NO. 193) | UAUCUUAUCAGACUGAUGUUGA |
| YXC-sRNA-77 (SEQ ID NO. 194) | UCUUACCGUGAGUAAUAAUG |
| YXC-sRNA-78 (SEQ ID NO. 195) | UGUUCAAAUCCAUGCAAAACUG |
| YXC-sRNA-79 (SEQ ID NO. 196) | UAUCACCAUCUGAAAUCGGU |
| YXC-sRNA-80 (SEQ ID NO. 197) | UGUUCAAAUCCAUGCAAAACUGA |
| YXC-sRNA-81 (SEQ ID NO. 198) | UCAUACCGUGAGUAAUAAUG |
| YXC-sRNA-82 (SEQ ID NO. 199) | UAUCACCAUCUGAAAUCGGUU |
| YXC-sRNA-83 (SEQ ID NO. 200) | UGAUAUGAAGCACUGUAGCUCA |
| CXL-sRNA-30 (SEQ ID NO. 201) | GGGAUUGUAGUUCAAUUGGUCAGAGC ACCGCCC |

TABLE 1-continued

The small RNA sequences used in the experiment,
all commercially synthesized.

| Name | Sequence |
|------|----------|
| PGY-sRNA-21 (SEQ ID NO. 202) | GUGCUUGAAAUUGUCGGGA |
| PGY-sRNA-22 (SEQ ID NO. 203) | UGAACUCUGAACUCCAGUCAC |
| PGY-sRNA-23 (SEQ ID NO. 204) | CCCUCCGCGGCCAGCUUCU |
| PGY-sRNA-24 (SEQ ID NO. 205) | GUGUCGUGAGAUGUUGGG |
| PGY-sRNA-25 (SEQ ID NO. 206) | GUUCAGAGUUCUACAGUCCGACGAUC UC |
| PGY-sRNA-26 (SEQ ID NO. 207) | UCCGGAAUGAUUGGGCGUAAAGCGU |
| PGY-sRNA-27 (SEQ ID NO. 208) | ACCGUGCGCUGGAUUAUGA |
| PGY-sRNA-28 (SEQ ID NO. 209) | UCUCAGGUAGACAGUUUCUAUGGG |
| PGY-sRNA-29 (SEQ ID NO. 210) | CGAUCCUGGCUCAGGAUGAACG |
| PGY-sRNA-30 (SEQ ID NO. 211) | UUUGGAUUGAAGGGAGCUCUG |
| PGY-sRNA-31 (SEQ ID NO. 212) | AGCUUACCAAGGCGAUGAU |
| PGY-sRNA-32 (SEQ ID NO. 213) | CCGGCCCCGAACCCGUCGGC |
| PGY-sRNA-6 (SEQ ID NO. 214) | GUUCAGAGUUCUACAGUCCGA |
| PGY-sRNA-18 (SEQ ID NO. 215) | CGGGGCUACGCCUGUCUGAGCGUCGC |
| sly-miR168b-5p(CXL-sRNA-7) (SEQ ID NO. 216) | UCGCUUGGUGCAGGUCGGGAC |
| Pab-miR3711(CXL-sRNA-8) (SEQ ID NO. 217) | GGCCCUCCUUCUAGCGCCA |
| CXL-sRNA-17 (SEQ ID NO. 218) | CAGAGUCGCGCAGCGGAA |
| CXL-sRNA-21 (SEQ ID NO. 219) | ACAGCAGGACGGUGGCCAUGGAAG |
| ppe-miR169c(HJT-sRNA-3) (SEQ ID NO. 220) | CAGCCAAGGAUGACUUGCCGG |
| HJT-sRNA-a2 (SEQ ID NO. 221) | UAGCACCAUCCGAAAUCGGUA |
| HJT-sRNA-h3 (SEQ ID NO. 222) | UGGGGCUACGCCUGUCUGAGCGUCGCU |

In the present invention, the concentration of the aforementioned small RNA used is 20 µM. In one embodiment, synthetic small RNAs are used to test their ability to inhibit any one or more pathway(s) or gene(s) listed in Table 3, or used to reduce or down-regulate the expression level of IL-1beta, IL-6 or/and TNF-alpha in vitro or in vivo, and/or to improve cell survival rate and/or to treat or prevent IL-1beta, IL-6 or/and TNF-alpha related diseases and/or H5N1 infection in a subject. In one embodiment, the small RNA used targets or reduces the same pathway(s) or gene(s) in Table 3. In one embodiment, the small RNA used reduces or down-regulates the expression level of one of IL-1beta, IL-6 and TNF-alpha. In one embodiment, the small RNA used improves cell survival rate. In one embodiment, the cell survival rate is the survival rate of H5N1 infected cells. In one embodiment, the small RNA used treats or prevents diseases related to the increase of the expression level of one of IL-1beta, IL-6 and TNF-alpha in a subject.

It should be understood that those skilled in the art can prepare the coding nucleic acid according to the small RNA of the present disclosure, and can introduce the coding nucleic acid into suitable expression vectors. The expression vector expressing the small RNA of the present disclosure can be directly introduced into a subject or a test cell, thus inhibiting any one or more pathway(s) or gene(s) listed in Table 3, or reducing or down-regulating the expression level of IL-1beta, IL-6 or/and TNF-alpha in vitro or in vivo, and/or improving cell survival rate and/or treating or preventing IL-1beta, IL-6 or/and TNF-alpha related diseases and/or H5N1 infection in a subject, provided that the expression vector can be expressed in the subject or the test cell. For example, see US Patent US 2017/0342410, which is incorporated herein by reference.

In addition, those skilled in the art can also prepare constructs for expressing small RNA in cells, for example retroviral constructs, and through transfecting the packaging cell line with the constructs to produce recombinant retroviral particles, therefore infect the target cells in vitro or in vivo to inhibit any one or more pathway(s) or gene(s) listed in Table 3, to reduce or down-regulate the expression level of IL-1beta, IL-6 or/and TNF-alpha and/or to improve cell survival, and/or to treat or prevent IL-1beta, IL-6 or/and TNF-alpha related diseases and/or H5N1 infection in a subject. For example, see US Patent US 2017/0342410, which is incorporated herein by reference.

Those skilled in the art can introduce the cells containing expression vectors or constructs into a subject or a cell in vitro or in vivo to achieve the above-mentioned objects of the present invention. Alternatively, those skilled in the art can isolate the small RNAs of the present disclosure from cells by conventional techniques. Therefore, the present invention encompasses methods for expressing small RNAs, which include the steps of expressing cells under suitable conditions and recovering small RNAs.

The invention also encompasses reagents for detecting small RNAs, constructs, recombinant viruses, expression vectors, cells and/or pharmaceutical compositions. Those skilled in the art can also use a detection reagent to detect cells from different sources to detect whether the small RNAs of the present disclosure are included therein. Preferably, the reagent is a primer and/or a probe. The design or use of reagents is well known to those skilled in the art.

In one embodiment, the small RNA is BZL-sRNA-20. The inventors found that BZL-sRNA-20 has a very favorable effect in inhibiting TNF-alpha, IL-1beta or IL-6 protein or mRNA thereof. Therefore, the inventors selected BZL-sRNA-20 as the basic small RNA, and combined it with other small RNAs to prepare the small RNA mixtures described in Table 2.

TABLE 2

Small RNA mixtures used in the present invention (the experimental results are shown in FIG. 35 to FIG. 41)

| Mixture-1 | BZL-sRNA-20 | BZL-sRNA-2 | BZL-sRNA-6 | BZL-sRNA-9 | BZL-sRNA-40 | BZL-sRNA-41 | |
|---|---|---|---|---|---|---|---|
| Mixture-2 | BZL-sRNA-20 | BZL-sRNA-4 | BZL-sRNA-8 | BZL-sRNA-12 | BZL-sRNA-21 | BZL-sRNA-31 | |
| Mixture-3 | BZL-sRNA-20 | BZL-sRNA-33 | BZL-sRNA-34 | BZL-sRNA-35 | BZL-sRNA-38 | BZL-sRNA-39 | |
| Mixture-4 | BZL-sRNA-20 | BZL-sRNA-11 | BZL-sRNA-13 | BZL-sRNA-19 | BZL-sRNA-23 | BZL-sRNA-28 | |
| Mixture-5 | BZL-sRNA-20 | BZL-sRNA-29 | BZL-sRNA-36 | BZL-sRNA-37 | BZL-sRNA-42 | | |
| Mixture-6 | BZL-sRNA-20 | CHu-sRNA-23 | CHu-sRNA-27 | CHu-sRNA-31 | CHu-sRNA-35 | CHu-sRNA-41 | |
| Mixture-7 | BZL-sRNA-20 | CHu-sRNA-46 | CHu-sRNA-47 | CHu-sRNA-48 | CHu-sRNA-49 | CHu-sRNA-50 | |
| Mixture-8 | BZL-sRNA-20 | CHu-sRNA-52 | CHu-sRNA-53 | CHu-sRNA-54 | CHu-sRNA-6 | CHu-sRNA-43 | |
| Mixture-9 | BZL-sRNA-20 | CHu-sRNA-51 | CHu-sRNA-55 | CHu-sRNA-5 | CHu-sRNA-8 | CHu-sRNA-10 | |
| Mixture-10 | BZL-sRNA-20 | CHu-sRNA-21 | CHu-sRNA-24 | CHu-sRNA-28 | CHu-sRNA-29 | CHu-sRNA-30 | CHu-sRNA-42 |
| Mixture-11 | BZL-sRNA-20 | LQi-sRNA-7 | DDi-sRNA-1 | HQi-sRNA-1 | XKC-sRNA-4 | XKC-sRNA-8 | |
| Mixture-12 | BZL-sRNA-20 | JYH-sRNA-1 | LQi-sRNA-5 | LQi-sRNA-8 | XKC-sRNA-2 | XKC-sRNA-7 | |
| Mixture-13 | BZL-sRNA-20 | YXC-sRNA-15 | YXC-sRNA-30 | YXC-sRNA-32 | YXC-sRNA-33 | YXC-sRNA-34 | |
| Mixture-14 | BZL-sRNA-20 | YXC-sRNA-35 | YXC-sRNA-38 | YXC-sRNA-39 | YXC-sRNA-40 | YXC-sRNA-43 | |
| Mixture-15 | BZL-sRNA-20 | YXC-sRNA-46 | YXC-sRNA-47 | YXC-sRNA-50 | YXC-sRNA-51 | YXC-sRNA-53 | |
| Mixture-16 | BZL-sRNA-20 | YXC-sRNA-56 | YXC-sRNA-62 | YXC-sRNA-64 | YXC-sRNA-70 | YXC-sRNA-71 | |
| Mixture-17 | BZL-sRNA-20 | YXC-sRNA-72 | YXC-sRNA-75 | YXC-sRNA-79 | YXC-sRNA-82 | | |
| Mixture-18 | BZL-sRNA-20 | YXC-sRNA-1 | YXC-sRNA-2 | YXC-sRNA-3 | YXC-sRNA-9 | YXC-sRNA-10 | |
| Mixture-19 | BZL-sRNA-20 | YXC-sRNA-12 | YXC-sRNA-13 | YXC-sRNA-16 | YXC-sRNA-19 | YXC-sRNA-24 | |
| Mixture-20 | BZL-sRNA-20 | YXC-sRNA-25 | YXC-sRNA-26 | YXC-sRNA-28 | YXC-sRNA-29 | YXC-sRNA-31 | |
| Mixture-21 | BZL-sRNA-20 | YXC-sRNA-36 | YXC-sRNA-37 | YXC-sRNA-41 | YXC-sRNA-42 | YXC-sRNA-44 | |
| Mixture-22 | BZL-sRNA-20 | YXC-sRNA-48 | YXC-sRNA-49 | YXC-sRNA-54 | YXC-sRNA-55 | YXC-sRNA-57 | |
| Mixture-23 | BZL-sRNA-20 | YXC-sRNA-58 | YXC-sRNA-60 | YXC-sRNA-66 | YXC-sRNA-68 | YXC-sRNA-69 | |
| Mixture-24 | BZL-sRNA-20 | YXC-sRNA-73 | YXC-sRNA-80 | YXC-sRNA-83 | | | |
| Mixture-25 | BZL-sRNA-20 | PGY-sRNA-21 | PGY-sRNA-22 | PGY-sRNA-23 | PGY-sRNA-25 | PGY-sRNA-26 | |
| Mixture-26 | BZL-sRNA-20 | PGY-sRNA-28 | PGY-sRNA-29 | PGY-sRNA-30 | PGY-sRNA-32 | | |
| Mixture-27 | BZL-sRNA-20 | CXL-sRNA-30 | PGY-sRNA-27 | PGY-sRNA-31 | PGY-sRNA-24 | | |
| Mixture-28 | BZL-sRNA-20 | BZL-sRNA-1 | BZL-sRNA-3 | BZL-sRNA-5 | BZL-sRNA-7 | BZL-sRNA-10 | |
| Mixture-29 | BZL-sRNA-20 | BZL-sRNA-14 | BZL-sRNA-15 | BZL-sRNA-16 | BZL-sRNA-17 | BZL-sRNA-18 | BZL-sRNA-30 |
| Mixture-30 | BZL-sRNA-20 | BZL-sRNA-22 | BZL-sRNA-24 | BZL-sRNA-25 | BZL-sRNA-26 | BZL-sRNA-27 | BZL-sRNA-32 |

TABLE 2-continued

Small RNA mixtures used in the present invention (the experimental results are shown in FIG. 35 to FIG. 41)

| Mixture-31 | BZL-sRNA-20 | CHu-sRNA-1 | CHu-sRNA-2 | CHu-sRNA-3 | CHu-sRNA-4 | CHu-sRNA-7 | |
|---|---|---|---|---|---|---|---|
| Mixture-32 | BZL-sRNA-20 | CHu-sRNA-9 | CHu-sRNA-11 | CHu-sRNA-12 | CHu-sRNA-13 | CHu-sRNA-14 | |
| Mixture-33 | BZL-sRNA-20 | CHu-sRNA-15 | CHu-sRNA-16 | CHu-sRNA-17 | CHu-sRNA-18 | CHu-sRNA-19 | |
| Mixture-34 | BZL-sRNA-20 | CHu-sRNA-20 | CHu-sRNA-22 | CHu-sRNA-25 | CHu-sRNA-26 | CHu-sRNA-32 | |
| Mixture-35 | BZL-sRNA-20 | CHu-sRNA-33 | CHu-sRNA-34 | CHu-sRNA-36 | CHu-sRNA-37 | CHu-sRNA-38 | |
| Mixture-36 | BZL-sRNA-20 | CHu-sRNA-39 | CHu-sRNA-40 | CHu-sRNA-44 | CHu-sRNA-45 | | |
| Mixture-37 | BZL-sRNA-20 | HQi-sRNA-2 | LQi-sRNA-1 | LQi-sRNA-2 | LQi-sRNA-3 | LQi-sRNA-4 | |
| Mixture-38 | BZL-sRNA-20 | LQi-sRNA-6 | XKC-sRNA-1 | XKC-sRNA-3 | XKC-sRNA-5 | XKC-sRNA-6 | |
| Mixture-39 | BZL-sRNA-20 | YXC-sRNA-4 | YXC-sRNA-5 | YXC-sRNA-6 | YXC-sRNA-7 | YXC-sRNA-8 | |
| Mixture-40 | BZL-sRNA-20 | YXC-sRNA-11 | YXC-sRNA-14 | YXC-sRNA-17 | YXC-sRNA-18 | YXC-sRNA-20 | |
| Mixture-41 | BZL-sRNA-20 | YXC-sRNA-21 | YXC-sRNA-22 | YXC-sRNA-23 | YXC-sRNA-27 | YXC-sRNA-45 | |
| Mixture-42 | BZL-sRNA-20 | YXC-sRNA-52 | YXC-sRNA-59 | YXC-sRNA-61 | YXC-sRNA-63 | YXC-sRNA-65 | |
| Mixture-43 | BZL-sRNA-20 | YXC-sRNA-67 | YXC-sRNA-74 | YXC-sRNA-81 | YXC-sRNA-76 | YXC-sRNA-77 | YXC-sRNA-78 |

In one embodiment, the small RNA mixtures in Table 2 are used for each test. In one embodiment, the siRNA mixtures are prepared by mixing 20 μM of BZL-sRNA-20 and 20 μM each of other small RNAs at a volume ratio of 2:1. In one embodiment of the small RNA mixtures, the molar concentration of BZL-sRNA-20 and other small RNAs is 2:1. In one embodiment of the small RNA mixtures, the molar concentration of total small RNA in the small RNA mixture is 20 μM. In the figures, the mixtures are indicated by the symbol MIX.

IL-6 Related Diseases

The small RNA of the present invention can treat IL-6 related diseases. IL-6 related diseases include:

(respiratory tract) obstructive airway diseases, including chronic obstructive pulmonary disease (COPD); asthma, such as bronchial, allergic, endogenous, exogenous and dust asthma, especially chronic or habitual asthma (for example advanced asthma and airway hyperresponsiveness); bronchitis; acute, allergic, atrophic rhinitis and chronic rhinitis, including caseous rhinitis, hypertrophic rhinitis, purulent rhinitis, rhinitis sicca and drug-induced rhinitis; membranous rhinitis, including croupous, fibrinous and pseudomembranous rhinitis, and adenopathic rhinitis; seasonal rhinitis, including neurological rhinitis (hay fever) and vasomotor rhinitis, sinusitis, idiopathic pulmonary fibrosis (IPF); sarcoidosis, farmer's lung and related diseases, adult respiratory distress syndrome, hypersensitivity pneumonia, fibroid lung and idiopathic interstitial pneumonia;

(bone and joint) rheumatoid arthritis, juvenile chronic arthritis, juvenile arthritis systemic disease, seronegative spondyloarthropathy (including ankylosing spondylitis, psoriatic arthritis and Reiter's disease), Behcet's disease, Sjogren syndrome and systemic sclerosis, gout, osteoporosis and osteoarthritis;

(skin) psoriasis, atopic dermatitis, contact dermatitis and other eczema skin diseases, allergic contact dermatitis, seborrheic dermatitis, lichen planus, scleroderma, pemphigus, bullous pemphigoid, epidermolysis bullosa, urticaria, xeroderma (angioderma), vasculitis, erythema, hypereosinophilic skin, uveitis, alopecia areata, allergic conjunctivitis and vernal conjunctivitis;

(gastrointestinal tract) gastric ulcer, abdominal disease, proctitis, eosinophilic gastroenteritis, mastocytosis, inflammatory bowel disease, Crohn's disease, ulcerative colitis, antiphospholipid syndrome, producing effects away from the organs, such as food-related allergy of migraine, rhinitis and eczema;

(other tissues and systemic diseases) cachexia, multiple sclerosis, atherosclerosis, acquired immunodeficiency syndrome (AIDS), mesangial proliferative glomerulonephritis, nephrotic syndrome, nephritis, glomerulonephritis, acute renal failure, hemodialysis, uremia, local or discoid lupus erythematosus, systemic lupus erythematosus, Castleman disease, Hashimoto's thyroiditis, myasthenia gravis, type I diabetes, type B insulin-resistant diabetes, sickle cell anemia, iridocyclitis/uveitis/optic neuritis, nephritis syndrome, eosinophilic fasciitis, high IgE syndrome, systemic vasculitis/Wegener's granulomatosis, orchitis/vasectomy reversal procedure, lepromatous leprosy, alcohol-induced hepatitis, Sezary syndrome and idiopathic thrombocytopenic purpura; postoperative adhesions, nephropathy, systemic inflammatory response syndrome, sepsis syndrome, gram-positive sepsis, gram-negative sepsis, culture-negative sepsis, fungal sepsis, neutropenic fever, acute pancreatitis, urosepsis, Graves' disease, Raynaud's disease, antibody-mediated cytotoxicity, type III hypersensitivity, POEMS syndrome (polyneuropathy, megaorganism, endocrine disease, monoclonal gammopathy, and skin alteration syndrome), mixed connective tissue disease, idiopathic Addison's disease, diabetes, chronic active hepatitis, primary biliary cirrhosis, vitiligo, post-MI (cardiotomy) syndrome, type IV hypersensitivity, granuloma caused by intracellular organisms, Wilson disease, hemochromatosis, α-I-antitrypsin deficiency, diabetic retinopathy, Hashimoto's thyroiditis, hypothalamic-pituitary-adrenal axis assessment, thyroiditis, encephalomyelitis, neonatal chronic lung disease, familial hemophagocytic lymphohistiocytosis, hair loss, radiotherapy (including, for example, but not limited to: weakness, anemia, cachexia, etc.), chronic salicylic acid poisoning, sleep apnea, obesity, heart failure and meningococcalemia;

(allograft rejection) acute and chronic rejection after transplantation of kidney, heart, liver, lung, pancreas, bone marrow, bone, small intestine, skin, cartilage and cornea; and chronic graft-versus-host disease;

(malignant disease) leukemia, acute lymphocytic leukemia (ALL), acute leukemia, T cell, B cell or FABALL, chronic myelogenous leukemia (CML), acute myelogenous leukemia (AML), chronic lymphocytic leukemia (CLL), hairy cell leukemia, myelodysplastic syndrome (MDS), lymphoma, Hodgkin's disease, non-Hodgkin's lymphoma, malignant lymphoma, Burkitt's lymphoma, multiple myeloma, Kaposi's sarcoma, renal cell carcinoma, colorectal cancer, prostate cancer, pancreatic cancer, nasopharyngeal carcinoma, malignant histiocytosis, tumor-associated syndrome/malignant hypercalcemia, solid tumor, adenocarcinoma, sarcoma, malignant melanoma, hemangioma, metastasis, cancer-related bone resorption, cancer-related bone pain; inhibition of cancer metastasis; improvement of cancer cachexia;

cystic fibrosis, stroke, reperfusion injury of the heart, brain, peripheral limbs and other organs; burns, trauma/hemorrhage, ionizing radiation exposure, chronic skin ulcers;

reproductive diseases (such as ovulation, menstruation and implantation diseases, premature birth, preeclampsia, endometriosis); (infection) acute or chronic bacterial infection, acute and chronic parasitic process or infection process, including bacteria, virus and fungi infection, HIV infection/HIV neuropathy, meningitis, hepatitis (A, B or C, or other viral hepatitis, etc.), septic arthritis, peritonitis, pneumonia, epiglottitis, hemolytic uremic syndrome/thrombotic thrombocytopenic purpura, malaria, dengue hemorrhagic fever, leishmaniasis, leprosy, toxic shock syndrome, streptococcal myositis, gas gangrene, *Mycobacterium tuberculosis, Mycobacterium avium-intracellulare, Pneumocystis carinii* pneumonia, pelvic inflammatory disease, orchitis/epididymitis, *Legionella*, Lyme disease, influenza A, Epstein-Barr virus, vital-associated hemophagocytic syndrome, viral encephalitis/aseptic meningitis, etc.

The small RNA of the present invention can be used in combination with one or more of the following:

agonists or antagonists of cytokines or cytokine functions (for example, agents that act on cytokine signaling pathways, such as modulators of the SOCS system), for example α-, β- and/or γ-interferon; type I insulin-like growth factor (IGF-1), its receptors and related binding proteins; interleukins (IL), such as one or more of IL-1-33, and/or interleukin antagonists or inhibitors, for example anakinra; inhibitors of receptors of interleukin family members or inhibitors of specific subunits of these receptors; inhibitors of tumor necrosis factor alpha (TNF-alpha), for example anti-TNF monoclonal antibodies (for example, infliximab; adalimumab and/or CDP-870), and/or TNF receptor antagonists, for example immunoglobulin molecules (for example etanercept) and/or low molecular weight agents, for example pentoxyfylline;

B cell modulators, for example monoclonal antibodies targeting B-lymphocytes (for example CD20 (rituximab) or MRA-aIL16R) or T-lymphocytes (for example, CTLA4-Ig, HuMaxIl-15 or Abatacept);

modulators that inhibit the activity of osteoclasts, for example RANKL antibodies;

modulators of chemokines or chemokine receptor function, for example antagonists of the following chemokines: CCR1, CCR2, CCR2A, CCR2B, CCR3, CCR4, CCR5, CCR6, CCR7, CCR8, CCR9, CCR10 and CCR11 (in terms of C-C family); CXCR1, CXCR2, CXCR3, CXCR4 and CXCR5 and CXCR6 (in terms of C-X-C family) and CX3CR1 of C-X3-C family;

matrix metalloproteinases (MMP), i.e. inhibitors of one or more of the following: stromelysin, collagenase, gelatinase as well as aggrecanase; especially collagenase-1 (MMP-1), collagenase-2 (MMP-8), collagenase-3 (MMP-13), stromelysin-1 (MMP-3), stromelysin-2 (MMP-10) and/or stromelysin-3 (MMP-11) and/or MMP-9 and/or MMP-12, for example doxycycline and other agent(s);

leukotriene biosynthesis inhibitors, 5-lipoxygenase (5-LO) inhibitors or 5-lipoxygenase activated protein (FLAP) antagonists, for example: zileuton; ABT-761; fenleuton; tepoxalin; Abbott-79175; Abbott-85761; N-(5-substituted)-thiophene-2-alkylsulfonamide; 2,6-di-tert-butylphenol hydrazone; methoxytetrahydropyran, for example Zenica ZD-2138; compound SB-210661; pyridyl-substituted 2-cyanonaphthalene compounds, for example L-739,010; 2-cyanoquinoline compounds, for example L-746,530; indole and/or quinoline compounds, for example MK-591, MK-886 and/or BAYx1005;

antagonists of leukotriene (LT) B4, LTC4, LTD4 and LTE4 receptors, selected from: phenothiazine-3-1s, for example L-651,392; amidino compounds, for example CGS-25019c; aminobenzoxazoles (benzoxalamines), for example ontazolast; benzamidines (benzenecarboximidamides), for example BIIL284/260; and compounds for example zafirlukast, ablukast, montelukast, pranlukast, verlukast (MK-679), RG-12525, Ro-245913, iralukast (CGP45715A) and BAYx7195, etc;

phosphodiesterase (PDE) inhibitors, for example methylxanthanine, such as theophylline and/or aminophylline; and/or selective PDE isoenzyme inhibitors, for example PDE4 inhibitors and/or PDE4D isotype inhibitors, and/or PDE5 inhibitors;

type 1 histamine receptor antagonists, for example cetirizine, loratadine, desloratadine, fexofenadine, acrivastine, terfenadine, astemizole, azelastine, levocarbastine, chlorpheniramine, promethazine, cyclizine and/or mizolastine (usually for oral, topical or parenteral application);

proton pump inhibitors (for example omeprazole) or gastroprotective type 2 histamine receptor antagonists;

type 4 histamine receptor antagonists;

α-1/α-2 adrenergic receptor agonists, vasoconstrictors, sympathomimetic agent(s), for example propylhexedrine, phenylephrine, phenylpropanolamine, ephedrine, pseudoephedrine, naphazoline hydrochloride, oxymetazoline hydrochloride, tetrahydrozoline hydrochloride, xylometazoline hydrochloride, tramazoline hydrochloride and ethyl norepinephrine hydrochloride;

anticholinergics, for example muscarinic receptor (M1, M2 and M3) antagonists, for example atropine, scopolamine, glycopyrrrolate, ipratropium bromide, tiotropium bromide, oxytropium bromide, pirenzepine and telenzepine;

beta-adrenergic receptor agonists (including beta receptor subtypes 1 to 4), for example isoprenaline, salbutamol, formoterol, salmeterol, terbutaline, m-hydroxy-isoproterenol, bitolterol mesylate and/or pirbuterol, for example their chiral enantiomers;

chromones, for example cromoglycate sodium and/or nedocromil sodium;

glucocorticoids, for example flunisolide, hydroxyprednisolone acetonide, beclomethasone dipropionate, budesonide, fluticasone propionate, ciclesonide and/or mometasone furoate;

agents that modulate nuclear hormone receptors, for example PPAR;

immunoglobulin (Ig) or Ig products or antagonists or antibodies that modulate Ig function, for example anti-IgE (for example, omalizumab);

other systemic or topical anti-inflammatory agent(s), for example thalidomide or derivatives thereof, retinoid, anthratriol and/or calcipotriol;

combination of aminosalicylate and sulfapyridine, for example sulfasalazine, mesalazine, balsalazide and olsalazine; immunomodulators, for example thiopurines and corticosteroids, for example budesonide;

antibacterial agents, for example penicillin derivatives, tetracyclines, macrolides, beta-lactams, fluoroquinolones, metronidazole and/or inhaled aminoglycosides; and/or antiviral agents, for example acyclovir, famciclovir, valcyclovir, ganciclovir, cidofovir; amantadine, rimantadine; ribavirin; zanamivir and/or oseltamivir; protease inhibitors, for example indinavir, nelfinavir, ritonavir, and/or saquinavir; nucleoside reverse transcriptase inhibitors, for example didanosine, lamivudine, stavudine, zalcitabine, zidovudine; non-nucleoside reverse transcriptase inhibitors, for example nevirapine and efavirenz;

cardiovascular agent(s), for example calcium channel blockers, beta-adrenergic receptor blockers, angiotensin converting enzyme (ACE) inhibitors, angiotensin-2 receptor antagonists;

lipid-lowering agents, for example statins and/or fibrates; regulators of blood cell morphology, for example pentoxifylline; thrombus-dissolving and/or anticoagulants, for example blood cell aggregation inhibitors;

CNS agent(s), for example antidepressants (for example sertraline), anti-Parkinson's agent(s) (for example selegiline, levodopa, ropinirole, pramipexole, MAOB inhibitors, for example selegine and rasagiline, comP inhibitors, for example tolcapone, A-2 inhibitors, dopamine reuptake inhibitors, NMDA antagonists, nicotinic agonists, dopamine agonists and/or neuronal nitric oxide synthase inhibitors) and anti-Alzheimer's disease agent(s), for example donepezil, rivastigmine, tacrine, COX-2 inhibitors, propentofylline or metrifonate;

agents for the treatment of acute and chronic pain, for example central or peripheral analgesics, for example opioid analogs or derivatives, carbamazepine, phenytoin, sodium valproate, amitryptiline or other antidepressants, acetaminophen or non-steroidal anti-inflammatory agent(s);

parenteral or topically-applied (including inhaled) local anesthetics, for example lignocaine or analogues thereof;

anti-osteoporosis agents, for example hormonal agent(s), such as raloxifene or bisphosphonates, such as alendronate;

(i) trypsin inhibitor; (ii) platelet activating factor (PAF) antagonist; (iii) interleukin converting enzyme (ICE) inhibitor; (iv) IMPDH inhibitor; (v) adhesion molecule inhibitor, including VLA-4 antagonists; (vi) cathepsin; (vii) kinase inhibitors, for example tyrosine kinase inhibitors (for example, examples of Btk, Itk and Jak3MAP inhibitors may include gefitinib and imatinib mesylate), serine/threonine kinases (for example, MAP kinases such as inhibitors of p38, JNK, protein kinase A, B and C and IKK), or kinases involved in cell cycle regulation (for example, cyclin-dependent kinases);

(viii) glucose-6 phosphate dehydrogenase inhibitors; (ix) bradykinin-B1- and/or B2-receptor antagonists; (x) anti-gout agents, for example colchicine; (xi) xanthine oxidase inhibitors, for example allopurinol; (xii) uricosuric agents, for example probenecid, sulfinpyrazone and/or benzbromarone; (xiii) growth hormone secretagogues; (xiv) transforming growth factor (TGFbeta); (xv) platelet-derived growth factor (PDGF); (xvi) fibroblast growth factor, for example basic fibroblast growth factor (bFGF); (xvii) granulocyte macrophage colony stimulating factor (GM-CSF); (xviii) capsaicin cream; (xix) tachykinin NK1 and/or NK3 receptor antagonists, for example NKP-608C, SB-233412 (talnetant) and/or D-4418; (xx) elastase inhibitors, for example UT-77 and/or ZD-0892; (xxi) TNF-alpha converting enzyme (TACE) inhibitor; (xxii) inducible nitric oxide synthase (iNOS) inhibitor or (xxiii) homologous molecules of chemoattractant receptor expressed on TH2 cells, (for example, CRTH2 antagonists); (xxiv) P38 inhibitors; (xxv) agents that modulate the function of Toll-like receptors (TLR) and (xxvi) agents that regulate the activity of purinergic receptors, for example P2X7; (xxvii) inhibitors of transcription factor activation, for example NFkB, API and/or STATS.

In order to treat inflammatory diseases, the small RNAs of the present invention can be used in combination with one or more of the following agent(s):

for example, non-steroidal anti-inflammatory agent(s) (hereinafter referred to as NSAIDs), including non-selective cyclooxygenase COX-1/COX-2 inhibitors, regardless of topical or systemic application (for example piroxicam, diclofenac, propionic acids, such as naproxen, flurbiprofen, fenoprofen, ketoprofen and ibuprofen, fenamates, such as mefenamic acid, indomethacin, sulindac, azapropazone, pyrazolones, for example phenylbutazone, salicylates, for example aspirin); selective COX-2 inhibitors (for example, meloxicam, celecoxib, rofecoxib, valdecoxib, lumarocoxib, parecoxib and etoricoxib); cyclooxygenase inhibiting nitric oxide donators (CINODs); glucocorticoids (whether through local, oral, intramuscular, intravenous or intraarticular routes); methotrexate, leflunomide; hydroxychloroquine, d-penicillamine, auranofin or other parenteral or oral gold products; analgesics; diacerein; intraarticular treatments, for example hyaluronic acid derivatives; and nutritional additives, for example glucosamine. The small RNAs of the present invention can also be used in combination with existing therapeutic agents for the treatment of cancer. Suitable agents that can be used in combination include: (i) anti-proliferative/anti-tumor agent(s) and combinations thereof used in medical oncology, for example gleevec (imatinib mesylate), alkylating agents (for example, cisplatin, carboplatin, cyclophosphamide, chlormethine, melphalan, chlorambucil, busulfan and nitrosourea); antimetabolites (for example, antifolates, such as fluoropyrimidines, such as 5-fluorouracil and tegafur, raltitrexed, methotrexate, cytarabine, hydroxyurea, gemcitabine and paclitaxel; antitumor antibiotics (for example, anthracycline antibiotics, such as adriamycin, bleomycin, doxorubicin, daunorubicin, epirubicin, idarubicin, mitomycin-C, dactinomycin and mithramycin); anti-(mitosis) division agents (for example, vinblastines, such as vincristine, vinblastine, vindesine and vinorelbine and taxanes, such as paclitaxel and taxotere); and topoisomerase inhibitors (for example, etoposides, such as etoposide and teniposide, amsacrine, topotecan and camptothecin); (ii) cytostatic agent(s), for example anti-estrogens (for example, tamoxifen, toremifene, raloxifene, droloxifene and iodoxyfene), estrogen receptor down-regulators (for example, fulvestrant), anti-androgens (for example, bicalutamide, flutamide, nilutamide and cyproterone acetate), LHRH antagonists or LHRH agonists (for example, goserelin, leuprorelin and buserelin), progestins (for example, megestrol acetate), aromatase inhibitors (for example, anastrozole, letrozole, vorazole and exemestane) and 5α-reductase inhibitors, for example finasteride;

(iii) agents that inhibit the invasion of cancer cells (for example, metalloproteinase inhibitors, such as marimastat and inhibitors of urokinase plasminogen activator receptor function);

(iv) inhibitors of growth factor function, for example, such inhibitors include growth factor antibodies, growth factor receptor antibodies (for example, anti-erbb2 antibody, trastuzumab and anti-erbb1 antibody cetuximab [C225]), farnesyl transferase inhibitors, tyrosine kinase inhibitors and serine/threonine kinase inhibitors, for example, epidermal growth factor family inhibitors (for example, EGFR family tyrosine kinase inhibitors, such as N-(3-chloro-4-fluorophenyl)-7-methoxy-6-(3-morpholinylpropoxy)quinazolin-4-amine (gefitinib, AZD1839), N-(3-ethynylphenyl)-6,7-bis(2-methoxyethoxy)quinazolin-4-amine (erlotinib, OSI-774) and 6-propenylamido-N-(3-chloro-4-fluorophenyl)-7-(3-morpholinopropoxy)quinazolin-4-amine (CI1033)), for example, the platelet-derived growth factor family inhibitors and for example, the hepatocyte growth factor family inhibitors;

(v) anti-angiogenic agents, for example those agents that inhibit the effect of vascular endothelial growth factor, (for example, anti-vascular endothelial growth factor antibody bevacizumab, the compounds disclosed in international patent applications WO97/22596, WO97/30035, WO97/32856 and WO98/13354, each patent is incorporated herein in its entirety) and compounds that act by other mechanisms (for example, linomide, inhibitors of integrin αvbeta3 function and angiostatin);

(vi) vascular disruptors, for example combretastatin A4 and the compounds disclosed in international patent applications WO99/02166, WO00/40529, WO00/41669, WO01/92224, WO02/04434 and WO02/08213 (each patent is incorporated herein in its entirety by reference);

(vii) antisense therapy, for example, those targeting the above targets, such as ISIS2503 and anti-ras antisense;

(viii) gene therapy methods, including for example, replacement of abnormal genes, such as abnormal p53 or abnormal BRCA1 or BRCA2, GDEPT (gene-directed enzyme prodrug therapy) methods, for example those methods using cytosine deaminase, thymidine kinase or bacterial nitroreductase, and methods to increase the tolerance of patients to chemotherapy or radiotherapy, for example multi-drug resistance gene therapy; and (ix) immunotherapy methods, including for example, ex vivo and in vivo methods to increase the immunogenicity of patient tumor cells, such as transfection with cytokines (such as interleukin 2, interleukin 4 or granulocyte macrophage colony stimulating factor) to reduce T cell non-responsiveness, methods using transfected immune cells, for example cytokine-transfected dendritic cells, methods using cytokine-transfected tumor cell lines, and methods using anti-idiotypic antibodies.

IL-1Beta Related Diseases

IL-1beta plays a key role in the pathology related to a variety of diseases involving immune and inflammatory elements. The small RNA of the present invention can treat IL-1beta related diseases. These diseases include but are not limited to: acquired immunodeficiency syndrome; acquired immunodeficiency-related diseases; acquired pernicious anemia; acute coronary syndrome; acute and chronic pain (different forms of pain); acute idiopathic polyneuropathy inflammation; acute immune diseases related to organ transplantation; acute or chronic immune diseases related to organ transplantation; acute inflammatory demyelinating polyneurotic neuropathy; acute ischemia; acute liver disease; acute rheumatic fever; acute transverse myelitis; Addison's disease; adult (acute) respiratory distress syndrome; adult Still's disease; alcohol-induced cirrhosis; alcohol-induced liver injury; allergic disease; allergy; alopecia; alopecia areata; Alzheimer's disease; allergic reaction; ankylosing spondylitis; ankylosing spondylitis-related lung disease; antiphospholipid antibody syndrome; aplastic anemia; arteriosclerosis; arthropathy; asthma; atherosclerotic disease/arteriosclerosis; atherosclerosis; atopic allergy; atopic eczema; atopic dermatitis; atrophy autoimmune hypothyroidism; autoimmune bullous disease; autoimmune dermatitis; autoimmune diabetes; autoimmune disorders related to streptococcal infection; autoimmune enteropathy; autoimmune hemolytic anemia; autoimmune hepatitis; autoimmune hearing loss; autoimmune lymphoproliferative syndrome (ALPS); autoimmune-mediated hypoglycemia; autoimmune myocarditis; autoimmune neutropenia; autoimmune premature ovarian failure; autoimmune thrombocytopenia (AITP); autoimmune thyroid disease; autoimmune uveitis; bronchiolitis obliterans; Behcet's disease; blepharitis; bronchiectasis; bullous pemphigoid; cachexia; cardiovascular disease; catastrophic antiphospholipid syndrome; celiac disease; cervical joint stiffness; chlamydia; choleosatatis; chronic active hepatitis; chronic eosinophilic pneumonia; chronic fatigue syndrome; chronic immune diseases related to organ transplantation; chronic ischemia; chronic liver disease; chronic mucocutaneous candidiasis; cicatricial pemphigoid; clinical isolation syndrome with risk of multiple sclerosis (CIS); common immunodeficiencies (common variable hypogammaglobulinemia); connective tissue disease-related interstitial lung disease; conjunctivitis; Coombs positive hemolytic anemia; childhood-onset psychosis; chronic obstructive pulmonary disease (COPD); Crohn's disease; cryptogenic autoimmune hepatitis; cryptogenic fibrotic alveolitis; dacryocystitis; depression; dermatitis scleroderma; dermatomyositis; dermatomyositis/polymyositis-related lung disease; diabetic retinopathy; diabetes; dilated cardiomyopathy; discoid lupus erythematosus; disc herniation; disc prolapse; disseminated intravascular coagulation; drug-induced hepatitis; drug-induced interstitial lung disease; drug-induced immune hemolytic anemia; endocarditis; endometriosis; endophthalmitis; enteropathic synovitis; episcleitis; erythema multiforme; severe erythema multiforme; female infertility; fibrosis; fibrotic lung disease; gestational pemphigoid; giant cell arteritis (GCA); glomerulonephritis; goiter autoimmune hypothyroidism (Hashimoto's disease); Goodpasture's syndrome; gouty arthritis; graft-versus-host disease (GVHD); Grave's disease; group B streptococcus (BGS) infection; Guillain-Barre syndrome (GBS); hemosiderinosis-related lung disease; hay fever; heart failure; hemolytic anemia; Henoch-Schonlein purpura; hepatitis B; hepatitis C; Hughes syndrome; Huntington's disease; hyperthyroidism; hypoparathyroidism; idiopathic leukopenia; idiopathic thrombocytopenia; idiopathic Parkinson's disease; idiopathic interstitial pneumonia; idiocratic liver disease; IgE mediated allergies; immune hemolytic anemia; inclusion body myositis; infectious diseases; infectious ophthalmic diseases; inflammatory bowel disease; inflammatory demyelinating disease; inflammatory heart disease; inflammatory nephropathy; insulin dependent diabetes; interstitial pneumonia; IPF/UIP; iritis; juvenile chronic arthritis; juvenile pernicious anemia; juvenile rheumatoid arthritis (JRA); Kawasaki's disease; keratitis; keratoconjunctivitis sicca; Kussmaul disease or Kussmaul-Meier disease; Landry's paralysis; Langerhans cell histiocytosis; linear IgA disease; livedo reticularis; Lyme arthritis; lymphocytic infiltrating lung disease; macular degeneration; male idiopathic infertility or NOS; malignant tumor; microvasculitis of the kidney; microscopic polyangiitis; mixed connective tissue disease-related lung disease; Morbus Bechterev; motor neuron disease; mucosal pemphigoid; multiple sclerosis (all subtypes: primary progressive, secondary progressive, relapsing remitting, etc.); multiple organ failure; myalgia encephalitis/Royal Free disease; myasthenia gravis; myelodysplastic syndrome; myocardial infarction; myocarditis; nephrotic syndrome; nerve root disorder; neuropathy; non-alcoholic steatohepatitis; non-A, non-B hepatitis; optic neuritis; organ transplant rejection; osteoarthritis; osteolysis; ovarian cancer; ovarian failure; pancreatitis; parasitic disease; Parkinson's disease; pauciarticular JRA; pemphigoid; pemphigus foliaceus; pemphigus vulgaris; peripheral arterial occlusive disease (PAOD); peripheral vascular disease (PVD); peripheral artery disease (PAD); phacolytic uveitis; phlebitis; polyarteritis nodosa (or nodular epiarteritis); polychondritis; polymyalgia rheumatica; poliosis; polyarticular JRA; polyendocrine deficiency syndrome; polymyositis; polyglandular type I and polyglandular type II deficiency; polymyalgia rheumatica (PMR); post-infection interstitial lung disease; post-inflammatory interstitial lung disease; postpump syndrome; premature ovarian failure; primary biliary cirrhosis; primary mucinous edema; primary Parkinson's syndrome; primary sclerosing cholangitis; primary sclerosing hepatitis; primary vasculitis; prostate and rectal cancer and hematopoietic malignancies (leukemia and lymphoma); prostatitis; psoriasis; psoriasis type 1; psoriasis type 2; psoriatic arthritis; psoriatic arthropathy; pulmonary hypertension secondary to connective tissue disease; pulmonary manifestations of polyarteritis nodosa; pure red cell aplasia; primary adrenal insufficiency; radiation fibrosis; reactive arthritis; Reiter's disease; recurrent neuromyelitis optica; renal disease NOS; restenosis; rheumatoid arthritis; rheumatoid arthritis-related interstitial lung disease; rheumatic heart disease; SAPHO (synovitis, acne, pustulosis, hyperostosis and osteitis); sarcoidosis; schizophrenia; Schmidt's syndrome; scleroderma; secondary amyloidosis; shock lung; scleritis; sciatica; secondary adrenal insufficiency; sepsis syndrome; septic arthritis; septic shock; seronegative arthropathy; silicone-related connective tissue disease; Sjogren's disease-related lung disease Sjogren's syndrome; Sneddon-Wilkinson skin disease; sperm autoimmunity; spondyloarthropathy; spondylitis ankylopoietica; Stevens-Johnson syndrome (SJS); Still's disease; stroke; sympathetic ophthalmia; Systemic inflammatory response syndrome; systemic lupus erythematosus; systemic lupus erythematosus-related lung disease; systemic scleroderma; systemic scleroderma-related interstitial lung disease; Takayasu's disease/arteritis; temporal arteritis; Th2 type and Th1 type mediated diseases; thyroiditis; Toxic shock syndrome; toxoplasma retinitis; toxic epidermal necrolysis; transverse myelitis; TRAPS (tumor necrosis factor receptor type I (TNFR) associated periodic syndrome); type B insulin resistance with acanthosis nigricans; type 1 allergy; type 1 autoimmune hepatitis (traditional autoimmune or lupus-like hepatitis); type 2 autoimmune hepatitis (anti-LKM antibody hepatitis); type II diabetes; ulcerative colitis arthropathy; ulcer colitis; urticaria; usual interstitial pneumonia (UIP); uveitis; vasculitis disseminated lung disease; vasculitis; vernal conjunctivitis; viral retinitis; vitiligo; Vogt-Koyanagi-Harada syndrome (VKH syndrome); Wegener's granulomatosis; wet macular degeneration; wound healing; *Yersinia* and *Salmonella* associated arthropathy.

The present invention encompasses a combination comprising the small RNAs described herein and at least one additional agent listed below. The combination may also include more than one additional agent, for example, 2 or 3 additional agents.

Exemplary combinations include the small RNAs described herein and non-steroidal anti-inflammatory drugs (NSAIDS), for example ibuprofen. Other exemplary combinations include the small RNAs described herein and corticosteroids, including prednisolone. Non-limiting examples of therapeutic agents with which the small RNAs of the present invention can be combined for rheumatoid arthritis include the following: cytokine suppressive anti-inflammatory drugs (CSAIDs); antibodies or antagonists against other human cytokines or growth factors, for example, TNF, LT, IL-1α, IL-2, IL-3, IL-4, IL-5, IL-6, IL-7, IL-8, IL-15, IL-16, IL-18, IL-21, interferon, EMAP-II, GM-CSF, FGF and PDGF. The small RNAs of the present invention can be combined with antibodies against cell surface molecules or ligands thereof including CD154 (gp39 or CD40L), said cell surface molecules are for example CD2, CD3, CD4, CD8, CD25, CD28, CD30, CD40, CD45, CD69, CD80 (B7.1), CD86 (B7.2), CD90 and CTLA.

Exemplary therapeutic agents used in combination with the small RNAs of the present invention can interfere at different points in the autoimmune and subsequent inflammatory cascades, for example TNF antagonists, such as chimeric, humanized or human TNF antibodies, D2E7 (PCT publication number WO 97/29131), CA2 (REMICADEa), CDP 571, and soluble p55 or p75 TNF receptors, derivatives thereof (p75TNFR1gG (ENBRELa) or p55TNFR1gG (Lenercept), and TNF-alpha converting enzyme (TACE) inhibitors, and other IL-1 inhibitors (interleukin-1 converting enzyme inhibitors, IL-1RA, etc.). Other reagents used in combination with small RNAs include interleukin 11, reagents that act in parallel with IL-1a function, depend on IL-1a function, or is consistent with IL-1a function, for example IL-18 antagonists (for example IL-18 binding proteins for example antibodies or soluble IL-18 receptors, or antigen-binding fragments thereof). Additional reagents used in combination with small RNAs include non-exhaustive anti-CD4 inhibitors, costimulatory pathway CD80 (B7.1) or CD86 (B7.2) antagonists, including antibodies, soluble receptors, antagonistic ligands or antigen-binding fragments thereof.

The small RNAs can also be combined with agents for the treatment of rheumatoid arthritis, for example methotrexate, 6-MP, azathioprine sulfasalazine, mesalazine, olsalazine chloroquinine/hydroxychloroquine, penicillamine, gold sodium thiomalate (intramuscular and oral), azathioprine, colchicine, corticosteroids (oral, inhalation and local injection), beta2 adrenergic receptor agonists (salbutamol, terbutaline and salmeterol), xanthine (theophylline and aminophylline), cromoglycates, nadocromil, ketotifen, ipratropium and oxitropium, cyclosporine, FK506, rapamycin, mycophenolate mofetil, leflunomide, NSAIDs for example ibuprofen, corticosteroids for example prednisolone, phosphodiesterase inhibitors, adenosine agonists, anticoagulants, complement inhibitors, adrenergics, reagents that interfere with the sinaling through pro-inflammatory cytokines for example TNF-alpha or IL-1 (for example IRAK, NIK, IKK, p38 and MAP kinase inhibitors), IL-1beta converting enzyme inhibitors, TNF-alpha converting enzyme (TACE) inhibitors, T cell signaling inhibitors for example kinase inhibitors, metalloproteinase inhibitors, sulfasalazine, azathioprine, 6-mercaptopurine, angiotensin converting enzyme inhibitors, soluble cytokine receptors and derivatives thereof (for example, soluble p55 or p75 TNF receptors and derivatives p75TNFRIgG (ENBREL™ and p55TNFRIgG (Lenercept)), sIL-1RI, sIL-1RII, sIL-6R), anti-inflammatory cytokines (for example, IL-4, IL-10, IL-11, IL-13 and TGFbeta), celecoxib, folic acid, hydroxychloroquine sulfate, profencoxib, etanercept, infliximab, naproxen, valdecoxib, sulfasalazine, methylprednisolone, meloxicam, methylprednisolone acetate, gold sodium thiomalate, aspirin, triamcinolone, dextropropoxyphene naphthalenesulfonate/paracetamol, folates, naproxen, voltarin, piroxicam, etodolac, diclofenac sodium, oxaprozin, oxycodone hydrochloride, dihydrocodeinone bitartrate/paracetamol, diclofenac sodium/misoprostol, fentanyl, anakinra, human recombinant, tramadol hydrochloride, salsalate, sulindac, cyanocobalamin/fa/pyridoxine, paracetamol, sodium alendronate, prednisolone, morphine sulfate, lidocaine hydrochloride, indomethacin, glucosamine sulfate (glucosamine sulf)/chondroitin, amitriptyline hydrochloride, sulfadiazine, oxycodone hydrochloride/paracetamol, olopatidine hydrochloride, misoprostol, sodium methoxy naphthyl propionate, omeprazole, cyclophosphamide, rituximab, IL-1 TRAP, MRA, CTLA4-IG, IL-18 BP, anti-IL-18, anti-IL15, BIRB-796, SCIO-469, VX-702, AMG-548, VX-740, roflumilast, IC-485, CDC-801 and mesopram.

Non-limiting examples of therapeutic agents with which the small RNAs of the present invention can be combined for inflammatory bowel disease include the following: budesonide; epidermal growth factors, corticosteroids, cyclosporine, sulfasalazine, aminosalicylates, 6-mercaptopurine, azathioprine, metronidazole, lipoxygenase inhibitors, mesalazine, olsalazine, balsalazide, antioxidants, thromboxane inhibitors, IL-1 receptor antagonists, anti-IL-1beta monoclonal antibodies, anti-IL-6 monoclonal antibodies, growth factors, elastase inhibitors, pyridyl-imidazole compounds, antibodies or antagonists against other human cytokines or growth factors for example TNF, LT, IL-1beta, IL-2, IL-6, IL-7, IL-8, IL-15, IL-16, IL-17, IL-18, EMAP-II, GM-CSF, FGF and PDGF. The small RNAs of the present invention can be combined with antibodies against cell surface molecules and ligands thereof, said cell surface molecules are for example CD2, CD3, CD4, CD8, CD25, CD28, CD30, CD40, CD45, CD69 and CD90. Small RNAs can also be combined with reagents for example methotrexate, cyclosporine, FK506, rapamycin, mycophenolate mofetil, leflunomide, NSAIDs for example ibuprofen, corticosteroids for example prednisolone, phosphodiesterase inhibitors, adenosine agonists, anticoagulants, complement inhibitors, adrenergic agent(s), reagents that interfere with the signaling via pro-inflammatory cytokines for example TNF-alpha or IL-1 (for example IRAK, NIK, IKK, p38 or MAP kinase inhibitors), IL-1beta converting enzyme inhibitors, TNF-alpha converting enzyme inhibitors, T cell signaling inhibitors for example kinase inhibitors, metalloproteinase inhibitors, sulfasalazine, azathioprine, 6-mercaptopurine, angiotensin-converting enzyme inhibitors, soluble cytokine receptors and derivatives thereof (for example soluble p55 or p75 TNF receptors, sIL-1RI, sIL-1RII, sIL-6R) and anti-inflammatory cytokines (for example, IL-4, IL-10, IL-11, IL-13 and TGFbeta).

Exemplary examples of therapeutic agents with which small RNAs as described herein can be combined for Crohn's disease include the following: TNF antagonists, for example anti-TNF antibodies, D2E7 (PCT publication number WO97/29131; HUMIRA®), CA2 (REMICADE®), CDP 571, TNFR-Ig constructs, (p75TNFRIgG (ENBREL®) and p55TNFRIgG (Lenercept)) inhibitors and PDE4 inhibitors. Small RNAs can be combined with corticosteroids, for example budesonide and dexamethasone. Small RNAs can also be combined with reagents for example sulfasalazine, 5-aminosalicylic acid and olsalazine, and reagents that interfere with the synthesis or action of pro-inflammatory cytokines (for example IL-1) (for example IL-1beta converting enzyme inhibitors and IL-1RA). Small RNAs can also be used together with T cell signaling inhibitors, for example, tyrosine kinase inhibitor 6-mercaptopurine. Small RNAs can be combined with IL-11. Small RNAs can be combined with the following reagents: mesalazine, prednisone, azathioprine, mercaptopurine, infliximab, methylprednisolone sodium succinate, diphenoxylate/atropine sulfate, loperamide hydrochloride, methotrexate, omeprazole, folates, ciprofloxacin/glucose-injection, dihydrocodeinone bitartrate/paracetamol, tetracycline hydrochloride, fluocinolone, metronidazole, thimerosal/boric acid, cholestyramine/sucrose, ciprofloxacin hydrochloride, hyoscyamine sulfate, pethidine hydrochloride, midazolam hydrochloride, oxycodone hydrochloride/paracetamol, promethazine hydrochloride, sodium phosphate, sulfamethoxazole/trimethoprim, celecoxib, polycarbophil, propoxyphene napsylate, hydrocortisone, multivitamins, balsalazide disodium, codeine phosphate/paracetamol, colesevelam hydrochloride (colesevelam hcl), cyanocobalamin, folic acid, levofloxacin, methylprednisolone, natalizumab and interferon γ.

Non-limiting examples of therapeutic agents with which the small RNAs of the present invention can be combined for multiple sclerosis include the following: corticosteroids, prednisolone, methylprednisolone, azathioprine, cyclophosphamide, cyclosporin, methotrexate, 4-aminopyridine, tizanidine, interferon-beta1a (AVONEX®, Biogen), interferon-beta1b (BETASERON®, Chiron/Berlex), interferon α-n3 (Interferon Sciences/Fujimoto), interferon-α (Alfa Wassermann/J&J), interferon beta1A-IF (Serono/Inhale Therapeutics), pegylated interferon (peginterferon) α2b (Enzon/Schering-Plough), copolymer 1 (Cop-1, COPAXONE®; Teva Pharmaceutical Industries, Inc.), hyperbaric oxygen, intravenous immunoglobulin, cladribine, antibodies, antagonists or inhibitors against other human cytokines or growth factors and receptors thereof, for example, TNF, LT, IL-1beta, IL-2, IL-6, IL-7, IL-8, IL-1A, IL-15, IL-16, IL-18, EMAP-II, GM-CSF, FGF and PDGF. The small RNAs of the present invention can be combined with antibodies against cell surface molecules or ligands thereof, said cell surface molecules are for example CD2, CD3, CD4, CD8, CD19, CD20, CD25, CD28, CD30, CD40, CD45, CD69, CD80, CD86 and CD90. Small RNAs of the present invention can also be combined with reagents for example FK506, rapamycin, mycophenolate mofetil, leflunomide, NSAIDs for example ibuprofen, phosphodiesterase inhibitors, adenosine agonists, anticoagulants, complement inhibitors, adrenergic agent(s), reagents that interfere with the signaling via pro-inflammatory cytokines for example TNF-alpha or IL-1 (for example IRAK, NIK, IKK, p38 or MAP kinase inhibitors), IL-1b converting enzyme inhibitors, TACE inhibitors, T cell signaling inhibitors for example kinase inhibitors, metalloproteinase inhibitors, sulfasalazine, azathioprine, 6-mercaptopurine, angiotensin-converting enzyme inhibitors, soluble cytokine receptors and derivatives thereof (for example soluble p55 or p75 TNF receptors, sIL-1RI, sIL-1RII, sIL-6R), anti-inflammatory cytokines (for example IL-4, IL-10, IL-13 and TGFbeta), COPAXONE®, and caspase inhibitors for example caspase-1 inhibitors.

The small RNAs of the present invention can also be combined with reagents for example alemtuzumab, dronabinol, Unimed, daclizumab, mitoxantrone, xaliproden hydrochloride, 4-aminopyridine, glatiramer acetate, natalizumab, sinnabidol, α-immunokine NNSO3, ABR-215062, AnergiX.MS, chemokine receptor antagonists, BBR-2778, calagualine, CPI-1189, LEM (liposome encapsulated mitoxantrone), THC.CBD (cannabinoid agonist), MBP-8298, mesopram (PDE4 inhibitor), MNA-715, anti-IL-6 receptor antibodies, neurovax, pirfenidone alltrap 1258 (RDP-1258), sTNF-R1, talampanel, teriflunomide, TGF-beta2, tiplimotide, VLA-4 antagonist (for example, TR-14035, VLA4 ultrahaler, antegran-ELAN/Biogen), interferon 7 antagonists and IL-4 agonists.

Non-limiting examples of therapeutic agents with which the small RNAs of the present invention can be combined for the treatment or prevention of angina include the following: aspirin, nitroglycerin, isosorbide mononitrate, metoprolol succinate, atenolol, metoprolol tartrate, amlodipine besylate, diltiazem hydrochloride, isosorbide dinitrate, clopidogrel disulfate, nifedipine, atorvastatin calcium, potassium chloride, furosemide, simvastatin, verapamil hydrochloride, digoxin, propranolol hydrochloride, carvedilol, lisinopril, spironolactone, hydrochlorothiazide, enalapril maleate, nadolol, ramipril, enoxaparin sodium, heparin sodium, valsartan, sotalol hydrochloride, fenofibrate, ezetimibe, bumetanide, losartan potassium, lisinopril/hydrochlorothiazide, felodipine, captopril and bisoprolol fumarate.

Non-limiting examples of therapeutic agents with which the small RNAs can be combined for the treatment or prevention of ankylosing spondylitis include the following: ibuprofen, voltaren and misoprostol, naproxen, meloxicam, indometacin, voltaren, celecoxib, lofencoxib, sulfasalazine, methotrexate, azathioprine, minocycline, prednisone, etanercept and infliximab.

Non-limiting examples of therapeutic agents with which the small RNAs of the present invention can be combined for the treatment or prevention of asthma include the following: salbutamol, salmeterol/fluticasone, montelukast sodium, fluticasone propionate, budesonide, prednisone, salmeterol xinafoate, levalbuterol hydrochloride, salbutamol sulfate/ipratropium, prednisolone sodium phosphate, triamcinolone, beclomethasone dipropionate, ipratropium bromide, azithromycin, pirbuterol acetate, prednisolone, anhydrous theophylline, methylprednisolone sodium succinate, clarithromycin, zafirlukast, formoterol fumarate, influenza virus vaccine, methylprednisolone, amoxicillin trihydrate, flunisolide, allergy injection, cromolyn sodium, fexonadine hydrochloride, flunisolide/menthol, amoxicillin/clavulanate potassium, levofloxacin, inhaler auxiliary device, guaifenesin, dexamethasone sodium phosphate, moxifloxacin hydrochloride, doxycycline hydrochloride, guaifenesin/d-methylmorphan, p-ephedrine/cod/chlorphenir, gatifloxacin, cetirizine hydrochloride, mometasone furoate, salmeterol xinafoate, benzonatate, cefalexin, dihydrocodeinone/chlorpheniramine, cetirizine hydrochloride/pseudoephedrine, phenylephrine/promethazine, codeine/promethazine, cefprozil, dexamethasone, guaifenesin/pseudoephedrine, chlorpheniramine/dihydrocodeinone, nedocromil sodium, terbutaline sulfate, epinephrine, methylprednisolone and m-hydroxy-isoproterenol sulfate.

Non-limiting examples of therapeutic agents with which the small RNAs of the present invention can be combined for the treatment or prevention of COPD include the following: salbutamol sulfate/ipratropium, ipratropium bromide, salmeterol/fluticasone, salbutamol, salmeterol xinafoate, fluticasone propionate, prednisone, anhydrous theophylline, methylprednisolone sodium succinate, montelukast sodium, budesonide, formoterol fumarate, triamcinolone, levofloxacin, guaifenesin, azithromycin, beclomethasone dipropionate, levalbuterol hydrochloride, funisolide, ceftriaxone sodium, amoxicillin trihydrate, gatifloxacin, zafirlukast, amoxicillin/clavulanate potassium, flunisolide/menthol, chlorpheniramine/dihydrocodeinone, m-hydroxy-isoproterenol sulfate, methylprednisolone, mometasone furoate, p-ephedrine/cod/chlorpheniramine, pirbuterol acetate, p-ephedrine/loratadine, terbutaline sulfate, tiotropium bromide, (R,R)-formoterol, TgAAT, cilomilast and roflumilast.

Non-limiting examples of therapeutic agents with which the small RNAs of the present invention can be combined for the treatment or prevention of HCV include the following: interferon-α-2a, interferon-α-2b, interferon-α con1, interferon-α-n1, pegylated interferon-α-2a, pegylated interferon-α-2b, ribavirin, peginterferon α-2b+ribavirin, ursodeoxycholic acid, glycyrrhizic acid, thymalfasin, Maxamine, VX-497 and any compound used to treat HCV by interfering with the following targets: HCV polymerase, HCV protease, HCV helicase, HCV IRES (internal ribosome entry site).

Non-limiting examples of therapeutic agents with which small RNAs can be combined for the treatment or prevention of idiopathic pulmonary fibrosis include the following: prednisone, azathioprine, salbutamol, colchicine, salbutamol sulfate, digoxin, γ interferon, methylprednisolone sodium succinate (sod succ), lorazepam, furosemide, lisinopril, nitroglycerin, spironolactone, cyclophosphamide, ipratropium bromide, actinomycetes D, alteplase, fluticasone propionate, levofloxacin, m-hydroxy-isoproterenol sulfate, morphine sulfate, oxycodone hydrochloride, potassium chloride, triamcinolone, anhydrous tacrolimus, calcium, interferon-α, methotrexate, mycophenolate mofetil and interferon-γ-1b.

Non-limiting examples of therapeutic agents with which the small RNA of the present invention can be combined for the treatment or prevention of myocardial infarction include the following: aspirin, nitroglycerin, metoprolol tartrate, enoxaparin sodium, heparin sodium, clopidogrel bisulfate, carvedilol, atenolol, morphine sulfate, metoprolol succinate, warfarin sodium, lisinopril, isosorbide mononitrate, digoxin, furosemide, simvastatin, ramipril, tenecteplase, enalapril maleate, torsemide, reteplase, losartan potassium, quinapril hydrochloride/mag carb, bumetanide, alteplase, enalaprilat, amiodarone hydrochloride, tirofiban hydrochloride monohydrate, diltiazem hydrochloride, captopril, irbesartan, valsartan, propranolole hydrochloride, fosinopril sodium, lidocaine hydrochloride, eptifibatide, cefazolin sodium, atropine sulfate, aminocaproic acid, spironolactone, interferon, sotalol hydrochloride, potassium chloride, docusate sodium, dobutamine hydrochloride, alprazolam, pravastatin sodium, atorvastatin calcium, midazole hydrochloride, pethidine hydrochloride, isosorbide dinitrate, epinephrine, dopamine hydrochloride, bivalirudin, rosuvastatin, ezetimibe/simvastatin, avasimibe and cariporide.

Non-limiting examples of therapeutic agents with which the small RNAs of the present invention can be combined for the treatment or prevention of psoriasis include the following: calcipotriene, clobetasol propionate, triamcinolone, halobatasol proionate, tazorotene, methotrexate, fluocinolone, enhanced betamethasone dipropionate, fluocinolone acetate, Acitretin, tar shampoo, betamethasone valerate, mometasone furoate, ketoconazole, pramocaine/fluocinolone, hydrocortisone valerate, fluoxycortisone, urea, betamethasone, clobetasol propionate/emollient (emoll), fluticasone propionate, azithromycin, hydrocortisone, moisturizing formula, folic acid, desonide, pimecrolimus, coal tar, diflorasone diacetate, etanercept folate, lactic acid, 8-methoxypsoralen, hc/bismuth subgal/znox/resor, methylprednisolone acetate, prednisone, sunscreen, clofloxasone, salicylic acid, anthralin, clocotrolone, coal extract, coal tar/salicylic acid, coal tar/salicylic acid/sulfur, desoximetasone, diazepam, emollient, fluocinolone/emollient, mineral oil/castor oil/na lact, mineral oil/peanut oil, petroleum/isopropyl myristate, psoralen, salicylic acid, saponificated/tribromsalan, thimerosal/boric acid, celecoxib, infliximab, cyclosporine, alacepril, efalizumab, tacrolimus, pimecrolimus, PUVA, UVB and salicylazosulfapyridine.

Non-limiting examples of therapeutic agents with which the small RNAs of the present invention can be combined for the treatment or prevention of psoriatic arthritis include the following: methotrexate, etanercept, lofencoxib, celecoxib, folic acid, sulfasalazine, naproxen, leflunomide, methylprednisolone acetate, indomethacin, hydroxychloroquine sulfate, prednisone, sulindac, enhanced betamethasone dipropionate, infliximab, methotrexate, folates, triamcinolone, voltarin, dimethyl sulfoxide, piroxicam, diclofenac sodium, ketoprofen, meloxicam, methylprednisolone, naproxen, tolmentin sodium, calcipotriol, cyclosporine, diclofenac sodium/misoprostol, fluocinolone, glucosamine sulfate, gold sodium thiomalate, dihydrocodeinone bitartrate/paracetamol, ibuprofen, risedronate sodium, sulfadiazine, thioguanine, valdecoxib, alacepril and efalizumab.

Non-limiting examples of therapeutic agents with which the small RNAs of the present invention can be combined for the treatment or prevention of restenosis include the following: sirolimus, paclitaxel, everolimus, tacrolimus, ABT-578 and paracetamol.

Non-limiting examples of therapeutic agents with which the small RNAs of the present invention can be combined for the treatment or prevention of sciatica include the following: dihydrocodeinone bitartrate/paracetamol, profencoxib, cyclobenzaprine hydrochloride, methylprednisolone, naproxen, ibuprofen, oxycodone hydrochloride/paracetamol, celecoxib, valdecoxib, methylprednisolone acetate, prednisone, codeine phosphate/paracetamol, tramadol hydrochloride/paracetamol, metaxalone, meloxicam, metopamol, lidocaine hydrochloride, diclofenac sodium, gabapentin, dexamethasone, cariprado, ketorolac tromethamine, indomethacin, paracetamol, diazepam, naproxen, oxycodone hydrochloride, tizanidine hydrochloride, sodium diclofenac/misoprostol, dextropropoxyphene naphthalenesulfonate/paracetamol, asa/oxycod/oxycodone, ibuprofen/dihydrocodeinone bit, tramadol hydrochloride, etodolic acid, propoxyphene hydrochloride, amitriptyline hydrochloride, cariprado/codeine phosphate/asa, morphine sulfate, multivitamins, sodium methoxy naphthyl propionate, orphenadrine citrate and temazepam.

Non-limiting examples of therapeutic agents in which the small RNAs of the present invention can be combined for the treatment or prevention of systemic lupus erythematosus (SLE) include the following: NSAIDS, for example, voltaren, naproxen, ibuprofen, piroxicam and indometacin; COX2 inhibitors, for example, celecoxib, profencoxib and valdecoxib; antimalarial agent(s), for example, hydroxychloroquine; steroids, for example, prednisone, prednisolone, budesonide and dexamethasone; cytotoxins, for example, azathioprine, cyclophosphamide, mycophenolate mofetil and methotrexate; PDE4 inhibitors or purine synthesis inhibitors, for example CELLCEPT®. The small RNAs can also be combined with reagents for example sulfasalazine, 5-aminosalicylic acid, olsalazine, imulan, and reagents that interfere with the synthesis, production or action of pro-inflammatory cytokines (for example IL-1) (for example caspase inhibitors, such as IL-1beta converting enzyme inhibitors and IL-1ra). The small RNAs can also be used together with T cell signaling inhibitors, for example tyrosine kinase inhibitors, or molecules that target T cell activation molecules, for example CTLA-4-IgG or anti-B7 family antibodies and anti-PD-1 family antibodies. The small RNAs of the present invention can be combined with IL-11 or anti-cytokine antibodies, for example fonotolizumab (anti-IFNg antibody), or anti-receptor receptor antibodies, for example anti-IL-6 receptor antibodies and antibodies against B cell surface molecules. The small RNAs can also be used together with the following reagents: UP 394 (abetimus), reagents that deplete or inactivate B cells, for example rituximab (anti-CD20 antibody), lymphostat-B (anti-BlyS antibody), TNF antagonists, for example, anti-TNF antibodies, D2E7 (PCT publication number WO 97/29131, HUMIRA®), CA2 (REMICADE®), CDP 571, TNFR-Ig constructs (p75TNFRIgG (ENBREL®) and p55TNFRIgG (Lenercept)).

TNF-Alpha Related Diseases

TNF-alpha has proven pathophysiological effects in various human diseases, especially inflammatory disorders, immune and immune regulation disorders, infections that cause septic, endotoxic and cardiovascular shock, neurodegenerative diseases and malignant diseases. The small RNAs of the present invention can be applied to treat the diseases listed below, which is not considered to be a complete or exclusive list. Other diseases directly or indirectly affected by TNF-alpha that are not specifically mentioned are also included.

Autoimmune or chronic inflammation: general chronic inflammation and/or autoimmune state, general immune-mediated inflammatory disorders, inflammatory CNS diseases, inflammatory diseases affecting eyes, joints, skin, mucous membrane, central nervous system, gastrointestinal tract, urinary tract or lung, general uveitis state, retinitis, HLA-B27+ uveitis, Behcet's disease, dry eye syndrome, glaucoma, Sjgren syndrome, diabetes (including diabetic neuropathy), insulin resistance, general arthritis state, rheumatoid arthritis, osteoarthritis, reactive arthritis and Reiter's syndrome, juvenile arthritis, ankylosing spondylitis, multiple sclerosis, Guillain-Barre syndrome, myasthenia gravis, amyotrophic lateral sclerosis, sarcoidosis, glomerulonephritis, chronic kidney disease, cystitis, psoriasis (including psoriatic arthritis), hidradenitis suppurativa, panniculitis, pyoderma gangrenosum, SAPHO syndrome (synovitis, acne, pustulosis, hyperostosis and osteitis), acne, Sweet syndrome, pemphigus, Crohn's disease (including extraintestinal manifestations), ulcerative colitis, bronchial asthma, allergic pneumonia, general allergies, allergic rhinitis, allergic sinusitis, chronic obstructive pulmonary disease (COPD), pulmonary fibrosis, Wegener granulomatosis, Kawasaki syndrome, giant cell arteritis, Churg-Strauss vasculitis, polyarteritis nodosa, burns, graft-versus-host disease, host-versus-graft reaction, rejection after organ or bone marrow transplantation, general systemic or local vasculitis state, systemic and discoid lupus erythematosus, multiple myositis and dermatomyositis, scleroderma, preeclampsia, acute and chronic pancreatitis, viral hepatitis and alcoholic hepatitis. Acute inflammation and/or prevention of post-operative or post-traumatic inflammation and pain: prevention of general post-operative inflammation, eye surgery (for example cataract (eye lens replacement) or glaucoma surgery), joint surgery (including arthroscopic surgery), joint-related structures (for example ligament) surgery, oral and/or dental surgery, minimal interventional cardiovascular procedures (for example PTCA, atherectomy, stent placement), laparoscopic and/or endoscopic abdominal and gynecological procedures, endoscopic urology procedures (for example prostate surgery, ureteroscopy, cystoscopy and interstitial cystitis), general pre- and post-operative inflammation (prevention). Neuropathy and neurodegenerative diseases: Alzheimer disease, Parkinson's disease, Huntington's disease, Bell's palsy and Creutzfeld-Jakob disease. Cancer: cancer-related osteolysis, cancer-related inflammation, cancer-related pain, cancer-related cachexia and bone metastasis. Pain: acute and chronic forms of pain (regardless of being caused by the central or peripheral effects of TNF-alpha and regardless of being classified as inflammatory, noxious or neuropathic forms of pain), sciatica, low back pain, carpal tunnel syndrome, complex regional pain syndrome (CRPS), gout, post-herpetic neuralgia, fibromyalgia, local pain state, chronic pain syndrome due to metastatic tumor and dismenorrhea. Infection: bacterial, viral or fungal sepsis, tuberculosis, AIDS. Cardiovascular diseases: atherosclerosis, coronary artery disease, hypertension, dyslipidemia, cardiac insufficiency and chronic heart failure. In one embodiment, the TNF-alpha-related disease is spondyloarthropathy, lung-related disorders, coronary heart disease, metabolic disorders, anemia, pain, liver disorders, skin disorders, nail disorders, or vasculitis. In another embodiment, the TNF-alpha-related disease is age-related cachexia, Alzheimer's disease, cerebral edema, inflammatory brain injury, chronic fatigue syndrome, dermatomyositis, drug reaction, intraspinal and/or peripheral edema, family periodic fever, Felty's syndrome, fibrosis, glomerular nephropathy (for example glomerulonephritis after streptococcal infection or IgA nephropathy), prosthesis relaxation, microscopic polyangiitis, mixed connective tissue disorder, multiple myeloma, cancer and cachexia, multiple organ disorders, myelodysplastic syndrome, orchitism, osteolysis, pancreatitis including acute, chronic and pancreatic abscess, periodontal polymyositis, progressive renal failure, pseudogout, pyoderma gangraenosum, recurrent polychondritis, rheumatic heart disease, sarcoidosis, cholangitis sclerosus, stroke, thoracic-abdominal aortic aneurysm (TAAA) repair, TNF receptor-associated periodic syndrome (TRAPS), and yellow fever vaccination-related syndromes, inflammatory diseases associated with ears, chronic otitis or pediatric otitis. In another embodiment of the present invention, the TNF-alpha related disease is Crohn's disease-related disease, juvenile arthritis/Still's disease (JRA), uveitis, sciatica, prostatitis, endometrial ectopic, choroidal neovascularization, lupus, Sjogren's syndrome and wet macular degeneration.

Non-limiting examples of therapeutic agent(s) with which the small RNAs of the present invention can be used in combination include the following: non-steroidal anti-inflammatory drugs (NSAIDs); cytokine suppressive anti-inflammatory drugs (CSAIDs); CDP-571/BAY-10-3356 (humanized anti-small RNA; Celltech/Bayer); cA2/infliximab (chimeric anti-small RNA; Centocor); 75 kd TNFR-IgG/etanercept (75 kD TNF receptor-IgG fusion protein; Immunex (J Invest. Med. (1996) Vol. 44, 235A); 55 kd TNF-IgG (55 kD TNF receptor-IgG fusion protein; Hoffmann-LaRoche); IDEC-CE 9.1/SB 210396 (non-depleted primatized anti-CD4 antibody); IDEC/SmithKline; DAB 486-IL-2 and/or DAB 389-IL-2 (IL-2 fusion protein; Seragen); Anti-Tac (humanized anti-IL-2Ra; Protein Design Labs/Roche); IL-4 (anti-inflammatory cytokine; DNAX/Schering); IL-10 (SCH 52000; recombinant IL-10, anti-inflammatory cytokine; DNAX/Schering); IL-4; IL-10 and/or IL-4 agonists (for example, agonist antibodies); IL-1RA (IL-1 receptor antagonist; Synergen/Amgen); TNF-bp/s-TNF (soluble TNF binding protein); R973401 (phosphodiesterase type IV inhibitor); MK-966 (COX-2 inhibitor); iloprost; methotrexate; thalidomide and thalidomide-related agent(s) (for example, Celgen); leflunomide (anti-inflammatory and cytokine inhibitor); tranexamic acid (plasminogen activation inhibitor); T-614 (cytokine inhibitor); prostaglandin El; tenidap (non-steroidal anti-inflammatory drug); naproxen (non-steroidal anti-inflammatory drug); mobic (non-steroidal anti-inflammatory drug); ibuprofen (non-steroidal anti-inflammatory drug) Drug); piroxicam (non-steroidal anti-inflammatory drug); diclofenac sodium (non-steroidal anti-inflammatory drug); indomethacin (non-steroidal anti-inflammatory drug); salicylazosulfapyridine; azathioprine; ICE inhibitors (inhibitor of the enzyme interleukin-1beta converting enzyme); zap-70 and/or Ick inhibitors (casein kinase inhibitor zap-70 or lck); VEGF inhibitors and/or VEGF-R inhibitors (vascular endothelial cell growth factor or vascular endothelial cell growth factor receptor; inhibitors of angiogenesis); corticosteroid anti-inflammatory agent(s) (for example, SB203580); TNF-converting enzyme inhibitors; anti-IL-12 antibodies; anti-IL-18 antibodies; interleukin-11; interleukin-13; interleukin-17 inhibitors; gold; penicillin; chloroquine; hydroxychloroquine; chlorambucil; cyclophosphamide; cyclosporine; total lymphocyte irradiation method; antithymocyte globulin; anti-CD4 antibodies; CD5-toxin; orally administered peptides and collagen; disodium lobenzarit; cytokine regulatory agents (CRAs) HP 228 and HP 466 (Houghten Pharmaceuticals, Inc.); ICAM-1 anti-allergy phosphorothioate oligodeoxynucleotide (ISIS 2302; Isis Pharmaceuticals, Inc.); soluble complement receptor 1 (TP10; T Cell Sciences, Inc.); prednisone; occulin; glycosaminoglycan polysulfate; minocycline; anti-IL2R antibodies; fish and plant seed fatty acids; auranofin; phenylbutazone; meclofenamic acid; flufenamic acid; intravenous immunoglobulin; zileuton; mycophenolic acid (RS-61443); tacrolimus (FK-506); sirolimus (rapamycin); amprilose (therafectin); cladribine (2-chlorodeoxyadenosine); azuridine; methotrexate; antiviral agents; and immunomodulators. Any of the above-mentioned agent(s) can be combined with the small RNAs of the present invention to treat TNF-alpha related diseases.

In one embodiment, the small RNAs of the present invention are combined with one of the following agent(s) to treat rheumatoid arthritis: small molecule inhibitor KDR (ABT-123), small molecule inhibitor of Tie-2; methotrexate; prednisone; celecoxib; folic acid; hydroxychloroquine sulfate; rofecoxib; etanercept; infliximab; leflunomide; naproxen; valdecoxib; sulfapyridine; methylhydropredniso-lone; ibuprofen; meloxicam; methylprednisolone acetate; gold sodium thiomalate; aspirin; azathiopurine; triamci-nolone acetate; propoxyphene naphthalenesulfonate/parac-etamol; folates; nabumetone; diclofenac sodium; piroxicam; etodolac; diclofenac sodium; oxaprazine; oxycodone hydro-chloride; hydrocodone ditartrate/paracetamol; diclofenac sodium/misoprote; fentanyl; anakinra, human recombinant; tramadol hydrochloride; salsalate; sulindac; vitamin B12/fa/ vitamin B6; acetaminophen; arsendronate sodium; hydro-prednisone; morphine sulfate; lidocaine hydrochloride; indomethacin; glucosamine sulfate/chondroitin; cyclosporine; amitriptyline hydrochloride; sulfadiazine; oxycodone hydrochloride/acetaminophen; olopatidine hydrochloride; misoprote; sodium methoxy naphthyl propi-onate; omeprazole; mycophenolate mofetil; cyclophosph-amide; rituximab; IL-1 TRAP; MRA; CTLA4-IG; IL-8BP; ABT-874; ABT-324 (anti-IL18); anti-IL15; BIRB-796; SCIO-469; VX-702; AMG-548; VX-740; roflumilast; IC-485; CDC-801; and mesopram. In another embodiment, the small RNAs of the present invention and the above-mentioned drug for the treatment of rheumatoid arthritis are used in combination for the treatment of TNF-alpha related diseases.

In one embodiment, the small RNAs of the present invention is combined with one of the following agent(s) to treat TNF-alpha related diseases in which TNF-alpha activ-ity is harmful: anti-IL12 antibody (ABT874); anti-IL18 antibody (ABT 325); small molecule inhibitors of LCK; small molecule inhibitors of COT; anti-Ill antibodies; small molecule inhibitors of MK2; anti-CD19 antibodies; small molecule inhibitors of CXCR3; small molecule inhibitors of CCR5; small molecule inhibitors of CCR11; anti-E/L selec-tin antibodies; small molecule inhibitors of P2X7; small molecule inhibitors of IRAK-4; Ssmall molecule agonists of glucocorticoid receptor; anti-C5a receptor antibodies; small molecule inhibitors of C5a receptor; anti-CD32 antibodies; and CD32 as therapeutic proteins.

In another embodiment, the small RNAs of the present invention are administered in combination with antibiotics and anti-infectives. Anti-infectives include those known in the art to treat viral, fungal, parasitic or bacterial infections. The term "antibiotic" used herein refers to a chemical substance that inhibits the growth of microorganisms or kills microorganisms. The term includes antibiotics produced by microorganisms known in the art, as well as synthetic antibiotics (for example, analogs). Antibiotics include, but are not limited to, clarithromycin (Biaxin), ciprofloxacin (Cipro), and metronidazole (Flagyl).

In another embodiment, the small RNAs of the present invention are administered in combination with other thera-peutic agent(s) for treating sciatica or pain. Examples of agent(s) that can be used to relieve or suppress the symptoms of sciatica or pain include hydrocodone ditartrate/paraceta-mol, rofecoxib, cyclobenzaprine hydrochloride, methylpred-nisone, naproxen, ibuprofen, oxycodone hydrochloride/ac-etaminophen, celecoxib, valdecoxib, methylprednisone acetate, prednisone, cocaine phosphate/paracetamol, tramadol hydrochloride/acetaminophen, metaxalone, meloxicam, methocarbamol, lidocaine hydrochloride, diclofenac sodium, gabapentin, dexamethasone, carlipodor, ketorolac, indometacin, acetaminophen, diazepam, nabumetone, oxy-codone hydrochloride, tizanidine hydrochloride, diclofenac sodium/misoprostol, propoxyfennaphthalene sulfonate/par-acetamol, a small amount of ibuprofen/hydrocodone; trama-dol hydrochloride, etodolic acid; propoxyphene hydrochlo-ride, amitriptyline hydrochloride, carliprol/codeine phosphate, morphine sulfate, multivitamins, sodium methoxy naphthyl propionate, orphenadrine citrate and temazepam.

In another embodiment, the small RNAs of the present invention are used in combination with hemodialysis to treat TNF-alpha related diseases.

In another embodiment, the small RNAs of the present invention are used in combination with agent(s) used to treat Crohn's disease or Crohn's disease-related diseases. Thera-peutic agent(s) that can be used to treat Crohn's disease include mesalazine, prednisone, azathioprine, mercaptopu-rine, infliximab, budesonide, salicylazosulfapyridine, meth-ylprednisolone, diphenoxylate, loperamide hydrochloride, methotrexate, folates, ciprofloxacin/glucose-injection, hydrocodone ditartrate, tetracycline hydrochloride, fluoci-nolone acetate, metronidazole, thimerosal/boric acid, cholestyramine/sucrose, ciprofloxacin hydrochloride, hyoscyamine sulfate, dolantin hydrochloride, midazolam hydrochloride, oxycodone hydrochloride/acetaminophen, promethazine hydrochloride, sodium phosphate, sulfame-thoxazole/trimethoprim, celecoxib, polyacrylic resin, propoxyphene napsylate, hydrocortisone, multivitamins, balsalazide disodium, cocaine phosphate/paracetamol, cole-sevelan hydrochloride, vitamin B12, folic acid, levofloxacin, methylprednisolone, natalizumab and T-interferon.

In another embodiment, the small RNAs of the present invention are administered in combination with other thera-peutic agent(s) for treating asthma. Examples of agent(s) that can be used to reduce or suppress asthma symptoms include the following: salbutamol; salmeterol/fludesone; sodium; fludexone propionate; budesonide; prednisone; sal-meterol xinafoate; levalbuterol hydrochloride; sulfate/ipra-tropium; prednisone sodium phosphate; triamcinolone acetonide; beclomethasone dipropionate; ipratropium bro-mide; azithromycin; pirbuterol acetate, prednisone, anhy-drous theophylline, methylprednisolone, clarithromycin, zafirlukast, formoterol fumarate, influenza virus vaccine, methylprednisolone trihydrate, flunisolide, allergic allergy injection, cromolyn sodium, fexofenadinehydrochloride, flunisolide/menthol, amoxicillin/potassium clavulanate, levofloxacin, inhalation aid device, guaifenesin, dexametha-sone sodium phosphate; moxifloxacin hydrochloride; hyclate; guaifenesin/dextromethorphan; chlorpheniramine; gatifloxacin; cetirizine hydrochloride; mometasone furoate; salmeterol xinafoate; cough syrup; cephalexin; hydroco-done/chlorpheniramine; cetirizine hydrochloride/ pseudoephedrine; phenylephrine/promethazine; codeine/ promethazine; cefprozil; dexamethasone; guaifenesin/ pseudoephedrine; chlorpheniramine/hydrocodone, nedocromil sodium, terbutaline sulfate, epinephrine and methylprednisone and orciprenaline sulfate.

In another embodiment, the small RNAs of the present invention are administered in combination with other thera-peutic agent(s) used for treating COPD. Examples of agent (s) that can be used to reduce or suppress COPD symptoms include salbutamol sulfate/ipratropium; ipratropium bro-mide; salmeterol/fludexone; salbutamol; salmeterol xin-afoate; fludexone propionate; prednisone; anhydrous theophylline; methylprednisolone sod succ; montelukast sodium; budesonide; formoterol fumarate; triamcinolone acetonide; levofloxacin; guaifenesin; azithromycin; beclomethasone; dipropionic acid; levalbuterol hydrochloride; flunisolide; sodium; trihydrates; gatifloxacin; zafirlukast; amoxicillin/clavulanate potassium; flunisolide/menthol; chlorpheniramine/hycodone; orciprenaline sulfate; methylprednisolone; furoates; -ephedrine/cod/chlorpheniramine; pirbuterol hydrochloride; -ephedrine/loratadine; terbutaline sulfate; tiotropium bromide; (R, R)-formoterol; TgAAT; cilomilast and roflumilast.

In another embodiment, the small RNAs of the present invention are administered in combination with other therapeutic agent(s) used for treating IPF. Examples of agent(s) that can be used to reduce or suppress the symptoms of IPF include prednisone; azathioprine; salbutanolamine; colchicine; sulfates; digoxin; γ interferon; methylprednisolone sod succ; furosemide; lisinopril; nitroglycerin; spironolactone; cyclophosphamide; ipratropium bromide; actinomycin d; alteplase; fluticasone propionate; levofloxacin; oxinaline sulfate; morphine sulfate; oxycodone hydrochloride; potassium chloride; triamcinolone acetonide; anhydrous tacrolimus; calcium; α-interferon; methotrexate; mycophenolate mofetil.

In another embodiment, the small RNAs of the present invention are administered in combination with other therapeutic agent(s) used for treating spondyloarthropathy. Examples of such agent(s) include non-steroidal anti-inflammatory drugs (NSAIDs), COX 2 inhibitors, including Celebrex, Vioxx; and Bextra, and etoricoxib. Physical therapy is also commonly used to treat spondyloarthropathy, usually in combination with non-steroidal anti-inflammatory drugs.

In another embodiment, the small RNAs of the present invention are administered in combination with other therapeutic agent(s) used for treating ankylosing spondylitis. Examples of agent(s) that can be used to reduce or suppress the symptoms of ankylosing spondylitis include ibuprofen, diclofenac and misoprostol, naproxen, meloxicam, indomethacin, diclofenac, celecoxib, rofecoxib, salicylazosulfapyridine, prednisone, methotrexate, azathioprine, minocycline, prednisone, etanercept and infumab.

In another embodiment, the small RNAs of the present invention are administered in combination with other therapeutic agent(s) used for treating psoriasis arthritis in patients. Examples of agent(s) that can be used to reduce or suppress the symptoms of arthritis in patients with psoriasis include methotrexate; etanercept; rofecoxib; celecoxib; folic acid; salicylazosulfapyridine; naproxen; leflunomide; methylprednisolone acetate; indomethacin; hydroxychloroquine sulfate; sulindac; prednisone; betamethasone (diprospan); infliximab; methotrexate; folic acid; triamcinolone acetonide; diclofenac; dimethyl sulfoxide; piroxicam; diclofenac sodium; ketoprofen; meloxicam; prednisone; methylprednisolone; nabumetone; sodium tetrabenzoylpyrrole acetate; calcipotriene; cyclosporine; diclofenac; sodium/misoprostol; fluocinolone acetate; glucosamine sulfate; gold sodium thiomalate; hydrocodone; ditartrate/paracetamol; ibuprofen; risedronate sodium; sulfadiazine; thioguanine; valdecoxib; alefacept; and efalizumab.

The small RNAs of the present invention can be administered in combination with other therapeutic agent(s) used for treating restenosis. Examples of agent(s) that can be used to reduce or inhibit restenosis include rapamycin, paclitaxel, everolimus, tacrolimus, ABT-578 and acetaminophen.

The small RNAs of the present invention can be administered in combination with other therapeutic agent(s) used for treating myocardial infarction. Examples of agent(s) that can be used to reduce or suppress myocardial infarction include aspirin, nitroglycerin, metoprolol tartrate, enoxaparin sodium, heparin sodium, clopidogrel hydrosulfate, carvedilol, atenolol, morphine sulfate, metoprolol succinate, warfarin sodium, lisinopril, isosorbide mononitrate, digoxin, furosemide, simvastatin, ramipril, tenecteplase, enalapril maleate, torsemide, reteplase, losartan potassium, quinapril hydrochloride/mag carb, bumetanib, alteplase, enalaprilat, amiodarone hydrochloride, tirofiban hydrochloride m-hydrate, diltiazem hydrochloride, captopril, irbesartan tablets, valsartan, propranolol hydrochloride, fosinopril sodium, lidocaine hydrochloride, eptifibatide, cefazolin sodium, atropine sulfate, leucine, spironolactone, interferon, sotalol hydrochloride, potassium chloride, docusate sodium, dobutamine hydrochloride, alprazolam, pravastatin sodium, lipitor, midazolam hydrochloride, dolantin hydrochloride, isosorbide dinitrate, epinephrine, dopamine hydrochloride, bivalirudin, rosuvastatin, ezetimibe/simvastatin, avasimibe, abciximab and cariporide.

The small RNAs of the present invention can be administered in combination with other therapeutic agent(s) used for treating angina. Examples of agent(s) that can be used to reduce or suppress angina include: aspirin; nitroglycerin; isosorbide mononitrate; metoprolol succinate; atenolol; metoprolol tartrate; alodipine sulfonate, dilitiazem hydropchloride, isosorbide dinitrate, clopidogrel hydrosulfate; nifedipine; lipitor; potassium chloride; furosemide; simvastatin; verapamil hydrochloride; digoxin; propranolol hydrochloride; carvedilol; lisinopril; sprionolactone; dihydrochlorothiazide; enalapril maleate; madolol; ramipril; enoxaparin sodium; heparin sodium; valsartan; sotalol hydrochloride; fenofibrate; ezetimibe; bumetanide; losartan potassium lisinopril/hydrochlorothiazide; felodipine; captopril; and bisoprolol fumarate.

In one embodiment of the present invention, the small RNAs of the present invention are administered in combination with agent(s) usually used for treating hepatitis C virus. Examples of such agent(s) include interferon-α-2a, interferon-α-2b, interferon-α con1, interferon-α-n1, pegylated interferon-α-2a, pegylated interferon-α-2b, ribavirin, pegylated interferon-α-2b and ribavirin, androdeoxycholic acid, glycyrrhizic acid, thymalfasin, maxamine and VX-497.

The small RNAs of the present invention are used in combination with corticosteroids, vitamin D analogs, and topical or oral retinoic acid, or a combination thereof, for the treatment of psoriasis. In addition, the small RNAs of the present invention is used in combination with one of the following agent(s) for the treatment of psoriasis: small molecule inhibitor of KDR (ABT-123), small molecule inhibitor of Tie-2, calcipotriene, clobetasol propionate, triamcinolone acetonide, halobetasol propionate, tazorotene, methotrexate, fluocinolone acetate, fluocinolone, Acitretin, tar shampoo, betamethasone valerate, mometasone furoate, ketoconazole, pramocaine/fluocinolone, hydrocortisone valerate, fludrolone, urea, betamethasone, clobetasol propionate/emoll, fludiasone propionate, azithromycin, hydrocortisone, prescription for increasing moisture, folic acid, desonide, coal tar, diflurazone acetate, etanercept, folates, lactic acid, methoxsalin, hc/bismuth subgallate/znox/resor, methylprednisolone acetate, prednisone, sunscreen substances, salicylic acid, hascinonide, anthranol, clocortolone pivalate, coal extracts, coal tar/salicylic acid, coal tar/salicylic acid/ sulfur, desoxymethasone, diazepam, emollient, pimecrolimus emollient, fluocinolone acetate/emollient, mineral oil/ castor oil/na lact, mineral oil/peanut oil, isopropyl petroleum myristate, psoralen, salicylic acid, saponificated/tribromosalen, thimerosal/boric acid, celecoxib, infliximab, ale- facept, efalizumab, tacrolimus, pimecrolimus, PUVA, UVB and salicylazosulfapyridine.

The small RNAs of the present invention can be admin- istered in combination with other therapeutic agent(s) for treating skin diseases. For example, the small RNAs of the present invention are combined with PUVA therapy. PUVA is a combination of psoralen (P) and long-wave ultraviolet rays, which is used to treat many different skin diseases. The small RNAs of the present invention can also be combined with pimecrolimus. In another embodiment, the antibody of the invention is used to treat psoriasis, in which the antibody is administered in combination with tacrolimus. In another embodiment, tacrolimus and the small RNAs of the inven- tion are administered in combination with methotrexate and/or cyclosporin. In another embodiment, the small RNAs of the present invention are administered in combination with stimulated excimer laser therapy for the treatment of psoriasis.

Non-limiting examples of other therapeutic agent(s) with which the small RNAs of the present invention can be combined to treat skin diseases or nail diseases include UVA and UVB phototherapy. Other non-limiting examples that can be used in combination with the small RNAs of the present invention include anti-IL-12 and anti-IL-18 thera- peutic agent(s), including antibodies.

In one embodiment, the small RNAs of the present invention are administered in combination with other thera- peutic agent(s) for the treatment of Behcet's disease. Other therapeutic agent(s) for the treatment of Behcet's disease include but are not limited to, prednisone, cyclophosph- amide (cytoxan), azathioprine (also referred to as imuran), methotrexate, timethoprim/sulfamethoxazole (also known as compound sulfamethoxazole tablets or TMP-SMZ) and folic acid.

Any of the above-mentioned therapeutic agent(s), alone or in combination, combined with the small RNAs of the present invention, can treat patients suffering from TNF- alpha-related diseases in which TNF-alpha activity is harm- ful.

The present invention is further illustrated below with reference to the examples. Those skilled in the art should understand that these embodiments are only illustrative and not restrictive. The scope of the invention is defined by the appended claims.

EXAMPLES

Experimental Materials and Methods

ELISA (enzyme-linked immunosorbent assay) and RT- qPCR (real-time fluorescent quantitative PCR).

Main experimental instruments and equipment: 10 cm cell culture dishes, 12-well cell culture plates, pipettors, pipettes, optical microscopes Main Experimental Reagents:

Cell culture: RPMI 1640 culture medium (MACGENE, cat. CM10041), fetal bovine serum (GE, cat. SV30160.03) added to the culture medium at 10%

Model establishment and transfection: artificially synthe- sized small RNAs (double-stranded, Genepharma) shown in Table 1, transfection reagent (RNAimax, invitrogen, 17338- 150), Opti-MEM (gibco, 31985-070 500 ml), LPS (sigma, cat. L4391-1MG)

RNA: Total RNA Rapid Extraction Kit (Shanghai Fasta- gen Biotech Co., Ltd., cat. no. 220011), TRIZOL reagent (SIGMA, T9424-200 ml), Reverse Transcription Kit (High Capacity cDNA Reverse Transcription Kit, Thermo, 4368813), LightCycler 480 SYBR Green I Master (Roche, 04887352001)

ELISA detection kit: (DuoSet Human IL-1beta/IL-6/ TNF-alpha, R&D, DY201/DY206/DY210), protease inhibi- tor (TargetMol, cat. no. C0001).

1. Functional Experiment of Artificially Synthesized Small RNAs at Protein Level Verified by Using the THP-1 Cell Model Stimulated by LPS 1.1 THP-1 cells (monocyte macrophages, purchased from the Cell Center of the Institute of Basic Medicine, Chinese Academy of Medical Sciences) were cultured in RPMI 1640 culture medium containing fetal bovine serum to the loga- rithmic growth phase. They were distributed into 12-well plates with 1 ml medium/well, incubated overnight at 37° C. for subsequent experiments.

1.2 The groups of the experiment were as follows:

Blank group, i.e. empty group, referred to untreated cells. This group served as a blank control;

LPS group: this group was treated as follows: 2 μl RNAimax was diluted with 200 μl Opti-MEM and added to the cells, which were stimulated with LPS. This group served as a negative control;

NC group: the random nonsense sequence 5' UUC UCC GAA CGU GUC ACG UTT-3 (SEQ ID No. 223) (double-stranded, Genepharma) was added to the cells with the same concentration and the same transfection method as that of the experimental group, and the cells were stimulated with LPS. This group served as a negative control.

1.3 The artificially synthesized plant small RNAs were transfected by using RNAimax at RNAimax 2/100 μl Opti- MEM, small RNA (20 μM) 5 μl/100 μl Opti-MEM. The above liquids were mixed and incubated for 10 minutes at room temperature and added to the cells.

1.4 LPS was added for stimulation 24 hours after the transfection, and the final concentration of LPS was 1 μg/ml.

1.5 The cell supernatant was collected 9 hours after LPS stimulation, and the concentration of the protease inhibitor added was 10 μl/ml.

1.6 The expressions of the three factors IL-1beta/IL-6/ TNF-alpha were detected by ELISA kit.

2. Functional Experiment of Artificially Synthesized Small RNAs at mRNA Level Verified By Using the THP-1 Cell Model Stimulated by LPS 2.1 THP-1 cells (monocyte macrophages, purchased from the Cell Center of the Institute of Basic Medicine, Chinese Academy of Medical Sciences) were cultured in RPMI 1640 culture medium containing fetal bovine serum to the loga- rithmic growth phase. They were distributed into 12-well plates with 1 ml medium/well, incubated overnight at 37° C. for subsequent experiments.

2.2 The groups of the experiment were as follows:

Blank group: empty group, referred to untreated cells. This group served as a blank control;

LPS group: in this group, 2 μl RNAimax was diluted with 200 μl Opti-MEM and added to the cells which were subjected to LPS stimulation. This group served as a negative control;

NC group: the random nonsense sequence 5' UUC UCC GAA CGU GUC ACG UTT-3 (SEQ ID No. 223) (Genepharma) was added to the cells with the same concentration and the same transfection method as that of the experimental group, and the cells were stimu- lated with LPS. This group served as a negative control.

2.3 The artificially synthesized plant small RNAs were transfected by using RNAimax at RNAimax 2 μl/100 μl Opti-MEM, small RNA (20 µM) 5 µl/100 µl Opti-MEM. The above liquids were mixed and incubated for 10 minutes at room temperature and added to the cells.

2.4 LPS was added for stimulation 24 hours after the transfection, and the final concentration of LPS was 1 µg/ml.

2.5 Nine hours after LPS stimulation, the cells were collected by centrifugation at 800 g for 5 minutes.

2.6 Total cell RNA was extracted by using Total RNA Rapid Extraction Kit according to the manufacturer's instructions.

2.7 Reverse transcription of RNA into cDNA: reverse transcription of small RNA into cDNA was carried out using a reverse transcription kit (High-Capacity cDNA Reverse Transcription Kits, Applied Biosystems, cat. no. 4368813) according to the manufacturer's instructions. The reverse transcription system was as follows: template RNA (150 ng/l) 10 µl, 10×RT Buffer 2.0 µl, 25×dNTP Mix (100 mM) 0.8 µl, 10× Random Primer (included in the kit) 2.0 µl, MultiScribe™ reverse transcriptase 1.0 µl, RNase inhibitor 1.0 µl, Nuclease-free H₂O 1.2 µl. After transient centrifugation, the system was put into the PCR instrument for reaction, and the reaction conditions were as follows: (1) 25° C., 10 min; (2) 37° C., 120 min; (3) 85° C., 5 min; (4) the reaction was stopped at 4° C. After the reaction, 20 µl RNase Free dH₂O was added to make up the final volume to 40 µl.

2.8 Quantitative PCR amplification reaction: the total volume of the qPCR reaction system was 10 µl, including: 5 µl 2×SYBR Green Master Mix, 0.5 µl forward primer (10 µM), 0.5 µl reverse primer (10 µM), 1 µl cDNA obtained by reverse transcription and 3 µl RNase Free dH₂O. A Light-Cycler 480 fluorescent quantitative PCR instrument was used and the PCR reaction conditions were: pre-denaturation for 5 minutes at 95° C., then PCR amplification cycle: (1) 95° C., 10 s; (2) 55° C., 10 s; (3) 72° C., 20 s; for a total of 40 cycles; finally 40° C. for 10 s to cool down. The forward primers and reverse primers for the amplification reaction were all designed and synthesized by Beijing Tsingke Xinye Biological Technology Co., Ltd. The primer sequences used are as follows:

The primers for UBC are:

```
Has-UBC-For
                        (SEQ ID No. 224)
CTGGAAGATGGTCGTACCCTG

Has-UBC-Rev
                        (SEQ ID No. 225)
GGTCTTGCCAGTGAGTGTCT
```

The primers for IL-1beta are:

```
Has-IL-1beta-For
                        (SEQ ID No. 226)
CTCGCCAGTGAAATGATGGCT Has-IL-1beta-Rev
                        (SEQ ID No. 227)
GTCGGAGATTCGTAGCTGGAT
```

The primers for IL-6 are:

```
Has-IL-6-For
                        (SEQ ID No. 228)
GGTACATCCTCGACGGCATCT

Has-IL-6 Rev
                        (SEQ ID No. 229)
GTGCCTCTTTGCTGCTTTCAC
```

The primers for TNF-alpha are:

```
Has-TNF-alpha For
                        (SEQ ID No. 230)
CTGCCCCAATCCCTTTATT Has-TNF-alpha Rev
                        (SEQ ID No. 231)
CCCAATTCTCTTTTTGAGCC
```

2.9 Calculation of the relative expression by using the 2-ΔΔCt method.

3. MTS Cell Viability Detection 3.1. Main experimental instruments and equipment: 10 cm cell culture dishes, 96-well cell culture plates, pipettors, pipette, optical microscopes, 1.5 ml centrifuge tubes, microplate reader, MTS detection kit (Promega, Celltiter 96 AQueous One Solution Cell Proliferation Assay, REF: G3581, LOT: 0000064219);

3.2. Main Experimental Reagents:

Cell culture: F12 culture medium (Hyclone), FBS (Gibico);

Model establishment and transfection: artificially synthesized small RNA, RNAimax, opti-MEM, H5N1 virus (A/Jilin/9/2004);

Cell survival rate: MTS cell viability detection kit;

3.3 The function of artificially synthesized small RNAs derived from Chinese herbal medicine in resisting H5N1 infection and alleviating cell death was verified by applying an A549 cell model infected by the H5N1 strain derived from 2004 Jilin (A/Jilin/9/2004).

3.3.1 A549 cells (human lung adenocarcinoma epithelial cells, purchased from American Type Culture Collection (ATCC, Rockville, MD, USA) were cultured in 10 cm cell culture dishes (cultured in Ham's F12 nutrient medium (HyClone, Logan, UT, USA), distributed into 96-well plates, 100 µl cell-containing culture medium per well);

3.3.2 When the cells were observed to grow to 90% confluence (about 12 hours) under an optical microscope, the artificially synthesized plant small RNAs were transfected by using a transfection reagent, transfection reagent 0.2 l/ml, small RNA 100 nmol/ml;

3.3.3 The cells were infected with H5N1 virus 24 hours after transfection, and the amount of challenge was 0.4 M.O.I;

3.3.4 The cell death status was detected by using the MTS kit 48 hours after challenge. The relevant reagents for MTS detection were mixed thoroughly according to: serum-free culture medium: solution A:solution B=100:20:1. The supernatant of the cells in the 96-well plates were aspirated. MTS detection reagent mixture was added to the 96-well plates at 100 µl/well and incubated in an oven at 37° C. for 30 min (protected from light) after adding;

3.3.5 The cell survival status was detected by using a microplate reader: the absorbance at 492 nm was detected three times per plate, and the result of the third time shall prevail.

4. Functional Experiment of Artificially Synthesized Small RNA Mixtures at Protein Level Verified by Using the THP-1 Cell Model Stimulated by LPS 4.1 THP-1 cells (monocyte macrophages, purchased from the Cell Center of the Institute of Basic Medicine, Chinese Academy of Medical Sciences) were cultured to the logarithmic growth phase. They were distributed into 12-well plates with 1 ml medium/well, incubated overnight at 37° C. for subsequent experiments.

4.2 The groups of the experiment were as follows:

Blank group: empty group, referred to untreated cells. This group served as a blank control;

LPS group: in this group, 2 μl RNAimax was diluted with 200 μl Opti-MEM and added to the cells which were subjected to LPS stimulation. This group served as a negative control;

NC (native) group: the random nonsense sequence 5' UUC UCC GAA CGU GUC ACG UTT-3 (SEQ ID No. 223) (double-stranded, Genepharma) was added to the cells with the same concentration and the same transfection method as that of the experimental group, and the cells were stimulated with LPS. This group served as a negative control.

4.3 The artificially synthesized plant small RNA mixtures (Table 2) were transfected by using RNAimax. The volume ratio of BZL-sRNA-20 to other small RNAs was 2:1 (the initial concentrations of various small RNAs were all 20 μM), RNAimax 2 μl/100 μl Opti-MEM, small RNA mixture (20 μM) 10 μl/100 μl Opti-MEM. The above liquids were mixed and incubated for 10 minutes at room temperature and added to the cells.

4.4 LPS was added for stimulation 24 hours after the transfection, and the final concentration of LPS was 1 μg/ml.

4.5 The cell supernatant was collected 9 hours after LPS stimulation, and the concentration of the protease inhibitor added was 10 μl/ml.

4.6 The expressions of the three factors IL-1beta/IL-6/TNF-alpha were detected by ELISA kit.

5. Functional Experiment of Artificially Synthesized Small RNA Mixtures at mRNA Level Verified by Using the THP-1 Cell Model Stimulated by LPS 5.1 THP-1 cells (monocyte macrophages, purchased from the Cell Center of the Institute of Basic Medicine, Chinese Academy of Medical Sciences) were cultured to the logarithmic growth phase. They were distributed into 12-well plates with 1 ml medium/well, incubated overnight at 37° C. for subsequent experiments.

5.2 The groups of the experiment were as follows:

Blank group: empty group, referred to untreated cells. This group served as a blank control;

LPS group: in this group, 2 μl RNAimax was diluted with 200 μl Opti-MEM and added to the cells which were subjected to LPS stimulation. This group served as a negative control; NC group: the random nonsense sequence 5' UUC UCC GAA CGU GUC ACG UTT-3 (SEQ ID No. 223) (double-stranded, Genepharma) was added to the cells with the same concentration and the same transfection method as that of the experimental group, and the cells were stimulated with LPS. This group served as a negative control.

5.3 The artificially synthesized plant small RNA mixtures (Table 2) were transfected by using RNAimax. The volume ratio of BZL-sRNA-20 to other small RNAs was 2:1, RNAimax 2 μl/100 μl Opti-MEM, small RNA mixture (20 μM) 10 μl/100 μl Opti-MEM. The above liquids were mixed and incubated for 10 minutes at room temperature and added to the cells.

5.4 LPS was added for stimulation 24 hours after the transfection, and the final concentration of LPS was 1 μg/ml.

5.5 Nine hours after LPS stimulation, the cells were collected by centrifugation at 800 g for 5 minutes.

5.6 The cells were lysed by 0.5 ml TRI Reagent (sigma, T9424-200ML), centrifuged at 12,000 rpm, 4° C. for 5 min and the precipitate was discard. Chloroform was added at the ratio of 200 μl/ml TRIzol, shaken and mixed throughly, and left at room temperature for 15 min. The mixture was centrifuged at 12,000 rpm, 4° C. for 15 min. The upper water phase was transferred to another centrifuge tube. The upper water phase was transferred to another new EP tube. Isopropanol was added at 0.5 ml/ml TRIzol, mixed well and left at room temperature for 5-10 min. The mixture was centrifuged at 12,000 rpm, 4° C. for 10 min. The supernatant was discarded, 1 ml of 75% ethanol was added and the centrifuge tube was gently shaken to suspend the precipitate. The mixture was centrifuged at 8000 g, 4° C. for 5 min. The supernatant was discarded to the greatest extent and the tube was dried at room temperature for 5-10 min. The RNA sample was dissolved by using 20 μl DEPC-treated $H_2O$.

5.7 Reverse transcription of RNA into cDNA: reverse transcription of small RNA into cDNA was carried out using a reverse transcription kit (High-Capacity cDNA Reverse Transcription Kits, Applied Biosystems, cat. no. 4368813). The reverse transcription system was as follows: template RNA (150 ng/l) 10 μl, 10× RT Buffer 2.0 μl, 25×dNTP Mix (100 mM) 0.8 μl, 10× Random Primer (included in the kit) 2.0 μl, MultiScribe™ reverse transcriptase 1.0 μl, RNase inhibitor 1.0 μl, Nuclease-free $H_2O$ 1.2 μl. After transient centrifugation, the system was put into the PCR instrument for reaction, and the reaction conditions were as follows: (1) 25° C., 10 min; (2) 37° C., 120 min; (3) 85° C., 5 min; (4) the reaction was stopped at 4° C. After the reaction, 20 μl RNase Free d$H_2O$ was added to make up the final volume to 40 μl.

5.8 Quantitative PCR amplification reaction: the total volume of the qPCR reaction system was 10 μl, including: 5 μl 2×SYBR Green Master Mix, 0.5 μl forward primer (10 μM), 0.5 μl reverse primer (10 μM), 1 μl cDNA obtained by reverse transcription and 3 μl RNase Free d$H_2O$. A Light-Cycler 480 fluorescent quantitative PCR instrument was used and the PCR reaction conditions were: pre-denaturation for 5 minutes at 95° C., then PCR amplification cycle: (1) 95° C., 10 s; (2) 55° C., 10 s; (3) 72° C., 20 s; for a total of 40 cycles; finally 40° C. for 10 s to cool down. The forward primers and reverse primers for the amplification reaction were all designed and synthesized by Beijing Tsingke Xinye Biological Technology Co., Ltd. The UBC gene was used as an internal reference gene. The primer sequences used are as follows:

```
Has-UBC-For
                          (SEQ ID No. 224)
CTGGAAGATGGTCGTACCCTG

Has-UBC-Rev
                          (SEQ ID No. 225)
GGTCTTGCCAGTGAGTGTCT

Has-IL-1beta-For
                          (SEQ ID No. 226)
CTCGCCAGTGAAATGATGGCT Has-IL-1beta-Rev
                          (SEQ ID No. 227)
GTCGGAGATTCGTAGCTGGAT Has-IL-6-For
                          (SEQ ID No. 228)
GGTACATCCTCGACGGCATCT Has-IL-6 Rev
                          (SEQ ID No. 229)
GTGCCTCTTTGCTGCTTTCAC Has-TNF-alpha For
                          (SEQ ID No. 230)
CTGCCCCAATCCCTTTATT
```

-continued

```
Has-TNF-alpha Rev
                               (SEQ ID NO. 231)
CCCAATTCTCTTTTTGAGCC
```

5.9 Calculation of the relative expression by using the 2-ΔΔCt method.

6. Experiment to Verify the Anti-Inflammatory Effect of BZL-sRNA-20 In Vivo 6.1 7-week-old male C57 mice weighing 20-23 g were divided into 4 groups, one of which remained untreated during the entire experiment, i.e. the blank group.

6.2 The mice were given a dose of 1 nmol/animal of BZL-sRNA-20 or NC small RNA by gavage 3 days, 2 days and 1 day in advance, respectively, and the groups were BZL-sRNA-20 or NC group (native group), respectively.

6.3 After 1% pentobarbital sodium anesthesia at 0 h, the mice were tracheally injected with a dose of LPS (1 mg/ml) 50 μl, at 50 μg/animal. Among them, the group only treated with LPS was denoted as the LPS group.

6.4 Nine hours after 1% pentobarbital sodium anesthesia, alveolar lavage (800 l) was performed for 2 times, each time with 800 μl PBS pipetted repeatedly for 3 times.

6.5 The obtained lavage fluid was centrifuged at 800 g for 5 min. The obtained exfoliated lung cells were lysed by 0.5 ml Trizol (Thermo), centrifuged at 12,000 rpm, 4° C. for 5 min and the precipitate was discard. Chloroform was added at the ratio of 200 μl/ml TRIzol, shaken and mixed throughly, and left at room temperature for 15 min. The mixture was centrifuged at 12,000 rpm, 4° C. for 15 min. The upper water phase was transferred to another centrifuge tube. The upper water phase was transferred to another new EP tube. Isopropanol was added at 0.5 ml/ml TRIzol, mixed well and left at room temperature for 5-10 min. The mixture was centrifuged at 12,000 rpm, 4° C. for 10 min. The supernatant was discarded, 1 ml of 75% ethanol was added and the centrifuge tube was gently shaken to suspend the precipitate. The mixture was centrifuged at 8000 g, 4° C. for 5 min. The supernatant was discarded to the greatest extent and the tube was dried at room temperature for 5-10 min. The RNA sample was dissolved by using 20 μl DEPC-treated H₂O.

6.6 Reverse transcription of RNA into cDNA: reverse transcription of small RNA into cDNA was carried out using a reverse transcription kit (High-Capacity cDNA Reverse Transcription Kits, Applied Biosystems, cat. no. 4368813). The reverse transcription system was as follows: template RNA (150 ng/l) 10 μl, 10× RT Buffer 2.0 μl, 25×dNTP Mix (100 mM) 0.8 μl, 10× Random Primer (included in the kit) 2.0 μl, MultiScribe™ reverse transcriptase 1.0 μl, RNase inhibitor 1.0 μl, Nuclease-free H₂O 1.2 μl. After transient centrifugation, the system was put into the PCR instrument for reaction, and the reaction conditions were as follows: (1) 25° C., 10 min; (2) 37° C., 120 min; (3) 85° C., 5 min; (4) the reaction was stopped at 4° C. After the reaction, 20 μl RNase free dH₂O was added to make up the final volume to 40 μl.

6.7 Quantitative PCR amplification reaction: the total volume of the qPCR reaction system was 10 μl, including: 5 μl 2×SYBR Green Master Mix, 0.5 μl forward primer (10 μM), 0.5 μl reverse primer (10 μM), 1 μl cDNA obtained by reverse transcription and 3 μl RNase Free dH₂O. A Light-Cycler 480 fluorescent quantitative PCR instrument was used and the PCR reaction conditions were: pre-denaturation for 5 minutes at 95° C., then PCR amplification cycle: (1) 95° C., 10 s; (2) 55° C., 10 s; (3) 72° C., 20 s; for a total of 40 cycles; finally 40° C. for 10 s to cool down. The forward primers and reverse primers for the amplification reaction were all designed and synthesized by Beijing Tsingke Xinye Biological Technology Co., Ltd. The GAPDH gene was used as an internal reference gene. The primer sequences used are as follows:

```
Mus-IL-1beta-For
                               (SEQ ID No. 232)
GTTCCCATTAGACAACTGC Mus-IL-1beta-Rev
                               (SEQ ID No. 233)
GATTCTTTCCTTTGAGGC Mus-IL-6-For
                               (SEQ ID No. 234)
TAGTCCTTCCTACCCCAATTTCC Mus-IL-6-Rev
                               (SEQ ID No. 235)
TTGGTCCTTAGCCACTCCTTC Mus-TNF-For
                               (SEQ ID No. 236)
CCTGTAGCCCACGTCGTAG Mus-TNF-Rev
                               (SEQ ID No. 237)
GGGAGTAGACAAGGTACAACCC Mus-GAPDH-For
                               (SEQ ID No. 238)
CACTCACGGCAAATTCAACGGCAC Mus-GAPDH-Rev
                               (SEQ ID No. 239)
GACTCCACGACATACTCAGCAC
```

6.8 Calculation of the relative expression by using the 2-ΔΔCt method.

6.9 The supernatant was centrifuged at 12000 rpm for 10 min, and the cell debris was removed. The expression of the factors was verified by detection with ELISA kits (DuoSet Mouse IL-1beta/IL-6/TNF-alpha, R&D, DY401/DY406/DY410).

7. Transcriptome Sequencing of Artificially Synthesized Small RNAs Verified by Using the THP-1 Cell Model Stimulated by LPS 7.1 Preparation and extraction of RNA for sequencing 7.1.1 The groups of the experiment:

Blank group: empty group, referred to untreated cells. This group served as a blank control;

LPS group: in this group, 2 μl RNAimax was diluted with 200 μl Opti-MEM and added to the cells which were subjected to LPS stimulation. This group served as a negative control;

NC group: the random nonsense sequence 5' UUC UCC GAA CGU GUC ACG UTT-3 (SEQ ID No. 223) (Genepharma) was added to the cells with the same concentration and the same transfection method as that of the experimental group, and the cells were stimulated with LPS. This group served as a negative control.

7.1.2 The artificially synthesized plant small RNAs were transfected by using RNAimax at RNAimax 2 μl/100 μl Opti-MEM, small RNA (20 μM) 5 μl/100 μl Opti-MEM. The above liquids were mixed and incubated for 10 minutes at room temperature and added to the cells.

7.1.3 LPS was added for stimulation 24 hours after the transfection, and the final concentration of LPS was 1 μg/ml.

7.1.4 Nine hours after LPS stimulation, the cells were collected by centrifugation at 800 g for 5 minutes.

7.1.5 The cells were fully lysed by using 0.5 ml Trizol Reagent (sigma). 100 µl chloroform was added, mixed well and centrifuged at 4° C., 13200 rpm for 25 min. 280 µl supernatant was taken and the same amount of isopropanol was added, mixed well and let stand at −40° C. for 30 min. The mixture was centrifuged at 4° C., 13200 rpm for 25 min. The supernatant was discarded and the precipitate was washed twice with 75% ethanol prepared with DEPC water. The precipitate was dried and dissolved with 20 µl DEPC water.

7.1.6 The obtained RNA solution was sent to the company for sequencing.

7.2 Data analysis 7.2.1 Uploading the sequencing data

A total of 194 sample data (including 2 NC) was uploaded to the 222.28.163.113 port 222 bioinformatics server using SSH protocol, using Xftp (version Xftp 5.0) as the transfer tool and XShell (version XShell 5.0) as the secure terminal simulation software on WINDOW10 platform.

7.2.2 Preparation of database data and calculation of sequencing data

The next step was carried out after uploading the data. The hg19 version of the human genome of UCSC was downloaded and the library was built by using bowtie2 (version bowtie2 2.1.0). The annotation file that matched hg19 in the UCSC database was used as the annotation file. The sequenced 150 bp fragments were matched to the human genome file of the gene name of each annotated segment by using the shell script to run Tophat (version 2.0.11) and cufflink (version 2.2.1), and the statistics of the expression count of each gene were completed.

Tophat Running Parameters:

The average separation distance between each sequenced fragment pair -r: 150

The standard deviation of the separation distance --mate-std-dev: 149 library-type (chain-specific): fr-secondstrand

Number of the threads -p: 16.

7.2.3 Summary of the sequencing data results

The sequencing data sorted by Tophat was written into a new text by using python (version 3.6.1) script.

7.2.4 Statistics of differential genes of 194 sequencing result samples

The running script was written by using DEGseq of R (version 3.3.2). The expressions of each sample and each gene were sorted out and compared with the expressions of each gene in the NC group to calculate the FC (fold change).

7.2.5 Statistics and clustering of differentially down-regulated genes

The results of step 4 were processed by screening the genes (wherein the gene expression level FC was down-regulated by more than 1.5 folds in each sample, when compared with that of the control group NC). These genes were uploaded to the Metacore database for analysis. The parameters were selected (ignore first line; species: *Homo sapiens*; type: down regulate; p-value and FDR: no limit).

7.2.6 Statistics of the number of differentially down-regulated genes

Statistics of 192 small RNA samples were performed by using the script in python (3.6.1). The expression levels of down-regulated genes (down-regulation level: fold change>1.5) was calculated, and the genes that could be down-regulated by small RNAs in 192 samples were obtained.

7.2.7 Classification tabulation of 192 small RNA target genes, and the pathways or biological processes involved by the target genes According to the pathways or biological processes to which the down-regulated genes of each sample belong, the data was divided to 6 categories and tabulated by referring to the PUBMED and KEGG databases, as well as the clustering results of the down-regulated genes (criteria: FC>1.5) for each sample in the Metacore database of 192 samples as described in 7.2.5.

Example 1: Verification of the Effect of Small RNAs in Table 1

1. As Mentioned Above in "Functional Experiment of Artificially Synthesized Small RNAs at Protein Level Verified by Using the THP-1 Cell Model Stimulated by LPS", the Small RNAs as Specified in FIG. 1 to FIG. 15 were Used for Experiment.

Figure 1:
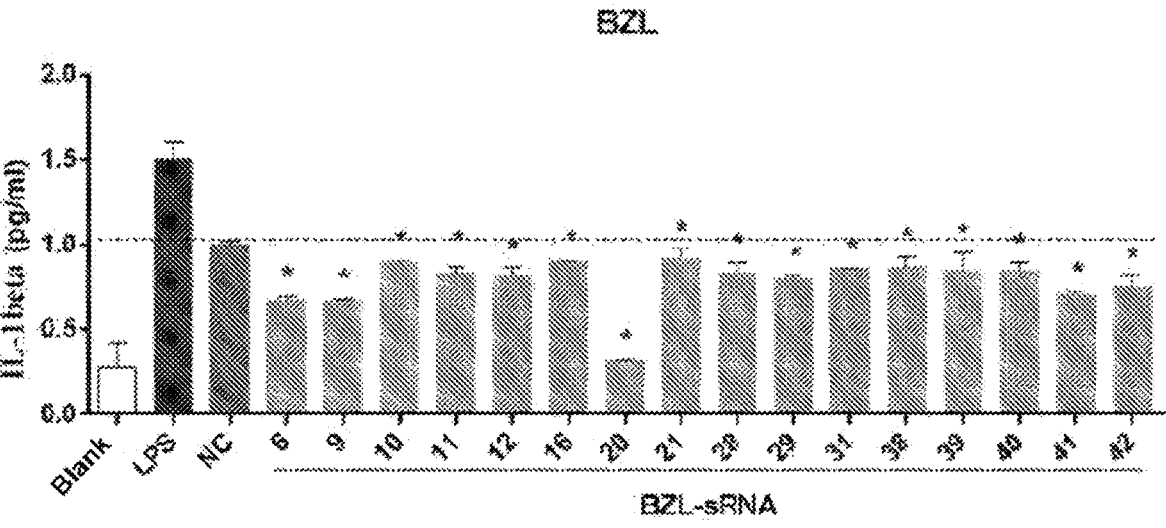
FIG. 1: The expression of the inflammatory factor IL-1beta at protein level compared to the control group, in the cell inflammation model after 9 hours of LPS stimulation, with the THP1 cells transfected with the *Scutellaria barbata* (BZL) small RNA 24 hours in advance, as specified in the figure.
Figure 2:
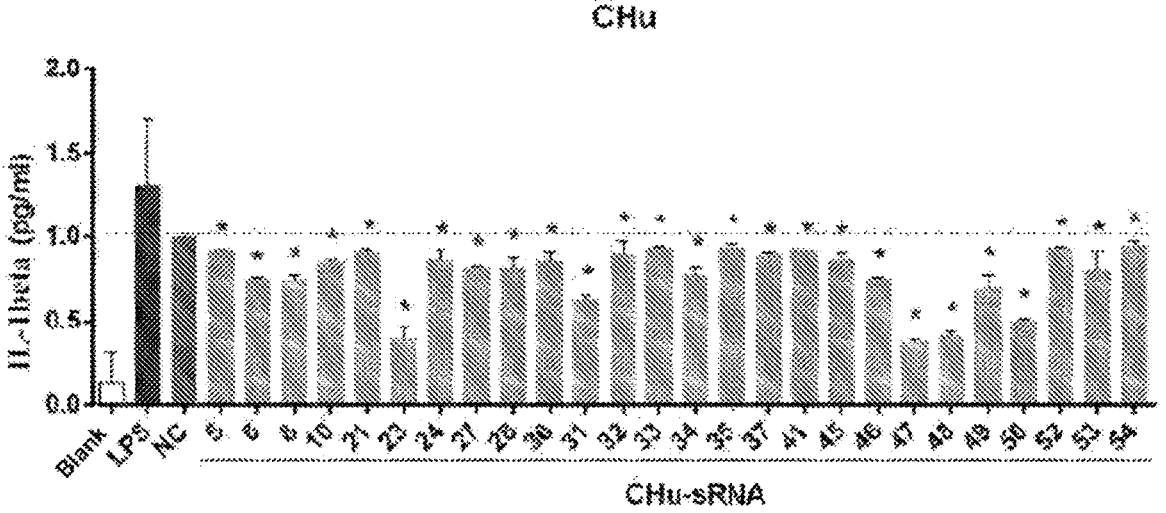
FIG. 2: The expression of the inflammatory factor IL-1beta at protein level compared to the control group, in the cell inflammation model after 9 hours of LPS stimulation, with the THP1 cells transfected with the *Bupleurum* (CHu) small RNA 24 hours in advance, as specified in the figure.
Figure 3:
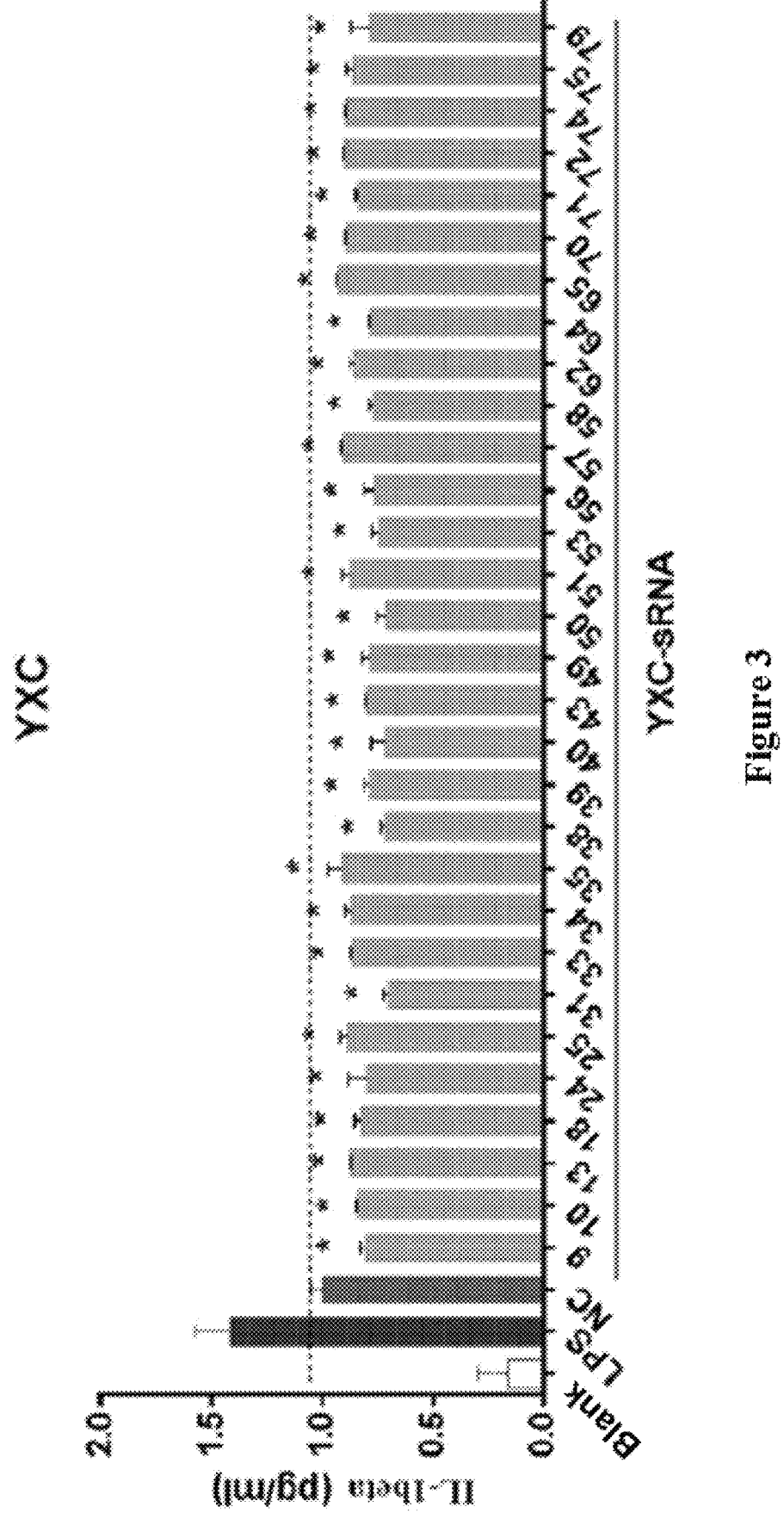
FIG. 3: The expression of the inflammatory factor IL-1beta at protein level compared to the control group, in the cell inflammation model after 9 hours of LPS stimulation, with the THP1 cells transfected with the *Houttuynia cordata* (YXC) small RNA 24 hours in advance, as specified in the figure.
Figure 4:
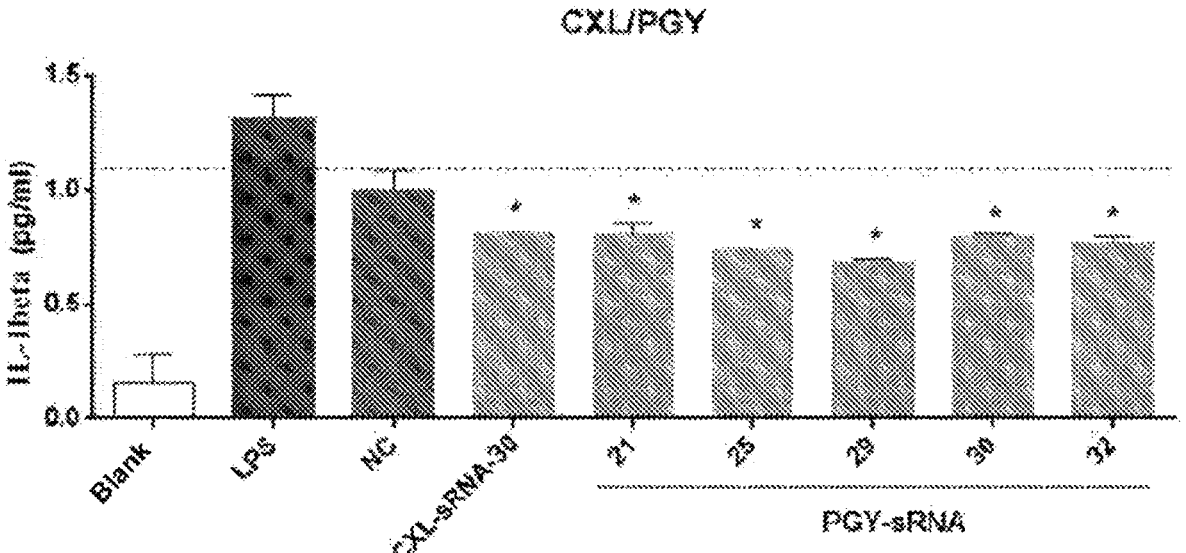
FIG. 4: The expression of the inflammatory factor IL-1beta at protein level compared to the control group, in the cell inflammation model after 9 hours of LPS stimulation, with the THP1 cells transfected with the *Andrographis paniculata* (CXL) and *Taraxacum* (PGY) small RNA 24 hours in advance, as specified in the figure.

FIG. 1: The expression of the inflammatory factor IL-1beta at protein level compared to the control group, in the cell inflammation model after 9 hours of LPS stimulation, with the THP1 cells transfected with the *Scutellaria barbata* (BZL) small RNA 24 hours in advance, as specified in the figure. FIG. 2: The expression of the inflammatory factor IL-1beta at protein level compared to the control group, in the cell inflammation model after 9 hours of LPS stimulation, with the THP1 cells transfected with the *Bupleurum* (CHu) small RNA 24 hours in advance, as specified in the figure. FIG. 3: The expression of the inflammatory factor IL-1beta at protein level compared to the control group, in the cell inflammation model after 9 hours of LPS stimulation, with the THP1 cells transfected with the *Houttuynia cordata* (YXC) small RNA 24 hours in advance, as specified in the figure. FIG. 4: The expression of the inflammatory factor IL-1beta at protein level compared to the control group, in the cell inflammation model after 9 hours of LPS stimulation, with the THP1 cells transfected with the *Andrographis paniculata* (CXL) and *Taraxacum* (PGY) small RNA 24 hours in advance, as specified in the figure. In FIG. 1 to FIG. 4, "*" means that unpaired t test P<0.05 was considered statistically significant in statistical analysis, indicating the effect of inhibiting the expression of inflammatory factors in in vitro experiments. The experimental results showed that the small RNAs shown in FIG. 1 to FIG. 4 had significantly higher effect in reducing the protein expression of IL-1beta than the NC group. The values in FIG. 1 to FIG. 4 were all values obtained by normalization relative to the NC group. BZL-sRNA-20 had the smallest value in ELISA of the inflammatory factor IL-1beta, indicating the best effect on inhibiting IL-1beta protein level among the small RNAs tested.

Figure 5:
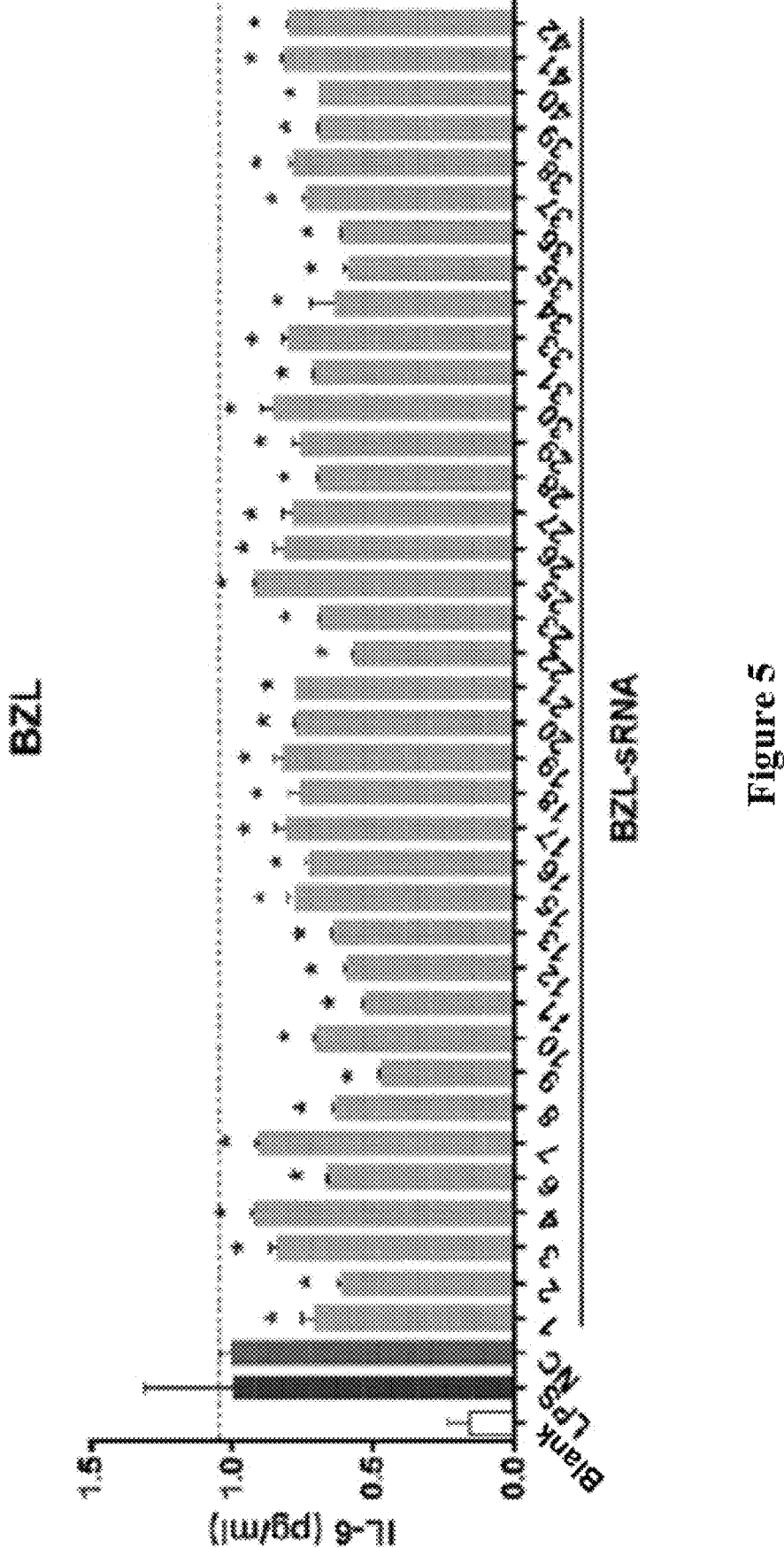
FIG. 5: The expression of the inflammatory factor IL-6 at protein level compared to the control group, in the cell inflammation model after 9 hours of LPS stimulation, with the THP1 cells transfected with the *Scutellaria barbata* (BZL) small RNA 24 hours in advance, as specified in the figure.
Figure 6:
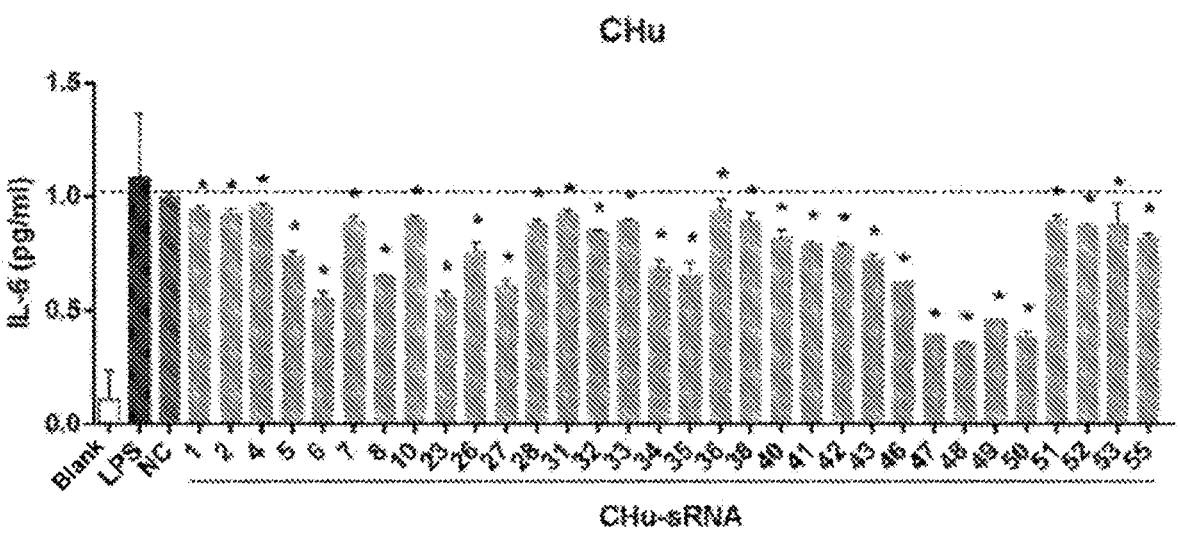
FIG. 6: The expression of the inflammatory factor IL-6 at protein level compared to the control group, in the cell inflammation model after 9 hours of LPS stimulation, with the THP1 cells transfected with the *Bupleurum* (CHu) small RNA 24 hours in advance, as specified in the figure.
Figure 7:
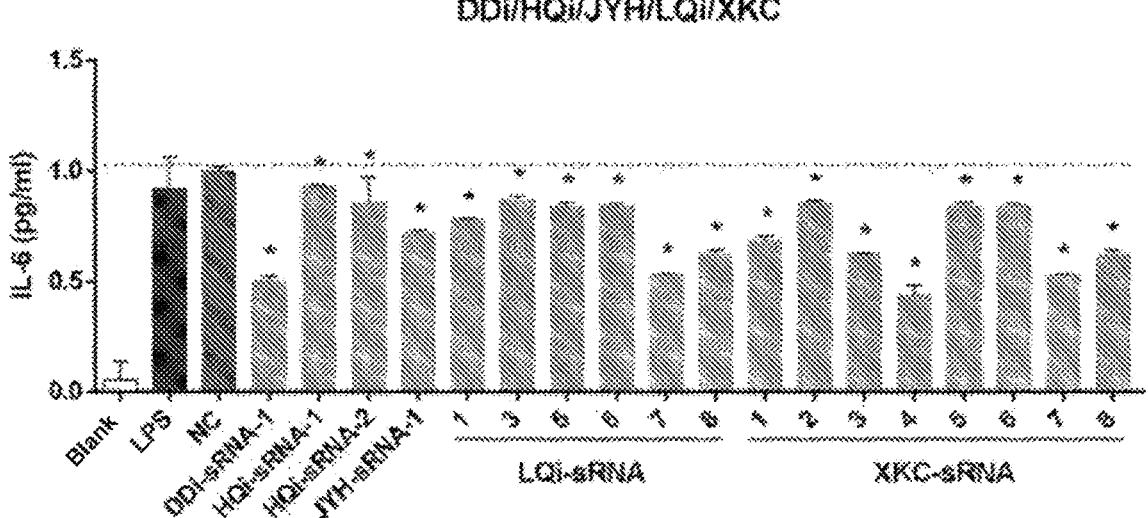
FIG. 7: The expression of the inflammatory factor IL-6 at protein level compared to the control group, in the cell inflammation model after 9 hours of LPS stimulation, with the THP1 cells transfected with the *Viola philippica* (DDi), *Scutellaria baicalensis* (HQi), *Lonicera japonica* (JYH), *Fructus forsythiae* (LQi) and *Prunella vulgaris* (XKC) small RNA 24 hours in advance, as specified in the figure.
Figure 8:
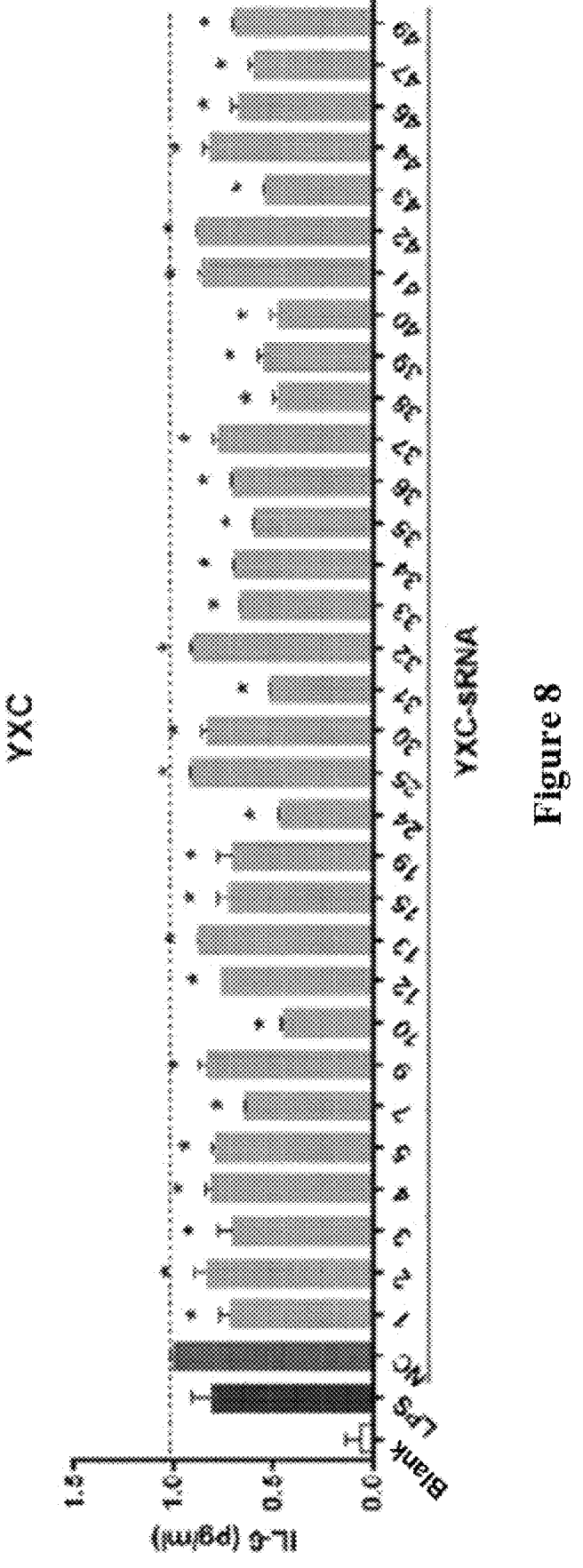
FIG. 8 to FIG. 9: The expression of the inflammatory factor IL-6 at protein level compared to the control group, in the cell inflammation model after 9 hours of LPS stimulation, with the THP1 cells transfected with the *Houttuynia cordata* (YXC) small RNA 24 hours in advance, as specified in the figure.
Figure 9:
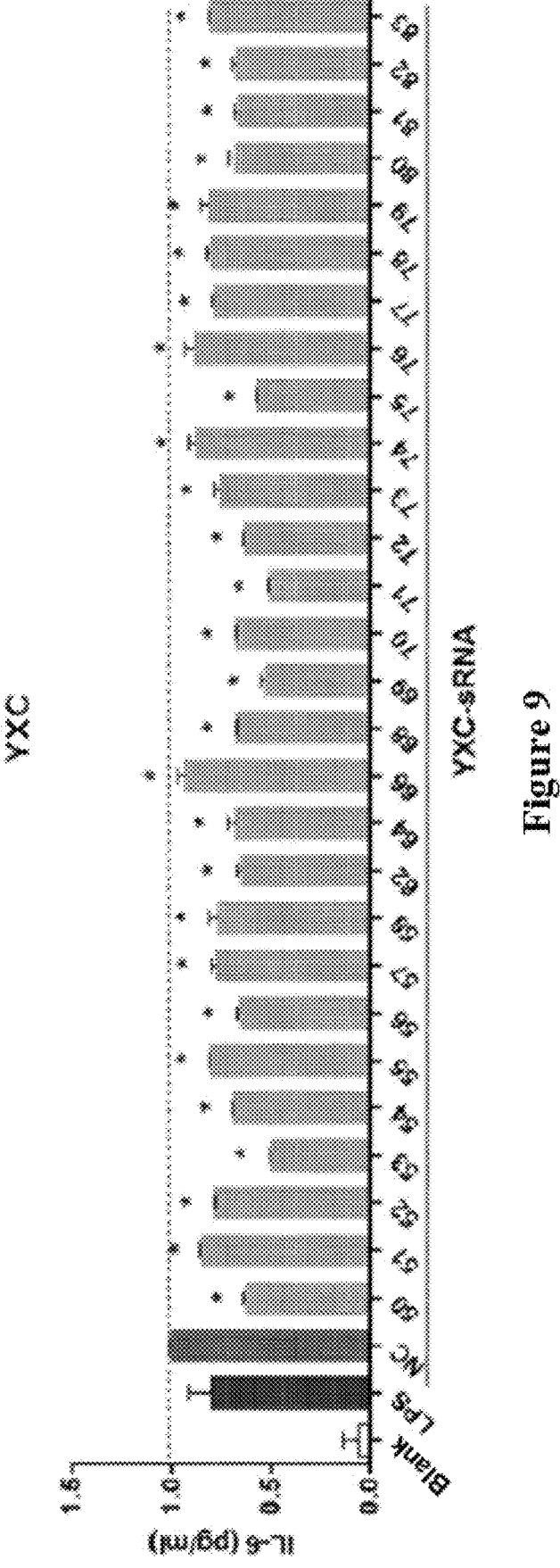
Figure 10:
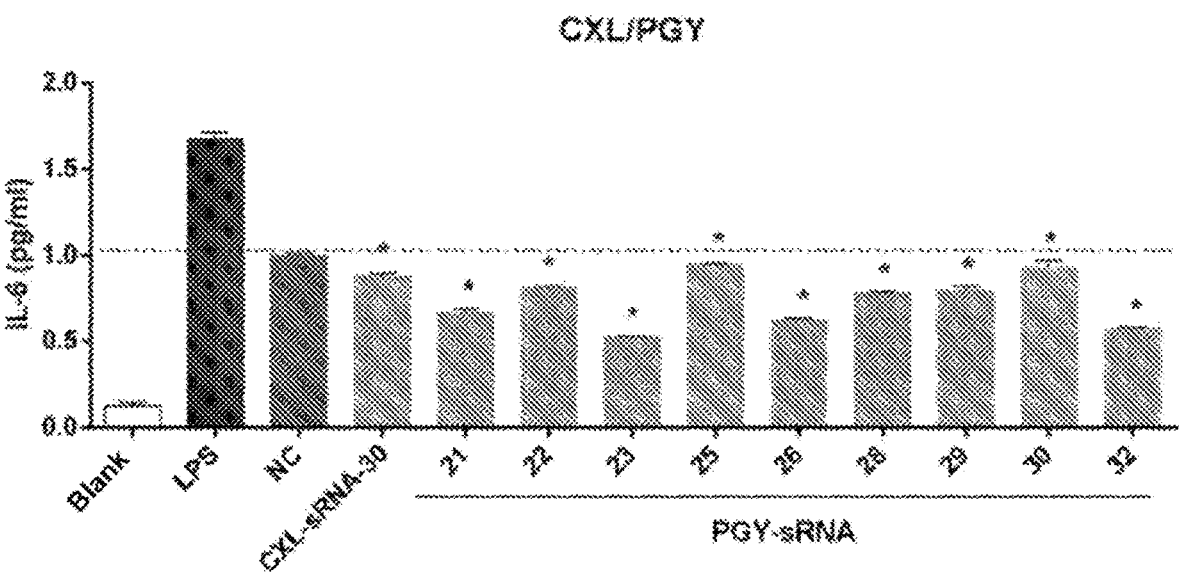
FIG. 10: The expression of the inflammatory factor IL-6 at protein level compared to the control group, in the cell inflammation model after 9 hours of LPS stimulation, with the THP1 cells transfected with the *Andrographis paniculata* (CXL) and *Taraxacum* (PGY) small RNA 24 hours in advance, as specified in the figure.

FIG. 5: The expression of the inflammatory factor IL-6 at protein level compared to the control group, in the cell inflammation model after 9 hours of LPS stimulation, with the THP1 cells transfected with the *Scutellaria barbata* (BZL) small RNA 24 hours in advance, as specified in the figure. FIG. 6: The expression of the inflammatory factor IL-6 at protein level compared to the control group, in the cell inflammation model after 9 hours of LPS stimulation, with the THP1 cells transfected with the *Bupleurum* (CHu) small RNA 24 hours in advance, as specified in the figure. FIG. 7: The expression of the inflammatory factor IL-6 at protein level compared to the control group, in the cell inflammation model after 9 hours of LPS stimulation, with the THP1 cells transfected with *Viola philippica* (DDi), *Scutellaria baicalensis* (HQi), *Lonicera japonica* (JYH), *Fructus forsythiae* (LQi), and *Prunella vulgaris* (XKC) small RNA 24 hours in advance, as specified in the figure. FIG. 8 to FIG. 9: The expression of the inflammatory factor IL-6 at protein level compared to the control group, in the cell inflammation model after 9 hours of LPS stimulation, with the THP1 cells transfected with the *Houttuynia cordata* (YXC) small RNA 24 hours in advance, as specified in the figure. FIG. 10: The expression of the inflammatory factor IL-6 at protein level compared to the control group, in the cell inflammation model after 9 hours of LPS stimulation, with the THP1 cells transfected with the *Andrographis paniculata* (CXL) and *Taraxacum* (PGY) small RNA 24 hours in advance, as specified in the figure. "*" means that unpaired t test P<0.05 was considered statistically significant in statistical analysis, indicating the effect of inhibiting the expression of inflammatory factors in in vitro experiments. The experimental results showed that the small RNAs shown in FIG. 5 to FIG. 10 had significantly higher effect in reducing the protein expression of IL-6 than the NC group. The values in FIG. 5 to FIG. 10 were all values obtained by normalization relative to the NC group. BZL-sRNA-20 inhibited IL-6 protein level very well.

Figure 11:
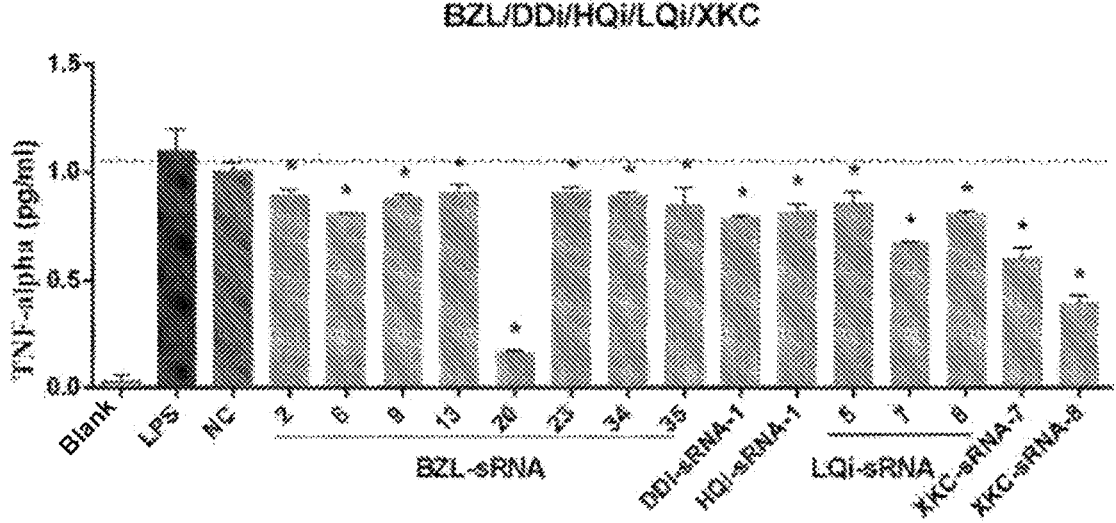
FIG. 11: The expression of the inflammatory factor TNF-alpha at protein level compared to the control group, in the cell inflammation model after 9 hours of LPS stimulation, with the THP1 cells transfected with the *Scutellaria barbata* (BZL), *Viola philippica* (DDi), *Scutellaria baicalensis* (HQi), *Fructus forsythiae* (LQi) and *Prunella vulgaris* (XKC) small RNA 24 hours in advance, as specified in the figure.
Figure 12:
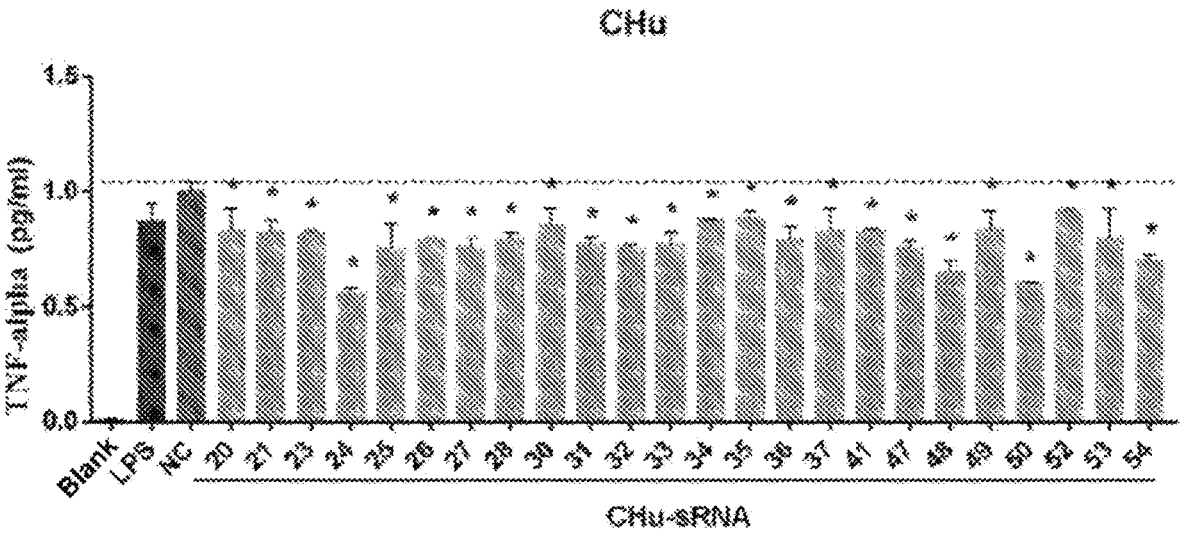
FIG. 12: The expression of the inflammatory factor TNF-alpha at protein level compared to the control group, in the cell inflammation model after 9 hours of LPS stimulation, with the THP1 cells transfected with the *Bupleurum* (CHu) small RNA 24 hours in advance, as specified in the figure.
Figure 13:
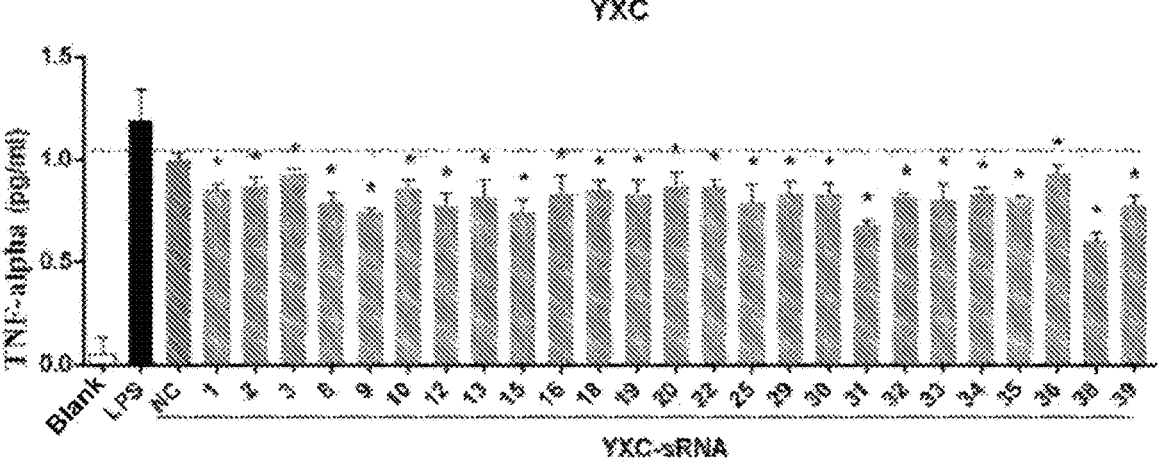
FIG. 13 to FIG. 14: The expression of the inflammatory factor TNF-alpha at protein level compared to the control group, in the cell inflammation model after 9 hours of LPS stimulation, with the THP1 cells transfected with the *Houttuynia cordata* (YXC) small RNA 24 hours in advance, as specified in the figure.
Figure 14:
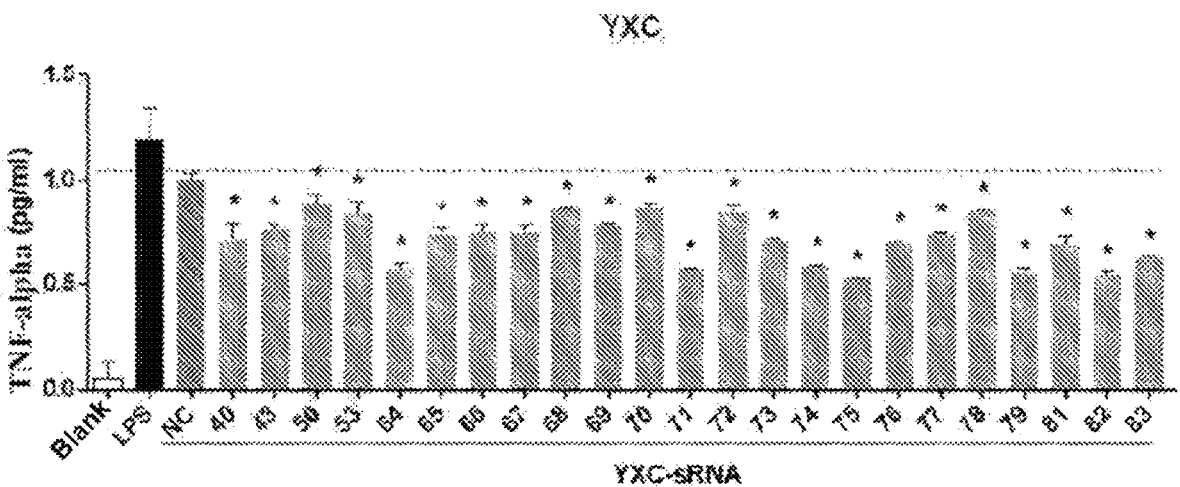
Figure 15:
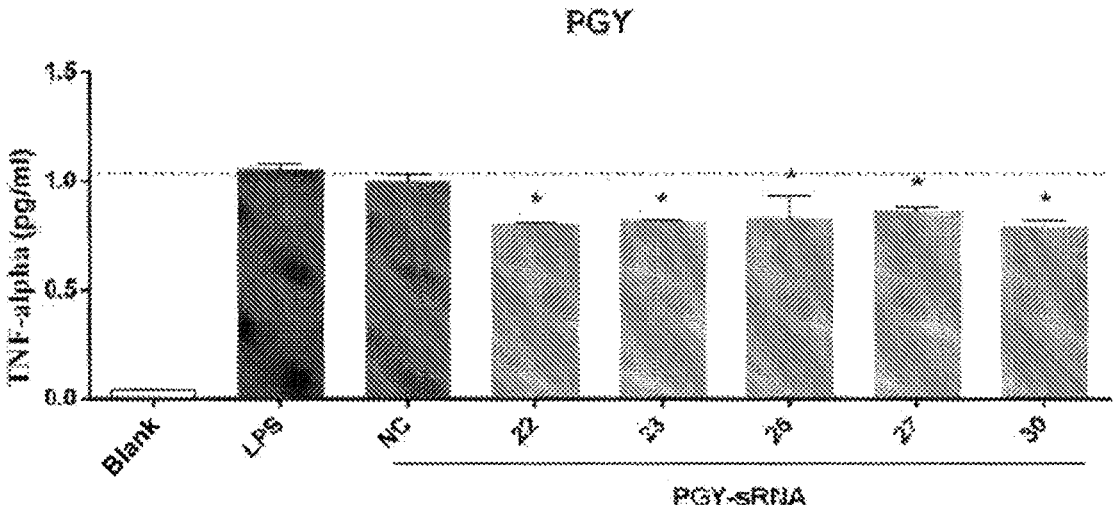
FIG. 15: The expression of the inflammatory factor TNF-alpha at protein level compared to the control group, in the cell inflammation model after 9 hours of LPS stimulation, with the THP1 cells transfected with the *Taraxacum* (PGY) small RNA 24 hours in advance, as specified in the figure.

FIG. 11: The expression of the inflammatory factor TNF-alpha at protein level compared to the control group, in the cell inflammation model after 9 hours of LPS stimulation, with the THP1 cells transfected with *Scutellaria barbata* (BZL), *Viola philippica* (DDi), *Scutellaria baicalensis* (HQi), *Fructus forsythiae* (LQi) and *Prunella vulgaris* (XKC) small RNA 24 hours in advance, as specified in the figure. FIG. 12: The expression of the inflammatory factor TNF-alpha at protein level compared to the control group, in the cell inflammation model after 9 hours of LPS stimulation, with the THP1 cells transfected with the *Bupleurum* (CHu) small RNA 24 hours in advance, as specified in the figure. FIG. 13 to FIG. 14: The expression of the inflammatory factor TNF-alpha at protein level compared to the control group, in the cell inflammation model after 9 hours of LPS stimulation, with the THP1 cells transfected with the *Houttuynia cordata* (YXC) small RNA 24 hours in advance, as specified in the figure. FIG. 15: The expression of the inflammatory factor TNF-alpha at protein level compared to the control group, in the cell inflammation model after 9 hours of LPS stimulation, with the THP1 cells transfected with the *Taraxacum* (PGY) small RNA 24 hours in advance, as specified in the figure. "*" means that unpaired t test P<0.05 was considered statistically significant in statistical analysis, indicating the effect of inhibiting the expression of inflammatory factors in in vitro experiments. The experimental results showed that the small RNAs shown in FIG. 11 to FIG. 15 had significantly higher effect in reducing the protein expression of TNF-alpha than the NC group. The values in FIG. 11 to FIG. 15 were all values obtained by normalization relative to the NC group. BZL-sRNA-20 had the smallest value in ELISA of the inflammatory factor TNF-alpha, indicating the best effect on inhibiting TNF-alpha protein level among the small RNAs tested.

2. As Mentioned Above in "Functional Experiment of Artificially Synthesized Small RNAs at mRNA Level Verified by Using the THP-1 Cell Model Stimulated by LPS", the Small RNAs as Specified in FIG. 14 to FIG. 33 Were Used for Experiment.

Figure 16:
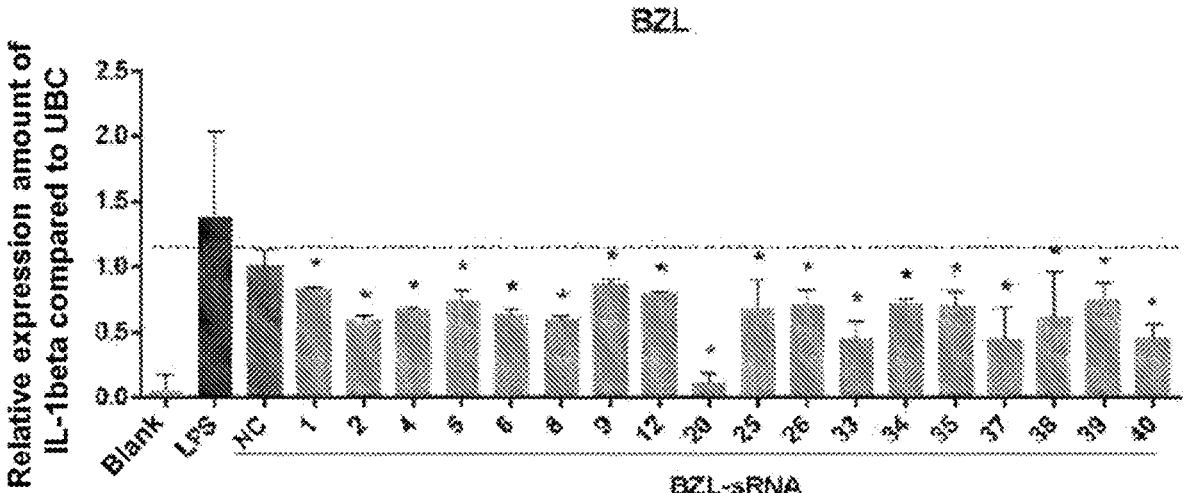
FIG. 16: The expression of the inflammatory factor IL-1beta at mRNA level compared to the control group, in the cell inflammation model after 9 hours of LPS stimulation, with the THP1 cells transfected with the *Scutellaria barbata* (BZL) small RNA 24 hours in advance, as specified in the figure.
Figure 17:
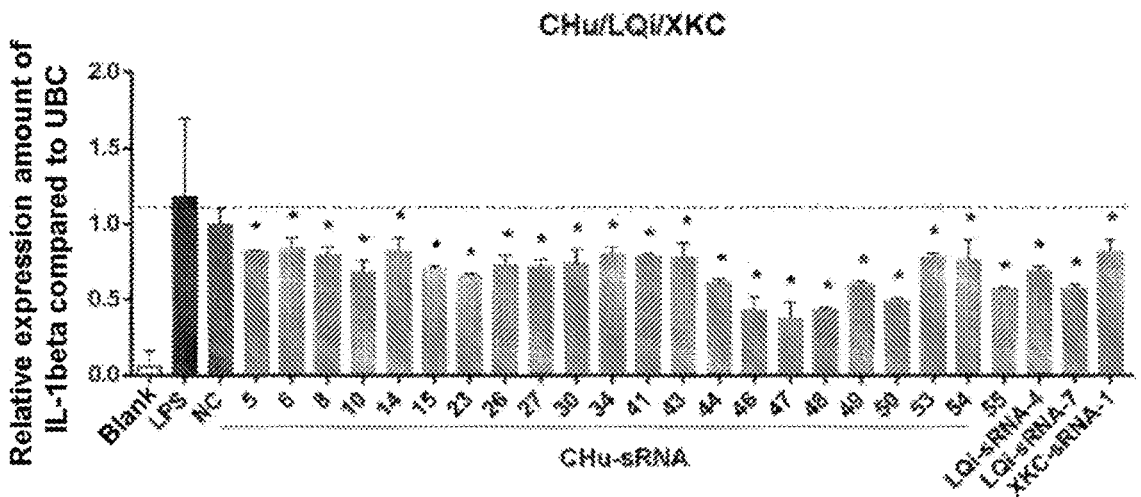
FIG. 17: The expression of the inflammatory factor IL-1beta at mRNA level compared to the control group, in the cell inflammation model after 9 hours of LPS stimulation, with the THP1 cells transfected with the *Bupleurum* (CHu), *Fructus forsythiae* (LQi) and *Houttuynia cordata* (YXC) small RNA 24 hours in advance, as specified in the figure.
Figure 18:
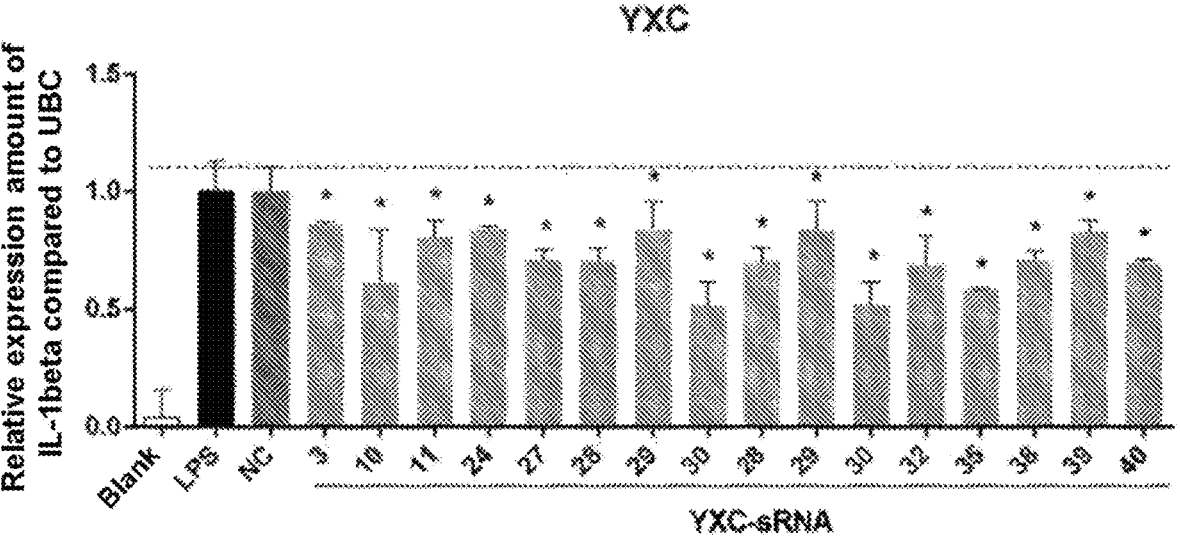
FIG. 18 to FIG. 19: The expression of the inflammatory factor IL-1beta at mRNA level compared to the control
Figure 19:
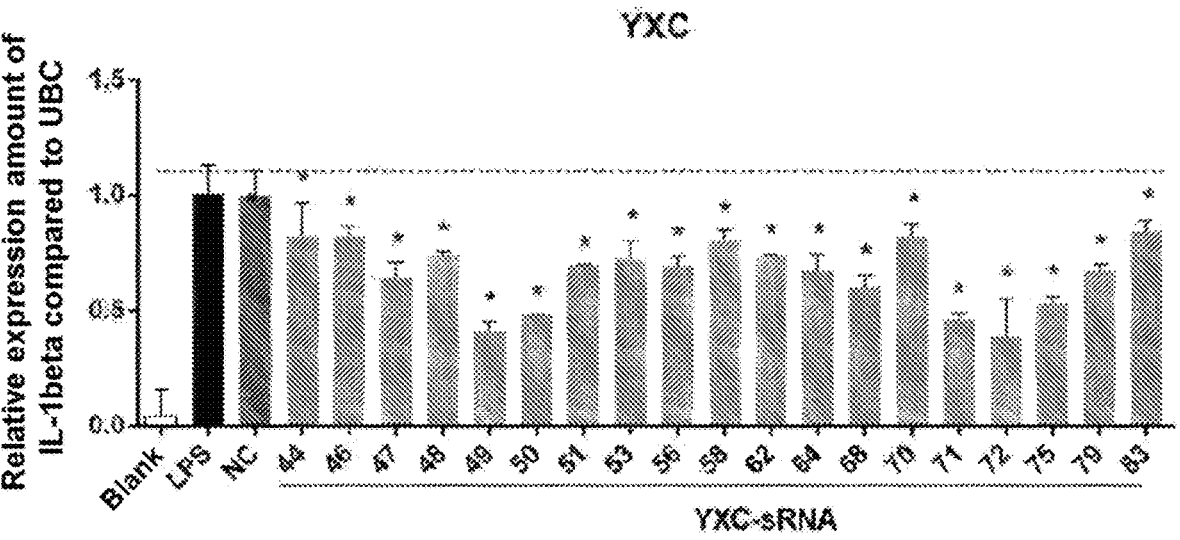

FIG. 16: The expression of the inflammatory factor IL-1beta at mRNA level (relative expression level of IL-1beta compared to UBC) compared to the control group, in the cell inflammation model after 9 hours of LPS stimulation, with the THP1 cells transfected with the *Scutellaria barbata* (BZL) small RNA 24 hours in advance, as specified in the figure. FIG. 17: The expression of the inflammatory factor IL-1beta at mRNA level compared to the control group, in the cell inflammation model after 9 hours of LPS stimulation, with the THP1 cells transfected with the *Bupleurum* (CHu), *Fructus forsythiae* (LQi) and *Houttuynia cordata* (YXC) small RNA 24 hours in advance, as specified in the figure. FIG. 18 to FIG. 19: The expression of the inflammatory factor IL-1beta at mRNA level compared to the control group, in the cell inflammation model after 9 hours of LPS stimulation, with the THP1 cells transfected with the *Houttuynia cordata* (YXC) small RNA 24 hours in advance, as specified in the figure. FIG. 20: The expression of the inflammatory factor IL-1beta at mRNA level compared to the control group, in the cell inflammation model after 9 hours of LPS stimulation, with the THP1 cells transfected with the *Taraxacum* (PGY) small RNA 24 hours in advance, as specified in the figure. "*" means that unpaired t test P<0.05 was considered statistically significant in statistical analysis, indicating the effect of inhibiting the expression of inflammatory factors in in vitro experiments. The experimental results showed that the small RNAs shown in FIG. 16 to FIG. 20 had significantly higher effect in reducing the mRNA expression of IL-1beta than the NC group. The values in FIG. 16 to FIG. 20 were all values obtained by normalization relative to the NC group. BZL-sRNA-20 had the smallest value in qPCR of the inflammatory factor IL-1beta, indicating the best effect on inhibiting IL-1beta mRNA level among the small RNAs tested.

FIG. 21 to FIG. 22: The expression of the inflammatory factor IL-6 at mRNA level compared to the control group, in the cell inflammation model after 9 hours of LPS stimulation, with the THP1 cells transfected with the *Scutellaria barbata* (BZL) small RNA 24 hours in advance, as specified in the figure. FIG. 23 to FIG. 24: The expression of the inflammatory factor IL-6 at mRNA level compared to the control group, in the cell inflammation model after 9 hours of LPS stimulation, with the THP1 cells transfected with the *Bupleurum* (CHu) small RNA 24 hours in advance, as specified in the figure. FIG. 25: The expression of the inflammatory factor IL-6 at mRNA level compared to the control group, in the cell inflammation model after 9 hours of LPS stimulation, with the THP1 cells transfected with the *Viola philippica* (DDi), *Scutellaria baicalensis* (HQi), *Lonicera japonica* (JYH), *Fructus forsythiae* (LQi) and *Prunella vulgaris* (XKC) small RNA 24 hours in advance, as specified in the figure. FIG. 26 to FIG. 27: The expression of the inflammatory factor IL-6 at mRNA level compared to the NC group, in the cell inflammation model after 9 hours of LPS stimulation, with the THP-1 cells transfected with the *Houttuynia cordata* (YXC) small RNA 24 hours in advance, as specified in the figure. FIG. 28: The expression of the inflammatory factor IL-6 at mRNA level compared to the NC group, in the cell inflammation model after 9 hours of LPS stimulation, with the THP1 cells transfected with the *Andrographis paniculata* (CXL) and *Taraxacum* (PGY) small RNA 24 hours in advance, as specified in the figure. "*" means that unpaired t test P<0.05 was considered statistically significant in statistical analysis, indicating the effect of inhibiting the expression of inflammatory factors in in vitro experiments. The experimental results showed that the small RNAs shown in FIG. 21 to FIG. 28 had significantly higher effect in reducing the mRNA expression of IL-6 than the NC group. The values in FIG. 21 to FIG. 22 were all values obtained by normalization relative to the NC group. BZL-sRNA-20 had relatively low value in qPCR of the inflammatory factor IL-6, indicating a relatively favorable effect on inhibiting IL-6 mRNA level among the small RNAs tested.

FIG. 29: The expression of the inflammatory factor TNF-alpha at mRNA level (relative expression level of TNF-alpha compared to UBC) compared to the NC group, in the cell inflammation model after 9 hours of LPS stimulation, with the THP1 cells transfected with the *Scutellaria barbata* (BZL) and *Bupleurum* (CHu) small RNA 24 hours in advance, as specified in the figure. FIG. 30: The expression of the inflammatory factor TNF-alpha at mRNA level compared to the NC group, in the cell inflammation model after 9 hours of LPS stimulation, with the THP1 cells transfected with the *Viola philippica* (DDi), *Lonicera japonica* (JYH), *Fructus forsythiae* (LQi) and *Prunella vulgaris* (XKC) small RNA 24 hours in advance, as specified in the figure. FIG. 31 to FIG. 32: The expression of the inflammatory factor TNF-alpha at mRNA level compared to the NC group, in the cell inflammation model after 9 hours of LPS stimulation, with the THP1 cells transfected with the *Houttuynia cordata* (YXC) small RNA 24 hours in advance, as specified in the figure. FIG. 33: The expression of the inflammatory factor TNF-alpha at mRNA level compared to the NC group, in the cell inflammation model after 9 hours of LPS stimulation, with the THP1 cells transfected with the *Taraxacum* (PGY) small RNA 24 hours in advance, as specified in the figure. "*" means that unpaired t test $P<0.05$ was considered statistically significant in statistical analysis, indicating the effect of inhibiting the expression of inflammatory factors in in vitro experiments. The experimental results showed that the small RNAs shown in FIG. 29 to FIG. 33 had significantly higher effect in reducing the mRNA expression of TNF-alpha than the NC group. The values in FIG. 29 to FIG. 33 were all values obtained by normalization relative to the NC group. BZL-sRNA-20 had the smallest value in qPCR of the inflammatory factor TNF-alpha, indicating the best effect on inhibiting TNF-alpha mRNA level among the small RNAs tested.

Figure 34N:
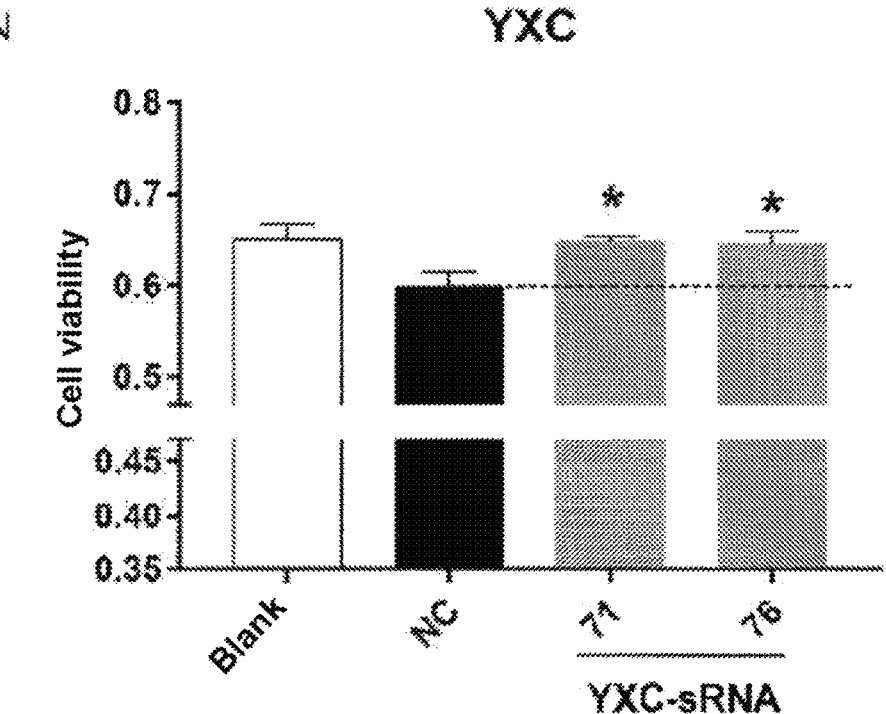

3. The Above-Mentioned MTS Cell Viability Detection by Using mRNAs Shown in FIG. 34A to FIG. 34N FIG. 34A-FIG. 34C: BZL: after H5N1 (0.4 M.O.I) infection, the rescue results of *Scutellaria barbata* (BZL) small RNA on cell death, as specified in the figure. FIG. 34D-FIG. 34G: CHu: after H5N1 (0.4 M.O.I) infection, the rescue results of the *Bupleurum* (CHu) small RNA on cell death, as specified in the figure. FIG. 34H: LQi/XKC: after H5N1 (0.4 M.O.I) infection, the rescue results of the *Fructus forsythiae* (LQi)/*Prunella vulgaris* (XKC) small RNA on cell death, as specified in the figure. FIG. 34I: XKC/YXC: after H5N1 (0.4 M.O.I) infection, the rescue results of the *Prunella vulgaris* (XKC)/*Houttuynia cordata* (YXC) small RNA on cell death, as specified in the figure. FIG. 34J-FIG. 34N: YXC: after H5N1 (0.4 M.O.I) infection, the rescue results of *Houttuynia cordata* (YXC) small RNA on cell death, as specified in the figure. In FIG. 34, unpaired t test $P<0.05$ was considered statistically significant in statistical analysis, indicating the rescuing effect on cell death caused by H5N1 infection. "*" represents $P<0.05$ in unpaired t test, and "" represents $P<0.01$ in unpaired t test. As shown in FIG. 34A-FIG. 34N, the small RNAs as specified in the figure significantly improved the cell survival rate, showing a more obvious effect of rescuing cell death compared with the NC group. The values in FIG. 34A-FIG. 34**N were all values obtained by normalization relative to the NC group. Among them, BZL-sRNA-20 was very effective in rescuing cell death.

Example 2: Verification of the Effect of the Mixtures in Table 2

As Mentioned Above in "Functional Experiment of Artificially Synthesized Small RNA Mixtures at Protein Level Verified by Using the THP-1 Cell Model Stimulated by LPS", the Effects of the Mixtures in Table 2 were Verified.

FIG. 35: The expression of the inflammatory factor IL-1beta at protein level compared to the NC group, in the cell inflammation model after 9 hours of LPS stimulation, with the THP1 cells transfected with the small RNA mixtures 24 hours in advance, as specified in the figure. The mixing ratio of BZL-sRNA-20 to other small RNAs was 2:1 (v/v). "*" means that unpaired t test $P<0.05$ was considered statistically significant in statistical analysis, indicating the effect of inhibiting the expression of inflammatory factors in in vitro experiments. The experimental results showed that the small RNA mixtures shown in FIG. 28 had significantly higher effect in reducing IL-1beta protein level than the NC group, among which MIX20, 24, 33, 36 and 42 had significantly higher effect in reducing IL-1beta protein level than the BZL-sRNA-20 group. The values in FIG. 35 were all values obtained by normalization relative to the NC group. For the mixture in the figure that was comparable effect in reducing IL-1beta protein level to that of BZL-sRNA-20 group, as the molar concentration of BZL-sRNA-20 small RNA in the mixture in the test cell liquid was much lower than that in the BZL-sRNA-20 group, this indicated that the various small RNAs in the mixture also had a favorable synergistic effect in reducing IL-1beta protein level.

FIG. 36 to FIG. 37: The expression of the inflammatory factor IL-6 at protein level compared to the NC group, in the cell inflammation model after 9 hours of LPS stimulation, with the THP1 cells transfected with the small RNA mixtures 24 hours in advance, as specified in the figure, wherein the mixing ratio of BZL-sRNA-20 to other small RNAs was 2:1 (v/v). "*" means that unpaired t test $P<0.05$ was considered statistically significant in statistical analysis, indicating the effect of inhibiting the expression of inflammatory factors in in vitro experiments. The results showed that the small RNA mixtures shown in FIG. 36 to FIG. 37 had significantly higher effect in reducing IL-6 protein level than the NC group, among which those in FIG. 36 (except MIX10), and MIX22, 25-28, 30-33 and 37-39 in FIG. 37 had significantly higher effect in reducing IL-6 protein level than the BZL-sRNA-20 group. The values in FIG. 36 to FIG. 37 were all values obtained by normalization relative to the NC group. Mixture 10 was comparable to the BZL-sRNA-20 group in reducing IL-1beta protein level. As the molar concentration of BZL-sRNA-20 small RNA in Mixture 10 in the test cell liquid was much lower than that in the BZL-sRNA-20 group, this indicated that the various small RNAs in Mixture 10 also had a favorable synergistic effect in reducing IL-6 protein level.

FIG. 38: The expression of the inflammatory factor IL-1beta at mRNA level compared to the NC group, in the cell inflammation model after 9 hours of LPS stimulation, with the THP1 cells transfected with the small RNA mixtures 24 hours in advance, as specified in the figure. The mixing ratio of BZL-sRNA-20 to other small RNAs was 2:1 (v/v). "*" means that unpaired t test $P<0.05$ was considered statistically significant in statistical analysis, indicating the effect of inhibiting the expression of inflammatory factors in in vitro experiments. The experimental results showed that the small RNA mixtures shown in FIG. 38 had significantly higher effect in reducing IL-1beta mRNA level than the NC group, among which MIX23, 42 and 43 had significantly higher effect in reducing IL-1beta mRNA level than the BZL-sRNA-20 group. The values in FIG. 38 were all values obtained by normalization relative to the NC group. For the mixture that was comparable to the BZL-sRNA-20 group in reducing IL-1beta mRNA level, as the molar concentration of BZL-sRNA-20 small RNA in the mixture in the test cell liquid was much lower than that in the BZL-sRNA-20 group, this indicated that the various small RNAs in the mixture also have a favorable synergistic effect in reducing IL-1beta mRNA level.

FIG. 39 to FIG. 40: The expression of the inflammatory factor IL-6 at mRNA level compared to the NC group, in the cell inflammation model after 9 hours of LPS stimulation, with the THP1 cells transfected with the small RNA mixtures 24 hours in advance, as specified in the figure, the mixing ratio of BZL-sRNA-20 to other small RNAs was 2:1 (v/v). "*" means that unpaired t test P<0.05 was considered statistically significant in statistical analysis, indicating the effect of inhibiting the expression of inflammatory factors in in vitro experiments. The results showed that the small RNA mixtures shown in FIG. 31 had significantly higher effect in reducing IL-6 mRNA level than the NC group, among which those in FIG. 39 (except MIX10 and 14), and MIX25-27, 30, 31 and 38 in FIG. 40 had significantly higher effect in reducing IL-6 mRNA level than the BZL-sRNA-20 group. The values in FIG. 39 to FIG. 40 were all values obtained by normalization relative to the NC group. For the mixture that was comparable to the BZL-sRNA-20 group in reducing IL-6 mRNA level, as the molar concentration of BZL-sRNA-20 small RNA in the mixture in the test cell liquid was much lower than that in the BZL-sRNA-20 group, this indicated that the various small RNAs in the mixture had a favorable synergistic effect in reducing IL-6 mRNA level.

FIG. 41: The expression of the inflammatory factor TNF-alpha at mRNA level compared to the NC group, in the cell inflammation model after 9 hours of LPS stimulation, with the THP1 cells transfected with the small RNA mixtures 24 hours in advance, as specified in the figure, the mixing ratio of BZL-sRNA-20 to other small RNAs was 2:1 (v/v). "*" means that unpaired t test P<0.05 was considered statistically significant in statistical analysis, indicating the effect of inhibiting the expression of inflammatory factors in in vitro experiments. The experimental results showed that the small RNA mixtures shown in FIG. 41 had significantly higher effect in reducing TNF-alpha mRNA level than the NC group, among which MIX32, 33, 40 and 42 had significantly higher effect in reducing TNF-alpha mRNA level than the BZL-sRNA-20 group. The values in FIG. 41 were all values obtained by normalization relative to the NC group. A mixture shows comparable effect in reducing TNF-alpha mRNA level to that of BZL-sRNA-20 group. As the molar concentration of BZL-sRNA-20 small RNA in the mixture in the test cell liquid was much lower than that in the BZL-sRNA-20 group, this indicated that the various small RNAs in the mixture also had a favorable synergistic effect in reducing TNF-alpha mRNA level.

Example 3: The in Vivo Effect of BZL-sRNA-20

The Experiment was Performed as Mentioned Above in "Experiment to Verify the Anti-Inflammatory Effect of BZL-sRNA-20 In Vivo".

FIG. 42: The expression of the inflammatory factor TNF-alpha at protein level compared to the NC group, in the alveolar lavage fluid of the animal inflammation model after 9 hours of LPS stimulation, wherein the mice were gavaged with small RNA, three days in advance. "*" means that unpaired t test P<0.05 was considered statistically significant in statistical analysis, indicating that BZL-sRNA-20 had the effect of inhibiting the expression of inflammatory factor TNF-alpha in in vivo experiments.

FIG. 43: The expression of the inflammatory factor IL-6 at mRNA level compared to the NC group, in the exfoliated lung cells of the animal inflammation model after 9 hours of LPS stimulation, wherein the mice were gavaged with small RNA, three days in advance. "**" means that unpaired t test P<0.01 was considered statistically significant in statistical analysis, indicating the effect of inhibiting the expression of inflammatory factor IL-6 in in vivo experiments.

Example 4: Classification of Target Genes Down-Regulated by Small RNA and the Pathways or Biological Processes they Involved, According to the Results of Transcriptome Sequencing of Artificially Synthesized Small RNAs Verified by Using the THP-1 Cell Model Stimulated by LPS Classification tabulation of 192 small RNA target genes and the pathways or biological processes they involved was performed as mentioned above.

TABLE 3

Classification table of small RNA target genes and the pathways
or biological processes they involved, obtained by calculation of
transcriptome sequencing of 192 small RNAs selected from Table 1.
This table shows that inflammatory factors and/or H5N1 infection
were inhibited by small RNAs through: the mechanism of action,
targets of action and pathways of action of chemokine related
signaling pathways, JAK/STAT signal transduction, amino acid
metabolism, mRNA activation and function, coenzyme metabolism,
small nucleolar RNA, etc., suggesting that different small RNAs had
the possibility of synergistic effects in related signaling
pathways and target genes.

| Positioning | Small RNA type |
|---|---|
| Chemokine related signaling pathway | (78) CHu-sRNA-34; CXL-sRNA-30; YXC-sRNA-75; PGY-sRNA-21; YXC-sRNA-17; YXC-sRNA-25; YXC-sRNA-70; CHu-sRNA-42; CHu-sRNA-45; CHu-sRNA-46; CHu-sRNA-47; YXC-sRNA-76; PGY-sRNA-30; YXC-sRNA-31; YXC-sRNA-47; YXC-sRNA-56; YXC-sRNA-68; YXC-sRNA-69; YXC-sRNA-71; YXC-sRNA-72; YXC-sRNA-78; YXC-sRNA-79; YXC-sRNA-81; CHu-sRNA-29; CHu-sRNA-32; CHu-sRNA-43; PGY-sRNA-24; PGY-sRNA-27; BZL-sRNA-39; BZL-sRNA-13; BZL-sRNA-16; BZL-sRNA-21; CHu-sRNA-4; CHu-sRNA-51; CHu-sRNA-6; CHu-sRNA-7; CHu-sRNA-8; PGY-sRNA-22; PGY-sRNA-26; PGY-sRNA-29; XKC-sRNA-2; XKC-sRNA-3; XKC-sRNA-4; YXC-sRNA-13; YXC-sRNA-15; YXC-sRNA-16; YXC-sRNA-19; YXC-sRNA-32; YXC-sRNA-35; YXC-sRNA-36; YXC-sRNA-37; YXC-sRNA-38; YXC-sRNA-41; YXC-sRNA-50; YXC-sRNA-57; YXC-sRNA-58; YXC-sRNA-64; YXC-sRNA-74; YXC-sRNA-7; YXC-sRNA-80; |

TABLE 3-continued

Classification table of small RNA target genes and the pathways
or biological processes they involved, obtained by calculation of
transcriptome sequencing of 192 small RNAs selected from Table 1.
This table shows that inflammatory factors and/or H5N1 infection
were inhibited by small RNAs through: the mechanism of action,
targets of action and pathways of action of chemokine related
signaling pathways, JAK/STAT signal transduction, amino acid
metabolism, mRNA activation and function, coenzyme metabolism,
small nucleolar RNA, etc., suggesting that different small RNAs had
the possibility of synergistic effects in related signaling
pathways and target genes.

| Positioning | Small RNA type |
|---|---|
| | YXC-sRNA-82; YXC-sRNA-83; YXC-sRNA-8; PGY-sRNA-6; CHu-sRNA-55; LQi-sRNA-7; BZL-sRNA-6; XKC-sRNA-1; YXC-sRNA-43; BZL-sRNA-34; BZL-sRNA-7; PGY-sRNA-31; YXC-sRNA-5; PGY-sRNA-23; YXC-sRNA-46; YXC-sRNA-33; YXC-sRNA-9; HQi-sRNA-2; |
| JAK/STAT signaling transduction | (63)CHu-sRNA-27; YXC-sRNA-65; LQi-sRNA-1; CHu-sRNA-30; CHu-sRNA-48; CHu-sRNA-41; LQi-sRNA-3; YXC-sRNA-39; YXC-sRNA-34; JYH-sRNA-1; CHu-sRNA-38; CHu-sRNA-20; CHu-sRNA-21; CHu-sRNA-33; CHu-sRNA-50; HQi-sRNA-1; LQi-sRNA-8; CHu-sRNA-35; CHu-sRNA-25; CHu-sRNA-23; CHu-sRNA-36; CHu-sRNA-40; DDi-sRNA-1; CHu-sRNA-24; CHu-sRNA-37; CHu-sRNA-5; CHu-sRNA-52; CHu-sRNA-54; YXC-sRNA-63; BZL-sRNA-28; BZL-sRNA-29; BZL-sRNA-31; BZL-sRNA-32; BZL-sRNA-33; BZL-sRNA-35; BZL-sRNA-36; BZL-sRNA-37; BZL-sRNA-38; BZL-sRNA-41; BZL-sRNA-26; BZL-sRNA-15; BZL-sRNA-25; BZL-sRNA-27; BZL-sRNA-30; BZL-sRNA-3; CHu-sRNA-2; XKC-sRNA-5; XKC-sRNA-7; XKC-sRNA-8; YXC-sRNA-10; YXC-sRNA-18; YXC-sRNA-22; YXC-sRNA-24; BZL-sRNA-8; CHu-sRNA-10; PGY-sRNA-32; LQi-sRNA-4; LQi-sRNA-5; CHu-sRNA-26#1; CHu-sRNA-26#2; CHu-sRNA-31; CHu-sRNA-53; LQi-sRNA-6; |
| Glycine, serine, cysteine and threonine metabolism | (25)CXL-sRNA-21; BZL-sRNA-1; BZL-sRNA-10; BZL-sRNA~11; BZL-sRNA-12; BZL-sRNA-17; BZL-sRNA-18; BZL-sRNA-19; BZL-sRNA-2; BZL-sRNA-20; BZL-sRNA-22; BZL-sRNA-23; BZL-sRNA-4; BZL-sRNA-40; BZL-sRNA-42; BZL-sRNA-9; CHu-sRNA-1; XKC-sRNA-6; YXC-sRNA-1; YXC-sRNA-12; YXC-sRNA-20; YXC-sRNA-4; YXC-sRNA-40; YXC-sRNA-42; YXC-sRNA-44; |
| Activation of the mRNA upon binding of the cap-binding complex and eIFs, and subsequent binding to 43S, organism-specific biosystem) (from REACTOME) | (11)CHu-sRNA-28; CXL-sRNA-7; HJT-sRNA-3; HJT-sRNA-A2; HJT-sRNA-H3; PGY-sRNA-18; YXC-sRNA-2; YXC-sRNA-29; YXC-sRNA-3; YXC-sRNA-30; Chu-sRNA-49; |
| Ubiquinone metabolism | (9)YXC-sRNA-54; YXC-sRNA-51; YXC-sRNA-53; YXC-sRNA-77; PGY-sRNA-28; YXC-sRNA-49; YXC-sRNA-62; YXC-sRNA-52; YXC-sRNA-73; |
| Small nucleolar RNA host gene | (4)YXC-sRNA-55; CXL-sRNA-17; CXL-sRNA-8; PGY-sRNA-25; |

The genes in the following table correspond to the pathways in the corresponding rows in the above table.

| sRNA | Associated genes |
|------|------------------|
| BZL-sRNA-1 | ['SERA', 'PSAT'] |
| BZL-sRNA-2 | |
| BZL-sRNA-3 | ['IFI27'] |
| BZL-sRNA-4 | |
| BZL-sRNA-6 | ['CCL3L1', 'IL-8'] |
| BZL-sRNA-7 | ['CCL3L1', 'IL-8', 'MIP-1-beta'] |
| BZL-sRNA-8 | ['IFI27', 'IFI6'] |
| BZL-sRNA-9 | ['SERA', 'PSAT'] |
| BZL-sRNA-10 | ['SERA', 'PSAT'] |
| BZL-sRNA-11 | ['SERA', 'PSAT'] |
| BZL-sRNA-12 | ['SERA', 'PSAT'] |
| BZL-sRNA-13 | ['CCL3L1'] |
| BZL-sRNA-15 | ['IFI27'] |
| BZL-sRNA-16 | ['CCL3L1'] |
| BZL-sRNA-17 | ['SERA', 'PSAT'] |
| BZL-sRNA-18 | ['SERA', 'PSAT'] |
| BZL-sRNA-19 | ['SERA', 'PSAT'] |
| BZL-sRNA-20 | ['SERA', 'PSAT'] |
| BZL-sRNA-21 | ['CCL3L1'] |
| BZL-sRNA-22 | |
| BZL-sRNA-23 | ['SERA', 'PSAT'] |
| BZL-sRNA-25 | ['IFI27'] |
| BZL-sRNA-26 | ['IFI27L2'] |
| BZL-sRNA-27 | ['IFI27'] |
| BZL-sRNA-28 | ['IFI6', 'IFI27'] |
| BZL-sRNA-29 | ['IFI6', 'IFI27'] |
| BZL-sRNA-30 | ['SERA', 'PSAT'] |
| BZL-sRNA-31 | ['IFI6', 'IFI27'] |
| BZL-sRNA-32 | ['IFI6', 'IFI27'] |
| BZL-sRNA-33 | ['IFI6', 'IFI27'] |
| BZL-sRNA-34 | ['CCL3L1', 'IL-8', 'MIP-1-beta'] |
| BZL-sRNA-35 | ['IFI6', 'IFI27'] |
| BZL-sRNA-36 | ['IFI6', 'IFI27'] |
| BZL-sRNA-37 | ['IFI6', 'IFI27'] |
| BZL-sRNA-38 | ['IFI6', 'IFI27'] |
| BZL-sRNA-39 | ['CCL3L1'] |
| BZL-sRNA-40 | ['SERA', 'PSAT'] |
| BZL-sRNA-41 | ['IFI6', 'IFI27'] |
| BZL-sRNA-42 | ['SERA', 'PSAT'] |
| CHu-sRNA-1 | ['SERA', 'PSAT'] |
| CHu-sRNA-10 | ['IFI27', 'IFI6'] |
| CHu-sRNA-20 | ['IL1RN'] |
| CHu-sRNA-21 | ['IL1RN'] |
| CHu-sRNA-23 | ['IL1RN', 'GBP1', 'IP10'] |
| CHu-sRNA-24 | ['IL1RN', 'GBP1', 'IP10'] |
| CHu-sRNA-25 | ['IL1RN', 'IP10', 'CCL2', 'GBP1'] |
| CHu-sRNA-26#1 | ['GBP1', 'IP10'] |
| CHu-sRNA-26#2 | ['GBP1', 'IP10'] |
| CHu-sRNA-27 | ['I-TAC', 'IP10', 'HIF1A', 'GBP1'] |
| CHu-sRNA-28 | ['EIF3CL'] |

-continued

| Identifier | Associated genes |
|---|---|
| CHu-sRNA-29 | ['CCL3L1', 'CCL8'] |
| CHu-sRNA-2 | ['IFI27'] |
| CHu-sRNA-30 | ['I-TAC', 'IL1RN', 'GBP1', 'MIG', 'IP10'] |
| CHu-sRNA-31 | ['GBP1', 'IP10'] |
| CHu-sRNA-32 | ['CCL3L1', 'CCL8'] |
| CHu-sRNA-33 | ['IL1RN'] |
| CHu-sRNA-34 | ['CCL8'] |
| CHu-sRNA-35 | ['IL1RN', 'IP10'] |
| CHu-sRNA-36 | ['IL1RN', 'GBP1'] |
| CHu-sRNA-37 | ['IL1RN', 'GBP1', 'IP10'] |
| CHu-sRNA-38 | ['CCL3L1'] |
| CHu-sRNA-4 | ['CCL3L1'] |
| CHu-sRNA-40 | ['IL1RN', 'GBP1'] |
| CHu-sRNA-41 | ['I-TAC', 'IL1RN', 'GBP1', 'IP10'] |
| CHu-sRNA-42 | ['CCL8'] |
| CHu-sRNA-43 | ['CCL3L1', 'CCL8'] |
| CHu-sRNA-45 | ['CCL8'] |
| CHu-sRNA-46 | ['CCL8'] |
| CHu-sRNA-47 | ['CCL8'] |
| CHu-sRNA-48 | ['I-TAC', 'IL1RN', 'GBP1', 'MIG', 'IP10'] |
| CHu-sRNA-49 | ['EIF3CL'] |
| CHu-sRNA-5 | ['IP10']; ['IL1RN', 'GBP1', 'IP10'] |
| CHu-sRNA-50 | ['IL1RN'] |
| CHu-sRNA-51 | ['CCL3L1'] |
| CHu-sRNA-52 | ['I-TAC', 'IL1RN', 'GBP1', 'IP10'] |
| CHu-sRNA-53 | |
| CHu-sRNA-54 | |
| CHu-sRNA-55 | ['CCL3L1', 'MIP-1-beta'] |
| CHu-sRNA-6 | ['CCL3L1'] |
| CHu-sRNA-7 | ['CCL3L1'] |
| CHu-sRNA-8 | ['CCL3L1'] |
| CXL-sRNA-17 | ['SNHG8'] |
| CXL-sRNA-21 | ['IL1RN'] |
| CXL-sRNA-30 | ['CCL4'] |
| CXL-sRNA-7 | ['IL1RN', 'GBP1', 'IP10'] |
| CXL-sRNA-8 | ['GBP1', 'IP10'] |
| DDi-sRNA-1 | ['IL1RN', 'CCL2'] |
| HJT-sRNA-3 | ['EIF3CL'] |
| HJT-sRNA-A2 | ['EIF3CL'] |
| HJT-sRNA-H3 | ['IL1RN'] |
| HQi-sRNA-1 | ['IL1RN'] |
| HQi-sRNA-2 | ['CCL8'] |
| JYH-sRNA-1 | ['ISG54', 'RSAD2', 'HIF1A', 'I-TAC', 'MIG', 'IP10', 'GBP1', 'ERAP140'] |
| LQi-sRNA-1 | ['I-TAC', 'IL1RN', 'MIG', 'GBP1', 'IP10'] |
| LQi-sRNA-3 | ['I-TAC', 'Apo-2L (TNFSF10)', 'MIG', 'IP10', 'IRF1', 'CCL2', 'TAP1 (PSF1)', 'GBP1'] |
| LQi-sRNA-4 | ['GBP1'] |
| LQi-sRNA-5 | ['GBP1'] |

Additional values shown: ['SERA', 'SHMT2', 'PSAT']; ['SNHG8']; ['EIF3CL']

-continued

| sRNA | Associated genes |
| --- | --- |
| LQi-sRNA-6 | ['GBP1', 'IP10'] |
| LQi-sRNA-7 | ['CCL3L1', 'MIP-1-beta', 'MIP-1-alpha', 'CCL8'] |
| LQi-sRNA-8 | ['IL1RN', 'ISG54'] |
| PGY-sRNA-18 | ['EIF3CL'] |
| PGY-sRNA-22 | ['CCL3L1'] |
| PGY-sRNA-23 | ['CCL2', 'CCL13', 'MIP-1-beta', 'CCL8'] |
| PGY-sRNA-24 | ['CCL3L1', 'CCL8'] |
| PGY-sRNA-25 | ['SNHG6'] |
| PGY-sRNA-26 | ['CCL3L1'] |
| PGY-sRNA-27 | ['CCL3L1'] |
| PGY-sRNA-28 | ['NDUFB1'] |
| PGY-sRNA-29 | ['CCL3L1'] |
| PGY-sRNA-30 | ['CCL4L2'] |
| PGY-sRNA-31 | ['CCL3L1', 'CCL4L2'] |
| PGY-sRNA-32 | ['IFI27', 'IFI6', 'CCL2'] |
| PGY-sRNA-6 | ['CCL3L1', 'TNF-alpha', 'CCL2', 'CCL13', 'MIP-1-beta', 'CCL8'] |
| XKC-sRNA-1 | ['CCL3L1', 'IL-8'] |
| XKC-sRNA-2 | ['CCL3L1'] |
| XKC-sRNA-3 | ['CCL3L1'] |
| XKC-sRNA-4 | |
| XKC-sRNA-5 | ['IFI27'] |
| XKC-sRNA-6 | ['SERA', 'PSAT'] |
| XKC-sRNA-7 | ['IFI27'] |
| XKC-sRNA-8 | ['IFI27'] |
| YXC-sRNA-1 | ['IFI27'] |
| YXC-sRNA-10 | ['IFI27'] |
| YXC-sRNA-12 | ['SERA', 'PSAT'] |
| YXC-sRNA-13 | ['CCL3L1'] |
| YXC-sRNA-15 | ['CCL3L1'] |
| YXC-sRNA-16 | ['CCL3L1'] |
| YXC-sRNA-18 | ['CCL3L1'] |
| YXC-sRNA-19 | ['CCL3L1'] |
| YXC-sRNA-2 | ['SERA', 'PSAT'] |
| YXC-sRNA-20 | ['SERA', 'PSAT'] |
| YXC-sRNA-22 | ['IFI27'] |
| YXC-sRNA-24 | ['IFI27'] |
| YXC-sRNA-29 | ['EIF3CL'] |
| YXC-sRNA-30 | ['EIF3CL'] |
| YXC-sRNA-31 | ['CCL3L1'] |
| YXC-sRNA-32 | ['CCL3L1'] |
| YXC-sRNA-33 | ['CCL4L2', 'CCL8'] |
| YXC-sRNA-3 | ['CCL4L2', 'CCL3L1'] |

-continued

| YXC-sRNA | Target genes |
| --- | --- |
| YXC-sRNA-34 | ['I-TAC', 'ERAP140', 'HIF1A'] |
| YXC-sRNA-35 | ['CCL3L1'] |
| YXC-sRNA-36 | ['CCL3L1'] |
| YXC-sRNA-37 | ['CCL3L1'] |
| YXC-sRNA-38 | ['CCL3L1'] |
| YXC-sRNA-39 | ['I-TAC', 'GBP1', 'ERAP140', 'HIF1A'] |
| YXC-sRNA-4 | ['SERA', 'PSAT'] |
| YXC-sRNA-40 | ['SERA', 'PSAT'] |
| YXC-sRNA-41 | ['CCL3L1'] |
| YXC-sRNA-42 | ['SERA', 'PSAT'] |
| YXC-sRNA-43 | ['CCL3L1', 'IL8'] |
| YXC-sRNA-44 | ['SERA', 'PSAT'] |
| YXC-sRNA-46 | ['CCL2', 'CCL13', 'CCL3L1', 'MIP-1-beta', 'CCL8'] |
| YXC-sRNA-47 | ['CCL4L2'] |
| YXC-sRNA-49 | ['CCL3L1'] |
| YXC-sRNA-50 | ['CCL3L1'] |
| YXC-sRNA-51 | ['NDUFB2', 'NDUFB1'] |
| YXC-sRNA-52 | ['NDUFA1', 'NDUFB2', 'NDUFA3', 'NDUFB1', 'NDUFB8', 'NDUFS6'] |
| YXC-sRNA-53 | ['NDUFB2', 'NDUFB1'] |
| YXC-sRNA-54 | ['NDUFB2', 'NDUFS6', 'NDUFA3', 'NDUFB1'] |
| YXC-sRNA-55 | ['SNHG9'] |
| YXC-sRNA-56 | ['CCL4L2'] |
| YXC-sRNA-57 | ['NDUFA3', 'NDUFB1'] |
| YXC-sRNA-58 | ['CCL3L1'] |
| YXC-sRNA-5 | ['CCL2', 'CCL13'] |
| YXC-sRNA-62 | ['NDUFA1', 'NDUFB2', 'NDUFB1'] |
| YXC-sRNA-63 | ['IFI6'] |
| YXC-sRNA-64 | ['CCL3L1'] |
| YXC-sRNA-65 | ['IFI6'] |
| YXC-sRNA-68 | ['CCL4L2'] |
| YXC-sRNA-69 | ['CCL4L2'] |
| YXC-sRNA-71 | ['CCL4L2'] |
| YXC-sRNA-72 | ['CCL4L2'] |
| YXC-sRNA-73 | ['NDUFA1', 'NDUFA13', 'NDUFB2', 'NDUFA3', 'NDUFB1'] |
| YXC-sRNA-74 | ['CCL3L1'] |
| YXC-sRNA-75 | ['CCL2'] |
| YXC-sRNA-76 | ['CCL8'] |

-continued

| YXC-sRNA-77 | YXC-sRNA-78 | YXC-sRNA-79 | YXC-sRNA-7 | YXC-sRNA-80 | YXC-sRNA-81 | YXC-sRNA-82 | YXC-sRNA-83 | YXC-sRNA-8 | YXC-sRNA-9 | PGY-sRNA-21 | YXC-sRNA-17 | YXC-sRNA-25 | YXC-sRNA-70 |
|---|---|---|---|---|---|---|---|---|---|---|---|---|---|
| ['NDUFB2', 'NDUFB1'] | ['CCL4L2'] | ['CCL4L2'] | ['CCL3L1'] | ['CCL3L1'] | ['CCL4L2'] | ['CCL3L1'] | ['CCL3L1'] | ['CCL3L1'] | ['CCL4'] | ['CCL4L2'] | ['CCL4L2', 'CCL3L3', 'CCL4L1'] | ['CCL4L2'] | ['CCL8'] |

| Abbreviation | English full name |
|---|---|
| CCL2 | C-C motif chemokine ligand 2 |
| CCL13 | C-C motif chemokine ligand 13 |
| CCL3L1 | C-C motif chemokine ligand 3 like 1 |
| MIP-1-beta (CCL4) | C-C motif chemokine ligand 4 |
| CCL8 | C-C motif chemokine ligand 8 |
| CCL4L2 | C-C motif chemokine ligand 4 like 2 |
| IL-8 | interleukin 8 |
| MIP-1-alpha | CCL3 C-C motif chemokine ligand 3 |
| TNF-alpha (TNF) | tumor necrosis factor |
| CCL4 | C-C motif chemokine ligand 4 |
| CCL3L3 | C-C motif chemokine ligand 3 like 3 |
| CCL4L1 | C-C motif chemokine ligand 4 like 1 |
| I-TAC (CXCL11) | C-X-C motif chemokine ligand 11 |
| IP10 (CXCL10) | C-X-C motif chemokine ligand 10 |
| HIF1A | hypoxia inducible factor 1 subunit alpha |
| GBP1 | guanylate binding protein 1 |
| IL1RN | interleukin 1 receptor antagonist |
| MIG (CXCL9) | C-X-C motif chemokine ligand 9 |
| Apo-2L(TNFSF10) | TNF superfamily member 10 |
| IRF1 | interferon regulatory factor 1 |
| TAP1(PSF1) | transporter 1, ATP binding cassette subfamily B member |
| ERAP140 | nuclear receptor coactivator 7 |
| ISG54 | interferon induced protein with tetratricopeptide repeats 2 |
| RSAD2 | RSAD2 radical S-adenosyl methionine domain containing 2 |

-continued

| Abbreviation | English full name |
|---|---|
| IFI6 | interferon alpha inducible protein 6 |
| IFI27 | interferon alpha inducible protein 27 |
| IFI27L2 | interferon alpha inducible protein 27 like 2 |
| SERA | phosphoglycerate dehydrogenase |
| SHMT2 | serine hydroxymethyltransferase 2 |
| PSAT | phosphoserine aminotransferase 1 |
| EIF3CL | eukaryotic translation initiation factor 3 subunit C like |
| NDUFB2 | NADH: ubiquinone oxidoreductase subunit B2 |
| NDUFS6 | NADH: ubiquinone oxidoreductase subunit S6 |
| NDUFA3 | NADH: ubiquinone oxidoreductase subunit A3 |
| NDUFB1 | NADH: ubiquinone oxidoreductase subunit B1 |
| NDUFA1 | NADH: ubiquinone oxidoreductase subunit A1 |
| NDUFB8 | NADH: ubiquinone oxidoreductase subunit B8 |
| NDUFA13 | NADH: ubiquinone oxidoreductase subunit A13 |
| SNHG9 | small nucleolar RNA host gene 9 |
| SNHG8 | small nucleolar RNA host gene 8 |
| SNHG6 | small nucleolar RNA host gene 6 |

The above are only the preferred embodiments of the present invention. It should be pointed out that for those of ordinary skill in the art, without departing from the principle of the present invention, several improvements and modifications can be made, and these improvements and modifications should also be deemed as the under the protection scope of the present invention.

What is claimed:

1. A method for reducing or down-regulating the expression level of IL-1 beta, IL-6 or/and TNF-alpha in vitro or in vivo, comprising administering to a cell or a subject having inflammation at least one of:

(a) a single-stranded small RNA consisting of SEQ ID NO: 20 or a double-stranded small RNA, wherein one strand consists of SEQ ID NO: 20 and the other strand consists of the complement thereof, (b) a construct comprising a sequence encoding the small RNA, (c) a recombinant virus comprising the construct of (b), (d) an expression vector comprising a sequence encoding the small RNA, (c) a cell comprising the construct of (b); and (f) a pharmaceutical composition comprising the (a), (b), (c), (d), or (e).

2. A method for improving cell survival rate in an H5N1 virus infection, comprising administering to a cell or a subject infected with the H5N1 virus at least one of:

(a) a single-stranded small RNA consisting of SEQ ID NO: 20 or a double-stranded small RNA wherein one strand consists of SEQ ID NO: 20 and the other strand consists of the complement thereof, (b) a construct comprising a sequence encoding the small RNA, (c) a recombinant virus comprising the construct of (b), (d) an expression vector comprising a sequence encoding the small RNA, (e) a cell comprising the construct of (b); and (f) a pharmaceutical composition comprising the (a), (b), (c), (d) or (e).

3. The method according to claim 2, wherein the cell survival rate is the cell survival rate in virus infection, wherein said cell survival rate is improved by rescuing the cell death caused by the virus.

4. The method according to claim 1, wherein the small RNA is siRNA.

5. The method according to claim 2, wherein the small RNA is siRNA.

6. The method according to claim 1, wherein the construct is a viral construct.

7. The method according to claim 2, wherein the construct is a viral construct.

8. The method according to claim 1, wherein the recombinant virus is a retrovirus.

9. The method according to claim 2, wherein the recombinant virus is a retrovirus.

10. The method according to claim 1, wherein the pharmaceutical composition is in prepared in a form for oral administration, intravenous administration subcutaneous administration, intramuscular administration, intraarterial administration, intraperitoneal administration, intrapulmonary administration, intracerebrospinal administration, intraarticular administration, intrasynovial administration, intrathecal administration, intralesional administration, or administration by inhalation.

11. The method according to claim 2, wherein the pharmaceutical composition is in prepared in a form for oral administration, intravenous administration subcutaneous administration, intramuscular administration, intraarterial administration, intraperitoneal administration, intrapulmonary administration, intracerebrospinal administration, intraarticular administration, intrasynovial administration, intrathecal administration, intralesional administration, or administration by inhalation.

12. The method according to claim 1, wherein the pharmaceutical composition comprises any one or more mixtures selected from the group consisting of:

| | | | | | | |
|---|---|---|---|---|---|---|
| Mixture-1 | BZL-sRNA-20 | BZL-sRNA-2 | BZL-sRNA-6 | BZL-sRNA-9 | BZL-sRNA-40 | BZL-sRNA-41 |
| Mixture-2 | BZL-sRNA-20 | BZL-sRNA-4 | BZL-sRNA-8 | BZL-sRNA-12 | BZL-sRNA-21 | BZL-sRNA-31 |
| Mixture-3 | BZL-sRNA-20 | BZL-sRNA-33 | BZL-sRNA-34 | BZL-sRNA-35 | BZL-sRNA-38 | BZL-sRNA-39 |
| Mixture-4 | BZL-sRNA-20 | BZL-sRNA-11 | BZL-sRNA-13 | BZL-sRNA-19 | BZL-sRNA-23 | BZL-sRNA-28 |
| Mixture-5 | BZL-sRNA-20 | BZL-sRNA-29 | BZL-sRNA-36 | BZL-sRNA-37 | BZL-sRNA-42 | |
| Mixture-6 | BZL-sRNA-20 | CHu-sRNA-23 | CHu-sRNA-27 | CHu-sRNA-31 | CHu-sRNA-35 | CHu-sRNA-41 |
| Mixture-7 | BZL-sRNA-20 | CHu-sRNA-46 | CHu-sRNA-47 | CHu-sRNA-48 | CHu-sRNA-49 | CHu-sRNA-50 |
| Mixture-8 | BZL-sRNA-20 | CHu-sRNA-52 | CHu-sRNA-53 | CHu-sRNA-54 | CHu-sRNA-6 | CHu-sRNA-43 |
| Mixture-9 | BZL-sRNA-20 | CHu-sRNA-51 | CHu-sRNA-55 | CHu-sRNA-5 | CHu-sRNA-8 | CHu-sRNA-10 |
| Mixture-10 | BZL-sRNA-20 | CHu-sRNA-21 | CHu-sRNA-24 | CHu-sRNA-28 | CHu-sRNA-29 | CHu-sRNA-30 | CHu-sRNA-42 |
| Mixture-11 | BZL-sRNA-20 | LQi-sRNA-7 | DDi-sRNA-1 | HQi-sRNA-1 | XKC-sRNA-4 | XKC-sRNA-8 |
| Mixture-12 | BZL-sRNA-20 | JYH sRNA-1 | LQi-sRNA-5 | LQi-sRNA-8 | XKC-sRNA-2 | XKC-sRNA-7 |
| Mixture-13 | BZL-sRNA-20 | YXC-sRNA-15 | YXC-sRNA-30 | YXC-sRNA-32 | YXC-sRNA-33 | YXC-sRNA-34 |
| Mixture-14 | BZL-sRNA-20 | YXC-sRNA-35 | YXC-sRNA-38 | YXC-sRNA-39 | YXC-sRNA-40 | YXC-sRNA-43 |
| Mixture-15 | BZL-sRNA-20 | YXC-sRNA-46 | YXC-sRNA-47 | YXC-sRNA-50 | YXC-sRNA-51 | YXC-sRNA-53 |
| Mixture-16 | BZL-sRNA-20 | YXC-sRNA-56 | YXC-sRNA-62 | YXC-sRNA-64 | YXC-sRNA-70 | YXC-sRNA-71 |
| Mixture-17 | BZL-sRNA-20 | YXC-sRNA-72 | YXC-sRNA-75 | YXC-sRNA-79 | YXC-sRNA-82 | |
| Mixture-18 | BZL-sRNA-20 | YXC-sRNA-1 | YXC-sRNA-2 | YXC-sRNA-3 | YXC-sRNA-9 | YXC-sRNA-10 |
| Mixture-19 | BZL-sRNA-20 | YXC-sRNA-12 | YXC sRNA-13 | YXC-sRNA-16 | YXC-sRNA-19 | YXC-sRNA-24 |
| Mixture-20 | BZL-sRNA-20 | YXC-sRNA-25 | YXC-sRNA-26 | YXC-sRNA-28 | YXC-sRNA-29 | YXC-sRNA-31 |
| Mixture-21 | BZL-sRNA-20 | YXC-sRNA-36 | YXC-sRNA-37 | YXC-sRNA-41 | YXC-sRNA-42 | YXC-sRNA-44 |
| Mixture-22 | BZL-sRNA-20 | YXC-sRNA-48 | YXC-sRNA-49 | YXC-sRNA-54 | YXC-sRNA-55 | YXC-sRNA-57 |
| Mixture-23 | BZL-sRNA-20 | YXC-sRNA-58 | YXC-sRNA-60 | YXC-sRNA-66 | YXC-sRNA-68 | YXC-sRNA-69 |
| Mixture-24 | BZL-sRNA-20 | YXC-sRNA-73 | YXC-sRNA-80 | YXC-sRNA-83 | | |
| Mixture-25 | BZL-sRNA-20 | PGY-sRNA-21 | PGY-sRNA-22 | PGY-sRNA-23 | PGY-sRNA-25 | PGY-sRNA-26 |
| Mixture-26 | BZL-sRNA-20 | PGY-sRNA-28 | PGY-sRNA-29 | PGY-sRNA-30 | PGY-sRNA-32 | |
| Mixture-27 | BZL-sRNA-20 | CXL-sRNA-30 | PGY-sRNA-27 | PGY-sRNA-31 | PGY-sRNA-24 | |

-continued

| Mixture | | | | | | |
|---|---|---|---|---|---|---|
| Mixture-28 | BZL-sRNA-20 | BZL-sRNA-1 | BZL-sRNA-3 | BZL-sRNA-5 | BZL-sRNA-7 | BZL-sRNA-10 |
| Mixture-29 | BZL-sRNA-20 | BZL-sRNA-14 | BZL-sRNA-15 | BZL-sRNA-16 | BZL-sRNA-17 | BZL-sRNA-18 | BZL-sRNA-30 |
| Mixture-30 | BZL-sRNA-20 | BZL-sRNA-22 | BZL-sRNA-24 | BZL-sRNA-25 | BZL-sRNA-26 | BZL-sRNA-27 | BZL-sRNA-32 |
| Mixture-31 | BZL-sRNA-20 | CHu-sRNA-1 | CHu-sRNA-2 | CHu-sRNA-3 | CHu-sRNA-4 | CHu-sRNA-7 |
| Mixture-32 | BZL-sRNA-20 | CHu-sRNA-9 | CHu-sRNA-11 | CHu-sRNA-12 | CHu-sRNA-13 | CHu-sRNA-14 |
| Mixture-33 | BZL-sRNA-20 | CHu-sRNA-15 | CHu-sRNA-16 | CHu-sRNA-17 | CHu-sRNA-18 | CHu-sRNA-19 |
| Mixture-34 | BZL-sRNA-20 | CHu-sRNA-20 | CHu-sRNA-22 | CHu-sRNA-25 | CHu-sRNA-26 | CHu-sRNA-32 |
| Mixture-35 | BZL-sRNA-20 | CHu-sRNA-33 | CHu-sRNA-34 | CHu-sRNA-36 | CHu-sRNA-37 | CHu-sRNA-38 |
| Mixture-36 | BZL-sRNA-20 | CHu-sRNA-39 | CHu-sRNA-40 | CHu-sRNA-44 | CHu-sRNA-45 | |
| Mixture-37 | BZL-sRNA-20 | HQi-sRNA-2 | LQi-sRNA-1 | LQi-sRNA-2 | LQi-sRNA-3 | LQi-sRNA-4 |
| Mixture-38 | BZL-sRNA-20 | LQi-sRNA-6 | XKC-sRNA-1 | XKC-sRNA-3 | XKC-sRNA-5 | XKC-sRNA-6 |
| Mixture-39 | BZL-sRNA-20 | YXC-sRNA-4 | YXC-sRNA-5 | YXC-sRNA-6 | YXC-sRNA-7 | YXC-sRNA-8 |
| Mixture-40 | BZL-sRNA-20 | YXC-sRNA-11 | YXC-sRNA-14 | YXC-sRNA-17 | YXC-sRNA-18 | YXC-sRNA-20 |
| Mixture-41 | BZL-sRNA-20 | YXC-sRNA-21 | YXC-sRNA-22 | YXC-sRNA-23 | YXC-sRNA-27 | YXC-sRNA-45 |
| Mixture-42 | BZL-sRNA-20 | YXC-sRNA-52 | YXC-sRNA-59 | YXC-sRNA-61 | YXC-sRNA-63 | YXC-sRNA-65 |
| Mixture-43 | BZL-sRNA-20 | YXC-sRNA-67 | YXC-sRNA-74 | YXC-sRNA-81 | YXC-sRNA-76 | YXC-sRNA-77 | YXC-sRNA-78. |

13. The method according to claim 2, wherein the pharmaceutical composition comprises any one or more mixtures selected from the group consisting of:

| Mixture | | | | | | |
|---|---|---|---|---|---|---|
| Mixture-1 | BZL-sRNA-20 | BZL-sRNA-2 | BZL-sRNA-6 | BZL-sRNA-9 | BZL-sRNA-40 | BZL-sRNA-41 |
| Mixture-2 | BZL-sRNA-20 | BZL-sRNA-4 | BZL-sRNA-8 | BZL sRNA-12 | BZL-sRNA-21 | BZL-sRNA-31 |
| Mixture-3 | BZL-sRNA-20 | BZL-sRNA-33 | BZL sRNA-34 | BZL sRNA-35 | BZL-sRNA-38 | BZL-sRNA-39 |
| Mixture-4 | BZL-sRNA-20 | BZL-sRNA-11 | BZL-sRNA-13 | BZL-sRNA-19 | BZL-sRNA-23 | BZL-sRNA-28 |
| Mixture-5 | BZL-sRNA-20 | BZL-sRNA-29 | BZL-sRNA-36 | BZL-sRNA-37 | BZL-sRNA-42 | |
| Mixture-6 | BZL-sRNA-20 | CHu-sRNA-23 | CHu-sRNA-27 | CHu-sRNA-31 | CHu-sRNA-35 | CHu-sRNA-41 |
| Mixture-7 | BZL-sRNA-20 | CHu-sRNA-46 | CHu-sRNA-47 | CHu-sRNA-48 | CHu-sRNA-49 | CHu-sRNA-50 |
| Mixture-8 | BZL-sRNA-20 | CHu-sRNA-52 | CHu-sRNA-53 | CHu-sRNA-54 | CHu-sRNA-6 | CHu-sRNA-43 |
| Mixture-9 | BZL-sRNA-20 | CHu-sRNA-51 | CHu-sRNA-55 | CHu-sRNA-5 | CHu-sRNA-8 | CHu-sRNA-10 |
| Mixture-10 | BLL-sRNA-20 | CHu-sRNA-21 | CHu-sRNA-24 | CHu-sRNA-28 | CHu-sRNA-29 | CHu-sRNA-30 | CHu-sRNA-42 |
| Mixture-11 | BZL-sRNA-20 | LQi-sRNA-7 | DDi-sRNA-1 | HQi-sRNA-1 | XKC-sRNA-4 | XKC-sRNA-8 |
| Mixture-12 | BZL-sRNA-20 | JYH-sRNA-1 | LQi-sRNA-5 | LQi-sRNA-8 | XKC-sRNA-2 | XKC-sRNA-7 |
| Mixture-13 | BZL-sRNA-20 | YXC-sRNA-15 | YXC-sRNA-30 | YXC-sRNA-32 | YXC-sRNA-33 | YXC-sRNA-34 |
| Mixture-14 | BZL-sRNA-20 | YXC-sRNA-35 | YXC-sRNA-38 | YXC-sRNA-39 | YXC-sRNA-40 | YXC-sRNA-43 |
| Mixture-15 | BZL-sRNA-20 | YXC-sRNA-46 | YXC-sRNA-47 | YXC-sRNA-50 | YXC-sRNA-51 | YXC-sRNA-53 |
| Mixture-16 | BZL-sRNA-20 | YXC-sRNA-56 | YXC sRNA-62 | YXC-sRNA-64 | YXC-sRNA-70 | YXC-sRNA-71 |
| Mixture-17 | BZL-sRNA-20 | YXC-sRNA-72 | YXC-sRNA-75 | YXC-sRNA-79 | YXC-sRNA-82 | |
| Mixture-18 | BZL-sRNA-20 | YXC-sRNA-1 | YXC sRNA-2 | YXC-sRNA-3 | YXC-sRNA-9 | YXC-sRNA-10 |
| Mixture-19 | BZL-sRNA-20 | YXC-sRNA-12 | YXC-sRNA-13 | YXC-sRNA-16 | YXC-sRNA-19 | YXC-sRNA-24 |

-continued

| | | | | | | |
|---|---|---|---|---|---|---|
| Mixture-20 | BZL-sRNA-20 | YXC-sRNA-25 | YXC sRNA-26 | YXC-sRNA-28 | YXC-sRNA-29 | YXC-sRNA-31 |
| Mixture-21 | BZL-sRNA-20 | YXC-sRNA-36 | YXC-sRNA-37 | YXC-sRNA-41 | YXC-sRNA-42 | YXC-sRNA-44 |
| Mixture-22 | BZL-sRNA-20 | YXC-sRNA-48 | YXC-sRNA-49 | YXC-sRNA-54 | YXC-sRNA-55 | YXC-sRNA-57 |
| Mixture-23 | BZL-sRNA-20 | YXC-sRNA-58 | YXC-sRNA-60 | YXC-sRNA-66 | YXC-sRNA-68 | YXC-sRNA-69 |
| Mixture-24 | BZL-sRNA-20 | YXC-sRNA-73 | YXC-sRNA-80 | YXC-sRNA-83 | | |
| Mixture-25 | BZL-sRNA-20 | PGY-sRNA-21 | PGY-sRNA-22 | PGY-sRNA-23 | PGY-sRNA-25 | PGY-sRNA-26 |
| Mixture-26 | BZL-sRNA-20 | PGY-sRNA-28 | PGY-sRNA-29 | PGY-sRNA-30 | PGY-sRNA-32 | |
| Mixture-27 | BZL-sRNA-20 | CXL-sRNA-30 | PGY-sRNA-27 | PGY-sRNA-31 | PGY-sRNA-24 | |
| Mixture-28 | BZL-sRNA-20 | BZL-sRNA-1 | BZL-sRNA-3 | BZL-sRNA-5 | BZL-sRNA-7 | BZL-sRNA-10 |
| Mixture-29 | BZL-sRNA-20 | BZL-sRNA-14 | BZL-sRNA-15 | BZL-sRNA-16 | BZL-sRNA-17 | BZL-sRNA-18 |
| Mixture-30 | BZL-sRNA-20 | BZL-sRNA-22 | BZL-sRNA-24 | BZL-sRNA-25 | BZL-sRNA-26 | BZL-sRNA-27 |
| Mixture-31 | BZL-sRNA-20 | CHu-sRNA-1 | CHu-sRNA-2 | CHu-sRNA-3 | CHu-sRNA-4 | CHu-sRNA-7 |
| Mixture-32 | BZL-sRNA-20 | CHu-sRNA-9 | CHu-sRNA-11 | CHu-sRNA-12 | CHu-sRNA-13 | CHu-sRNA-14 |
| Mixture-33 | BZL-sRNA-20 | CHu-sRNA-15 | CHu-sRNA-16 | CHu-sRNA-17 | CHu-sRNA-18 | CHu-sRNA-19 |
| Mixture-34 | BZL-sRNA-20 | CHu-sRNA-20 | CHu-sRNA-22 | CHu-sRNA-25 | CHu-sRNA-26 | CHu-sRNA-32 |
| Mixture-35 | BZL-sRNA-20 | CHu-sRNA-33 | CHu-sRNA-34 | CHu-sRNA-36 | CHu-sRNA-37 | CHu-sRNA-38 |
| Mixture-36 | BZL-sRNA-20 | CHu-sRNA-39 | CHu-sRNA-40 | CHu-sRNA-44 | CHu-sRNA-45 | |
| Mixture-37 | BZL-sRNA-20 | HQi-sRNA-2 | LQi-sRNA-1 | LQi-sRNA-2 | LQi-sRNA-3 | LQi-sRNA-4 |
| Mixture-38 | BZL-sRNA-20 | LQi-sRNA-6 | XKC-sRNA-1 | XKC-sRNA-3 | XKC-sRNA-5 | XKC-sRNA-6 |
| Mixture-39 | BZL-sRNA-20 | YXC-sRNA-4 | YXC-sRNA-5 | YXC-sRNA-6 | YXC-sRNA-7 | YXC-sRNA-8 |
| Mixture-40 | BZL-sRNA-20 | YXC-sRNA-11 | YXC-sRNA-14 | YXC-sRNA-17 | YXC-sRNA-18 | YXC-sRNA-20 |
| Mixture-41 | BZL-sRNA-20 | YXC-sRNA-21 | YXC-sRNA-22 | YXC-sRNA-23 | YXC-sRNA-27 | YXC-sRNA-45 |
| Mixture-42 | BZL-sRNA-20 | YXC-sRNA-52 | YXC-sRNA-59 | YXC-sRNA-61 | YXC-sRNA-63 | YXC-sRNA-65 |
| Mixture-43 | BZL-sRNA-20 | YXC-sRNA-67 | YXC-sRNA-74 | YXC-sRNA-81 | YXC-sRNA-76 | YXC-sRNA-77 |

(Mixture-29 additional: BZL-sRNA-30; Mixture-30 additional: BZL-sRNA-32; Mixture-43 additional: YXC-sRNA-78.)

14. The method according to claim 12, wherein the molar concentration ratio of the small RNA consisting of SEQ ID NO: 20 to other small RNA(s) in the pharmaceutical composition is about 2:1.

15. The method according to claim 13, wherein the molar concentration ratio of the small RNA consisting of SEQ ID NO: 20 to other small RNA(s) in the pharmaceutical composition is about 2:1.

\*    \*    \*    \*    \*